(12) United States Patent
Freed et al.

(10) Patent No.: US 12,384,829 B2
(45) Date of Patent: Aug. 12, 2025

(54) POCKET ENGINEERING OF HLA ALLELES FOR TREATING AUTOIMMUNITY

(71) Applicant: THE REGENTS OF THE UNIVERSITY OF COLORADO, Denver, CO (US)

(72) Inventors: Brian Freed, Centennial, CO (US); Christina Roark, Englewood, CO (US); Elizabeth Sunderhaus, W. Henrietta, NY (US)

(73) Assignee: The Regents of The University of Colorado, A Body Corporate, Denver, CO (US)

( * ) Notice: Subject to any disclaimer, the term of this patent is extended or adjusted under 35 U.S.C. 154(b) by 0 days.

(21) Appl. No.: 18/156,887

(22) Filed: Jan. 19, 2023

(65) Prior Publication Data
US 2023/0295265 A1    Sep. 21, 2023

Related U.S. Application Data

(63) Continuation of application No. 17/741,438, filed on May 10, 2022, now Pat. No. 12,202,880.

(60) Provisional application No. 63/186,770, filed on May 10, 2021.

(51) Int. Cl.
| | |
|---|---|
| C07K 14/74 | (2006.01) |
| A61K 35/17 | (2025.01) |
| A61K 35/28 | (2015.01) |
| A61K 40/10 | (2025.01) |
| A61K 40/22 | (2025.01) |
| A61K 40/41 | (2025.01) |
| A61P 37/02 | (2006.01) |
| A61P 37/06 | (2006.01) |
| C12N 5/0775 | (2010.01) |
| C12N 15/62 | (2006.01) |
| C12N 15/86 | (2006.01) |
| C12Q 1/6881 | (2018.01) |
| A61K 38/00 | (2006.01) |

(52) U.S. Cl.
CPC ........ *C07K 14/70539* (2013.01); *A61K 35/28* (2013.01); *A61K 40/10* (2025.01); *A61K 40/22* (2025.01); *A61K 40/416* (2025.01); *A61P 37/02* (2018.01); *A61P 37/06* (2018.01); *C12N 5/0663* (2013.01); *C12N 15/625* (2013.01); *C12N 15/86* (2013.01); *C12Q 1/6881* (2013.01); *A61K 38/00* (2013.01); *C12N 2740/10043* (2013.01)

(58) Field of Classification Search
CPC .. C07K 14/70539; A61K 35/17; A61K 35/28; A61K 40/10; A61K 38/00; A61P 37/06; A61P 37/02; C12Q 1/6881; C12N 5/0663; C12N 2740/10043
See application file for complete search history.

(56) References Cited

U.S. PATENT DOCUMENTS

| | | |
|---|---|---|
| 5,965,787 A | 10/1999 | Luthra |
| 11,932,867 B2 | 3/2024 | Freed et al. |
| 2003/0017143 A1 | 1/2003 | Suciu-Foca |
| 2004/0033516 A1 | 2/2004 | Mougin |
| 2012/0264627 A1 | 10/2012 | Reinherz |
| 2015/0166616 A1 | 6/2015 | Bancel |
| 2018/0296603 A1 | 10/2018 | Gori |
| 2020/0123611 A1 | 4/2020 | Grant et al. |
| 2020/0199616 A1 | 6/2020 | Freed |
| 2021/0071249 A1 | 3/2021 | Irani |
| 2023/0091257 A1 | 3/2023 | Freed |
| 2023/0123094 A1 | 4/2023 | Freed et al. |
| 2023/0126183 A1 | 4/2023 | Freed et al. |
| 2023/0159617 A1 | 5/2023 | Freed et al. |
| 2023/0192808 A1 | 6/2023 | Freed et al. |
| 2024/0327862 A1 | 10/2024 | Freed |

FOREIGN PATENT DOCUMENTS

| | | | |
|---|---|---|---|
| JP | 2004535173 A | * 11/2004 | ............. C07K 14/56 |
| WO | 2016021972 | 2/2016 | |
| WO | 2016/201047 | 12/2016 | |

(Continued)

OTHER PUBLICATIONS

Christelle Pommie et al. IMGT standardized criteria for statistical analysis of immunoglobulin V-REGION amino acid properties; J. Mol. Recognit. 2004; 17: 17-32 (Year: 2004).*

International Search Report and Written Opinion for International Application No. PCT/US2022/028643, Oct. 11, 2022.

International Search Report and Written Opinion for International Application No. PCT/US2022/028644, Oct. 11, 2022.

(Continued)

*Primary Examiner* — Fereydoun G Sajjadi
*Assistant Examiner* — Masudur Rahman
(74) *Attorney, Agent, or Firm* — Womble Bond Dickinson (US) LLP

(57) ABSTRACT

Methods of preventing or treating autoimmune disease are disclosed. In some cases, subjects with having or at risk of developing autoimmune disease are identified as possessing one or more autoimmunity-susceptibility HLA alleles at one or more HLA loci. In many cases, the HLA loci are selected from Class I and Class II loci, for example Class I A, B, and C, and Class II DQ, DR, and DP. In many cases, subjects suffering from or at risk of developing an autoimmune disease may be administered a plurality engineered autologous HSCs modified to carry and express a variant susceptibility allele having at least one mutation in the antigen binding cleft that alters antigen binding and/or specificity of that variant HLA molecule. In many embodiments, the engineered HSCs are CD34+ immune cells that express one or more modified HLA proteins.

13 Claims, 45 Drawing Sheets

Specification includes a Sequence Listing.

(56) References Cited

FOREIGN PATENT DOCUMENTS

| WO | 2017/044672 | 3/2017 |
| WO | 2018200635 | 11/2018 |
| WO | 2019/126818 | 6/2019 |
| WO | 2019/158602 | 8/2019 |
| WO | 2020/006357 | 1/2020 |
| WO | 2020/180501 | 9/2020 |
| WO | 2020/181062 | 9/2020 |
| WO | 2020/181272 | 9/2020 |
| WO | 2020/201467 | 10/2020 |

OTHER PUBLICATIONS

International Search Report and Written Opinion for International Application No. PCT/US2022/028645, Dec. 2, 2022.
Zubillaga et al., "HLA-DQA1 and HLA-DQB1 genetic markers and clinical presentation in celiac disease", Journal of Pediatric Gastroenterology and Nutrition, Lippincott Williams Wilkins, Inc, US, vol. 34, No. 5, May 1, 2002, pp. 548-554.
Percival D Sampaio-Barros et al., "Characterization and outcome of uveitits in 350 patients with spondyloarthropathies", Rheumatology International; Clinical and Experimental Investigations, Springer, Berlin, DE, vol. 26, No. 12, Sep. 7, 2006), pp. 1143-1146.
Misra et al., "Structure-based selection of human metabolite binding P4 pocket of DRB1*15:01 and DRB1*15:03, with implications for multiple sclerosis", Genes and Immunity, Nature Publishing Group, GB, vol. 20, No. 1, Jan. 20, 2018, pp. 46-55.
Misra et al., "The immunogenetics of neurological disease", Immunology, Wiley-Blackwell Publishing Ltd, GB, vol. 153, No. 4, Dec. 11, 2017, pp. 399-414.
Ryan et al., "Genetic markers of treatment response to tumour necrosis factor-[alpha] inhibitors in the treatment of psoriasis", Clinical and Experimental Dermatology, Blackwell Scientific Publications, GB, vol. 39, No. 4, Apr. 23, 2014, pp. 519-524.
Johannes R Hov et al., "Electrostatic modifications of the human leukocyte antigen-DR P9 peptide-binding pocket and susceptibility to primary sclerosing cholangitis", Hepatology, John Wiley & Sons, Inc, US, vol. 53, No. 6, May 13, 2011, pp. 1967-1976.
Ling et al., "HLA-DRB1 amino acid positions 11/13, 71, and 74 are associated with inflammation level, disease activity, and the health assessment questionnaire score in patients with inflammatory polyarthritis", Arthritis & Rheumatology 68.11 (2016), 2618-2628.
Extended European Search Report for EP 18791113.6 dated Mar. 10, 2021, 8 pages.
Anderson, Kirsten M., "A Molecular Analysis of the Shared Epitope Hypothesis: Binding of Arthritogenic Peptides to DRB1*04 Alleles 11", Arthritis & Rheumatology, vol. 68, No. 7, Jul. 2016, pp. 1627-1636.
Roark et al., "Progress towards gene editing of HLA-DRB1*04:01 by CRISPR/Cas9", Human Immunology, vol. 79, No. Suppl., p. 162, 31 (Aug. 31, 2018), p. 186.
Roark et al., "Arthritogenic peptide binding to DRB1*01 alleles correlates with susceptibility to rheumatoid arthritis", Journal of Autoimmunity, vol. 72, Apr. 30, 2016, pp. 25-35.

Office Action dated Apr. 5, 2022 in connection with Japanese patent application No. 2019-558446, 6 pages with English translation.
National Center for Biotechnology Information, "Amycolatopsiskeratiniphilia strain FH 1893 genome assembly, chromosome: I", GenBank: LT629789, Oct. 21, 2016, 499 pages.
National Center for Biotechnology Information, "Microlunatus phosphovorous NM-1 DNA, complete genome", GenBank: AP012204.1, Oct. 7, 2016, 746 pages.
National Center for Biotechnology Information, "Myodes glareolus MHC class II antigen (Mygl-DRB) gene, Mygl-DRB*48 allele, exon 2 and partial cds", GenBank: GQ901819.1, Jul. 24, 2016, 1 page.
PCT, International Search Report and Written Opinion, Application No. PCT/US2018/029302, Sep. 11, 2018, 15 pages.
Raychaudhuri, Soumya et al., "Five amino acids in three HLA proteins explain most of the association between MHC and seropositive rheumatoid arthritis", Nat. Genet., vol. 44 No. 3, Mar. 2012, pp. 291-296.
PHLA 3D, HLA Molecule DRB1*04:01, retrieved online at https://www.phla3d.com.br/alleles/view/DRB1*04:01/1, Apr. 17, 2023.
HLA Nomenclature, HLA Alleles Numbers, retrieved online at http://hla.alleles.org/nomenclature/stats.html, Apr. 17, 2023.
Coppin et al., "Position 71 in the a helix of the DRB domain is predicted to influence peptide binding and plays a central role in allorecognition", European Journal Immunology, 23, 343-349, 1993.
Young et al., "HLA-DRB1 amino acid disparity is the major stimulus of interleukin-2 production by alloreactive helper T-lymphocytes", Immunogenetics, 47, 310-317, 1998.
Fleischhauer et al., "Bone Marrow-Allograft Rejection by T Lymphocytes Recognizing a Single Amino Acid Difference in HLA-B44", The New England Journal of Medicine, 323:1818-1822, Dec. 27, 1990.
Schulman et al., "Mismatches at the HLA-DR and the HLA-B Loci Are Risk Factors for Acute Rejection after Lung Transplantation", American Journal of Respiratory and Critical Care Medicine, vol. 157, 1833-1837, 1998.
McInnes et al., "The Pathogenesis of Rheumatoid Arthritis", The New England Journal of Medicine, 365: 2205-2219, Dec. 8, 2011.
Watanabe et al., STN Accession No. 20200609125 (abstract for Watanabe et al., 2020, 4 pages) (Year: 2020).
Diller, R. et al., "Metal-triggered conformational reorientation of a self-peptide bound to a disease-associated HLA-B*27 subtype", J. Biol. Chem., Jul. 2019, vol. 294 (36), pp. 13269-13279.
Morel, P.A. et al. (1988). Aspartic acid at position 57 of the HLA-DQ beta chain protects against type I diabetes: a family study. Proceedings of the National Academy of Sciences, 85(21), 8111-8115 (Year: 1988).
Dever et al., "CRISPR / Cas9 (Beta)-globin gene targeting in human haematopoietic stem cells", Nature, vol. 539, pp. 384-389, Nov. 17, 2016.
Hoban et al., "CRISPR / Cas9-Mediated Correction of the Sickle Mutation in Human CD34+ cells", Molecular Therapy, vol. 24, No. 9, pp. 1561-1569, Sep. 2016.
Khodthong et al. "Optimization of DNA, RNA and RNP Delivery for Efficient Mammalian Cell Engineering", Mirus Bio LLC, 2016.
Extended European Search Report for EP Application No. 24162513.6 dated Aug. 28, 2024.

* cited by examiner

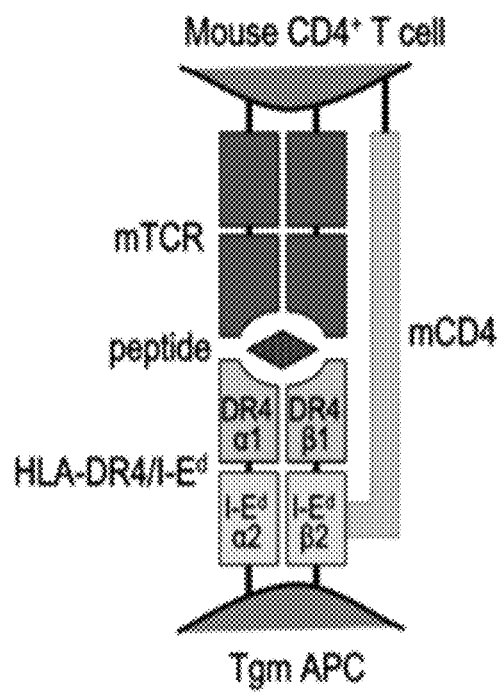
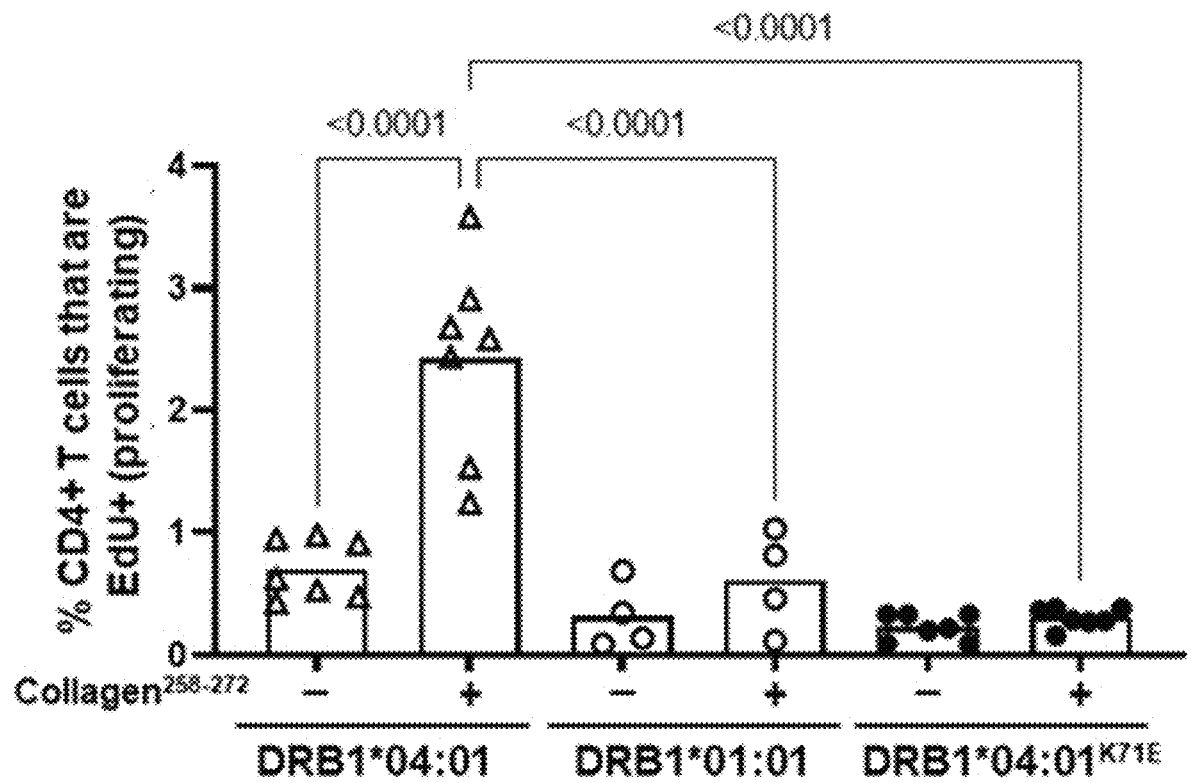
Fig. 2

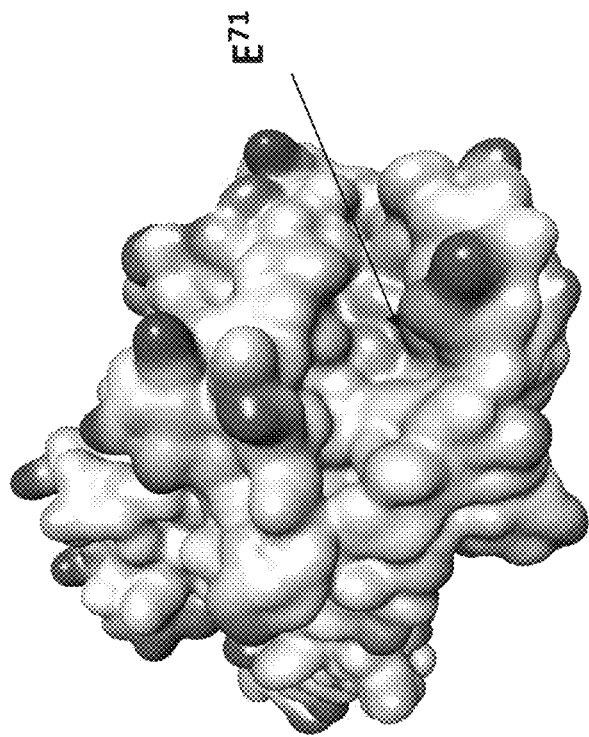
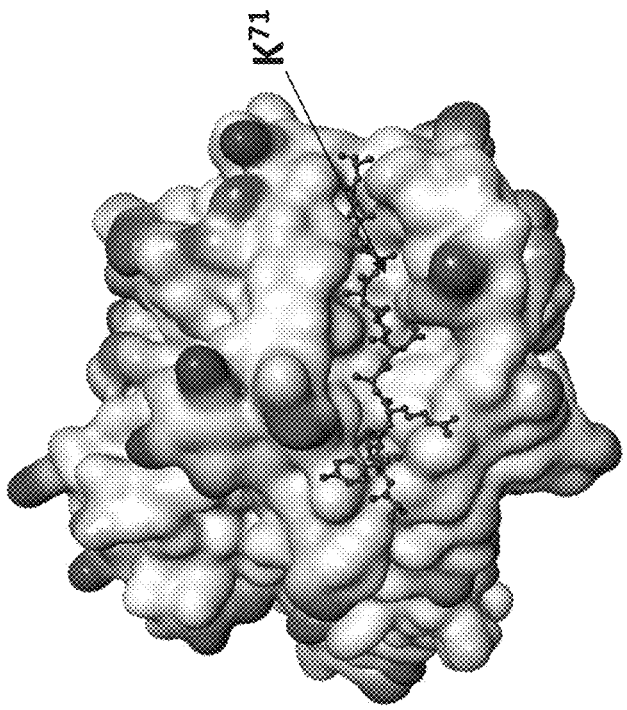
Fig. 3A

Binding of Aquaporin Peptides to DRB1 Alleles

Susceptible DRB1*03:01    AQP4-5    Resistant DRB1*07:01

3.56

0.95

AQP4-6

2.68

0.79

Peptide Binding (Mean Fluorescence Intensity)

Fig.9

Sequence alignment DRB1*04:01 and *04:05

Fig.10

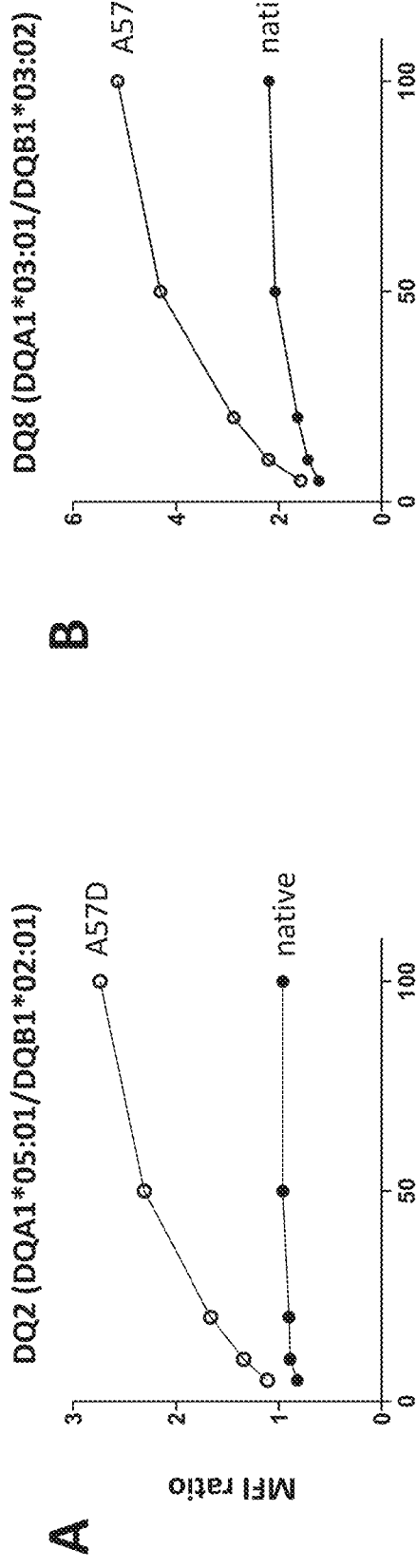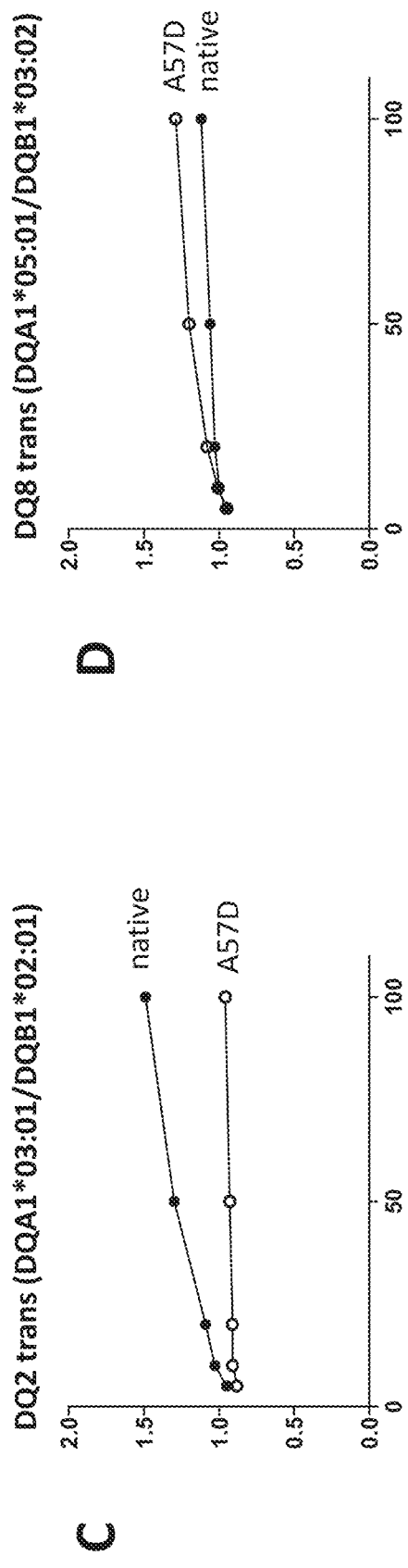
Fig. 12

Fig.16   Peptide Binding (Mean Fluorescence Intensity)

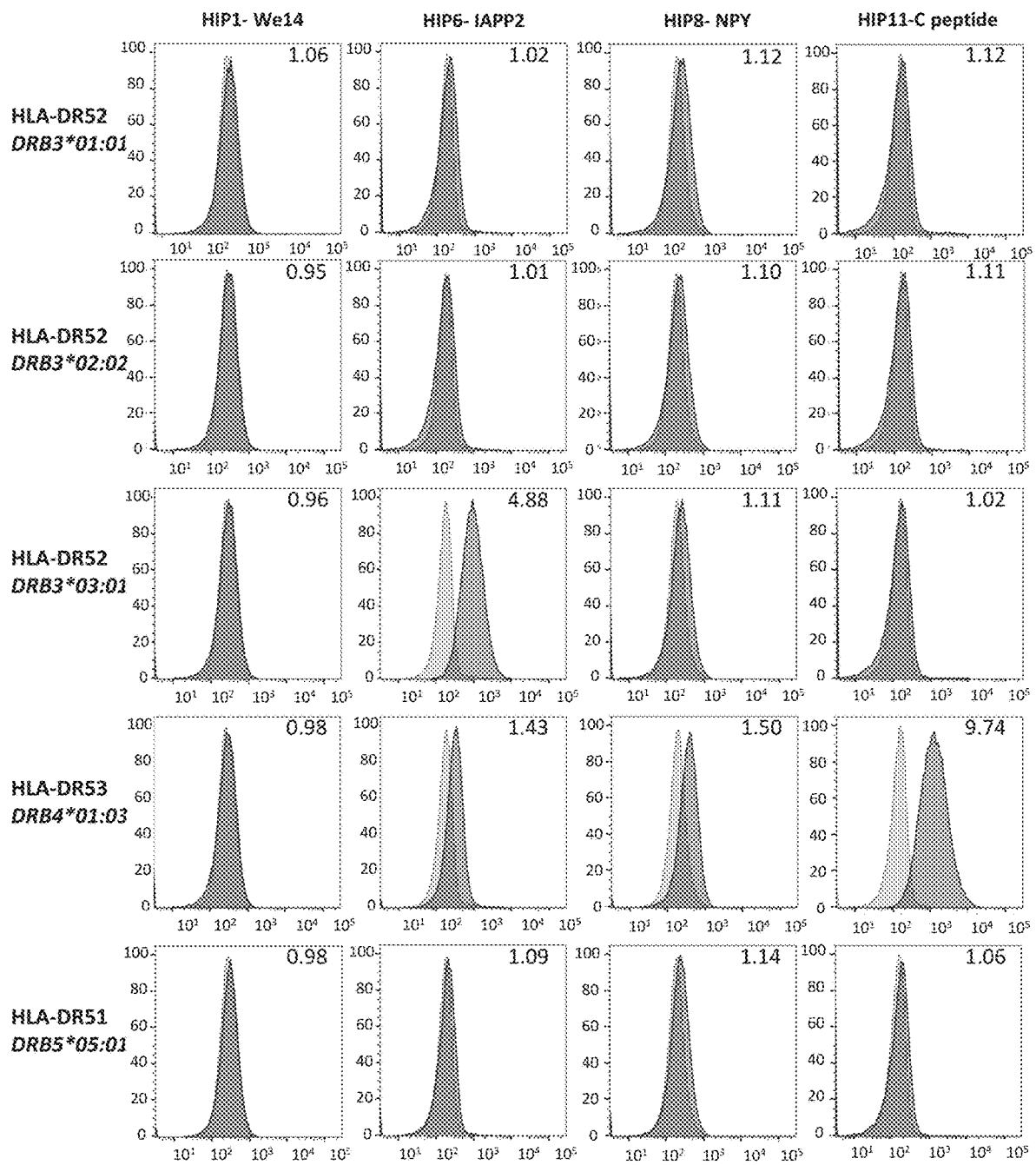
Fig. 20  Peptide Binding (Mean Fluorescence Intensity)

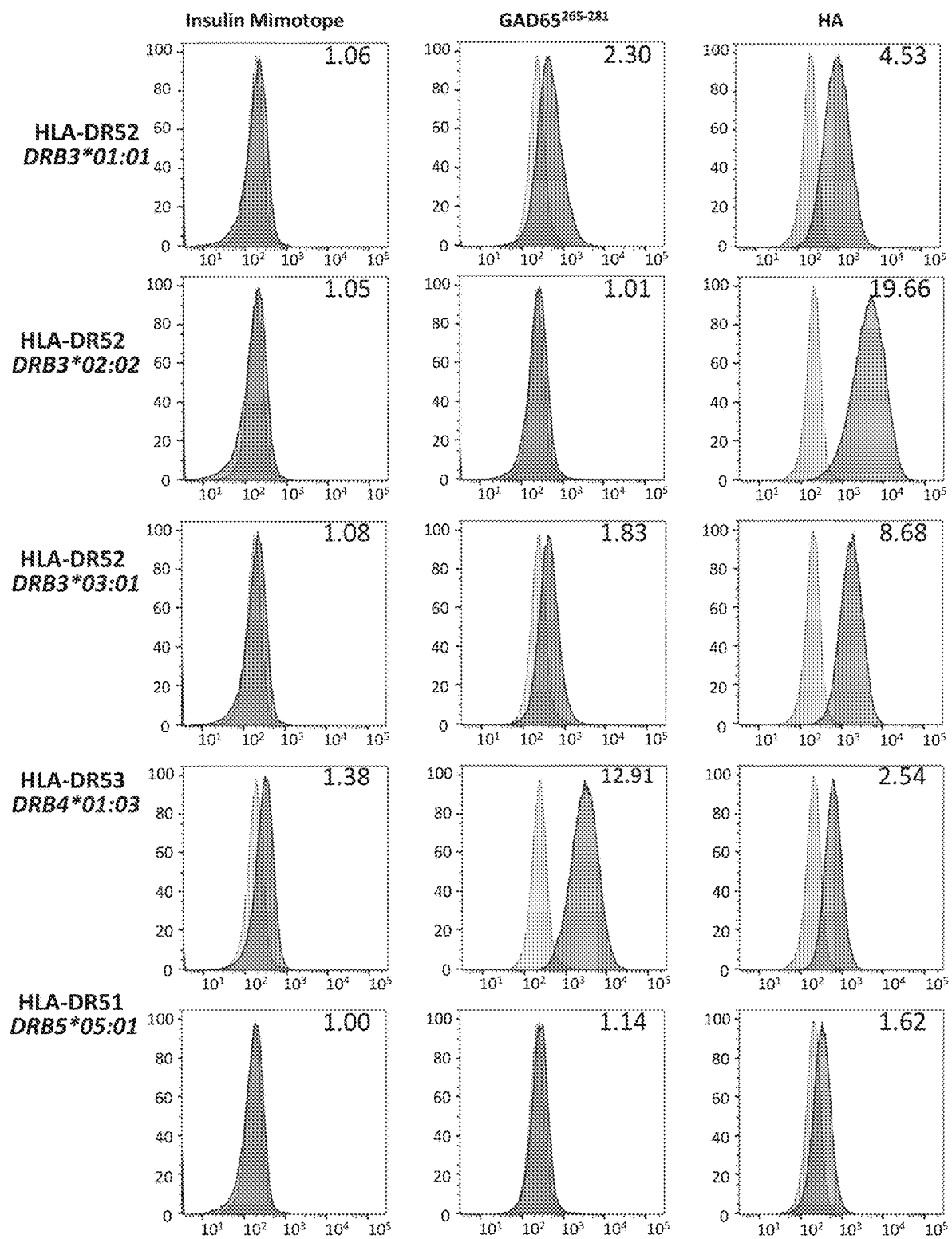
Fig. 21     Peptide Binding (Mean Fluorescence Intensity)

| Disease | Peptide | Sequence | SEQ ID NO: |
|---|---|---|---|
| MS | MBP(83-101) | ENPVVHFFKNIVTPRTPPP | 123 |
|  | RASGRP2(78-87) | LVRYWISAFP | 122 |
|  | MOG(97-109) | FFRDHSYQEEA | 121 |
|  | MBP(146-170) | AQGTLSKIFKLGGRDSRSGSPMARR | 124 |
| Diabetes | HIP 1 | GQVELGG-WSKMDQLA | 97 |
|  | HIP6 | GQVELGGG-NAVEVLK | 98 |
|  | HIP8 | GQVELGGG-SSPETLI | 99 |
|  | HIP11 | SLQPLA-LEAEDLQV | 100 |
|  | Insulin Mimotope | HLVEELYLVAGEEG | 102 |
|  | GAD65(265-281) | AMMIARFKMFPEVKEKG | 101 |
|  | Insulin B9-23 | SHLVEALYLVCGERG | 104 |
| NMO | AQP4(284-298) (AQP4-5) | RSQVETDDLILKPGV | 105 |
|  | AQP4(285-299) (AQP4-6) | SQVETDDLILKPGVV | 106 |
| RA | Type II Collagen(258-272) | PGIAGFKGEQGPKGE | 107 |
|  | carbamylated collagen |  |  |
|  | alpha enolase(11-25) | IFDSRGNPTVEVDLF | 108 |
|  | citrullinated a enolase | IFDS{CIT}GNPTVEVDLF | 109 |
|  | Native Vimentin (66-78) | SAVRLRSSVPGVR | 110 |
|  | Citrullinated vimentin | SAVRL{CIT}SSVPGVR | 111 |
|  | carbamylated vimentin |  |  |
|  | fibrinogen(79-91) | QDFTNRINKLKNS | 112 |
|  | citrullinated fibrinogen(79-91) | QDFTN{CIT}INKLKNS | 113 |
|  | carbamylated fibrongen(79-91) |  |  |
|  | aggrecan(89-103) | ATEGRVRVNSAYQDK | 114 |
|  | citrullinated aggrecan | ATEG{CIT}VRVNSAYQDK | 115 |
|  | cartilage intermediate layer protein - CILP(297-311) | ATIKAEFVRAETPYM | 116 |
|  | citrullinated CILP | ATIKAEFV{CIT}AETPYM | 117 |
|  | Asparagine Synthase Peptide Derived from Streptomyces | AVRLQGSVAGVR | 118 |
| Other | BK virus | PYHFKYHEKHFANAI | 119 |
|  | CLIP | PVSKMRMATPLLMQA | 120 |
|  | Influenza hemagglutinin (HA(306-318)) | PKYVKQNTLKLAT | 103 |

Fig. 22

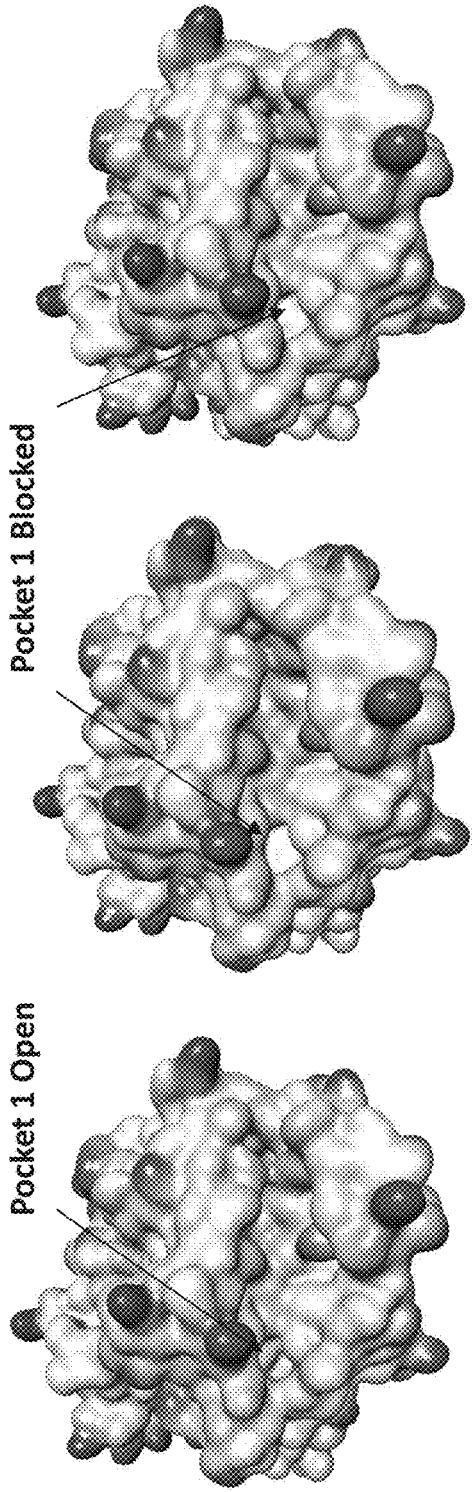
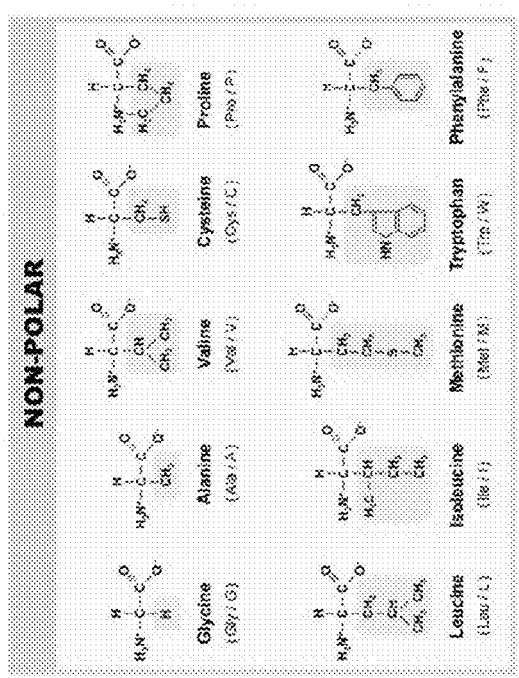
Fig. 23A

Representative alleles, positions, mutations

| Allele | Specific positions/specific mutatns |
|---|---|
| DRB1*01:01 | L67I  Q70D  V85A  G86V  R71E |
| DRB1*01:02 | |
| DRB1*01:03 | |
| DRB1*03:01 | V86L  V86M |
| DRB1*04:01 | L67I  Q70D  K71E  G86V  K71R  L67F  A74L  G86M  G86L  A74E  G86F  L67I-Q70D  L67F-A74F |
| DRB1*04:02 | |
| DRB1*04:03 | R71E |
| DRB1*04:04 | R71E |
| DRB1*04:05 | R71E |
| DRB1*04:08 | R71E |
| DRB1*07:01 | |
| DRB1*09:01 | |
| DRB1*10:01 | |
| DRB1*11:01 | |
| DRB1*11:02 | |
| DRB1*11:03 | |
| DRB1*12:01 | |
| DRB1*13:01 | V86L  V86M |
| DRB1*14:01 | |
| DRB1*15:01 | F47Y  A71R  A71R-V86G (DRB1*15:122) |
| DRB1*15:02 | |
| DRB1*16:01 | |
| DRB3*01:01 | |
| DRB3*02:02 | |
| DRB3*03:01 | |
| DRB4*01:03 | |
| DRB5*01:01 | |

| Alleles | DQA1 | DQB1 | Specific positions/specific mutatns |
|---|---|---|---|
| DQ5 | DQA1*01:01 | DQB1*05:01 | |
| DQ6 | DQA1*01:02 | DQB1*06:02 | |
| DQ2 | DQA1*05:01 | DQB1*02:01 | A57D  K71E  K71T |
| DQ2 Trans | DQA1*03:01 | DQB1*02:01 | A57D |
| DQ8 | DQA1*03:01 | DQB1*03:02 | A57D |
| DQ8 trans | DQA1*05:01 | DQB1*03:02 | A57D |
| | DQA1*05:05 | DQB1*03:01 | |
| | DQA1*03:01 | DQB1*03:01 | |

| Alleles | Specific positions/specific mutatns |
|---|---|
| B27:03 | |
| B27:05 | Y59H (E D116H (B*27:09) |
| B27:09 | |

Fig.28

| SEQ ID NO. | HLA Allele Name | Mature Protein Sequence |
|---|---|---|
| 1 | A*02:01:01:01 | GSHSMRYFFTSVSRPGRGEPRFIAVGYVDDTQFVRFDSDAASQRMEPRAPWIEQEGPEYW DGETRKVKAHSQTHRVDLGTLRGYYNQSEAGSHTVQRMYGCDVGSDWRFLRGYHQYAYDG KDYIALKEDLRSWTAADMAAQTTKHKWEAAHVAEQLRAYLEGTCVEWLRRYLENGKETLQ RTDAPKTHMTHHAVSDHEATLRCWALSFYPAEITLTWQRDGEDQTQDTELVETRPAGDGT FQKWAAVVVPSGQEQRYTCHVQHEGLPKPLTLRWEPSSQPTIPIVGIIAGLVLFGAVITG AVVAAVMWRRKSSDRKGGSYSQAASSDSAQGSDVSLTACKV |
| 2 | A*03:01:01:01 | GSHSMRYFFTSVSRPGRGEPRFIAVGYVDDTQFVRFDSDAASQRMEPRAPWIEQEGPEYW DQETRNVKAQSQTDRVDLGTLRGYYNQSEAGSHTIQIMYGCDVGSDGRFLRGYRQDAYDG KDYIALNEDLRSWTAADMAAQITKRKWEAAHEAEQLRAYLDGTCVEWLRRYLENGKETLQ RTDPPKTHMTHHPISDHEATLRCWALGFYPAEITLTWQRDGEDQTQDTELVETRPAGDGT FQKWAAVVVPSGEEQRYTCHVQHEGLPKPLTLRWELSSQPTIPIVGIIAGLVLLGAVITG AVVAAVMWRRKSSDRKGGSYTQAASSDSAQGSDVSLTACKV |
| 3 | A*29:01:01:01 | GSHSMRYFTTSVSRPGRGEPRFIAVGYVDDTQFVRFDSDAASQRMEPRAPWIEQEGPEYW DLQTRNVKAQSQTDRANLGTLRGYYNQSEAGSHTIQMMYGCHVGSDGRFLRGYRQDAYDG KDYIALNEDLRSWTAADMAAQITQRKWEAARVAEQLRAYLEGTCVEWLRRYLENGKETLQ RTDAPKTHMTHHAVSDHEATLRCWALSFYPAEITLTWQRDGEDQTQDTELVETRPAGDGT FQKWASVVVPSGQEQRYTCHVQHEGLPKPLTLRWEPSSQPTIPIVGIIAGLVLFGAVFAG AVVAAVRWRRKSSDRKGGSYSQAASSDSAQGSDMSLTACKV |
| 4 | B*07:02:01:01 | GSHSMRYFYTSVSRPGRGEPRFISVGYVDDTQFVRFDSDAASPREEPRAPWIEQEGPEYW DRNTQIYKAQAQTDRESLRNLRGYYNQSEAGSHTLQSMYGCDVGPDGRLLRGHDQYAYDG KDYIALNEDLRSWTAADTAAQITQRKWEAAREAEQRRAYLEGECVEWLRRYLENGKDKLE RADPPKTHVTHHPISDHEATLRCWALGFYPAEITLTWQRDGEDQTQDTELVETRPAGDRT FQKWAAVVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA |
| 5 | B*08:01:01:01 | GSHSMRYFDTAMSRPGRGEPRFISVGYVDDTQFVRFDSDAASPREEPRAPWIEQEGPEYW DRNTQIFKTNTQTDRESLRNLRGYYNQSEAGSHTLQSMYGCDVGPDGRLLRGHNQYAYDG KDYIALNEDLRSWTAADTAAQITQRKWEAARVAEQDRAYLEGTCVEWLRRYLENGKDTLE RADPPKTHVTHHPISDHEATLRCWALGFYPAEITLTWQRDGEDQTQDTELVETRPAGDRT FQKWAAVVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA |
| 6 | B*27:05:02:01 | GSHSMRYFHTSVSRPGRGEPRFITVGYVDDTLFVRFDSDAASPREEPRAPWIEQEGPEYW DRETQICKAKAQTDREDLRTLLRYYNQSEAGSHTLQMMYGCDVGPDGRLLRGYHQDAYDG KDYIALNEDLSSWTAADTAAQITQRKWEAARVAEQLRAYLEGECVEWLRPYLENGKETLQ RADPPKTHVTHHPISDHEATLRCWALGFYPAEITLTWQRDGEDQTQDTELVETRPAGDRT FQKWAAVVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA |
| 7 | B*27:01 | GSHSMRYFHISVSRPGRGEPRFITVGYVDDTLFVRFDSDAASPREEPPAPWIEQEGPEYW DRETQICKAKAQTDRENLRTALRYYNQSEAGSHTLQNMYGCDVGPDGRLLRGYHQDAYDG KDYIALNEDLSSWTAADTAAQITQRKWEAARVAEQLRAYLEGECVEWLRRYLENGKETLQ RADPPKTHVTHHPISDHEATLRCWALGFYPAEITLTWQRDGEDQTQDTELVETRPAGDRT FQKWAAVVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA |

Fig. 29

| SEQ ID NO. | HLA Allele Name | Mature Protein Sequence |
|---|---|---|
| 8 | B*27:03 | GSHSMRYFHTSVSRPGRGEPRFITVGYVDDTLFVRFDSDAASPREEPRAPWIEQEGPEHW DRETQICKAKAQTDREDLRTLLRYYNQSEAGSHTLQNMYGCDVGPDGRLLRGYHQDAYDG KDYIALNEDLSSWTAADTAAQITQRKWEAARVAEQLRAYLEGECVEWLRRYLENGKETLQ RADPPKTHVTHHPISDHEATLRCWALGFYPAEITLTWQRDGEDQTQDTELVETRPAGDRT FQKWAAVVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA |
| 9 | B*27:05:02:01 | GSHSMRYFHTSVSRPGRGEPRFITVGYVDDTLFVRFDSDAASPREEPRAPWIEQEGPEYW DRETQICKAKAQTDREDLRTLLRYYNQSEAGSHTLQNMYGCDVGPDGRLLRGYHQDAYDG KDYIALNEDLSSWTAADTAAQITQRKWEAARVAEQLRAYLEGECVEWLRRYLENGKETLQ RADPPKTHVTHHPISDHEATLRCWALGFYPAEITLTWQRDGEDQTQDTELVETRPAGDRT FQKWAAVVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA |
| 10 | B*27:09 | GSHSMRYFHTSVSRPGRGEPRFITVGYVDDILFVRFDSDAASPREEPRAPWIEQEGPEYW DRETQICKAKAQTDREDLRTLLRYYNQSEAGSHTLQNMYGCDVGPDGRLLRGYHQHAYDG KDYIALNEDLSSWTAADTAAQITQRKWEAARVAEQLRAYLEGECVEWLPRYLENGKETLQ RADPPKTHVTHHPISDHEATLRCWALGFYPAEITLTWQRDGEDQTQDTELVETRPAGDRT FQKWAAVVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA |
| 11 | B*51:01:01:01 | GSHSMRYFYTAMSRPGRGEPRFIAVGYVDDTQFVRFDSDAASPRTEPRAPWIEQEGPEYW DRNTQIFKTNTQTYRENLRIALRYYNQSEAGSHTWQTMYGCDVGPDGRLLRGHNQYAYDG KDYIALNEDLSSWTAADTAAQITQRKWEAAREAEQLRAYLEGLCVEWLRRHLENGKETLQ RADPPKTHVTHHPVSDHEATLRCWALGFYPAEITLTWQRDGEDQTQDTELVETRPAGDRT FQKWAAVVVPSGEEQRYTCHVQHEGLPKPLILRWEPSSQSTIPIVGIVAGLAVLAVVVIG AVVATVMCRRKSSGGKGGSYSQAASSDSAQGSDVSLTA |
| 12 | B*54:01:01:01 | GSHSMRYFYTAMSRPGRGEPRFIAVGYVDDTQFVRFDSDAASPRGEPRAPWVEQEGPEYW DRNTQIYKAQAQTDRESLRNLRGYYNQSEAGSHIWQTMYGCDLGPDGRLLRGHNQLAYDG KDYIALNEDLSSWTAADTAAQITQRKWEAARVAEQLRAYLEGTCVEWLRRYLENGKETLQ RADPPKTHVTHHPISDHEATLRCWALGFYPAEITLTWQRDGEDQTQDTELVETRPAGDRT FQKWAAVVVPSGEEQRYTCHVQHEGLPKPLTLRWEPSSQSTIPIVGIVAGLAVLAVVVIG AVVATVMCRRKSSGGKGGSYSQAASSDSAQGSDVSLTA |
| 13 | B*57:01:01:01 | GSHSMRYFYTAMSRPGRGEPRFIAVGYVDDTQFVRFDSDAASPRMAPRAPWIEQEGPEYW DGETRNMKASAQTYPENLRIALRYYNQSEAGSHIIQVMYGCDVGPDGRLLRGHDQSAYDG KDYIALNEDLSSWTAADTAAQITQRKWEAARVAEQLRAYLEGLCVEWLPRYLENGKETLQ RADPPKTHVTHHPISDHEATLRCWALGFYPAEITLTWQRDGEDQTQDTELVETRPAGDRT FQKWAAVVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA |
| 14 | C*06:02:01:01 | CSHSMRYFDTAVSRPGRGEPRFISVGYVDDTQFVRFDSDAASPRGEPRAPWVEQEGPEYW DRETQKYKRQAQADRVNLRKLRGYYNQSEDGSHTLQWMYGCDLGPDGRLLRGYDQSAYDG KDYIALNEDLRSWTAADTAAQITQRKWEAAREAEQWRAYLEGTCVEWLRRYLENGKETLQ PAEBPKTHVTHHPVSDHEATLRCWALGFYPAEITLTWQRDGEDQTQDTELVETRPAGDGT FQKWAAVVVPSGEEQRYTCHVQHEGLPEPLILRWEPSSQPTIPIVGIVAGLAVLAVLAVL GAVMAVVMCRRKSSGGKGGSCSQAASSNSAQGSDESLIACKA |

Fig. 29 continued

| SEQ ID NO. | HLA Allele Name | Mature Protein Sequence |
|---|---|---|
| 15 | C*18:01:01:01 | CSHSMRYFDTAVSRPGRGEPRFISVGYVDDTQFVRFDSDAASPRGEPRAPWVEQEGPEYW BRETQKYKRQAQADRVNLRKLRGYYNQSEDGSHTLQRMFGCDLGPDGRLLRGYNQFAYDG KDYIALNEDLRSWTAADTAAQITQRKWEAAREAEQRRAYLEGTCVEWLRRYLENGKETLQ RAEHPKTHVTHHPVSDHEATLRCWALGFYPAEITLTWQRDGEDQTQDTELVETRPAGDGT FQKWAAVVVPSGEEQRYTCHVQHEGLPEPLTLRWKPSSQPTIPIVGIVAGLAVLVVLAVL GAVVAVVMCRRKSSGGKGGSCSQAASSNSAQGSDESLIACKA |
| 16 | DPA1*02:01:01:01 | IKADHVSTYAAFVQTHRPTGEFMFEFDEDEQFYVDLDKKETVWHLEEFGRAFSFEAQGGL ANIAILNNNLNTLIQRSNHTQAANDPPEVTVFPKEPVELGQPNTLICHIDRFFPPVLNVT WLCNGEPVTEGVAESLFLPRTDYSFHKFHYLTFVPSAEDVYDCRVEHWGLDQPLLKHWEA QEPIQMPETTETVLCALGLVLGLVGIIVGTVLIIKSLRSGHDPRAQGPL |
| 17 | DPB1*13:01:01:01 | RATPENYVYQLRQECYAFNGTQRFLERYIYNREEYARFDSDVGEFRAVTELGRPAAEYWN SQKDILEEERAVPDRMCRHNYELDEAVTLQRRVQPKVNVSPSKKGPLQHHNLLVCHVTDF YPGSIQVRWFLNGQEETAGVVSTNLIRNGDWTFQILVMLEMTPQQGDVYICQVEHTSLDS PVTVEWKAQSDSARSKTLTGAGGFVLGLIICGVGIFMHRRSHKVQRGSA |
| 18 | DQA1*01:01:01:01 | EDIVADHVASCGVNLYQFYGPSGQYTHEFDGDEEFYVDLERKETAWRWPEFSKFGSFDPQ GALRNMAVAKHNLNIMIKRYNSTAATNEVPEVTVFSKSPVTLGQPNTLICLVDNIFPPVV NITWLSNGQSVTEGVSETSFLSKSDHSFFKISYLTFLPSADEIYDCKVEHWGLDQPLLKH WEPEIPAPMSELTETVVCALGLSVGLVGIVVGTVFIIQGLRSVGASRHQGPL |
| 19 | DQA1*01:02:01:01 | EDIVADHVASCGVNLYQFYGPSGQYTHEFDGDEQFYVDLERKETAWRWPEFSKFGSFDPQ GALRNMAVAKHNLNIMIKRYNSTAATNEVPEVTVFSKSPVTLGQPNTLICLVDNIFPPVV NITWLSNGQSVTEGVSETSFLSKSDHSFFKISYLTFLPSADEIYDCKVEHWGLIQPLLKH WEPEIPAPMSELTETVVCALGLSVGLMGIVVGTVFIIQGLRSVGASRHQGPL |
| 20 | DQA1*02:01:01:01 | EDIVADHVASYGVNLYQSYGPSGQFTHEFDGDEEFYVDLERKETVWKLPLFHRLRFDPQF ALTNIAVLKHNLNILIKRSNSTAATNEVPEVTVFSKSPVTLGQPNTLICLVDNIFPPVVN ITWLSNGHSVTEGVSETSFLSKSDHSFFKISYLTFLPSADEIYDCKVEHWGLDEPLLKHW EPEIPAPMSELTETVVCALGLSVGLVGIVVGTVLIIRGLRSVGASRHQGPL |
| 21 | DQA1*03:01:01:01 | EDIVADHVASYGVNLYQSYGPSGQYSHEFDGDEEFYVDLERKETVWQLPLFRRFRRFDPQ FALTNIAVLKHNLNIVIKRSNSTAATNEVPEVTVFSKSPVTLGQPNTLICLVDNIFPPVV NITWLSNGHSVTEGVSETSFLSKSDRSFFKISYLTFLPSADEIYDCKVEHWGLDEPLLKH WEPEIPTPMSELTETVVCALGLSVGLVGIVVGTVLIIRGLRSVGASRHQGPL |
| 22 | DQA1*05:01:01:01 | EDIVADHVASYGVNLYQSYGPSGQYTHEFDGDEQFYVDLGRKETVWCLPVLRQFRFDPQF ALTNIAVLKHNLNSLIKRSNSTAATNEVPEVTVFSKSPVTLGQPNILICLVDNIFPPVVN ITWLSNGHSVTEGVSETSFLSKSDHSFFKISYLTLLPSAEESYDCKVEHWGLDKPLLKHW EPEIPAPMSELTETVVCALGLSVGLVGIVVGTVFIIRGLRSVGASRHQGPL |
| 23 | DQA1*05:05:01:01 | EDIVADHVASYGVNLYQSYGPSGQYTHEFDGDEQFYVDLGRKETVWCLPVLRQFRFDPQF ALTNIAVLKHNLNSLIKRSNSTAATNEVPEVTVFSKSPVTLGQPNILICLVDNIFPPVVN ITWLSNGHSVTEGVSETSFLSKSDRSFFKISYLTLLPSAEESYDCKVEHWGLDKPLLKHW EPEIPAPMSELTETVVCALGLSVGLVGIVVGTVFIIRGLRSVGASRHQGPL |
| 24 | DQB1*02:01:01:01 | RDSPEDFVYQFKGMCYFTNGTERVRLVSRSIYNREEIVRFDSDVGEFRAVTLLGLPAAEY WNSQKDILERKRAAVDRVCRHNYQLELRTTLQRRVEPTVTISPSRTEALNHHNLLVCSVT DFYPAQIKVRWFRNDQEETAGVVSTPLIRNGDWTFQILVMLEMTPQRGDVYTCHVEHPSL QSPITVEWRAQSESAQSKMLSGIGGFVLGLIFLSLGLIIHHRSQKGLLH |

Fig. 29 continued

| SEQ ID NO. | HLA Allele Name | Mature Protein Sequence |
|---|---|---|
| 25 | DQB1*03:01:01:01 | RDSPEDFVYQFKAMCYFTNGTERVRYVTRYIYNREEYARFDSDVEVYRAVTPLGPPDAEYWNSQKEVLERTRAELDTVCRHNYQLELRTTLQRRVEPTVTISPSRTEALNHHNLLVCSVTDFYPAQIKVRWFRNDQEEITGVVSTPLIRNGDWTFQILVMLEMTPQHGDVYTCHVEHPSLQNPITVEWRAQSESAQSKMLSGIGGFVLGLIFLGLGLIIHHRSQKGLLH |
| 26 | DQB1*03:02:01:01 | RDSPEDFVYQFKGMCYFTNGTERVRLVTRYIYNREEYARFDSDVGVYRAVTPLGPPAAEYWNSQKEVLERTRAELDTVCRHNYQLELRTTLQRRVEPTVTISPSRTEALNHHNLLVCSVTDFYPAQIKVRWFRNDQEEITGVVSTPLIRNGDWTFQILVMLEMTPQRGDVYTCHVEHPSLQNPIIVEWRAQSESAQSKMLSGIGGFVLGLIFLGLGLIIHHRSQKGLLH |
| 27 | DQB1*05:01:01:01 | RDSPEDFVYQFKGLCYFTNGTERVRGVTRHIYNREEYVRFDSDVGVYRAVTPQGRPVAEYWNSQKEVLEGARASVDRVCRHNYEVAYRGILQRRVEPTVTISPSRTEALNHHNLLICSVTDFYPSQIKVRWFRNDQEETAGVVSTPLIRNGDWTFQILVMLEMTPQRGEVYTCHVEHPSLQSPITVEWRAQSESAQSKMLSGVGGFVLGLIFLGLGLIIRQRSRKGLLH |
| 28 | DQB1*06:01:01:01 | RDPPEDFVLQFKAMCYFTNGTERVRYVTRYIYNREEDVRFDSDVGVYRAVTPQGRPDAEYWNSQKDILERTRAELDTVCRHNYEVAFRGILQRRVEPTVTISPSRTEALNHHNLLVCSVTDFYPGQIKVRWFRNDQEETAGVVSIPLIRNGDWTFQILVMLEMTPQHGEVYTCHVEHPSLQSPITVEWRAQSESAQNRMLSGIGGFVLGLIFLGLGLIIRQRSQKGPQGPPAGLLH |
| 29 | DQB1*06:02:01:01 | RDSPEDFVFQFKGMCYFTNGTERVRLVTRYIYNREEYARFDSDVGVYRAVTPQGRPDAEYWNSQKEVLEGTRAELDTVCRHNYEVAFRGILQRRVEPTVTISPSRTEALNHHNLLVCSVTDFYPGQIKVRWFRNDQEEIAGVVSIPLIRNGDWTFQILVMLEMTPQRGEVYTCHVEHPSLQSPITVEWRAQSESAQSKMLSGVGGFVLGLIFLGLGLIIRQRSQKGLLH |
| 30 | DRB1*01:01:01:01 | GDTRPRFLWQLKFECHFFNGTERVRLLERCIYNQEESVRFDSDVGEYRAVTELGRPDAEYWNSQKDLLEQRRAAVDTYCRHNYGVGESFTVQRRVEPKVTVYPSKTQPLQHHNLLVCSVSGFYPGSIEVRWFRNGQEEKAGVVSTGLIQNGDWTFQTLVMLETVPRSGEVYTCQVEHPSVTSPLTVEWRARSESAQSKMLSGVGGFVLGLLFLGAGLFIYFRNQKGHSGLQPTGFLS |
| 31 | DRB1*01:02:01:01 | GDTRPRFLWQLKFECHFFNGTERVRLLERCIYNQEESVRFDSDVGEYRAVTELGRPDAEYWNSQKDLLEQRRAAVDTYCRHNYGAVESFTVQRRVEPKVTVYPSKTQPLQHHNLLVCSVSGFYPGSIEVRWFRNGQEEKAGVVSTGLIQNGDWTFQTLVMLETVPRSGEVYTCQVEHPSVTSPLTVEWRARSESAQSKMLSGVGGFVLGLLFLGAGLFIYFRNQKGHSGLQPTGFLS |
| 32 | DRB1*01:03:01 | GDTRPRFLWQLKFECHFFNGTERVRLLERCIYNQEESVRFDSDVGEYRAVTELGRPDAEYWNSQKDILEDERAAVDTYCRHNYGVGESFTVQRRVEPKVTVYPSKTQPLQHHNLLVCSVSGFYPGSIEVRWFRNGQEEKAGVVSTGLIQNGDWTFQTLVMLETVPRSGEVYTCQVEHPSVTSPLTVEWRARSESAQSKMLSGVGGFVLGLLFLGAGLFIYFRNQKGHSGLQPTGFLS |
| 33 | DRB1*03:01:01:01 | GDTRPRFLEYSTSECHFFNGTERVRYLDRYFHNQEENVRFDSDVGEFRAVTELGRPDAEYWNSQKDLLEQRRGRVDNYCRHNYGVVESFTVQRRVEPKVTVYPSKTQPLQHHNLLVCSVSGFYPGSIEVRWFRNGQEEKTGVVSIGLIHNGDWTFQTLVMLETVPRSGEVYTCQVEHPSVTSPLTVEWRARSESAQSKMLSGVGGFVLGLLFLGAGLFIYFRNQKGHSGLQFRGFLS |
| 34 | DRB1*04:01:01:01 | GDTRPRFLEQVKHECHFFNGTERVRFLDRYFYHQEEYVRFDSDVGEYRAVTELGRPDAEYWNSQKDLLEQKRAAVDTYCRHNYGVGESFTVQRRVPEVTVYPAKTQPLQHHNLLVCSVNGFYPGSIEVRWFRNGQEEKTGVVSTGLIQNGDWTFQTLVMLETVPRSGEVYTCQVEHPSLTSPLTVEWRARSESAQSKMLSGVGGFVLGLLFLGAGLFIYFRNQKGHSGLQFTGFLS |

Fig. 29 continued

| SEQ ID NO. | HLA Allele Name | Mature Protein Sequence |
|---|---|---|
| 35 | DRB1*04:02:01 | GDTRPRFLEQVKHECHFFNGTERVRFLDRYFYHQEEYVRFDSDVGEYRAVTELGRPDAEY WNSQKDILEDERAAVDTYCRHNYGVVESFTVQRRVYPEVTVYPAKTQPLQHHNLLVCSVN GFYPGSIEVRWFRNGQEEKTGVVSTGLIQNGDWTFQTLVMLETVPRSGEVYTCQVEHPSL TSPLTVEWRARSESAQSKMLSGVGGFVLGLLFLGAGLFIYFRNQKGHSGLQPTGFLS |
| 36 | DRB1*04:03:01:01 | GDTRPRFLEQVKHECHFFNGTERVRFLDRYFYHQEEYVRFDSDVGEYRAVTELGRPDAEY WNSQKDLLEQRRAAVDTYCRHNYGVVESFTVQRRVYPEVTVYPAKTQPLQHHNLLVCSVN GFYPGSIEVRWFRNGQEEKTGVVSTGLIQNGDWTFQTLVMLETVPRSGEVYTCQVEHPSL TSPLTVEWRARSESAQSKMLSGVGGFVLGLLFLGAGLFIYFRNQKGHSGLQPTGFLS |
| 37 | DRB1*04:04:01:01 | GDTRPRFLEQVKHECHFFNGTERVRFLDRYFYHQEEYVRFDSDVGEYRAVTELGRPDAEY WNSQKDLLEQRRAAVDTYCRHNYGVVESFTVQRRVYPEVTVYPAKTQPLQHHNLLVCSVN GFYPGSIEVRWFRNGQEEKTGVVSTGLIQNGDWTFQTLVMLETVPRSGEVYTCQVEHPSL TSPLTVEWRARSESAQSKMLSGVGGFVLGLLFLGAGLFIYFRNQKGHSGLQPTGFLS |
| 38 | DRB1*04:05:01:01 | GDTRPRFLEQVKHECHFFNGTERVRFLDRYFYHQEEYVRFDSDVGEYRAVTELGRPSAEY WNSQKDLLEQRRAAVDTYCRHNYGVGESFTVQRRVYPEVTVYPAKTQPLQHHNLLVCSVN GFYPGSIEVRWFRNGQEEKTGVVSTGLIQNGDWTFQTLVMLETVPRSGEVYTCQVEHPSL TSPLTVEWRARSESAQSKMLSGVGGFVLGLLFLGAGLFIYFRNQKGHSGLQPTGFLS |
| 39 | DRB1*04:08:01:01 | GDTRPRFLEQVKHECHFFNGTERVRFLDRYFYHQEEYVRFDSDVGEYRAVTELGRPDAEY WNSQKDLLEQRRAAVDTYCRHNYGVGESFTVQRRVYPEVTVYPAKTQPLQHHNLLVCSVN GFYPGSIEVRWFRNGQEEKTGVVSTGLIQNGDWTFQTLVMLETVPRSGEVYTCQVEHPSL TSPLTVEWRARSESAQSKMLSGVGGFVLGLLFLGAGLFIYFRNQKGHSGLQPTGFLS |
| 40 | DRB1*07:01:01:01 | GDTQPRFLWQGKYKCHFFNGTERVQFLERLFYNQEEFVRFDSDVGEYRAVTELGRPVAES WNSQKDILEDRRSQVDTYCRHNYGVGESFTVQRRVHPEVTVYPAKTQPLQHHNLLVCSVS GFYPGSIEVRWFRNGQEEKAGVVSTGLIQNGDWTFQTLVMLETVPRSGEVYTCQVEHPSV MSPLTVEWRARSESAQSKMLSGVGGFVLGLLFLGAGLFIYFRNQKGHSGLQPTGFLS |
| 41 | DRB1*08:01:01 | GDTRPRFLEYSTSECYFFNGTERVRFLDRYFYNQEEYVRFDSDVGEYRAVTELGRPSAEY WNSQKDFLEDRRALVDTYCRHNYGVGESFTVQRRVHPKVTVYPSKTQPLQHHNLLVCSVS GFYPGSIEVRWFRNGQEEKTGVVSTGLIHNGDWTFQTLVMLETVPRSGEVYTCQVEHPSV TSPLTVEWSARSESAQSKMLSGVGGFVLGLLFLGAGLFIYFRNQKGHSGLQPTGFLS |
| 42 | DRB1*09:01:02:01 | GDTQPRFLKQDKFECHFFNGTERVRYLHRGIYNQEENVRFDSDVGEYRAVTELGRPVAES WNSQKDFLERRRAEVDTYCRHNYGVGESFTVQRRVHPEVTVYPAKTQPLQHHNLLVCSVS GFYPGSIEVRWFRNGQEEKAGVVSTGLIQNGDWTFQTLVMLETVPRSGEVYTCQVEHPSV MSPLTVEWRARSESAQSKMLSGVGGFVLGLLFLGAGLFIYFRNQKGHSGLQPTGFLS |
| 43 | DRB1*10:01:01:01 | GDTRPRFLEEVKFECHFFNGTERVRLLERVHNQEEYARYDSDVGEYRAVTELGRPDAEY WNSQKDLLERRRAAVDTYCRHNYGVGESFTVQRRVQPKVTVYPSKTQPLQHHNLLVCSVN GFYPGSIEVRWFRNGQEEKTGVVSTGLIQNGDWTFQTLVMLETVPQSGEVYTCQVEHPSV MSPLTVEWRARSESAQSKMLSGVGGFVLGLLFLGAGLFIYFRNQKGHSGLPPTGFLS |

Fig. 29 continued

| SEQ ID NO. | HLA Allele Name | Mature Protein Sequence |
|---|---|---|
| 44 | DRB1*11:01:01:01 | GDTRPRFLEYSTSECHFFNGTERVRFLDRYFYNQEEYVRFDSDVGEFRAVTELGRPDEEY<br>WNSQKDFLEDRRAAVDTYCRHNYGVGESFTVQRRVHPKVTVYPSKTQPLQHHNLLVCSVS<br>GFYPGSIEVRWFRNGQEEKTGVVSTGLIHNGDWTFQTLVMLETVPRSGEVYTCQVEHPSV<br>TSPLTVEWRARSESAQSKMLSGVGGFVLGLLFLGAGLFIYFRNQKGHSGLQPRGFLS |
| 45 | DRB1*11:02:01:01 | GDTRPRFLEYSTSECHFFNGTERVRFLDRYFYNQEEYVRFDSDVGEFRAVTELGRPDEEY<br>WNSQKDILEDERAAVDTYCRHNYGVVESFTVQRRVHPKVTVYPSKTQPLQHHNLLVCSVS<br>GFYPGSIEVRWFRNGQEEKTGVVSTGLIHNGDWTFQTLVMLETVPRSGEVYTCQVEHPSV<br>TSPLTVEWRARSESAQSKMLSGVGGFVLGLLFLGAGLFIYFRNQKGHSGLQPRGFLS |
| 46 | DRB1*11:03:01 | GDTRPRFLEYSTSECHFFNGTERVRFLDRYFYNQEEYVRFDSDVGEFRAVTELGRPDEEY<br>WNSQKDFLEDRRAAVDTYCRHNYGVVESFTVQRRVHPKVTVYPSKTQPLQHHNLLVCSVS<br>GFYPGSIEVRWFRNGQEEKTGVVSTGLIHNGDWTFQTLVMLETVPRSGEVYTCQVEHPSV<br>TSPLTVEWRARSESAQSKMLSGVGGFVLGLLFLGAGLFIYFRNQKGHSGLQPRGFLS |
| 47 | DRB1*11:04:01:01 | GDTRPRFLEYSTSECHFFNGTERVRFLDRYFYNQEEYVRFDSDVGEFRAVTELGRPDEEY<br>WNSQKDFLEDRRAAVDTYCRHNYGVVESFTVQRRVHPKVTVYPSKTQPLQHHNLLVCSVS<br>GFYPGSIEVRWFRNGQEEKTGVVSTGLIHNGDWTFQTLVMLETVPRSGEVYTCQVEHPSV<br>TSPLTVEWRARSESAQSKMLSGVGGFVLGLLFLGAGLFIYFRNQKGHSGLQPRGFLS |
| 48 | DRB1*12:01:01:01 | GDTRPRFLEYSTGECYFFNGTERVRLLERHFHNQEELLRFDSDVGEFRAVTELGRPVAES<br>WNSQKDILEDRRAAVDTYCRHNYGAVESFTVQRRVHPKVTVYPSKTQPLQHHNLLVCSVS<br>GFYPGSIEVRWFRNGQEEKTGVVSTGLIHNGDWTFQTLVMLETVPRSGEVYTCQVEHPSV<br>TSPLTVEWRARSESAQSKMLSGVGGFVLGLLFLGAGLFIYFRNQKGHSGLQPRGFLS |
| 49 | DRB1*13:01:01:01 | GDTRPRFLEYSTSECHFFNGTERVRFLDRYFHNQEENVRFDSDVGEFRAVTELGRPDAEY<br>WNSQKDILEDERAAVDTYCRHNYGVVESFTVQRRVHPKVTVYPSKTQPLQHHNLLVCSVS<br>GFYPGSIEVRWFRNGQEEKTGVVSTGLIHNGDWTFQTLVMLETVPRSGEVYTCQVEHPSV<br>TSPLTVEWRARSESAQSKMLSGVGGFVLGLLFLGAGLFIYFRNQKGHSGLQPRGFLS |
| 50 | DRB1*14:01:01 | GDTRPRFLEYSTSECHFFNGTERVRFLDRYFHNQEEFVRFDSDVGEYRAVTELGRPAAEH<br>WNSQKDLLERRAEVDTYCRHNYGVVESFTVQRRVHPKVTVYPSKTQPLQHYNLLVCSVS<br>GFYPGSIEVRWFRNGQEEKTGVVSTGLIHNGDWTFQTLVMLETVPRSGEVYTCQVEHPSV<br>TSPLTVEWRARSESAQSKMLSGVGGFVLGLLFLGAGLFIYFRNQKGHSGLQPRGFLS |
| 51 | DRB1*15:01:01:01 | GDTRPRFLWQPKRECHFFNGTERVRFLDRYFYNQEESVRFDSDVGEFRAVTELGRPDAEY<br>WNSQKDILEQARAAVDTYCRHNYGVVESFTVQRVQPKVTVYPSKTQPLQHHNLLVCSVS<br>GFYPGSIEVRWFLNGEEKAGMVSTGLIQNGDWTFQTLVMLETVPRSGEVYTCQVEHPSV<br>TSPLTVEWRARSESAQSKMLSGVGGFVLGLLFLGAGLFIYFRNQKGHSGLQPTGFLS |
| 52 | DRB1*15:02:02:01 | GDTRPRFLWQPKRECHFFNGTERVRFLDRYFYNQEESVRFDSDVGEFRAVTELGRPDAEY<br>WNSQKDILEQARAAVDTYCRHNYGVGESFTVQRVQPKVTVYPSKTQPLQHHNLLVCSVS<br>GFYPGSIEVRWFLNGEEKAGMVSTGLIQNGDWTFQTLVMLETVPRSGEVYTCQVEHPSV<br>TSPLTVEWRARSESAQSKMLSGVGGFVLGLLFLGAGLFIYFRNQKGHSGLQPTGFLS |

Fig. 29 continued

| SEQ ID NO. | HLA Allele Name | Mature Protein Sequence |
|---|---|---|
| 53 | DRB1*16:01:01:01 | GDTRPRFLWQPKRECHFFNGTERVRFLDRYFYNQEESVRFDSDVGEYRAVTELGRPDAEY WNSQKDFLEDRRAAVDTYCRHNYGVGESFTVQRRVQPKVTVYPSKTQPLQHHNLLVCSVS GFYPGSIEVRWFLNGQEEKAGMVSTGLIQNGDWTFQTLVMLETVPRSGEVYTCQVEHPSV TSPLTVEWRARSESAQSKMLSGVGGFVLGLLFLGAGLFIYFRNQKGHSGLQPTGFLS |
| 54 | DPB3*01:01:02:01 | GDTRPRFLELRKSECHFFNGTERVRYLDRYFHNQEEFLRFDSDVGEYRAVTELGRPVAES WNSQKDLLEQKRGRVDNYCRHNYGVGESFTVQRRVHPQVTVYPAKTQPLQHHNLLVCSVS GFYPGSIEVRWFRNGQEEKAGVVSTGLIQNGDWTFQTLVMLETVPRSGEVYTCQVEHPSV TSALTVEWRARSESAQSKMLSGVGGFVLGLLFLGAGLFIYFRNQKGHSGLQPTGFLS |
| 55 | DPB3*02:02:01:01 | GDTRPRFLELLKSECHFFNGTERVRFLERHFHNQEEYARFDSDVGEYRAVRELGRPDAEY WNSQKDLLEQKRGQVDNYCRHNYGVGESFTVQRRVHPQVTVYPAKTQPLQHHNLLVCSVS GFYPGSIEVRWFRNGQEEKAGVVSTGLIQNGDWTFQTLVMLETVPRSGEVYTCQVEHPSV TSPLTVEWSARSESAQSKMLSGVGGFVLGLLFLGAGLFIYFRNQKGHSGLQPTGFLS |
| 56 | DPB3*03:01:01:01 | GDTRPRFLELLKSECHFFNGTERVRFLERYFHNQEEFVRFDSDVGEYRAVTELGRPVAES WNSQKDLLEQKRGQVDNYCRHNYGVVESFTVQRRVHPQVTVYPAKTQPLQHHNLLVCSVS GFYPGSIEVRWFRNGQEEKTGVVSTGLIHNGDWTFQTLVMLETVPRSGEVYTCQVEHPSV TSPLTVEWRARSESAQSKMLSGVGGFVLGLLFLGAGLFIYFRNQKGHSGLQPTGFLS |
| 57 | DPB4*01:03:01:01 | GDTQPRFLEQAKCECHFLNGTERVWNLIRYIYNQEEYARYNSDLGEYQAVTELGRPDAEY WNSQKDLLERRRAEVDTYCRYNYGVVESFTVQRRVQPKVTVYPSKTQPLQHHNLLVCSVN GFYPGSIEVRWFRNGQEEKAGVVSTGLIQNGDWTFQTLVMLETVPRSGEVYTCQVEHPSM MSPLTVQWSARSESAQSKMLSGVGGFVLGLLFLGTGLFIYFRNQKGHSGLQPTGLLS |
| 58 | DPB5*01:01:01:01 | GDTRPRFLQQDKYECHFFNGTERVRFLHRDIYNQEEDLRFDSDVGEYRAVTELGRPDAEY WNSQKDFLEDRRAAVDTYCRHNYGVGESFTVQRRVEPKVTVYPARTQTLQHHNLLVCSVS GFYPGSIEVRWFRNSQEEKAGVVSTGLIQNGDWTFQTLVMLETVPRSGEVYTCQVEHPSV TSPLTVEWRAQSESAQSKMLSGVGGFVLGLLFLGAGLFIYFKNQKGHSGLHPTGLVS |

| | | |
|---|---|---|
| DQA1*<br>05:05 | GATCAGATCTACCACCATGATCCTAAACAAAGCTCTGATGCTGGGGACCCTTGCCCTGACCACCGTGATGAGCCCCTGTGGAGGTGAAGAC<br>ATTGTGGCTGACCACGTCGCCTCTTATGGTGTAAACTTGTACCAGTCTTACGGTCCCTCTGGCCAGTACACCCATGAATTTGATGGAGATGAG<br>CAGTTCTACGTGGACCTGGGGAGGAAGGAGACTCTCTGGTGTTTGCCTGTTCTCAGACAATTTAGATTTGACCCGCAATTTGCACTGACAAA<br>CATCGCTGTCCTAAAACATAACTTGAACAGTCTGATTAAACGCTCCAACTCTACCGCTGCTACCAATGAGGTTCCTGAGGTCACAGTGTTTCC<br>AAGTCTCCCGTGACACTGGGTCAGCCCAACATCCTCATCTGTCTTGTGGACAACATCTTTCCTCCTGTGGTCAACATCACATGGCTGAGCAAT<br>GGGCACTCAGTCACAGAAGGTGTTTCTGAGACCAGCTTCCTCTCCAAGAGTGATCATTCCTTCTTCAAGATCAGTTACCTCACCCTCTCCCTT<br>CTGCTGAGGAGAGTTATGACTGCAAGGTGGAGCACTGGGGACTGGACAAGCCTCTTCTGAAACACTGGGAGCCTGAGATTCCAGCCCCTA<br>TGTCAGAGCTCACAGAGACTGTGGTCTGCGCCCTGGGGTTGTCTGTGGGCCTCGTGGGCATTGTGGTGGGCACTGTCTTCATCATCCGAG<br>GCCTGCGTTCAGTTGGTGCTTCCAGACACCAAGGGCCCTTGTGACTCGAGGATC | 63 |
| DQA1*0<br>5:05 | GATCAGATCTACCACCATGATCCTAAACAAAGCTCTGATGCTGGGGACCCTTGCCCTGACCACCGTGATGAGCCCCTGTGGAGGTGAAGAC<br>ATTGTGGCTGACCACGTCGCCTCTTATGGTGTAAACTTGTACCAGTCTTACGGTCCCTCTGGCCAGTACACCCATGAATTTGATGGAGATGAG<br>CAGTTCTACGTGGACCTGGGGAGGAAGGAGACTCTCTGGTGTTTGCCTGTTCTCAGACAATTTAGATTTGACCCGCAATTTGCACTGACAAA<br>CATCGCTGTCCTAAAACATAACTTGAACAGTCTGATTAAACGCTCCAACTCTACCGCTGCTACCAATGAGGTTCCTGAGGTCACAGTGTTTCC<br>AAGTCTCCCGTGACACTGGGTCAGCCCAACATCCTCATCTGTCTTGTGGACAACATCTTTCCTCCTGTGGTCAACATCACATGGCTGAGCAAT<br>GGGCACTCAGTCACAGAAGGTGTTTCTGAGACCAGCTTCCTCTCCAAGAGTGATCATTCCTTCTTCAAGATCAGTTACCTCACCCTCTCCCTT<br>CTGCTGAGGAGAGTTATGACTGCAAGGTGGAGCACTGGGGACTGGACAAGCCTCTTCTGAAACACTGGGAGCCTGAGATTCCAGCCCCTA<br>TGTCAGAGCTCACAGAGACTGTGGTCTGCGCCCTGGGGTTGTCTGTGGGCCTCGTGGGCATTGTGGTGGGCACTGTCTTCATCATCCGAG<br>GCCTGCGTTCAGTTGGTGCTTCCAGACACCAAGGGCCCTTGTGACTCGAGGATC | 64 |
| DQB1*0<br>2:01<br>K71E | GATCAGATCTACCACCATGTCTTGGAAAAAGGCTTTGCGGATCCCCGGAGGCCTTCGGGCAGCAACTGTGACCTTGATGCTGTCGATGCTG<br>AGCACCCCAGTGGCTGAGGGCAGAGACTCTCCCGAGGGATTCGTGTACCAGTTTAAGGGCATGTGCTACTTCACCAACGGGACAGAGCGC<br>GTGCGTCTTGTGAGCAGAAGCATCTATAACCGAGAAGAGATCGTGCGCTTCGACAGCGACGTGGGGGAGTTCCGGGCGGTGACGCTGCT<br>GGGGCTGCCTGCCGCCGAGTACTGGAACAGCCAGAAGGACATCCTGGAGAGGCGACGGGCCGGTGGACAGGGTGTGCAGACACA<br>ACTACCGTTGGAGCTCCGCACGACCTTGCAGCGGCGAGTGGAGCCACAGTGACCATCTCCCCATCCAGGACAGAGGCCCTCAACCACC<br>ACAACCTGCTGGTCTGCTCGGTGACAGATTTCTATCCAGCCCAGATCAAAGTCCGGTGGTTTCGGAATGACCAGGAGGAGACAGCTGGCG<br>TTGTGTCCACCCCCCTTATTAGGAATGGTGACTGGACCTTCCAGATCCTGGTGATGCTGGAAATGACTCCCCAGCGTGGAGACGTCTACACC<br>TGCCACGTGGAGCACCCCAGCCTCCAGAGCCCCATCACCGTGGAGTGGCGGGCTCAATCTGAATCTGCCCAGAGCAAGATGCTGAGTGG<br>CATTGGAGGCTTCGTGCTGGGGCTGATCTTCCTCGGGCTGGGCCTTATCATCCATCACAGGAGTCAGAAAGGGCTCCTGCACTGACTCGAG<br>GATC | 65 |
| DQB1*0<br>2:01<br>K71T | GATCAGATCTACCACCATGTCTTGGAAAAAGGCTTTGCGGATCCCCGGAGGCCTTCGGGCAGCAACTGTGACCTTGATGCTGTCGATGCTG<br>AGCACCCCAGTGGCTGAGGGCAGAGACTCTCCCGAGGGATTCGTGTACCAGTTTAAGGGCATGTGCTACTTCACCAACGGGACAGAGCGC<br>GTGCGTCTTGTGAGCAGAAGCATCTATAACCGAGAAGAGATCGTGCGCTTCGACAGCGACGTGGGGGAGTTCCGGGCGGTGACGCTGCT<br>GGGGCTGCCTGCCGCCGAGTACTGGAACAGCCAGAAGGACATCCTGGAGAGGCGACGGGCCGGTGGACAGGGTGTGCAGACACA<br>CTACCAGTGGAGCTCCGCACGACCTTGCAGCGGCGAGTGGAGCCACAGTGACCATCTCCCCATCCAGGACAGAGGCCCTCAACCACCA<br>CAACCTGCTGGTCTGCTCGGTGACAGATTTCTATCCAGCCCAGATCAAAGTCCGGTGGTTTCGGAATGACCAGGAGGAGACAGCTGGCGTT<br>GTGTCCACCCCCCTTATTAGGAATGGTGACTGGACCTTCCAGATCCTGGTGATGCTGGAAATGACTCCCCAGCGTGGAGACGTCTACACCT<br>GCCACGTGGAGCACCCCAGCCTCCAGAGCCCCATCACCGTGGAGTGGCGGGCTCAATCTGAATCTGCCCAGAGCAAGATGCTGAGTGGC<br>ATTGGAGGCTTCGTGCTGGGGCTGATCTTCCTCGGGCTGGGCCTTATCATCCATCACAGGAGTCAGAAAGGGCTCCTGCACTGACTCGAG<br>GATC | 66 |
| DQB1*0<br>3:01 | GATCAGATCTACCACCATGTCTTGGAAAAAGGCTTTGCGGATCCCCGGAGGCCTTCGGGCAGCAACTGTTACCTTGATGCTGGCGATGCTG<br>AGCACCCCAGTGGCTGAGGGCAGAGACTCTCCCGAGGGATTCGTGTACCAGTTTAAGGGCATGTGCTACTTCACCAACGGGACGGAGCGC<br>GTGCGTTATGTGACCAGATACATCTATAACCGAGAGGAGTACGCACGCTTCGACAGCGACGTGGAGGTGTACCGGGCGGTGACGCCGCT<br>GGGGCCGCCTGACGCGGAGTACTGGAACAGCCAGAAGGAAGTCCTGGAGAGGACCCGGGCGGAGTTGGACACGGTGTGCAGACACAA<br>CTACCAGTTGGAGCTCCGCACGACCTTGCAGCGGCGAGTGGAGCCCACAGTGACCATCTCCCCATCCAGGACAGAGGCCTCAACCACCA<br>CAACCTGCTGGTCTGCTCAGTGACAGATTTCTATCCAGCCCAGATCAAAGTCCGGTGGTTTCGGAATGACCAGGAGGAGACAACCGGCGTT<br>GTGTCCACCCCCCTTATTAGGAACGGTGACTGGACCTTCCAGATCCTGGTGATGCTGGAAATGACTCCCCAGCATGGAGACGTCTACACCT<br>GCCACGTGGAGCACCCCAGCCTCCATCACCCATCACCGTGGAGTGGCGGGCTCAGTCTGAATCTGCCCAGAGCAAGATGCTGAGTGGC<br>ATTGGAGGCTTCGTGCTGGGGCTCATCTTCCTCGGGCTGGGCCTTATTATCCATCACAGGAGTCAGAAAGG | 67 |

Fig. 30 continued

| | | |
|---|---|---|
| DQB1*0 382 A57D | GATCAGATCTACCACCATGTCTTGGAAGAAGGCTTTGCGGATCCCTGGAGGCCTTCGGGTAGCAACTGTGACCTTGATGCTGGCGATGCTG AGCACGCCGGTGGCTGAGGGCAGAGACTCTCCCGAGGATTCGTGTACCAGTTTAAGGGCATGTGCTACTTCACCAACGGGACGGAGCG CGTGCGTCTTGTGACCAGATACATCTATAACCGAGAGGAGTACGCACGCTTCGACAGCGACGTGGGGGTGTATCGGCGGTGACGCCGC TGGGGCCGCCTGACGCCGAGTACTGGAACAGCCAGAAGGAAGTCCTGGAGAGGACCCGGGCCGGAGTTGGACACGGTGTGCAGACACA ACTACCAGTTGGAGCTCCGCACGACCTTGCAGCGGCGAGTGGAGCCCACAGTGACCATCTCCCCATCCAGGACAGAGGCCCTCAACCACC ACAACCTGCTGGTCTGCTCAGTGACAGATTTCTATCCAGCCAGATCAAAGTCCGGTGGTTTCGGAATGACCAGGAGGAGACAACTGGCGT TGTGTCCACCCCCCTTATTAGGAACGGTGACTGGACCTTCCAGATCCTGGTGATGCTGGAAATGACTCCCCAGCGTGGAGACGTCTACACCT GCCACGTGGAGCACCCCAGCCTCCAGAACCCCATCATCGTGGAGTGGCGGGCTCAGTCTGAATCTGCCCAGAGCAAGATGCTGAGTGGC ATTGGAGGCTTCGTGCTGGGGCTGATCTTCCTCGGGCTGGGCCTTATTATCCATCACAGGAGTCAGAAAGGGCTCCTGCACTGACTCGAGG ATCGCTCCTGCACTGACTCGAGGATC | 68 |
| DQB1*0 387 | GATCAGATCTACCACCATGTCTTGGAAGAAGGCTTTGCGGATCCCTGGAGGCCTTCGGGTAGCAACTGTGACCTTGATGCTGGCGATGCTG AGCACGCCGGTGGCTGAGGGCAGAGACTCTCCCGAGGATTCGTGTACCAGTTTAAGGGCATGTGCTACTTCACCAACGGGACGGAGCG CGTGCGTCTTGTGACCAGATACATCTATAACCGAGAGGAGTACGCACGCTTCGACAGCGACGTGGGGGTGTATCGGCGGTGACGCCGC TGGGGCCGCCTGACGCCGAGTACTGGAACAGCCAGAAGGAAGTCCTGGAGAGGACCCGGGCCGGAGTTGGACACGGTGTGCAGACACA ACTACCAGTTGGAGCTCCGCACGACCTTGCAGCGGCGAGTGGAGCCCACAGTGACCATCTCCCCATCCAGGACAGAGGCCCTCAACCACC ACAACCTGCTGGTCTGCTCAGTGACAGATTTCTATCCAGCCAGATCAAAGTCCGGTGGTTTCGGAATGACCAGGAGGAGACAACTGGCGT TGTGTCCACCCCCCTTATTAGGAACGGTGACTGGACCTTCCAGATCCTGGTGATGCTGGAAATGACTCCCCAGCGTGGAGACGTCTACACCT GCCACGTGGAGCACCCCAGCCTCCAGAACCCCATCATCGTGGAGTGGCGGGCTCAGTCTGAATCTGCCCAGAGCAAGATGCTGAGTGGC ATTGGAGGCTTCGTGCTGGGGCTGATCTTCCTCGGGCTGGGCCTTATTATCCATCACAGGAGTCAGAAAGGGCTCCTGCACTGACTCGAGG ATC | 69 |
| DQB1*0 604 | GATCAGATCTACCACCATGTCTTGGAAGAAGGCTTTGCGGATCCCCGGAGACCTTCGGGTAGCAACTGTCACCTTGATGCTGGCGATGCTG AGCTCCCTACTGGCTGAGGGCAGAGACTCTCCCGAGGATTCGTGTACCAGTTTAAGGGCATGTGCTACTTCACCAACGGGACGGAGCGC GTGCGTCTTGTAACCAGACACATCTATAACCGAGAGGAGTACGCGCGCTTCGACAGCGACGTGGGGGTGTACCGGCGGTGACGCCGCA GGGGCGGCCGTTGCCGGACTACTGGAACAGCCAGAAGGAAGTCCTGGAGGAGACCCGGCCGGAGTTGGACACGGTGTGCAGACACAA CTACGAGGTGGGGTACGGCGGGATCCTGCAGAGGAGAGTGGAGCCCACAGTGACCCATCTCCCCATCCAGGACAGAGGCCCTCAACCACC ACAACCTGCTGGTCTGCTCGGTGACAGATTTCTATCCAGGCCAGATCAAAGTCCAGTGGTTTCGGAATGATCAGGAGGAGACAGCCGGCG TTGTGTCCACCCCCCTTATTAGGAATGGTGACTGGACTTCCAGATCCTGGTGATGCTGGAAATGACTCCCCAGCGTGGAGATGTCTACACC TGCCACGTGGAGCACCCAGCCTCCAGAGCCCCATCACCGTGGAGTGGCGGGCTCAGTCTGAATCTGCCCAGAGCAAGATGCTGAGTGG CGTTGGAGGCTTCGTGCTGGGGCTGATCTTCCTTGGGCTGGGCCTTATCATCCGTCAAAGGAGTCAGAAAGGGCTTCTGCACTGACTCGAG GATC | 70 |
| DRB1*0 301 V86L | GATCAGATCTACCACCATGGTGTGTCTGAGGCTCCCTGGAGGCTCCTGCATGGCAGTTCTGACAGTGACACTGATGGTGCTGAGCTCCCCA CTGGCTTTGGCTGGGGACACCAGACCACGTTTCTTGGAGTACTCTACGTCTGAGTGTCATTTCTTCAATGGGACGGAGCGGGTGCGGTACC TGGACAGATACTTCCATAACCAGGAGGAGAACGTGCGCTTCGACAGCGACGTGGGGGAGTTCCGGGCGGTGACGGAGCTGGGGCGGCC CTGATGCCGAGTACTGGAACAGCCAGAAGGACCTCCTGGAGCAGAAGCGGGCCGGGTGGACAACTACTGCAGACACAACTACGGGGT TCTGGAGAGCTTCACAGTGCAGCGGCGAGTCCATCCTAAGGTGACTGTGTATCCTTCAAAGACCCAGCCCCTGCAGCACCATAACCTCCTG GTCTGTTCTGTGAGTGGTTTCTATCCAGGCAGCATTGAAGTCAGGTGGTTCCGGAATGGCCAGGAAGAGAAGACTGGGGTGGTGTCCACA GGCCTGATCCACAATGGAGACTGGACCTTCCAGACCCTGGTGATGCTGGAAACAGTTCCTCGGAGTGGAGAGGTTTACACCTGCCAAGTG GAGCACCCAAGCGTGACAAGCCCTCTCACAGTGGAATGGAGAGCACGGTCTGAATCTGCACAGAGCAAGATGCTGAGTGGAGTCGGGG GCTTTGTGCTGGGCCTGCTCTTCCTGGGGCCGGGCTGTTCATCTACTTCAGGAATCAGAAAGGACACTCTGGACTTCAGCCAAGAGGATTC CTGAGCTGACTCGAGGATC | 71 |
| DRB1*0 301 V86M | GATCAGATCTACCACCATGGTGTGTCTGAGGCTCCCTGGAGGCTCCTGCATGGCAGTTCTGACAGTGACACTGATGGTGCTGAGCTCCCCA CTGGCTTTGGCTGGGGACACCAGACCACGTTTCTTGGAGTACTCTACGTCTGAGTGTCATTTCTTCAATGGGACGGAGCGGGTGCGGTTC CTGGACAGATACTTCCATAACCAGGAGGAGAACGTGCGCTTCGACAGCGACGTGGGGGAGTTCCGGGCGGTGACGGAGCTGGGGCGGCC CTGATGCCGAGTACTGGAACAGCCAGAAGGACCTCCTGGAGCAGAAGCGGGCCGGGTGGACAACTACTGCAGACACAACTACGGGGT TATGGAGAGCTTCACAGTGCAGCGGCGAGTCCATCCTAAGGTGACTGTGTATCCTTCAAAGACCCAGCCCCTGCAGCACCATAACCTCCTG GTCTGTTCTGTGAGTGGTTTCTATCCAGGCAGCATTGAAGTCAGGTGGTTCCGGAATGGCCAGGAAGAGAAGACTGGGGTGGTGTCCACA GGCCTGATCCACAATGGAGACTGGACCTTCCAGACCCTGGTGATGCTGGAAACAGTTCCTCGGAGTGGAGAGGTTTACACCTGCCAAGTG GAGCACCCAAGCGTGACAAGCCCTCTCACAGTGGAATGGAGAGCACGGTCTGAATCTGCACAGAGCAAGATGCTGAGTGGAGTCGGGG GCTTTGTGCTGGGCCTGCTCTTCCTGGGGCCGGGCTGTTCATCTACTTCAGGAATCAGAAAGGACACTCTGGACTTCAGCCAAGAGGATTC CTGAGCTGACTCGAGGATC | 72 |

Fig. 30 continued

| | | |
|---|---|---|
| DRB1*0 4.01 G86F | GATCAGATCTACCACCATGGTGTGTCTGAAGTTCCCTGGAGGCTCCTGCATGGCAGCTCTGACAGTGACACTGATGGTGCTGAGCTCCCA CTGGCTTTGGCTGGGGACACCCGACCACGTTTCTTGGAGCAGGTTAAACATGAGTGTCATTTCTTCAACGGGACGGAGCGGGTGCGGTTC CTGGACAGATACTTCTATCACCAAGAGGAGTACGTGCGCTTCGACAGCGACGTGGGGGAGTACCGGGCGGTGACGGAGCTGGGGCGGC CTGATGCCGAGTACTGGAACAGCCAGAAGGACCTCCTGGAGCAGAAGCGGGCCGCGGTGGACACCTACTGCAGACACAACTACGGGGT TTTTGAGAGCTTCACAGTGCAGCGGCGAGTCTATCCTGAGGTGACTGTGTATCCTGCAAAGACCCAGCCCCTGCAGCACCACAACCTCCTG GTCTGCTCTGTGAATGGTTTCTATCCAGGCAGCATTGAAGTCAGGTGGTTCCGGAACGGCCAGGAAGAGAAGACTGGGGTGGTGTCCACA GGCCTGATCCAGAATGGAGACTGGACCTTCCAGACCCTGGTGATGCTGGAAACAGTTCCTCGGAGTGGAGAGGTTTACACCTGCCAAGTG GAGCACCCAAGCCTGACGAGCCCTCTCACAGTGGAATGGAGAGCACGGTCTGAATCTGCACAGAGCAAGATGCTGAGTGAGTCGGGG GCTTCGTGCTGGGCCTGCTCTTCCTTGGGGCCGGGCTGTTCATCTACTTCAGGAATCAGAAAGGACACTCTGGACTTCAGCCAACAGGATTC CTGAGCTGACTCGAGGATC | 73 |
| DRB1*0 4.01 G86L | GATCAGATCTACCACCATGGTGTGTCTGAAGTTCCCTGGAGGCTCCTGCATGGCAGCTCTGACAGTGACACTGATGGTGCTGAGCTCCCA CTGGCTTTGGCTGGGGACACCCGACCACGTTTCTTGGAGCAGGTTAAACATGAGTGTCATTTCTTCAACGGGACGGAGCGGGTGCGGTTC CTGGACAGATACTTCTATCACCAAGAGGAGTACGTGCGCTTCGACAGCGACGTGGGGGAGTACCGGGCGGTGACGGAGCTGGGGCGGC CTGATGCCGAGTACTGGAACAGCCAGAAGGACCTCCTGGAGCAGAAGCGGGCCGCGGTGGACACCTACTGCAGACACAACTACGGGGT TCTTGAGAGCTTCACAGTGCAGCGGCGAGTCTATCCTGAGGTGACTGTGTATCCTGCAAAGACCCAGCCCCTGCAGCACCACAACCTCCTG GTCTGCTCTGTGAATGGTTTCTATCCAGGCAGCATTGAAGTCAGGTGGTTCCGGAACGGCCAGGAAGAGAAGACTGGGGTGGTGTCCACA GGCCTGATCCAGAATGGAGACTGGACCTTCCAGACCCTGGTGATGCTGGAAACAGTTCCTCGGAGTGGAGAGGTTTACACCTGCCAAGTG GAGCACCCAAGCCTGACGAGCCCTCTCACAGTGGAATGGAGAGCACGGTCTGAATCTGCACAGAGCAAGATGCTGAGTGAGTCGGGG GCTTCGTGCTGGGCCTGCTCTTCCTTGGGGCCGGGCTGTTCATCTACTTCAGGAATCAGAAAGGACACTCTGGACTTCAGCCAACAGGATTC CTGAGCTGACTCGAGGATC | 74 |
| DRB1*0 4.01 G86M | GATCAGATCTACCACCATGGTGTGTCTGAAGTTCCCTGGAGGCTCCTGCATGGCAGCTCTGACAGTGACACTGATGGTGCTGAGCTCCCA CTGGCTTTGGCTGGGGACACCCGACCACGTTTCTTGGAGCAGGTTAAACATGAGTGTCATTTCTTCAACGGGACGGAGCGGGTGCGGTTC CTGGACAGATACTTCTATCACCAAGAGGAGTACGTGCGCTTCGACAGCGACGTGGGGGAGTACCGGGCGGTGACGGAGCTGGGGCGGC CTGATGCCGAGTACTGGAACAGCCAGAAGGACCTCCTGGAGCAGAAGCGGGCCGCGGTGGACACCTACTGCAGACACAACTACGGGGT TATGGAGAGCTTCACAGTGCAGCGGCGAGTCTATCCTGAGGTGACTGTGTATCCTGCAAAGACCCAGCCCCTGCAGCACCACAACCTCCTG GTCTGCTCTGTGAATGGTTTCTATCCAGGCAGCATTGAAGTCAGGTGGTTCCGGAACGGCCAGGAAGAGAAGACTGGGGTGGTGTCCACA GGCCTGATCCAGAATGGAGACTGGACCTTCCAGACCCTGGTGATGCTGGAAACAGTTCCTCGGAGTGGAGAGGTTTACACCTGCCAAGTG GAGCACCCAAGCCTGACGAGCCCTCTCACAGTGGAATGGAGAGCACGGTCTGAATCTGCACAGAGCAAGATGCTGAGTGAGTCGGGG GCTTCGTGCTGGGCCTGCTCTTCCTTGGGGCCGGGCTGTTCATCTACTTCAGGAATCAGAAAGGACACTCTGGACTTCAGCCAACAGGATTC CTGAGCTGACTCGAGGATC | 75 |
| DRB1*0 4.03 R71E | GATCAGATCTACCACCATGGTGTGTCTGAAGTTCCCTGGAGGCTCCTGCATGGCAGCTCTGACAGTGACACTGATGGTGCTGAGCTCCCA CTGGCTTTGGCTGGGGACACCCGACCACGTTTCTTGGAGCAGGTTAAACATGAGTGTCATTTCTTCAACGGGACGGAGCGGGTGCGGTTC CTGGACAGATACTTCTATCACCAAGAGGAGTACGTGCGCTTCGACAGCGACGTGGGGGAGTACCGGGCGGTGACGGAGCTGGGGCGGC CTGATGCCGAGTACTGGAACAGCCAGAAGGACCTCCTGGAGCAGGAGCGGGCCGAGGTGGACACCTACTGCAGACACAACTACGGGGT TGTGGAGAGCTTCACAGTGCAGCGGCGAGTCTATCCTGAGGTGACTGTGTATCCTGCAAAGACCCAGCCCCTGCAGCACCACAACCTCCTG GTCTGCTCTGTGAATGGTTTCTATCCAGGCAGCATTGAAGTCAGGTGGTTCCGGAACGGCCAGGAAGAGAAGACTGGGGTGGTGTCCACA GGCCTGATCCAGAATGGAGACTGGACCTTCCAGACCCTGGTGATGCTGGAAACAGTTCCTCGGAGTGGAGAGGTTTACACCTGCCAAGTG GAGCACCCAAGCCTGACGAGCCCTCTCACAGTGGAATGGAGAGCACGGTCTGAATCTGCACAGAGCAAGATGCTGAGTGAGTCGGGG GCTTCGTGCTGGGCCTGCTCTTCCTTGGGGCCGGGCTGTTCATCTACTTCAGGAATCAGAAAGGACACTCTGGACTTCAGCCAACAGGATTC CTGAGCTGACTCGAGGATC | 76 |
| DRB1*0 4.04 R71E | GATCAGATCTACCACCATGGTGTGTCTGAAGTTCCCTGGAGGCTCCTGCATGGCAGCTCTGACAGTGACACTGATGGTGCTGAGCTCCCA CTGGCTTTGGCTGGGGACACCCGACCACGTTTCTTGGAGCAGGTTAAACATGAGTGTCATTTCTTCAACGGGACGGAGCGGGTGCGGTTC CTGGACAGATACTTCTATCACCAAGAGGAGTACGTGCGCTTCGACAGCGACGTGGGGGAGTACCGGGCGGTGACGGAGCTGGGGCGGC CTGATGCCGAGTACTGGAACAGCCAGAAGGACCTCCTGGAGCAGGAGCGGCCGCGGTGGACACCTACTGCAGACACAACTACGGGGT TGTGGAGAGCTTCACAGTGCAGCGGCGAGTCTATCCTGAGGTGACTGTGTATCCTGCAAAGACCCAGCCCCTGCAGCACCACAACCTCCTG GTCTGCTCTGTGAATGGTTTCTATCCAGGCAGCATTGAAGTCAGGTGGTTCCGGAACGGCCAGGAAGAGAAGACTGGGGTGGTGTCCACA GGCCTGATCCAGAATGGAGACTGGACCTTCCAGACCCTGGTGATGCTGGAAACAGTTCCTCGGAGTGGAGAGGTTTACACCTGCCAAGTG GAGCACCCAAGCCTGACGAGCCCTCTCACAGTGGAATGGAGAGCACGGTCTGAATCTGCACAGAGCAAGATGCTGAGTGAGTCGGGG GCTTCGTGCTGGGCCTGCTCTTCCTTGGGGCCGGGCTGTTCATCTACTTCAGGAATCAGAAAGGACACTCTGGACTTCAGCCAACAGGATTC CTGAGCTGACTCGAGGATC | 77 |

Fig. 30 continued

| DRB1*04.05 R71E | GATCAGATCTACCACCATGGTGTGTCTGAAGTTCCCTGGAGGCTCCTGCATGGCAGCTCTGACAGTGACACTGATGGTGCTGAGCTCCCA CTGGCTTTGGCTGGGGACACCCGACCACGTTTCTTGGAGCAGGTTAAACATGAGTGTCATTTCTTCAACGGGACGGAGCGGGTGCGGTTC CTGGACAGATACTTCTATCACCAAGAGGAGTACGTGCGCTTCGACAGCGACGTGGGGGAGTACCGGGCGGTGACGGAGCTGGGGCGGC CTAGCCGGAGTACTGGAACAGCCAGAAGGACCTCCTGGAGCAGGAGCGGGCCGCGGTGGACACCTACTGCAGACACAACTACGGGGT TGGTGAGAGCTTCACAGTGCAGCGGCGAGTCTATCCTGAGGTGACTGTGTATCCTGCAAAGACCCAGCCCCTGCAGCACCACAACCTCCTG GTCTGCTCTGTGAATGGTTTCTATCCAGGCAGCATTGAAGTCAGGTGGTTCCGGAACGGCCAGGAAGAGAAGACTGGGGTGGTGTCCACA GGCCTGATCCAGAATGGAGACTGGACCTTCCAGACCCTGGTGATGCTGGAAACAGTTCCTCGGAGTGGAGAGGTTTACACCTGCCAAGTG GAGCACCCAAGCCTGACGAGCCCTCTCACAGTGGAATGGAGAGCACGGTCTGAATCTGCACAGAGCAAGATGCTGAGTGGAGTCGGGG GCTTCGTGCTGGGCCTGCTCTTCCTTGGGGCCGGGCTGTTCATCTACTTCAGGAATCAGAAAGGACACTCTGGACTTCAGCCAACAGGATTC CTGAGCTGACTCGAGGATC | 78 |
|---|---|---|
| DRB1*04.08 R71E | GATCAGATCTACCACCATGGTGTGTCTGAAGTTCCCTGGAGGCTCCTGCATGGCAGCTCTGACAGTGACACTGATGGTGCTGAGCTCCCA CTGGCTTTGGCTGGGGACACCCGACCACGTTTCTTGGAGCAGGTTAAACATGAGTGTCATTTCTTCAACGGGACGGAGCGGGTGCGGTTC CTGGACAGATACTTCTATCACCAAGAGGAGTACGTGCGCTTCGACAGCGACGTGGGGGAGTACCGGGCGGTGACGGAGCTGGGGCGGC CTGATGCCGAGTACTGGAACAGCCAGAAGGACCTCCTGGAGCGGAGGCGGGCCGCGGTGGACACCTACTGCAGACACAACTACGGGGT TGGTGAGAGCTTCACAGTGCAGCGGCGAGTCTATCCTGAGGTGACTGTGTATCCTGCAAAGACCCAGCCCCTGCAGCACCACAACCTCCTG GTCTGCTCTGTGAATGGTTTCTATCCAGGCAGCATTGAAGTCAGGTGGTTCCGGAACGGCCAGGAAGAGAAGACTGGGGTGGTGTCCACA GGCCTGATCCAGAATGGAGACTGGACCTTCCAGACCCTGGTGATGCTGGAAACAGTTCCTCGGAGTGGAGAGGTTTACACCTGCCAAGTG GAGCACCCAAGCCTGACGAGCCCTCTCACAGTGGAATGGAGAGCACGGTCTGAATCTGCACAGAGCAAGATGCTGAGTGGAGTCGGGG GCTTCGTGCTGGGCCTGCTCTTCCTTGGGGCCGGGCTGTTCATCTACTTCAGGAATCAGAAAGGACACTCTGGACTTCAGCCAACAGGATTC CTGAGCTGACTCGAGGATC | 79 |
| DRB1*07.01 | GATCAGATCTACCACCATGGTGTGTCTGAAGCTCCCTGGAGGCTCCTGCATGGCAGCTCTGACAGTGACACTGATGGTGCTGAGCTCCCCA CTGGCTTTGGCTGGGGACACCCAACCACGTTTCCTGTGGCAGGGTAAGTATAAGTGTCATTTCTTCAACGGGACGGAGCGGGTGCAGTTCC TGGAAAGACTCTTCTATAACCAGGAGGAGTTCGTGCGCTTCGACAGCGACGTGGGGGAGTACCGGGCGGTGACGGAGCTGGGGCGGCC TGTCGCCGAGTACTGGAACAGCCAGAAGGACATCCTGGAGGACAGGCGGGCCGCGGTGGACACCGTGTGCAGACACAACTACGGGGTT GGTGAGAGCTTCACAGTGCAGCGGCGAGTCCATCCTGAGGTGACTGTGTATCCTGCCAAGACTCAGCCCCTGCAGCACCACAACCTCCTG GTCTGCTCTGTGAATGGTTTCTATCCAGGCAGCATTGAAGTCAGGTGGTTCCGGAACGGCCAGGAAGAGAAGGCTGGGGTGGTGTCCAC AGGCCTGATCCAGAATGGAGACTGGACCTTCCAGACCCTGGTGATGCTGGAAACAGTTCCTCGGAGTGGAGAAGTTTACACCTGCCAAGT GGAGCACCCAAGTGTGATGAGCCCTCTCACAGTGGAATGGAGAGCACGGTCTGAATCTGCACAGAGCAAGATGCTGAGTGGAGTCGGG GCTTTGTGCTGGGCCTGCTCTTCCTTGGGGCCGGGTTGTTCATCTACTTCAGGAATCAGAAAGGACACTCTGGACTTCAGCCAACAGGATT CCTGAGCTGACTCGAGGATC | 80 |
| DRB1*09.01 | GATCAGATCTACCACCATGGTGTGTCTGAAGCTCCCTGGAGGCTCCTGCATGGCAGCTCTGACAGTGACACTGATGGTGCTGAGCTCCCA CTGGCTTTGGCTGGGGACACCCAACCACGTTTCTTGAAGCAGGATAAGTTTGAGTGTCATTTCTTCAACGGGACGGAGCGGGTGCGGTATC TGCACAGAGCATCTATAACCAAGAGGAGTACGTGCGCTTCGACAGCGACGTGGGGGAGTACCGGCCGGTGACGGAGCTGGGGCGGC CTGTCGCCGAGTACTCCGAACAGCCAGAAGGACTTCCTGGAGCGGAGGCGGGCCGAGGTGGACACCGGTCGCAGACAACTACGGGGT TGGTGAGAGCTTCACAGTGCAGAGGCGAGTCCATCCTGAGGTGACTGTGTATCCTGCCAAGACTCAGCCCCTGCAGCACCACAACCTCCTG GTCTGCTCTGTGAGTGGTTTCTATCCAGGCAGCATTGAAGTCAGGTGGTTCCGGAACGGCCAGGAAGAGAAGGCTGGGGTGGTGTCCAC AGGCCTGATCCAGAATGGAGACTGGACCTTCCAGACCCTGGTGATGCTGGAAACAGTTCCTCGGAGTGGAGAAGTTTACACCTGCCAAGT GGAGCACCCAAGTGTGATGAGCCCTCTCACAGTGGAATGGAGAGCACGGTCTGAATCTGCACAGAGCAAGATGCTGAGTGGAGTCGGG GGCTTGTGCTGGGCCTGCTCTTCCTTGGGGCCGGGCTGTTCATCTACTTCAGGAATCAGAAAGGACACTCTGGACTTCAGCCAACAGGATT CCTGAGCTGACTCGAGGATC | 81 |
| DRB1*10.01 | GATCAGATCTACCACCATGGTGTGTCTGAGGCTCCCTGGAGGCTCCTGCATGGCAGTCTGACAGTGACACTGATGGTGCTGAGCTCCCCA CTGGCTTTGGCTGGGGACACCCGACCACGTTTCTTGGAGGAGGTTAAGTTTGAGTGTCATTTCTTCAACGGGACGGAGCGGGTGCGGTTG CTGGAAAGACGCGTCCATAACCAAGAGGAGTACGTGCGCTTCGACAGCGACGTGGGGGAGTACCGGGCGGTGACGGAGCTGGGGCGG GCCCTGATGCCGAGTACTGGAACAGCCAGAAGGACCTCCTGGAGCGGAGGCGGTCCGCGGTGGACACCTACTGCAGACACAACTACGCG GTTGGTGAGAGCTTCACAGTGCAGCGGCGAGTTCAACCTAAGGTGACTGTGTATCCTTCAAAGACCCAGCCCCTGCAGCACCACAACCTCC TGGTCTGTCTCTGTGAATGGTTTCTATCCAGGCAGCATTGAAGTCAGGTGGTTCCGGAACGGCCAGGAAGAGAAGACTGGGGTGGTTCCA CGGGCCTGATCCAGAATGGAGACTGGACCTTCCAGACCCTGGTGATGCTGGAAACAGTTCCTCAGAGTGGAGAGGTTTACACCTGCCAAG TGGAGCACCCAAGTGTGATGAGCCCTCTCACAGTGGAATGGAGAGCACGGTCTGAATCTGCACAGAGCAAGATGCTGAGTGGAGTCGGG GCTTCGTGCTGGGCCTGCTCTTCCTTGGGGCCGGGCTGTTCATCTACTTCAGGAATCAGAAAGGACACTCTGGACTTCAGCCAACAGGATT CCTGAGCTGACTCGAGGATC | 82 |

Fig. 30 continued

| | | |
|---|---|---|
| DRB1*1 1.01 | GATCAGATCTACCACCATGGTGTGTCTGAGGCTCCCTGGAGGCTCCTGCATGGCAGTTCTGACAGTGACACTGATGGTGCTGAGCTCCCCA CTGGCTTTGGCTGGGACACCAGACCACGTTTCTTGGAGTACTCTACGTCTGAGTGTCATTTCTTCAATGGGACGGAGCGGGTGCGGTTCC TGGACAGATACTTCTATAACCAAGAGGAGTACGTGCGCTTCGACAGCGACGTGGGGGAGTTCCGGGCGGTGACGGAGCTGGGGCGGCC TGATGAGGAGTACTGGAACAGCCAGAAGGACTTCCTGGAAGACAGGCGGGCCGCGGTGGACAACCTACTGCAGACACAACTACGGGGTT GGTGAGAGCTTCACAGTGCAGCGGCGAGTCCATCCTAAGGTGACTGTGTATCCTTCAAAGACCCAGCCCCTGCAGCACCACAACCTCCTGG TCTGTTCTGTGAGTGGTTTCTATCCAGGCAGCATTGAAGTCAGGTGGTTCCCGGAATGGCCAGGAAGAGAAGACTGGGGTGGTGTCCACAG GCCTGATCCACAATGGAGACTGGACCTTCCAGACCCTGGTGATGCTGGAAACAGTTCCTCGGAGTGGAGAGGTTTACACCTGCCAAGTGG AGCACCCAAGCGTGACAAGCCCTCTCACAGTGGAATGGAGAGCACGGTCTGAATCTGCACAGAGCAAGATGCTGAGTGGAGTCGGGGG CTTTGTGCTGGGCCTGCTCTTCCTTGGGGCGGGCTGTTCATCTACTTCAGGAATCAGAAAGGACACTCTGGACTTCAGCCAAGAGGATTCC TGAGCTGACTCGAGGATC | 83 |
| DRB1*1 1.02 | GATCAGATCTACCACCATGGTGTGTCTGAGGCTCCCTGGAGGCTCCTGCATGGCAGTTCTGACAGTGACACTGATGGTGCTGAGCTCCCCA CTGGCTTTGGCTGGGACACCAGACCACGTTTCTTGGAGTACTCTACGTCTGAGTGTCATTTCTTCAATGGGACGGAGCGGGTGCGGTTCC TGGACAGATACTTCTATAACCAAGAGGAGTACGTGCGCTTCGACAGCGACGTGGGGGAGTTCCGGGCGGTGACGGAGCTGGGGCGGCC TGATGAGGAGTACTGGAACAGCCAGAAGGACATCCTGGAAGACGAGCGGGCCGCGGTGGACAACCTACTGCAGACACAACTACGGGGTT GTGGAGAGCTTCACAGTGCAGCGGCGAGTCCATCCTAAGGTGACTGTGTATCCTTCAAAGACCCAGCCCCTGCAGCACCACAACCTCCTGG TCTGTTCTGTGAGTGGTTTCTATCCAGGCAGCATTGAAGTCAGGTGGTTCCCGGAATGGCCAGGAAGAGAAGACTGGGGTGGTGTCCACAG GCCTGATCCACAATGGAGACTGGACCTTCCAGACCCTGGTGATGCTGGAAACAGTTCCTCGGAGTGGAGAGGTTTACACCTGCCAAGTGG AGCACCCAAGCGTGACAAGCCCTCTCACAGTGGAATGGAGAGCACGGTCTGAATCTGCACAGAGCAAGATGCTGAGTGGAGTCGGGGG CTTTGTGCTGGGCCTGCTCTTCCTTGGGGCGGGCTGTTCATCTACTTCAGGAATCAGAAAGGACACTCTGGACTTCAGCCAAGAGGATTCC TGAGCTGACTCGAGGATC | 84 |
| DRB1*1 103 | GATCAGATCTACCACCATGGTGTGTCTGAGGCTCCCTGGAGGCTCCTGCATGGCAGTTCTGACAGTGACACTGATGGTGCTGAGCTCCCCA CTGGCTTTGGCTGGGACACCAGACCACGTTTCTTGGAGTACTCTACGTCTGAGTGTCATTTCTTCAATGGGACGGAGCGGGTGCGGTTCC TGGACAGATACTTCTATAACCAAGAGGAGTACGTGCGCTTCGACAGCGACGTGGGGGAGTTCCGGGCGGTGACGGAGCTGGGGCGGCC TGATGAGGAGTACTGGAACAGCCAGAAGGACTTCCTGGAAGACAGGCGGGCCGCGGTGGACAACCTACTGCAGACACAACTACGGGGTT GTGGAGAGCTTCACAGTGCAGCGGCGAGTCCATCCTAAGGTGACTGTGTATCCTTCAAAGACCCAGCCCCTGCAGCACCACAACCTCCTGG TCTGTTCTGTGAGTGGTTTCTATCCAGGCAGCATTGAAGTCAGGTGGTTCCCGGAATGGCCAGGAAGAGAAGACTGGGGTGGTGTCCACAG GCCTGATCCACAATGGAGACTGGACCTTCCAGACCCTGGTGATGCTGGAAACAGTTCCTCGGAGTGGAGAGGTTTACACCTGCCAAGTGG AGCACCCAAGCGTGACAAGCCCTCTCACAGTGGAATGGAGAGCACGGTCTGAATCTGCACAGAGCAAGATGCTGAGTGGAGTCGGGGG CTTTGTGCTGGGCCTGCTCTTCCTTGGGGCGGGCTGTTCATCTACTTCAGGAATCAGAAAGGACACTCTGGACTTCAGCCAAGAGGATTCC TGAGCTGACTCGAGGATC | 85 |
| DRB1*1 2.01 | GATCAGATCTACCACCATGGTGTGTCTGAGGCTCCCTGGAGGCTCCTGCATGGCAGTTCTGACAGTGACACTGATGGTGCTGAGCTCCCCA CTGGCTTTGGCTGGGACACCAGACCACGTTTCTTGGAGTACTCTACGGGTGAGTGTTATTTCTTCAATGGGACGGAGCGGGTCGGTTAC TGGAGAGACACTTCCATAACCAGGAGGAGTCCGTGCGCTTCGACAGCGACGTGGGCGAGTTCCGGGCGGTGACGGAGCTGGGGCGGC CTGTCGCCGAGTCCTGGAACAGCCAGAAGGACATCCTGGAAGACAGGCGGGCCGCGGTGGACACCTATTGCAGACACAACTACGGGGCT GTGGAGAGCTTCACAGTGCAGCGGCGAGTCCATCCTAAGGTGACTGTGTATCCTTCAAAGACCCAGCCCCTGCAGCACCACAACCTCCTGG TCTGTTCTGTGAGTGGTTTCTATCCAGGCAGCATTGAAGTCAGGTGGTTCCCGGAATGGCCAGGAAGAGAAGACTGGGGTGGTGTCCACGG GCCTGATCCACAATGGAGACTGGACCTTCCAGACCCTGGTGATGCTGGAAACAGTTCCTCGGAGTGGAGAGGTTTACACCTGCCAAGTGG AGCACCCAAGCGTGACAAGCCCTCTCACAGTGGAATGGAGAGCACGGTCTGAATCTGCACAGAGCAAGATGCTGAGTGGAGTCGGGGG CTTTGTGCTGGGCCTGCTCTTCCTTGGGGCGGGCTGTTCATCTACTTCAGGAATCAGAAAGGACACTCTGGACTTCAGCCAAGAGGATTCC TGAGCTGACTCGAGGATC | 86 |
| DRB1*1 501 A71R | GATCAGATCTACCACCATGGTGTGTCTGAAGCTCCCTGGAGGCTCCTGCATGACAGCGCTGACAGTGACACTGATGGTGCTGAGCTCCCCA CTGGCTTTGTCTGGGGACACCAGACCCTGGCAGTCCGGAGTGTCATTTCTTCAATGGGACGGAGCGGGTGCGGTTC CTGGACAGATACTTCTATAACCAGGAGGAGTACGTGCGCTTCGACAGCGACGTGGGGGAGTTCCGGGCGGTGACGGAGCTGGGCGGCC CTGACGCTGAGTACTGGAACAGCCAGAAGGACATCCTGGAGCAGAGGCGGGCCGCGGTGGACACCTACTGCAGACACAACTACGGGGT TGTGGAGAGCTTCACAGTGCAGCGGCGGAGTCCAACCTAAGGTGACTGTATATCCTTCAAAGACCCAGCCCCTGCAGCACCACAAGCTCCTG GTCTGCTCTGTGAGTGGTTTCTATCCAGGCAGCATTGAAGTCAGGTGGTTCCTGAACGGCCAGCAAGAAGAAGCTGGCGATGGTGTCCACA GGCCTGATCAGAATGGAGACTGGACCTTCCAGACCCTGGTGATGCTGGAAACAGTTCCTCGGAAGTGGAGAGGTTTACACCTGCCAAGTG GAGCACCCAAGCGTGACAAGCCCTCTCACAGTGGAATGGAGAGCACGGTCTGAATCTGCACAGAGCAAGATGCTGAGTGGAGTCGGGGG GCTTTGTGCTGGCCTGCTCTTCCTTGGGGCCGGGCTGTTCATCTACTTCAGGAATCAGAAAGGACACTCTGGACTTCAGCCAACAGGATTC CTGAGCTGACTCGAGGATC | 87 |

Fig. 30 continued

| | | |
|---|---|---|
| DRB1*1 5.01 F47Y | GATCAGATCTACCACCATGGTGTGTCTGAAGCTCCCTGGAGGCTCCTGCATGACAGCGCTGACAGTGACACTGATGGTGCTGAGCTCCCA CTGGCTTTGTCTGGGGACACCCGACCACGTTTCCTGTGGCAGCCTAAGAGGGAGTGTCATTTCTTCAATGGGACGGAGCGGGTGCGGTTC CTGGACAGATACTTCTATAACCAGGAGGAGTCCGTGCGCTTCGACAGCGACGTGGGGGAGTACGGGCGGTGACGGAGCTGGGGCGG CCTGACGCTGAGTACTGGAACAGCCAGAAGGACATCCTGGAGCAGGCGCGGGCCGCGGTGACACCTACTGCAGACACAACTACGGGG TTGTGGAGAGCTTCACAGTGCAGGGCGAGTCCAACCTAAGGTGACTGTATATCCTTCAAAGACCCAGCCCCTGCAGCACCACAACCTCCT GGTCTGCTCTGTGAGTGGTTTCTATCCAGGCAGCATTGAAGTCAGGTGGTTCCTGAACGGCCAGGAAGAGAAGGCTGGGATGGTGTCCAC AGGCCTGATCCAGAATGGAGACTGGACCTTCCAGACCCTGGTGATGCTGGAAACAGTTCCTCGAAGTGGAGAGGTTTACACCTGCCAAGT GGAGCACCCAAGCGTGACAAGCCCTCTCACAGTGGAATGGAGAGCACGGTCTGAATCTGCACAGAGCAAGATGCTGAGTGGAGTCGGG GGCTTTGTGCTGGGCCTGCTCTTCCTTGGGGCCGGGCTGTTCATCTACTTCAGGAATCAGAAAGGACACTCTGGACTTCAGCCAACAGGATT CCTGAGCTGACTCGAGGATC | 88 |
| DRB1*1 501 V86L | GATCAGATCTACCACCATGGTGTGTCTGAAGCTCCCTGGAGGCTCCTGCATGACAGCGCTGACAGTGACACTGATGGTGCTGAGCTCCCA CTGGCTTTGTCTGGGGACACCCGACCACGTTTCCTGTGGCAGCCTAAGAGGGAGTGTCATTTCTTCAATGGGACGGAGCGGGTGCGGTTC CTGGACAGATACTTCTATAACCAGGAGGAGTCCGTGCGCTTCGACAGCGACGTGGGGGAGTCCGGGCGGTGACGGAGCTGGGGCGGC CTGACGCTGAGTACTGGAACAGCCAGAAGGACATCCTGGAGCAGGCGCGGGCCGCGGTGACACCTACTGCAGACACAACTACGGGGT TCTGGAGAGCTTCACAGTGCAGCGGCGAGTCCAACCTAAGGTGACTGTATATCCTTCAAAGACCCCAGCCCCTGCAGCACCACAACCTCCTG GTCTGCTCTGTGAGTGGTTTCTATCCAGGCAGCATTGAAGTCAGGTGGTTCCTGAACGGCCAGGAAGAGAAGGCTGGGATGGTGTCCACA GGCCTGATCCAGAATGGAGACTGGACCTTCCAGACCCTGGTGATGCTGGAAACAGTTCCTCGAAGTGGAGAGGTTTACACCTGCCAAGTG GAGCACCCAAGCGTGACAAGCCCTCTCACAGTGGAATGGAGAGCACGGTCTGAATCTGCACAGAGCAAGATGCTGAGTGGAGTCGGGG GCTTTGTGCTGGGCCTGCTCTTCCTTGGGGCCGGGCTGTTCATCTACTTCAGGAATCAGAAAGGACACTCTGGACTTCAGCCAACAGGATTC CTGAGCTGACTCGAGGATC | 89 |
| DRB1*1 501 V86M | GATCAGATCTACCACCATGGTGTGTCTGAAGCTCCCTGGAGGCTCCTGCATGACAGCGCTGACAGTGACACTGATGGTGCTGAGCTCCCA CTGGCTTTGTCTGGGGACACCCGACCACGTTTCCTGTGGCAGCCTAAGAGGGAGTGTCATTTCTTCAATGGGACGGAGCGGGTGCGGTTC CTGGACAGATACTTCTATAACCAGGAGGAGTCCGTGCGCTTCGACAGCGACGTGGGGGAGTACGGGCGGTGACGGAGCTGGGGCGGC CTGACGCTGAGTACTGGAACAGCCAGAAGGACATCCTGGAGCAGGCGCGGGCCGCGGTGACACCTACTGCAGACACAACTACGGGGT TATGGAGAGCTTCACAGTGCAGCGGCGAGTCCAACCTAAGGTGACTGTATATCCTTCAAAGACCCAGCCCCTGCAGCACCACAACCTCCTG GTCTGCTCTGTGAGTGGTTTCTATCCAGGCAGCATTGAAGTCAGGTGGTTCCTGAACGGCCAGGAAGAGAAGGCTGGGATGGTGTCCACA GGCCTGATCCAGAATGGAGACTGGACCTTCCAGACCCTGGTGATGCTGGAAACAGTTCCTCGAAGTGGAGAGGTTTACACCTGCCAAGTG GAGCACCCAAGCGTGACAAGCCCTCTCACAGTGGAATGGAGAGCACGGTCTGAATCTGCACAGAGCAAGATGCTGAGTGGAGTCGGGG GCTTTGTGCTGGGCCTGCTCTTCCTTGGGGCCGGGCTGTTCATCTACTTCAGGAATCAGAAAGGACACTCTGGACTTCAGCCAACAGGATTC CTGAGCTGACTCGAGGATC | 90 |
| DRB1*1 5.02_86 G_(Gly@ pos86) | GATCAGATCTACCACCATGGTGTGTCTGAAGCTCCCTGGAGGCTCCTGCATGACAGCGCTGACAGTGACACTGATGGTGCTGAGCTCCCA CTGGCTTTGTCTGGGGACACCCGACCACGTTTCCTGTGGCAGCCTAAGAGGGAGTGTCATTTCTTCAATGGGACGGAGCGGGTGCGGTTC CTGGACAGATACTTCTATAACCAGGAGGAGTCCGTGCGCTTCGACAGCGACGTGGGGGAGTTCCGGGCGGTGACGGAGCTGGGGCGGC CTGACGCTGAGTACTGGAACAGCCAGAAGGACATCCTGGAGCAGGCGCGGGCCGCGGTGACACCTACTGCAGACACAACTACGGGGT TGGTGAGAGCTTCACAGTGCAGCGGCGAGTCCAACCTAAGGTGACTGTATATCCTTCAAAGACCCAGCCCCTGCAGCACCACAACCTCCTG GTCTGCTCTGTGAGTGGTTTCTATCCAGGCAGCATTGAAGTCAGGTGGTTCCTGAACGGCCAGGAAGAGAAGGCTGGGATGGTGTCCACA GGCCTGATCCAGAATGGAGACTGGACCTTCCAGACCCTGGTGATGCTGGAAACAGTTCCTCGAAGTGGAGAGGTTTACACCTGCCAAGTG GAGCACCCAAGCGTGACAAGCCCTCTCACAGTGGAATGGAGAGCACGGTCTGAATCTGCACAGAGCAAGATGCTGAGTGGAGTCGGGG GCTTTGTGCTGGGCCTGCTCTTCCTTGGGGCCGGGCTGTTCATCTACTTCAGGAATCAGAAAGGACACTCTGGACTTCAGCCAACAGGATC CTGAGCTGACTCGAGGATC | 91 |
| DRB1*1 5.122_7 1R/86G_ (Arg@po s71/Gly @pos86 ) | GATCAGATCTACCACCATGGTGTGTCTGAAGCTCCCTGGAGGCTCCTGCATGACAGCGCTGACAGTGACACTGATGGTGCTGAGCTCCCA CTGGCTTTGTCTGGGGACACCCGACCACGTTTCCTGTGGCAGCCTAAGAGGGAGTGTCATTTCTTCAATGGGACGGAGCGGGTGCGGTTC CTGGACAGATACTTCTATAACCAGGAGGAGTCCGTGCGCTTCGACAGCGACGTGGGGGAGTTCCGGGCGGTGACGGAGCTGGGGCGGC CTGACGCTGAGTACTGGAACAGCCAGAAGGACATCCTGGAGCAGGCGCGGGCCGCGGTGACACCTACTGCAGACACAACTACGGGGT TGGTGAGAGCTTCACAGTGCAGCGGCGAGTCCAACCTAAGGTGACTGTATATCCTTCAAAGACCCAGCCCCTGCAGCACCACAACCTCCTG GTCTGCTCTGTGAGTGGTTTCTATCCAGGCAGCATTGAAGTCAGGTGGTTCCTGAACGGCCAGGAAGAGAAGGCTGGGATGGTGTCCACA GGCCTGATCCAGAATGGAGACTGGACCTTCCAGACCCTGGTGATGCTGGAAACAGTTCCTCGAAGTGGAGAGGTTTACACCTGCCAAGTG GAGCACCCAAGCGTGACAAGCCCTCTCACAGTGGAATGGAGAGCACGGTCTGAATCTGCACAGAGCAAGATGCTGAGTGGAGTCGGGG GCTTTGTGCTGGGCCTGCTCTTCCTTGGGGCCGGGCTGTTCATCTACTTCAGGAATCAGAAAGGACACTCTGGACTTCAGCCAACAGGATTC CTGAGCTGACTCGAGGATC | 92 |

Fig. 30 continued

| | | |
|---|---|---|
| DRB3*0 101 | GATCAGATCTACCACCATGGTGTGTCTGAAGCTCCCTGGAGGCTCCAGCTTGGCAGCGTTGACAGTGACACTGATGGTGCTGAGCTCCCGA CTGGCTTTCGCTGGGGACACCCGACCACGTTTCTTGGAGCTCCGTAAGTCTGAGTGTCATTTCTTCAATGGCACGGAGCGGGTGCGGTACC TGGACAGATACTTCCATAACCAGGAGGAGTTCCTGCGCTTCGACAGCGACGTGGGGGAGTACCGGGCGGTGACGGAGCTGGGGCGGCC TGTCGCCGAGTCCTGGAACAGCCAGAAGGACCTCCTGGAGCAGAAGCGGGCCGGGTGGACAATTACTGCAGACACAACTACGGGGTT GGTGAGAGCTTCACAGTGCAGCGGCGAGTCCATCCTCAGGTGACTCTGTATCCTGCAAAGACCCAGCCCCTGCAGCACCACAACCTCCTG GTCTGCTCTGTGAGTGGTTTCTATCCAGGCAGCATTGAAGTCAGGTGGTTCCGGAACGGCCAGGAAGAGAAGGCTGGGGTTGGTGTCCAC GGGCCTGATCCAGAATGGAGACTGGACCTTCCAGACCCTGGTGATGCTAGAAACAGTTCCTCGGAGTGGAGAGGTTTACACTTGCCAAGT GGAGCACCCAAGCGTAACGAGCGCTCTCACACGTGGAATGGAGAGCACGGTCTGAATCTGCACAGAGCAAGATGCTGAGTGGAGTCGGG GGCTTTGTGCTGGGCCTGCTCTTCCTTGGGGCCGGGCTTGTTCATCTACTTCAGGAATCAGAAAGGACACTCTGGACTTCAGCCAACAGGATT CCTGAGCTGACTCGAGGATC | 93 |
| HLA-A7A-B* 27:03 | GATCCTCGAGACCACCATGCGGGTCACGGCGCCCCGAACCCTCCTCCTGCTGCTCTGGGGGGCAGTGGCCCTGACCGAGACCTGGGCTG GCTCCCACTCCATGAGGTATTTCCACACCTCCGTGTCCCGGCCCGGCCGCGGGGAGCCCCGCTTCATCACGGTGGGCTACGTGGACGACA CGCTGTTCGTGAGGTTCGACAGCGACGCCGCGAGTCGGAGAGGAGCCGCGGGCGCCGTGGATAGAGCAGGAGGGCCGGAGCAT TGGGACCGGGAGACACAGATCTGCAAGGCCAAGGCACAGACTGACCGAGAGGACCTGCGGACCCTGCTCCGCTACTACAACCAGAGCG AGGCCGGGTCTCACACCCTCCAGAATATGTATGGCTGCGACGTGGGGCCGGACGGGCGCCTCCTCCGCGGGTACCACCAGGACGCCTAC GACGGCAAGGATTACATCGCCCTGAACGAGGACCTGAGCTCCTGGACCGCCGCGGACACGGCGGCTCAGATCACCCAGCGCAAGTGGG AGGCGGCCCGTGTGGCGGGAGCAGCTGAGAGCCTACCTGGAGGGCGAGTGCGTGGAGTGGCTCCGCAGATACCTGGAGAACGGGAAGG GAGACGCTGCAGCGCGCGGACCCCCAAAGACACACGTGACCCACCACCCCATCTCTGACCATGAGGCCACCCTGAGGTGCTGGGCCCT GGGCTTCTACCCTGCGGAGATCACACTGACCTGGCAGCGGGATGGCGAGGACCAAACTCAGGACACTGAGCTTGTGGAGACCAGACCAG CAGGAGATAGAACCTTCCAGAAGTGGGCAGCTGTGGTGGTGCCTTCTGGAGAAGAGCAGAGATACACATGCCATGTACAGCATGAGGGG CTGCCGAAGCCCCTCACCCTGAGATGGGAGCCGTCTTCCCAGTCCACCGTCCCCATCGTGGGCATTGTTGCTGGCCTGGCTGTCCTAGCAG TTGTGGTCATCGGAGCTGTGTCGCTGCTGTGATGTGTAGGAGGAAGAGCTCAGGTGGAAAAGGAGGGAGCTACTCTCAGGCTGCGTGC AGCGACAGTGCCCAGGGCTCTGATGTGTCTCTCACAGCTTGAGAATTCGATC | 94 |
| HLA-B*27:09 | GATCCTCGAGACCACCATGCGGGTCACGGCGCCCCGAACCCTCCTCCTGCTGCTCTGGGGGGCAGTGGCCCTGACCGAGACCTGGGCTG GCTCCCACTCCATGAGGTATTTCCACACCTCCGTGTCCCGGCCCGGCCGCGGGGAGCCCCGCTTCATCACGGTGGGCTACGTGGACGACA CGCTGTTCGTGAGGTTCGACAGCGACGCCGCGAGTCGGAGAGGAGCCGCGGGCGCCGTGGATAGAGCAGGAGGGCGGGAGTATT GGGACCGGGAGACACAGATCTGCAAGGCCAAGGCACAGACTGACCGAGAGGACCTGCGGACCCTGCTCCGCTACTACAACCAGAGCGA GGCCGGGTCTCACACCCTCCAGAATATGTATGGCTGCGACGTGGGGCCGGACGGGCGGCTCCTCCGCGGGTACCACCAGCACGCCTACG ACGGCAAGGATTACATCGCCCTGAACGAGGACCTGAGCTCCTGGACCGCGGCGGACACGGCGGCTCAGATCACCCAGCGCAAGTGGGA GGCGGCCCGTGTGGCGGAGCAGCTGAGAGCCTACCTGGAGGGCGAGTGCGTGGAGTGGCTCCGCAGATACCTGGAGAACGGGAAGG AGACGCTGCAGCGCGCGGACCCCCAAAGACACACGTGACCCACCACCCCATCTCTGACCATGAGGCCACCCTGAGGTGCTGGGCCCTG GGCTTCTACCCTGCGGAGATCACACTGACCTGGCAGCGGGATGGCGAGGACCAAACTCAGGACACTGAGCTTGTGGAGACCAGACCAGC AGGAGATAGAACCTTCCAGAAGTGGGCAGCTGTGGTGGTGCCTTCTGGAGAAGAGCAGAGATACACATGCCATGTACAGCATGAGGGC TGCCGAAGCCCCTCACCCTGAGATGGGAGCCGTCTTCCCAGTCCACCGTCCCCATCGTGGGCATTGTTGCTGGCCTGGCTGTCCTAGCAGT TGTGGTCATCGGAGCTGTGTCGCTGCTGTGATGTGTAGGAGGAAGAGCTCAGGTGGAAAAGGAGGGAGCTACTCTCAGGCTGCGTGCA GCGACAGTGCCCAGGGCTCTGATGTGTCTCTCACAGCTTGAGAATTCGATC | 95 |
| HLA-B*27:05: 02 | GATCCTCGAGACCACCATGCGGGTCACGGCGCCCCGAACCCTCCTCCTGCTGCTCTGGGGGGCAGTGGCCCTGACCGAGACCTGGGCTG GCTCCCACTCCATGAGGTATTTCCACACCTCCGTGTCCCGGCCCGGCCGCGGGGAGCCCCGCTTCATCACGGTGGGCTACGTGGACGACA CGCTGTTCGTGAGGTTCGACAGCGACGCCGCGAGTCGGAGAGGAGCCGCGGGCGCCGTGGATAGAGCAGGAGGGCCGGAGTATT GGGACCGGGAGACACAGATCTGCAAGGCCAAGGCACAGACTGACCGAGAGGACTGCGGACCCTGCTCCGCTACTACAACCAGAGCGA GGCCGGGTCTCACACCCTCCAGAATATGTATGGCTGCGACGTGGGGCCGGACGGGCGCCTCCTCCGCGGGTACCACCAGGACGCCTAC GACGGCAAGGATTACATCGCCCTGAACGAGGACCTGAGCTCCTGGACCGCGCGGACACGGCGGCTCAGATCACCCAGCGCAAGTGGG AGGCGGCCCGTGTGGCGGAGCAGCTGAGAGCCTACCTGGAGGGCGAGTGCGTGGAGTGGCTCCGCAGATACCTGGAGAACGGGAAG GAGACGCTGCAGCGCGCGGACCCCCAAAGACACACGTGACCCACCACCCCATCTCTGACCATGAGGCCACCCTGAGGTGCTGGGCCCT GGGCTTCTACCCTGCGGAGATCACACTGACCTGGCAGCGGGATGGCGAGGACCAAACTCAGGACACTGAGCTTGTGGAGACCAGACCAG CAGGAGATAGAACCTTCCAGAAGTGGGCAGCTGTGGTGGTGCCTTCTGGAGAAGAGCAGAGATACACATGCCATGTACAGCATGAGGGG CTGCCGAAGCCCCTCACCCTGAGATGGGAGCCGTCTTCCCAGTCCACCGTCCCCATCGTGGGCATTGTTGCTGGCCTGGCTGTCCTAGCAG TTGTGGTCATCGGAGCTGTGTCGCTGCTGTGATGTGTAGGAGGAAGAGCTCAGGTGGAAAAGGAGGGAGCTACTCTCAGGCTGCGTGC AGCGACAGTGCCCAGGGCTCTGATGTGTCTCTCACAGCTTGAGAATTCGATC | 96 |

Fig. 30 continued

SEQUENCE LISTING

```
Sequence total quantity: 124
SEQ ID NO: 1            moltype = AA  length = 341
FEATURE                 Location/Qualifiers
source                  1..341
                        mol_type = protein
                        organism = synthetic construct
SEQUENCE: 1
GSHSMRYFFT SVSRPGRGEP RFIAVGYVDD TQFVRFDSDA ASQRMEPRAP WIEQEGPEYW   60
DGETRKVKAH SQTHRVDLGT LRGYYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWAAVVVP SGQEQRYTCH VQHEGLPKPL TLRWEPSSQP TIPIVGIIAG LVLFGAVITG  300
AVVAAVMWRR KSSDRKGGSY SQAASSDSAQ GSDVSLTACK V                     341

SEQ ID NO: 2            moltype = AA  length = 341
FEATURE                 Location/Qualifiers
```

```
source                  1..341
                        mol_type = protein
                        organism = synthetic construct
SEQUENCE: 2
GSHSMRYFFT SVSRPGRGEP RFIAVGYVDD TQFVRFDSDA ASQRMEPRAP WIEQEGPEYW    60
DQETRNVKAQ SQTDRVDLGT LRGYYNQSEA GSHTIQIMYG CDVGSDGRFL RGYRQDAYDG   120
KDYIALNEDL RSWTAADMAA QITKRKWEAA HEAEQLRAYL DGTCVEWLRR YLENGKETLQ   180
RTDPPKTHMT HHPISDHEAT LRCWALGFYP AEITLTWQRD GEDQTQDTEL VETRPAGDGT   240
FQKWAAVVVP SGEEQRYTCH VQHEGLPKPL TLRWELSSQP TIPIVGIIAG LVLLGAVITG   300
AVVAAVMWRR KSSDRKGGSY TQAASSDSAQ GSDVSLTACK V                      341

SEQ ID NO: 3            moltype = AA  length = 341
FEATURE                 Location/Qualifiers
source                  1..341
                        mol_type = protein
                        organism = synthetic construct
SEQUENCE: 3
GSHSMRYFTT SVSRPGRGEP RFIAVGYVDD TQFVRFDSDA ASQRMEPRAP WIEQEGPEYW    60
DLQTRNVKAQ SQTDRANLGT LRGYYNQSEA GSHTIQMMYG CHVGSDGRFL RGYRQDAYDG   120
KDYIALNEDL RSWTAADMAA QITQRKWEAA RVAEQLRAYL EGTCVEWLRR YLENGKETLQ   180
RTDAPKTHMT HHAVSDHEAT LRCWALSFYP AEITLTWQRD GEDQTQDTEL VETRPAGDGT   240
FQKWASVVVP SGQEQRYTCH VQHEGLPKPL TLRWEPSSQP TIPIVGIIAG LVLFGAVFAG   300
AVVAAVRWRR KSSDRKGGSY SQAASSDSAQ GSDMSLTACK V                      341

SEQ ID NO: 4            moltype = AA  length = 338
FEATURE                 Location/Qualifiers
source                  1..338
                        mol_type = protein
                        organism = synthetic construct
SEQUENCE: 4
GSHSMRYFYT SVSRPGRGEP RFISVGYVDD TQFVRFDSDA ASPREPRAP WIEQEGPEYW    60
DRNTQIYKAQ AQTDRESLRN LRGYYNQSEA GSHTLQSMYG CDVGPDGRLL RGHDQYAYDG   120
KDYIALNEDL RSWTAADTAA QITQRKWEAA REAEQRRAYL EGECVEWLRR YLENGKDKLE   180
RADPPKTHVT HHPISDHEAT LRCWALGFYP AEITLTWQRD GEDQTQDTEL VETRPAGDRT   240
FQKWAAVVVP SGEEQRYTCH VQHEGLPKPL TLRWEPSSQS TVPIVGIVAG LAVLAVVVIG   300
AVVAAVMCRR KSSGGKGGSY SQAACSDSAQ GSDVSLTA                          338

SEQ ID NO: 5            moltype = AA  length = 338
FEATURE                 Location/Qualifiers
source                  1..338
                        mol_type = protein
                        organism = synthetic construct
SEQUENCE: 5
GSHSMRYFDT AMSRPGRGEP RFISVGYVDD TQFVRFDSDA ASPREPRAP WIEQEGPEYW    60
DRNTQIFKTN TQTDRESLRN LRGYYNQSEA GSHTLQSMYG CDVGPDGRLL RGHNQYAYDG   120
KDYIALNEDL RSWTAADTAA QITQRKWEAA RVAEQDRAYL EGTCVEWLRR YLENGKDTLE   180
RADPPKTHVT HHPISDHEAT LRCWALGFYP AEITLTWQRD GEDQTQDTEL VETRPAGDRT   240
FQKWAAVVVP SGEEQRYTCH VQHEGLPKPL TLRWEPSSQS TVPIVGIVAG LAVLAVVVIG   300
AVVAAVMCRR KSSGGKGGSY SQAACSDSAQ GSDVSLTA                          338

SEQ ID NO: 6            moltype = AA  length = 338
FEATURE                 Location/Qualifiers
source                  1..338
                        mol_type = protein
                        organism = synthetic construct
SEQUENCE: 6
GSHSMRYFHT SVSRPGRGEP RFITVGYVDD TLFVRFDSDA ASPREPRAP WIEQEGPEYW    60
DRETQICKAK AQTDREDLRT LLRYYNQSEA GSHTLQNMYG CDVGPDGRLL RGYHQDAYDG   120
KDYIALNEDL SSWTAADTAA QITQRKWEAA RVAEQLRAYL EGECVEWLRR YLENGKETLQ   180
RADPPKTHVT HHPISDHEAT LRCWALGFYP AEITLTWQRD GEDQTQDTEL VETRPAGDRT   240
FQKWAAVVVP SGEEQRYTCH VQHEGLPKPL TLRWEPSSQS TVPIVGIVAG LAVLAVVVIG   300
AVVAAVMCRR KSSGGKGGSY SQAACSDSAQ GSDVSLTA                          338

SEQ ID NO: 7            moltype = AA  length = 338
FEATURE                 Location/Qualifiers
source                  1..338
                        mol_type = protein
                        organism = synthetic construct
SEQUENCE: 7
GSHSMRYFHT SVSRPGRGEP RFITVGYVDD TLFVRFDSDA ASPREPRAP WIEQEGPEYW    60
DRETQICKAK AQTYRENLRT ALRYYNQSEA GSHTLQNMYG CDVGPDGRLL RGYHQDAYDG   120
KDYIALNEDL SSWTAADTAA QITQRKWEAA RVAEQLRAYL EGECVEWLRR YLENGKETLQ   180
RADPPKTHVT HHPISDHEAT LRCWALGFYP AEITLTWQRD GEDQTQDTEL VETRPAGDRT   240
FQKWAAVVVP SGEEQRYTCH VQHEGLPKPL TLRWEPSSQS TVPIVGIVAG LAVLAVVVIG   300
AVVAAVMCRR KSSGGKGGSY SQAACSDSAQ GSDVSLTA                          338

SEQ ID NO: 8            moltype = AA  length = 338
FEATURE                 Location/Qualifiers
source                  1..338
```

```
                            mol_type = protein
                            organism = synthetic construct
SEQUENCE: 8
GSHSMRYFHT SVSRPGRGEP RFITVGYVDD TLFVRFDSDA ASPREEPRAP WIEQEGPEHW    60
DRETQICKAK AQTDREDLRT LLRYYNQSEA GSHTLQNMYG CDVGPDGRLL RGYHQDAYDG   120
KDYIALNEDL SSWTAADTAA QITQRKWEAA RVAEQLRAYL EGECVEWLRR YLENGKETLQ   180
RADPPKTHVT HHPISDHEAT LRCWALGFYP AEITLTWQRD GEDQTQDTEL VETRPAGDRT   240
FQKWAAVVVP SGEEQRYTCH VQHEGLPKPL TLRWEPSSQS TVPIVGIVAG LAVLAVVVIG   300
AVVAAVMCRR KSSGGKGGSY SQAACSDSAQ GSDVSLTA                          338

SEQ ID NO: 9                moltype = AA  length = 338
FEATURE                     Location/Qualifiers
source                      1..338
                            mol_type = protein
                            organism = synthetic construct
SEQUENCE: 9
GSHSMRYFHT SVSRPGRGEP RFITVGYVDD TLFVRFDSDA ASPREEPRAP WIEQEGPEYW    60
DRETQICKAK AQTDREDLRT LLRYYNQSEA GSHTLQNMYG CDVGPDGRLL RGYHQDAYDG   120
KDYIALNEDL SSWTAADTAA QITQRKWEAA RVAEQLRAYL EGECVEWLRR YLENGKETLQ   180
RADPPKTHVT HHPISDHEAT LRCWALGFYP AEITLTWQRD GEDQTQDTEL VETRPAGDRT   240
FQKWAAVVVP SGEEQRYTCH VQHEGLPKPL TLRWEPSSQS TVPIVGIVAG LAVLAVVVIG   300
AVVAAVMCRR KSSGGKGGSY SQAACSDSAQ GSDVSLTA                          338

SEQ ID NO: 10               moltype = AA  length = 338
FEATURE                     Location/Qualifiers
source                      1..338
                            mol_type = protein
                            organism = synthetic construct
SEQUENCE: 10
GSHSMRYFHT SVSRPGRGEP RFITVGYVDD TLFVRFDSDA ASPREEPRAP WIEQEGPEYW    60
DRETQICKAK AQTDREDLRT LLRYYNQSEA GSHTLQNMYG CDVGPDGRLL RGYHQHAYDG   120
KDYIALNEDL SSWTAADTAA QITQRKWEAA RVAEQLRAYL EGECVEWLRR YLENGKETLQ   180
RADPPKTHVT HHPISDHEAT LRCWALGFYP AEITLTWQRD GEDQTQDTEL VETRPAGDRT   240
FQKWAAVVVP SGEEQRYTCH VQHEGLPKPL TLRWEPSSQS TVPIVGIVAG LAVLAVVVIG   300
AVVAAVMCRR KSSGGKGGSY SQAACSDSAQ GSDVSLTA                          338

SEQ ID NO: 11               moltype = AA  length = 338
FEATURE                     Location/Qualifiers
source                      1..338
                            mol_type = protein
                            organism = synthetic construct
SEQUENCE: 11
GSHSMRYFYT AMSRPGRGEP RFIAVGYVDD TQFVRFDSDA ASPRTEPRAP WIEQEGPEYW    60
DRNTQIFKTN TQTYRENLRI ALRYYNQSEA GSHTWQTMYG CDVGPDGRLL RGHNQYAYDG   120
KDYIALNEDL SSWTAADTAA QITQRKWEAA REAEQLRAYL EGLCVEWLRR HLENGKETLQ   180
RADPPKTHVT HHPVSDHEAT LRCWALGFYP AEITLTWQRD GEDQTQDTEL VETRPAGDRT   240
FQKWAAVVVP SGEEQRYTCH VQHEGLPKPL TLRWEPSSQS TIPIVGIVAG LAVLAVVVIG   300
AVVATVMCRR KSSGGKGGSY SQAASSDSAQ GSDVSLTA                          338

SEQ ID NO: 12               moltype = AA  length = 338
FEATURE                     Location/Qualifiers
source                      1..338
                            mol_type = protein
                            organism = synthetic construct
SEQUENCE: 12
GSHSMRYFYT AMSRPGRGEP RFIAVGYVDD TQFVRFDSDA ASPRGEPRAP WVEQEGPEYW    60
DRNTQIYKAQ AQTDRESLRN LRGYYNQSEA GSHTWQTMYG CDLGPDGRLL RGHNQLAYDG   120
KDYIALNEDL SSWTAADTAA QITQRKWEAA RVAEQLRAYL EGTCVEWLRR YLENGKETLQ   180
RADPPKTHVT HHPISDHEAT LRCWALGFYP AEITLTWQRD GEDQTQDTEL VETRPAGDRT   240
FQKWAAVVVP SGEEQRYTCH VQHEGLPKPL TLRWEPSSQS TIPIVGIVAG LAVLAVVVIG   300
AVVATVMCRR KSSGGKGGSY SQAASSDSAQ GSDVSLTA                          338

SEQ ID NO: 13               moltype = AA  length = 338
FEATURE                     Location/Qualifiers
source                      1..338
                            mol_type = protein
                            organism = synthetic construct
SEQUENCE: 13
GSHSMRYFYT AMSRPGRGEP RFIAVGYVDD TQFVRFDSDA ASPRMAPRAP WIEQEGPEYW    60
DGETRNMKAS AQTYRENLRI ALRYYNQSEA GSHIIQVMYG CDVGPDGRLL RGHDQSAYDG   120
KDYIALNEDL SSWTAADTAA QITQRKWEAA RVAEQLRAYL EGLCVEWLRR YLENGKETLQ   180
RADPPKTHVT HHPISDHEAT LRCWALGFYP AEITLTWQRD GEDQTQDTEL VETRPAGDRT   240
FQKWAAVVVP SGEEQRYTCH VQHEGLPKPL TLRWEPSSQS TVPIVGIVAG LAVLAVVVIG   300
AVVAAVMCRR KSSGGKGGSY SQAACSDSAQ GSDVSLTA                          338

SEQ ID NO: 14               moltype = AA  length = 342
FEATURE                     Location/Qualifiers
source                      1..342
                            mol_type = protein
```

```
                              organism = synthetic construct
SEQUENCE: 14
CSHSMRYFDT AVSRPGRGEP RFISVGYVDD TQFVRFDSDA ASPRGEPRAP WVEQEGPEYW    60
DRETQKYKRQ AQADRVNLRK LRGYYNQSED GSHTLQWMYG CDLGPDGRLL RGYDQSAYDG   120
KDYIALNEDL RSWTAADTAA QITQRKWEAA REAEQWRAYL EGTCVEWLRR YLENGKETLQ   180
RAEHPKTHVT HHPVSDHEAT LRCWALGFYP AEITLTWQRD GEDQTQDTEL VETRPAGDGT   240
FQKWAAVVVP SGEEQRYTCH VQHEGLPEPL TLRWEPSSQP TIPIVGIVAG LAVLAVLAVL   300
GAVMAVVMCR RKSSGGKGGS CSQAASSNSA QGSDESLIAC KA                     342

SEQ ID NO: 15              moltype = AA  length = 342
FEATURE                    Location/Qualifiers
source                     1..342
                           mol_type = protein
                           organism = synthetic construct
SEQUENCE: 15
CSHSMRYFDT AVSRPGRGEP RFISVGYVDD TQFVRFDSDA ASPRGEPRAP WVEQEGPEYW    60
DRETQKYKRQ AQADRVNLRK LRGYYNQSED GSHTLQRMFG CDLGPDGRLL RGYNQFAYDG   120
KDYIALNEDL RSWTAADTAA QITQRKWEAA REAEQRRAYL EGTCVEWLRR YLENGKETLQ   180
RAEHPKTHVT HHPVSDHEAT LRCWALGFYP AEITLTWQWD GEDQTQDTEL VETRPAGDGT   240
FQKWAAVVVP SGEEQRYTCH VQHEGLPEPL TLRWKPSSQP TIPIVGIVAG LAVLVVLAVL   300
GAVVAVVMCR RKSSGGKGGS CSQAASSNSA QGSDESLIAC KA                     342

SEQ ID NO: 16              moltype = AA  length = 229
FEATURE                    Location/Qualifiers
source                     1..229
                           mol_type = protein
                           organism = synthetic construct
SEQUENCE: 16
IKADHVSTYA AFVQTHRPTG EFMFEFDEDE QFYVDLDKKE TVWHLEEFGR AFSFEAQGGL    60
ANIAILNNNL NTLIQRSNHT QAANDPPEVT VFPKEPVELG QPNTLICHID RFFPPVLNVT   120
WLCNGEPVTE GVAESLFLPR TDYSFHKFHY LTFVPSAEDV YDCRVEHWGL DQPLLKHWEA   180
QEPIQMPETT ETVLCALGLV LGLVGIIVGT VLIIKSLRSG HDPRAQGPL              229

SEQ ID NO: 17              moltype = AA  length = 229
FEATURE                    Location/Qualifiers
source                     1..229
                           mol_type = protein
                           organism = synthetic construct
SEQUENCE: 17
RATPENYVYQ LRQECYAFNG TQRFLERYIY NREEYARFDS DVGEFRAVTE LGRPAAEYWN    60
SQKDILEEER AVPDRICRHN YELDEAVTLQ RRVQPKVNVS PSKKGPLQHH NLLVCHVTDF   120
YPGSIQVRWF LNGQEETAGV VSTNLIRNGD WTFQILVMLE MTPQQGDVYI CQVEHTSLDS   180
PVTVEWKAQS DSARSKTLTG AGGFVLGLII CGVGIFMHRR SKKVQRGSA              229

SEQ ID NO: 18              moltype = AA  length = 232
FEATURE                    Location/Qualifiers
source                     1..232
                           mol_type = protein
                           organism = synthetic construct
SEQUENCE: 18
EDIVADHVAS CGVNLYQFYG PSGQYTHEFD GDEEFYVDLE RKETAWRWPE FSKFGGFDPQ    60
GALRNMAVAK HNLNIMIKRY NSTAATNEVP EVTVFSKSPV TLGQPNTLIC LVDNIFPPVV   120
NITWLSNGQS VTEGVSETSF LSKSDHSFFK ISYLTFLPSA DEIYDCKVEH WGLDQPLLKH   180
WEPEIPAPMS ELTETVVCAL GLSVGLVGIV VGTVFIIQGL RSVGASRHQG PL          232

SEQ ID NO: 19              moltype = AA  length = 232
FEATURE                    Location/Qualifiers
source                     1..232
                           mol_type = protein
                           organism = synthetic construct
SEQUENCE: 19
EDIVADHVAS CGVNLYQFYG PSGQYTHEFD GDEQFYVDLE RKETAWRWPE FSKFGGFDPQ    60
GALRNMAVAK HNLNIMIKRY NSTAATNEVP EVTVFSKSPV TLGQPNTLIC LVDNIFPPVV   120
NITWLSNGQS VTEGVSETSF LSKSDHSFFK ISYLTFLPSA DEIYDCKVEH WGLDQPLLKH   180
WEPEIPAPMS ELTETVVCAL GLSVGLMGIV VGTVFIIQGL RSVGASRHQG PL          232

SEQ ID NO: 20              moltype = AA  length = 231
FEATURE                    Location/Qualifiers
source                     1..231
                           mol_type = protein
                           organism = synthetic construct
SEQUENCE: 20
EDIVADHVAS YGVNLYQSYG PSGQFTHEFD GDEEFYVDLE RKETVWKLPL FHRLRFDPQF    60
ALTNIAVLKH NLNILIKRSN STAATNEVPE VTVFSKSPVT LGQPNTLICL VDNIFPPVVN   120
ITWLSNGHSV TEGVSETSFL SKSDHSFFKI SYLTFLPSAD EIYDCKVEHW GLDEPLLKHW   180
EPEIPAPMSE LTETVVCALG LSVGLVGIVV GTVLIIRGLR SVGASRHQGP L           231

SEQ ID NO: 21              moltype = AA  length = 232
FEATURE                    Location/Qualifiers
```

```
source                   1..232
                         mol_type = protein
                         organism = synthetic construct
SEQUENCE: 21
EDIVADHVAS YGVNLYQSYG PSGQYSHEFD GDEEFYVDLE RKETVWQLPL FRRFRRFDPQ    60
FALTNIAVLK HNLNIVIKRS NSTAATNEVP EVTVFSKSPV TLGQPNTLIC LVDNIFPPVV   120
NITWLSNGHS VTEGVSETSF LSKSDHSFFK ISYLTFLPSA DEIYDCKVEH WGLDEPLLKH   180
WEPEIPTPMS ELTETVVCAL GLSVGLVGIV VGTVLIIRGL RSVGASRHQG PL           232

SEQ ID NO: 22            moltype = AA  length = 231
FEATURE                  Location/Qualifiers
source                   1..231
                         mol_type = protein
                         organism = synthetic construct
SEQUENCE: 22
EDIVADHVAS YGVNLYQSYG PSGQYTHEFD GDEQFYVDLG RKETVWCLPV LRQFRFDPQF    60
ALTNIAVLKH NLNSLIKRSN STAATNEVPE VTVFSKSPVT LGQPNILICL VDNIFPPVVN   120
ITWLSNGHSV TEGVSETSFL SKSDHSFFKI SYLTLLPSAE ESYDCKVEHW GLDKPLLKHW   180
EPEIPAPMSE LTETVVCALG LSVGLVGIVV GTVFIIRGLR SVGASRHQGP L            231

SEQ ID NO: 23            moltype = AA  length = 231
FEATURE                  Location/Qualifiers
source                   1..231
                         mol_type = protein
                         organism = synthetic construct
SEQUENCE: 23
EDIVADHVAS YGVNLYQSYG PSGQYTHEFD GDEQFYVDLG RKETVWCLPV LRQFRFDPQF    60
ALTNIAVLKH NLNSLIKRSN STAATNEVPE VTVFSKSPVT LGQPNILICL VDNIFPPVVN   120
ITWLSNGHSV TEGVSETSFL SKSDHSFFKI SYLTLLPSAE ESYDCKVEHW GLDKPLLKHW   180
EPEIPAPMSE LTETVVCALG LSVGLVGIVV GTVFIIRGLR SVGASRHQGP L            231

SEQ ID NO: 24            moltype = AA  length = 229
FEATURE                  Location/Qualifiers
source                   1..229
                         mol_type = protein
                         organism = synthetic construct
SEQUENCE: 24
RDSPEDFVYQ FKGMCYFTNG TERVRLVSRS IYNREEIVRF DSDVGEFRAV TLLGLPAAEY    60
WNSQKDILER KRAAVDRVCR HNYQLELRTT LQRRVEPTVT ISPSRTEALN HHNLLVCSVT   120
DFYPAQIKVR WFRNDQEETA GVVSTPLIRN GDWTFQILVM LEMTPQRGDV YTCHVEHPSL   180
QSPITVEWRA QSESAQSKML SGIGGFVLGL IFLGLGLIIH HRSQKGLLH               229

SEQ ID NO: 25            moltype = AA  length = 229
FEATURE                  Location/Qualifiers
source                   1..229
                         mol_type = protein
                         organism = synthetic construct
SEQUENCE: 25
RDSPEDFVYQ FKAMCYFTNG TERVRYVTRY IYNREEYARF DSDVEVYRAV TPLGPPDAEY    60
WNSQKEVLER TRAELDTVCR HNYQLELRTT LQRRVEPTVT ISPSRTEALN HHNLLVCSVT   120
DFYPAQIKVR WFRNDQEETT GVVSTPLIRN GDWTFQILVM LEMTPQHGDV YTCHVEHPSL   180
QNPITVEWRA QSESAQSKML SGIGGFVLGL IFLGLGLIIH HRSQKGLLH               229

SEQ ID NO: 26            moltype = AA  length = 229
FEATURE                  Location/Qualifiers
source                   1..229
                         mol_type = protein
                         organism = synthetic construct
SEQUENCE: 26
RDSPEDFVYQ FKGMCYFTNG TERVRLVTRY IYNREEYARF DSDVGVYRAV TPLGPPAAEY    60
WNSQKEVLER TRAELDTVCR HNYQLELRTT LQRRVEPTVT ISPSRTEALN HHNLLVCSVT   120
DFYPAQIKVR WFRNDQEETT GVVSTPLIRN GDWTFQILVM LEMTPQRGDV YTCHVEHPSL   180
QNPIIVEWRA QSESAQSKML SGIGGFVLGL IFLGLGLIIH HRSQKGLLH               229

SEQ ID NO: 27            moltype = AA  length = 229
FEATURE                  Location/Qualifiers
source                   1..229
                         mol_type = protein
                         organism = synthetic construct
SEQUENCE: 27
RDSPEDFVYQ FKGLCYFTNG TERVRGVTRH IYNREEYVRF DSDVGVYRAV TPQGRPVAEY    60
WNSQKEVLEG ARASVDRVCR HNYEVAYRGI LQRRVEPTVT ISPSRTEALN HHNLLICSVT   120
DFYPSQIKVR WFRNDQEETA GVVSTPLIRN GDWTFQILVM LEMTPQRGDV YTCHVEHPSL   180
QSPITVEWRA QSESAQSKML SGVGGFVLGL IFLGLGLIIR QRSRKGLLH               229

SEQ ID NO: 28            moltype = AA  length = 237
FEATURE                  Location/Qualifiers
source                   1..237
                         mol_type = protein
```

```
                      organism  = synthetic construct
SEQUENCE: 28
RDPPEDFVLQ FKAMCYFTNG TERVRYVTRY IYNREEDVRF DSDVGVYRAV TPQGRPDAEY     60
WNSQKDILER TRAELDTVCR HNYEAVFRGI LQRRVEPTVT ISPSRTEALN HHNLLVCSVT    120
DFYPGQIKVR WFRNDQEETA GVVSTPLIRN GDWTFQILVM LEMTPQHGDV YTCHVEHPSL    180
QSPITVEWRA QSESAQNKML SGIGGFVLGL IFLGLGLIIR QRSQKGPQGP PPAGLLH       237

SEQ ID NO: 29            moltype = AA  length = 229
FEATURE                  Location/Qualifiers
source                   1..229
                         mol_type = protein
                         organism = synthetic construct
SEQUENCE: 29
RDSPEDFVFQ FKGMCYFTNG TERVRLVTRY IYNREEYARF DSDVGVYRAV TPQGRPDAEY     60
WNSQKEVLEG TRAELDTVCR HNYEVAFRGI LQRRVEPTVT ISPSRTEALN HHNLLVCSVT    120
DFYPGQIKVR WFRNDQEETA GVVSTPLIRN GDWTFQILVM LEMTPQRGDV YTCHVEHPSL    180
QSPITVEWRA QSESAQSKML SGVGGFVLGL IFLGLGLIIR QRSQKGLLH                229

SEQ ID NO: 30            moltype = AA  length = 237
FEATURE                  Location/Qualifiers
source                   1..237
                         mol_type = protein
                         organism = synthetic construct
SEQUENCE: 30
GDTRPRFLWQ LKFECHFFNG TERVLLLERC IYNQEESVRF DSDVGEYRAV TELGRPDAEY     60
WNSQKDLLEQ RRAAVDTYCR HNYGVGESFT VQRRVEPKVT VYPSKTQPLQ HHNLLVCSVS    120
GFYPGSIEVR WFRNGQEEKA GVVSTGLIQN GDWTFQTLVM LETVPRSGEV YTCQVEHPSV    180
TSPLTVEWRA RSESAQSKML SGVGGFVLGL LFLGAGLFIY FRNQKGHSGL QPTGFLS       237

SEQ ID NO: 31            moltype = AA  length = 237
FEATURE                  Location/Qualifiers
source                   1..237
                         mol_type = protein
                         organism = synthetic construct
SEQUENCE: 31
GDTRPRFLWQ LKFECHFFNG TERVLLLERC IYNQEESVRF DSDVGEYRAV TELGRPDAEY     60
WNSQKDLLEQ RRAAVDTYCR HNYGAVESFT VQRRVEPKVT VYPSKTQPLQ HHNLLVCSVS    120
GFYPGSIEVR WFRNGQEEKA GVVSTGLIQN GDWTFQTLVM LETVPRSGEV YTCQVEHPSV    180
TSPLTVEWRA RSESAQSKML SGVGGFVLGL LFLGAGLFIY FRNQKGHSGL QPTGFLS       237

SEQ ID NO: 32            moltype = AA  length = 237
FEATURE                  Location/Qualifiers
source                   1..237
                         mol_type = protein
                         organism = synthetic construct
SEQUENCE: 32
GDTRPRFLWQ LKFECHFFNG TERVLLLERC IYNQEESVRF DSDVGEYRAV TELGRPDAEY     60
WNSQKDILED ERAAVDTYCR HNYGVGESFT VQRRVEPKVT VYPSKTQPLQ HHNLLVCSVS    120
GFYPGSIEVR WFRNGQEEKA GVVSTGLIQN GDWTFQTLVM LETVPRSGEV YTCQVEHPSV    180
TSPLTVEWRA RSESAQSKML SGVGGFVLGL LFLGAGLFIY FRNQKGHSGL QPTGFLS       237

SEQ ID NO: 33            moltype = AA  length = 237
FEATURE                  Location/Qualifiers
source                   1..237
                         mol_type = protein
                         organism = synthetic construct
SEQUENCE: 33
GDTRPRFLEY STSECHFFNG TERVRYLDRY FHNQEENVRF DSDVGEFRAV TELGRPDAEY     60
WNSQKDLLEQ KRGRVDNYCR HNYGVVESFT VQRRVHPKVT VYPSKTQPLQ HHNLLVCSVS    120
GFYPGSIEVR WFRNGQEEKT GVVSTGLIHN GDWTFQTLVM LETVPRSGEV YTCQVEHPSV    180
TSPLTVEWRA RSESAQSKML SGVGGFVLGL LFLGAGLFIY FRNQKGHSGL QPRGFLS       237

SEQ ID NO: 34            moltype = AA  length = 237
FEATURE                  Location/Qualifiers
source                   1..237
                         mol_type = protein
                         organism = synthetic construct
SEQUENCE: 34
GDTRPRFLEQ VKHECHFFNG TERVRFLDRY FYHQEEYVRF DSDVGEYRAV TELGRPDAEY    60
WNSQKDLLEQ KRAAVDTYCR HNYGVGESFT VQRRVYPEVT VYPAKTQPLQ HHNLLVCSVN   120
GFYPGSIEVR WFRNGQEEKT GVVSTGLIQN GDWTFQTLVM LETVPRSGEV YTCQVEHPSL   180
TSPLTVEWRA RSESAQSKML SGVGGFVLGL LFLGAGLFIY FRNQKGHSGL QPTGFLS      237

SEQ ID NO: 35            moltype = AA  length = 237
FEATURE                  Location/Qualifiers
source                   1..237
                         mol_type = protein
                         organism = synthetic construct
SEQUENCE: 35
```

```
GDTRPRFLEQ VKHECHFFNG TERVRFLDRY FYHQEEYVRF DSDVGEYRAV TELGRPDAEY     60
WNSQKDILED ERAAVDTYCR HNYGVVESFT VQRRVYPEVT VYPAKTQPLQ HHNLLVCSVN    120
GFYPGSIEVR WFRNGQEEKT GVVSTGLIQN GDWTFQTLVM LETVPRSGEV YTCQVEHPSL    180
TSPLTVEWRA RSESAQSKML SGVGGFVLGL LFLGAGLFIY FRNQKGHSGL QPTGFLS       237

SEQ ID NO: 36          moltype = AA   length = 237
FEATURE                Location/Qualifiers
source                 1..237
                       mol_type = protein
                       organism = synthetic construct
SEQUENCE: 36
GDTRPRFLEQ VKHECHFFNG TERVRFLDRY FYHQEEYVRF DSDVGEYRAV TELGRPDAEY     60
WNSQKDLLEQ RRAEVDTYCR HNYGVVESFT VQRRVYPEVT VYPAKTQPLQ HHNLLVCSVN    120
GFYPGSIEVR WFRNGQEEKT GVVSTGLIQN GDWTFQTLVM LETVPRSGEV YTCQVEHPSL    180
TSPLTVEWRA RSESAQSKML SGVGGFVLGL LFLGAGLFIY FRNQKGHSGL QPTGFLS       237

SEQ ID NO: 37          moltype = AA   length = 237
FEATURE                Location/Qualifiers
source                 1..237
                       mol_type = protein
                       organism = synthetic construct
SEQUENCE: 37
GDTRPRFLEQ VKHECHFFNG TERVRFLDRY FYHQEEYVRF DSDVGEYRAV TELGRPDAEY     60
WNSQKDLLEQ RRAAVDTYCR HNYGVVESFT VQRRVYPEVT VYPAKTQPLQ HHNLLVCSVN    120
GFYPGSIEVR WFRNGQEEKT GVVSTGLIQN GDWTFQTLVM LETVPRSGEV YTCQVEHPSL    180
TSPLTVEWRA RSESAQSKML SGVGGFVLGL LFLGAGLFIY FRNQKGHSGL QPTGFLS       237

SEQ ID NO: 38          moltype = AA   length = 237
FEATURE                Location/Qualifiers
source                 1..237
                       mol_type = protein
                       organism = synthetic construct
SEQUENCE: 38
GDTRPRFLEQ VKHECHFFNG TERVRFLDRY FYHQEEYVRF DSDVGEYRAV TELGRPSAEY     60
WNSQKDLLEQ RRAAVDTYCR HNYGVGESFT VQRRVYPEVT VYPAKTQPLQ HHNLLVCSVN    120
GFYPGSIEVR WFRNGQEEKT GVVSTGLIQN GDWTFQTLVM LETVPRSGEV YTCQVEHPSL    180
TSPLTVEWRA RSESAQSKML SGVGGFVLGL LFLGAGLFIY FRNQKGHSGL QPTGFLS       237

SEQ ID NO: 39          moltype = AA   length = 237
FEATURE                Location/Qualifiers
source                 1..237
                       mol_type = protein
                       organism = synthetic construct
SEQUENCE: 39
GDTRPRFLEQ VKHECHFFNG TERVRFLDRY FYHQEEYVRF DSDVGEYRAV TELGRPDAEY     60
WNSQKDLLEQ RRAAVDTYCR HNYGVGESFT VQRRVYPEVT VYPAKTQPLQ HHNLLVCSVN    120
GFYPGSIEVR WFRNGQEEKT GVVSTGLIQN GDWTFQTLVM LETVPRSGEV YTCQVEHPSL    180
TSPLTVEWRA RSESAQSKML SGVGGFVLGL LFLGAGLFIY FRNQKGHSGL QPTGFLS       237

SEQ ID NO: 40          moltype = AA   length = 237
FEATURE                Location/Qualifiers
source                 1..237
                       mol_type = protein
                       organism = synthetic construct
SEQUENCE: 40
GDTQPRFLWQ GKYKCHFFNG TERVQFLERL FYNQEEFVRF DSDVGEYRAV TELGRPVAES     60
WNSQKDILED RRGQVDTVCR HNYGVGESFT VQRRVHPEVT VYPAKTQPLQ HHNLLVCSVS    120
GFYPGSIEVR WFRNGQEEKA GVVSTGLIQN GDWTFQTLVM LETVPRSGEV YTCQVEHPSV    180
MSPLTVEWRA RSESAQSKML SGVGGFVLGL LFLGAGLFIY FRNQKGHSGL QPTGFLS       237

SEQ ID NO: 41          moltype = AA   length = 237
FEATURE                Location/Qualifiers
source                 1..237
                       mol_type = protein
                       organism = synthetic construct
SEQUENCE: 41
GDTRPRFLEY STGECYFFNG TERVRFLDRY FYNQEEYVRF DSDVGEYRAV TELGRPSAEY     60
WNSQKDFLED RRALVDTYCR HNYGVGESFT VQRRVHPEVT VYPSKTQPLQ HHNLLVCSVS    120
GFYPGSIEVR WFRNGQEEKT GVVSTGLIHN GDWTFQTLVM LETVPRSGEV YTCQVEHPSV    180
TSPLTVEWSA RSESAQSKML SGVGGFVLGL LFLGAGLFIY FRNQKGHSGL QPTGFLS       237

SEQ ID NO: 42          moltype = AA   length = 237
FEATURE                Location/Qualifiers
source                 1..237
                       mol_type = protein
                       organism = synthetic construct
SEQUENCE: 42
GDTQPRFLKQ DKFECHFFNG TERVRYLHRG IYNQEENVRF DSDVGEYRAV TELGRPVAES     60
WNSQKDFLER RRAEVDTVCR HNYGVGESFT VQRRVHPEVT VYPAKTQPLQ HHNLLVCSVS    120
```

```
GFYPGSIEVR WFRNGQEEKA GVVSTGLIQN GDWTFQTLVM LETVPRSGEV YTCQVEHPSV    180
MSPLTVEWRA RSESAQSKML SGVGGFVLGL LFLGAGLFIY FRNQKGHSGL QPTGFLS      237

SEQ ID NO: 43           moltype = AA  length = 237
FEATURE                 Location/Qualifiers
source                  1..237
                        mol_type = protein
                        organism = synthetic construct
SEQUENCE: 43
GDTRPRFLEE VKFECHFFNG TERVRLLERR VHNQEEYARY DSDVGEYRAV TELGRPDAEY    60
WNSQKDLLER RRAAVDTYCR HNYGVGESFT VQRRVQPKVT VYPSKTQPLQ HHNLLVCSVN    120
GFYPGSIEVR WFRNGQEEKT GVVSTGLIQN GDWTFQTLVM LETVPQSGEV YTCQVEHPSV    180
MSPLTVEWRA RSESAQSKML SGVGGFVLGL LFLGAGLFIY FRNQKGHSGL PPTGFLS      237

SEQ ID NO: 44           moltype = AA  length = 237
FEATURE                 Location/Qualifiers
source                  1..237
                        mol_type = protein
                        organism = synthetic construct
SEQUENCE: 44
GDTRPRFLEY STSECHFFNG TERVRFLDRY FYNQEEYVRF DSDVGEFRAV TELGRPDEEY    60
WNSQKDFLED RRAAVDTYCR HNYGVGESFT VQRRVHPKVT VYPSKTQPLQ HHNLLVCSVS    120
GFYPGSIEVR WFRNGQEEKT GVVSTGLIHN GDWTFQTLVM LETVPRSGEV YTCQVEHPSV    180
TSPLTVEWRA RSESAQSKML SGVGGFVLGL LFLGAGLFIY FRNQKGHSGL QPRGFLS      237

SEQ ID NO: 45           moltype = AA  length = 237
FEATURE                 Location/Qualifiers
source                  1..237
                        mol_type = protein
                        organism = synthetic construct
SEQUENCE: 45
GDTRPRFLEY STSECHFFNG TERVRFLDRY FYNQEEYVRF DSDVGEFRAV TELGRPDEEY    60
WNSQKDILED ERAAVDTYCR HNYGVVESFT VQRRVHPKVT VYPSKTQPLQ HHNLLVCSVS    120
GFYPGSIEVR WFRNGQEEKT GVVSTGLIHN GDWTFQTLVM LETVPRSGEV YTCQVEHPSV    180
TSPLTVEWRA RSESAQSKML SGVGGFVLGL LFLGAGLFIY FRNQKGHSGL QPRGFLS      237

SEQ ID NO: 46           moltype = AA  length = 237
FEATURE                 Location/Qualifiers
source                  1..237
                        mol_type = protein
                        organism = synthetic construct
SEQUENCE: 46
GDTRPRFLEY STSECHFFNG TERVRFLDRY FYNQEEYVRF DSDVGEFRAV TELGRPDEEY    60
WNSQKDFLED ERAAVDTYCR HNYGVVESFT VQRRVHPKVT VYPSKTQPLQ HHNLLVCSVS    120
GFYPGSIEVR WFRNGQEEKT GVVSTGLIHN GDWTFQTLVM LETVPRSGEV YTCQVEHPSV    180
TSPLTVEWRA RSESAQSKML SGVGGFVLGL LFLGAGLFIY FRNQKGHSGL QPRGFLS      237

SEQ ID NO: 47           moltype = AA  length = 237
FEATURE                 Location/Qualifiers
source                  1..237
                        mol_type = protein
                        organism = synthetic construct
SEQUENCE: 47
GDTRPRFLEY STSECHFFNG TERVRFLDRY FYNQEEYVRF DSDVGEFRAV TELGRPDEEY    60
WNSQKDFLED RRAAVDTYCR HNYGVVESFT VQRRVHPKVT VYPSKTQPLQ HHNLLVCSVS    120
GFYPGSIEVR WFRNGQEEKT GVVSTGLIHN GDWTFQTLVM LETVPRSGEV YTCQVEHPSV    180
TSPLTVEWRA RSESAQSKML SGVGGFVLGL LFLGAGLFIY FRNQKGHSGL QPRGFLS      237

SEQ ID NO: 48           moltype = AA  length = 237
FEATURE                 Location/Qualifiers
source                  1..237
                        mol_type = protein
                        organism = synthetic construct
SEQUENCE: 48
GDTRPRFLEY STGECYFFNG TERVRLLERH FHNQEELLRF DSDVGEFRAV TELGRPVAES    60
WNSQKDILED RRAAVDTYCR HNYGAVESFT VQRRVHPKVT VYPSKTQPLQ HHNLLVCSVS    120
GFYPGSIEVR WFRNGQEEKT GVVSTGLIHN GDWTFQTLVM LETVPRSGEV YTCQVEHPSV    180
TSPLTVEWRA RSESAQSKML SGVGGFVLGL LFLGAGLFIY FRNQKGHSGL QPRGFLS      237

SEQ ID NO: 49           moltype = AA  length = 237
FEATURE                 Location/Qualifiers
source                  1..237
                        mol_type = protein
                        organism = synthetic construct
SEQUENCE: 49
GDTRPRFLEY STSECHFFNG TERVRFLDRY FHNQEENVRF DSDVGEFRAV TELGRPDAEY    60
WNSQKDILED ERAAVDTYCR HNYGVVESFT VQRRVHPKVT VYPSKTQPLQ HHNLLVCSVS    120
GFYPGSIEVR WFRNGQEEKT GVVSTGLIHN GDWTFQTLVM LETVPRSGEV YTCQVEHPSV    180
TSPLTVEWRA RSESAQSKML SGVGGFVLGL LFLGAGLFIY FRNQKGHSGL QPRGFLS      237
```

```
SEQ ID NO: 50            moltype = AA   length = 237
FEATURE                  Location/Qualifiers
source                   1..237
                         mol_type = protein
                         organism = synthetic construct
SEQUENCE: 50
GDTRPRFLEY STSECHFFNG TERVRFLDRY FHNQEEFVRF DSDVGEYRAV TELGRPAAEH   60
WNSQKDLLER RRAEVDTYCR HNYGVVESFT VQRRVHPKVT VYPSKTQPLQ HYNLLVCSVS  120
GFYPGSIEVR WFRNGQEEKT GVVSTGLIHN GDWTFQTLVM LETVPRSGEV YTCQVEHPSV  180
TSPLTVEWRA RSESAQSKML SGVGGFVLGL LFLGAGLFIY FRNQKGHSGL QPRGFLS     237

SEQ ID NO: 51            moltype = AA   length = 237
FEATURE                  Location/Qualifiers
source                   1..237
                         mol_type = protein
                         organism = synthetic construct
SEQUENCE: 51
GDTRPRFLWQ PKRECHFFNG TERVRFLDRY FYNQEESVRF DSDVGEFRAV TELGRPDAEY   60
WNSQKDILEQ ARAAVDTYCR HNYGVVESFT VQRRVQPKVT VYPSKTQPLQ HHNLLVCSVS  120
GFYPGSIEVR WFLNGQEEKA GMVSTGLIQN GDWTFQTLVM LETVPRSGEV YTCQVEHPSV  180
TSPLTVEWRA RSESAQSKML SGVGGFVLGL LFLGAGLFIY FRNQKGHSGL QPTGFLS     237

SEQ ID NO: 52            moltype = AA   length = 237
FEATURE                  Location/Qualifiers
source                   1..237
                         mol_type = protein
                         organism = synthetic construct
SEQUENCE: 52
GDTRPRFLWQ PKRECHFFNG TERVRFLDRY FYNQEESVRF DSDVGEFRAV TELGRPDAEY   60
WNSQKDILEQ ARAAVDTYCR HNYGVGESFT VQRRVQPKVT VYPSKTQPLQ HHNLLVCSVS  120
GFYPGSIEVR WFLNGQEEKA GMVSTGLIQN GDWTFQTLVM LETVPRSGEV YTCQVEHPSV  180
TSPLTVEWRA RSESAQSKML SGVGGFVLGL LFLGAGLFIY FRNQKGHSGL QPTGFLS     237

SEQ ID NO: 53            moltype = AA   length = 237
FEATURE                  Location/Qualifiers
source                   1..237
                         mol_type = protein
                         organism = synthetic construct
SEQUENCE: 53
GDTRPRFLWQ PKRECHFFNG TERVRFLDRY FYNQEESVRF DSDVGEYRAV TELGRPDAEY   60
WNSQKDFLED RRAAVDTYCR HNYGVGESFT VQRRVQPKVT VYPSKTQPLQ HHNLLVCSVS  120
GFYPGSIEVR WFLNGQEEKA GMVSTGLIQN GDWTFQTLVM LETVPRSGEV YTCQVEHPSV  180
TSPLTVEWRA RSESAQSKML SGVGGFVLGL LFLGAGLFIY FRNQKGHSGL QPTGFLS     237

SEQ ID NO: 54            moltype = AA   length = 237
FEATURE                  Location/Qualifiers
source                   1..237
                         mol_type = protein
                         organism = synthetic construct
SEQUENCE: 54
GDTRPRFLEL RKSECHFFNG TERVRYLDRY FHNQEEFLRF DSDVGEYRAV TELGRPVAES   60
WNSQKDLLEQ KRGRVDNYCR HNYGVGESFT VQRRVHPQVT VYPAKTQPLQ HHNLLVCSVS  120
GFYPGSIEVR WFRNGQEEKA GVVSTGLIQN GDWTFQTLVM LETVPRSGEV YTCQVEHPSV  180
TSALTVEWRA RSESAQSKML SGVGGFVLGL LFLGAGLFIY FRNQKGHSGL QPTGFLS     237

SEQ ID NO: 55            moltype = AA   length = 237
FEATURE                  Location/Qualifiers
source                   1..237
                         mol_type = protein
                         organism = synthetic construct
SEQUENCE: 55
GDTRPRFLEL LKSECHFFNG TERVRFLERH FHNQEEYARF DSDVGEYRAV RELGRPDAEY   60
WNSQKDLLEQ KRGQVDNYCR HNYGVGESFT VQRRVHPQVT VYPAKTQPLQ HHNLLVCSVS  120
GFYPGSIEVR WFRNGQEEKA GVVSTGLIQN GDWTFQTLVM LETVPRSGEV YTCQVEHPSV  180
TSPLTVEWSA RSESAQSKML SGVGGFVLGL LFLGAGLFIY FRNQKGHSGL QPTGFLS     237

SEQ ID NO: 56            moltype = AA   length = 237
FEATURE                  Location/Qualifiers
source                   1..237
                         mol_type = protein
                         organism = synthetic construct
SEQUENCE: 56
GDTRPRFLEL LKSECHFFNG TERVRFLERY FHNQEEFVRF DSDVGEYRAV TELGRPVAES   60
WNSQKDLLEQ KRGQVDNYCR HNYGVVESFT VQRRVHPQVT VYPAKTQPLQ HHNLLVCSVS  120
GFYPGSIEVR WFRNGQEEKT GVVSTGLIHN GDWTFQTLVM LETVPRSGEV YTCQVEHPSV  180
TSPLTVEWRA RSESAQSKML SGVGGFVLGL LFLGAGLFIY FRNQKGHSGL QPTGFLS     237

SEQ ID NO: 57            moltype = AA   length = 237
```

```
FEATURE                 Location/Qualifiers
source                  1..237
                        mol_type = protein
                        organism = synthetic construct
SEQUENCE: 57
GDTQPRFLEQ AKCECHFLNG TERVWNLIRY IYNQEEYARY NSDLGEYQAV TELGRPDAEY    60
WNSQKDLLER RRAEVDTYCR YNYGVVESFT VQRRVQPKVT VYPSKTQPLQ HHNLLVCSVN   120
GFYPGSIEVR WFRNGQEEKA GVVSTGLIQN GDWTFQTLVM LETVPRSGEV YTCQVEHPSM   180
MSPLTVQWSA RSESAQSKML SGVGGFVLGL LFLGTGLFIY FRNQKGHSGL QPTGLLS     237

SEQ ID NO: 58           moltype = AA  length = 237
FEATURE                 Location/Qualifiers
source                  1..237
                        mol_type = protein
                        organism = synthetic construct
SEQUENCE: 58
GDTRPRFLQQ DKYECHFFNG TERVRFLHRD IYNQEEDLRF DSDVGEYRAV TELGRPDAEY    60
WNSQKDFLED RRAAVDTYCR HNYGVGESFT VQRRVEPKVT VYPARTQTLQ HHNLLVCSVN   120
GFYPGSIEVR WFRNSQEEKA GVVSTGLIQN GDWTFQTLVM LETVPRSGEV YTCQVEHPSV   180
TSPLTVEWRA QSESAQSKML SGVGGFVLGL LFLGAGLFIY FKNQKGHSGL HPTGLVS     237

SEQ ID NO: 59           moltype = DNA  length = 1089
FEATURE                 Location/Qualifiers
source                  1..1089
                        mol_type = other DNA
                        organism = synthetic construct
SEQUENCE: 59
atgcgggtca cggcgccccg aaccctcctc ctgctgctct ggggggcagt ggccctgacc    60
gagacctggg ctggctccca ctccatgagg tatttccaca cctccgtgtc ccggcccggc   120
cgcggggagc cccgcttcat caccgtgggc tacgtggacg acacgctgtt cgtgaggttc   180
gacagcgacg ccgcgagtcc gagagaggag ccgcgggcgc cgtggataga gcaggagggg   240
ccggagtatt gggaccggga gacacagatc tgcaaggcca aggcacagac tgaccgagag   300
gacctgcgga ccctgctccg ctactacaac cagagcgagg ccgggtctca caccctccag   360
aatatgtatg gctgcgacgt ggggccggac gggcgcctcc tccgcgggta ccaccaggac   420
gcctacgacg gcaaggatta catcgccctg aacgaggacc tgagctcctg gaccgccgcg   480
gacacggcgg ctcagatcac ccagcgcaag tgggaggcgg cccgtgtggc ggagcagctg   540
agagcctacc tggagggcga gtgcgtggag tggctccgca gatacctgga gaacgggaag   600
gagacgctgc agcgcgcgga ccccccaaag acacacgtga cccaccaccc catctctgac   660
catgaggcca ccctgaggtg ctgggccctg gcttctacc tgcggagat cacactgacc   720
tggcagcggg atggcgagga ccaaaactcag gacactgagc ttgtggagac cagaccagca   780
ggagatagaa ccttccagaa gtgggcagct gtggtggtgc cttctggaga agagcagaga   840
tacacatgcc atgtacagca tgaggggctg ccgaagcccc tcaccctgag atgggagccg   900
tcttcccagt ccaccgtccc catcgtgggc attgttgctg gcctggctgt cctagcagtt   960
gtggtcatcg gagctgtggt cgctgctgtg atgtgtagga ggaagagctc aggtggaaaa  1020
ggagggagct actctcaggc tgcgtgcagc gacagtgccc agggctctga tgtgtctctc  1080
acagcttga                                                         1089

SEQ ID NO: 60           moltype = DNA  length = 1089
FEATURE                 Location/Qualifiers
source                  1..1089
                        mol_type = other DNA
                        organism = synthetic construct
SEQUENCE: 60
atgcgggtca cggcgccccg aaccctcctc ctgctgctct ggggggcagt ggccctgacc    60
gagacctggg ctggctccca ctccatgagg tatttccaca cctccgtgtc ccggcccggc   120
cgcggggagc cccgcttcat caccgtgggc tacgtggacg acacgctgtt cgtgaggttc   180
gacagcgacg ccgcgagtcc gagagaggag ccgcgggcgc cgtggataga gcaggagggg   240
ccggagcatt gggaccggga gacacagatc tgcaaggcca aggcacagac tgaccgagag   300
gacctgcgga ccctgctccg ctactacaac cagagcgagg ccgggtctca caccctccag   360
aatatgtatg gctgcgacgt ggggccggac gggcgcctcc tccgcgggta ccaccaggac   420
gcctacgacg gcaaggatta catcgccctg aacgaggacc tgagctcctg gaccgccgcg   480
gacacggcgg ctcagatcac ccagcgcaag tgggaggcgg cccgtgtggc ggagcagctg   540
agagcctacc tggagggcga gtgcgtggag tggctccgca gatacctgga gaacgggaag   600
gagacgctgc agcgcgcgga ccccccaaag acacacgtga cccaccaccc catctctgac   660
catgaggcca ccctgaggtg ctgggccctg gcttctacc tgcggagat cacactgacc   720
tggcagcggg atggcgagga ccaaaactcag gacactgagc ttgtggagac cagaccagca   780
ggagatagaa ccttccagaa gtgggcagct gtggtggtgc cttctggaga agagcagaga   840
tacacatgcc atgtacagca tgaggggctg ccgaagcccc tcaccctgag atgggagccg   900
tcttcccagt ccaccgtccc catcgtgggc attgttgctg gcctggctgt cctagcagtt   960
gtggtcatcg gagctgtggt cgctgctgtg atgtgtagga ggaagagctc aggtggaaaa  1020
ggagggagct actctcaggc tgcgtgcagc gacagtgccc agggctctga tgtgtctctc  1080
acagcttga                                                         1089

SEQ ID NO: 61           moltype = DNA  length = 1089
FEATURE                 Location/Qualifiers
source                  1..1089
                        mol_type = other DNA
                        organism = synthetic construct
SEQUENCE: 61
```

```
atgcgggtca cggcgccccg aaccctcctc ctgctgctct gggggcagt ggccctgacc    60
gagacctggg ctggctccca ctccatgagg tatttccaca cctccgtgtc ccggccggc   120
cgcggggagc cccgcttcat caccgtgggc tacgtggacg acacgctgtt cgtgaggttc   180
gacagcgacg ccgcgagtcc gagagaggag ccgcggggcgc cgtggataga gcaggagggg   240
ccggagtatt gggaccggga gacacagatc tgcaaggcca aggcacagac tgaccgagag   300
agcctgcgga ccctgctccg ctactacaac cagagcgagg ccgggtctca caccctccag   360
aatatgtatg gctgcgacgt ggggccggac gggcgcctcc tccgcgggta tgaccagtac   420
gcctacgacg gcaaggatta catcgccctg aacgaggacc tgagctcctg gaccgccgcg   480
gacacggcgg ctcagatcac ccagcgcaag tgggaggcgg cccgtgaggc ggagcagctg   540
agagcctacc tggagggcga gtgcgtggag tggctccgca gatacctgga gaacgggaag   600
gagacgctgc agcgcgcgga ccccccaaag acacacgtga cccaccaccc catctctgac   660
catgaggcca ccctgaggtg ctgggccctg gcttctacc ctgggagat cacactgacc   720
tggcagcggg atggcgagga ccaaactcag gacactgagc ttgtggagac cagaccagca   780
ggagatagaa ccttccagaa gtgggcagct gtggtggtgc cttctggaga agagcagaga   840
tacacatgcc atgtacagca tgaggggctg ccgaagcccc tcaccctgag atgggagccg   900
tcttcccagt ccaccgtccc catcgtgggc attgttgctg gctggctgt cctagcagtt   960
gtggtcatcg gagctgtggt cgctgctgtg atgtgtagga ggaagagctc aggtggaaaa  1020
ggagggagct actctcaggc tgcgtgcagc gacagtgccc agggctctga tgtgtctctc  1080
acagcttga                                                          1089

SEQ ID NO: 62               moltype = DNA  length = 1089
FEATURE                     Location/Qualifiers
source                      1..1089
                            mol_type = other DNA
                            organism = synthetic construct
SEQUENCE: 62
atgcgggtca cggcgccccg aaccctcctc ctgctgctct gggggcagt ggccctgacc    60
gagacctggg ctggctccca ctccatgagg tatttccaca cctccgtgtc ccggccggc   120
cgcggggagc cccgcttcat caccgtgggc tacgtggacg acacgctgtt cgtgaggttc   180
gacagcgacg ccgcgagtcc gagagaggag ccgcggggcgc cgtggataga gcaggagggg   240
ccggagtatt gggaccggga gacacagatc tgcaaggcca aggcacagac tgaccgagag   300
gacctgcgga ccctgctccg ctactacaac cagagcgagg ccgggtctca caccctccag   360
aatatgtatg gctgcgacgt ggggccggac gggcgcctcc tccgcgggta ccaccagcac   420
gcctacgacg gcaaggatta catcgccctg aacgaggacc tgagctcctg gaccgccgcg   480
gacacggcgg ctcagatcac ccagcgcaag tgggaggcgg cccgtgtgcg ggagcagctg   540
agagcctacc tggagggcga gtgcgtggag tggctccgca gatacctgga gaacgggaag   600
gagacgctgc agcgcgcgga ccccccaaag acacacgtga cccaccaccc catctctgac   660
catgaggcca ccctgaggtg ctgggccctg gcttctacc ctgcggagat cacactgacc   720
tggcagcggg atggcgagga ccaaactcag gacactgagc ttgtggagac cagaccagca   780
ggagatagaa ccttccagaa gtgggcagct gtggtggtgc cttctggaga agagcagaga   840
tacacatgcc atgtacagca tgaggggctg ccgaagcccc tcaccctgag atgggagccg   900
tcttcccagt ccaccgtccc catcgtgggc attgttgctg gctggctgt cctagcagtt   960
gtggtcatcg gagctgtggt cgctgctgtg atgtgtagga ggaagagctc aggtggaaaa  1020
ggagggagct actctcaggc tgcgtgcagc gacagtgccc agggctctga tgtgtctctc  1080
acagcttga                                                          1089

SEQ ID NO: 63               moltype = DNA  length = 791
FEATURE                     Location/Qualifiers
source                      1..791
                            mol_type = other DNA
                            organism = synthetic construct
SEQUENCE: 63
gatcagatct accaccatga tcctaaacaa agctctgatg ctggggaccc ttgccctgac    60
caccgtgatg agccctgtg gaggtgaaga cattgtggct gaccacgtcg cctcttatgg   120
tgtaaacttg taccagtctt acggtcccct tggccagtac acccatgaat ttgatggaga   180
tgagcagttc tacgtggacc tggggaggaa ggagactgtc tggtgtttgc ctgttctcag   240
acaatttaga tttgacccgc aatttgcact gacaaacatc gctgtcctaa acataacttt   300
gaacagtctg attaaacgct ccaactctac cgctgctacc aatgaggttc ctgaggtcac   360
agtgttttcc aagtctcccg tgacactggg tcagcccaac atcctcatct gtcttgtgga   420
caacatcttt cctcctgtgg tcaacatcat atggctgagc aatgggcact cagtcacaga   480
aggtgtttct gagaccagct tcctctccaa gagtgatcat tccttcttca agatcagtta   540
cctcaccctc ctccctttctg ctgaggagag ttatgactgc aaggtggagc actgggact   600
ggacaagcct cttctgaaac actgggagcc tgagattcca gccccatgt cagagctcac   660
agagactgtg gtctgcgccc tgggggttgtc tgtgggcctc gtgggcattg tggtgggcac   720
tgtcttcatc atccgaggcc tgcgttcagt tggtgcttcc agacaccaag ggcccttgtg   780
actcgaggat c                                                        791

SEQ ID NO: 64               moltype = DNA  length = 791
FEATURE                     Location/Qualifiers
source                      1..791
                            mol_type = other DNA
                            organism = synthetic construct
SEQUENCE: 64
gatcagatct accaccatga tcctaaacaa agctctgatg ctggggaccc ttgccctgac    60
caccgtgatg agccctgtg gaggtgaaga cattgtggct gaccacgtcg cctcttatgg   120
tgtaaacttg taccagtctt acggtcccct tggccagtac acccatgaat ttgatggaga   180
tgagcagttc tacgtggacc tggggaggaa ggagactgtc tggtgtttgc ctgttctcag   240
acaatttaga tttgacccgc aatttgcact gacaaacatc gctgtcctaa acataacttt   300
gaacagtctg attaaacgct ccaactctac cgctgctacc aatgaggttc ctgaggtcac   360
```

```
agtgttttcc aagtctcccg tgacactggg tcagcccaac atcctcatct gtcttgtgga    420
caacatcttt cctcctgtgg tcaacatcac atggctgagc aatgggcact cagtcacaga    480
aggtgtttct gagaccagct tcctctccaa gagtgatcat tccttcttca agatcagtta    540
cctcaccctc ctcccttctg ctgaggagag ttatgactgc aaggtggagc actgggggact   600
ggacaagcct cttctgaaac actgggagcc tgagattcca gccctatgt cagagctcac     660
agagactgtg gtctgcgccc tggggttgtc tgtgggcctc gtgggcattg tggtgggcac    720
tgtcttcatc atccgaggcc tgcgttcagt tggtgcttcc agacaccaag ggcccttgtg    780
actcgaggat c                                                          791

SEQ ID NO: 65           moltype = DNA   length = 812
FEATURE                 Location/Qualifiers
source                  1..812
                        mol_type = other DNA
                        organism = synthetic construct
SEQUENCE: 65
gatcagatct accaccatgt cttggaaaaa ggctttgcgg atccccgag gccttcgggc      60
agcaactgtg accttgatgc tgtcgatgct gagcacccca gtggctgagg cagagactc     120
tcccgaggat ttcgtgtacc agtttaaggg catgtgctac ttcaccaacg gaacagagcg    180
cgtgcgtctt gtgagcagaa gcatctataa ccgagaagag atcgtgcgct tcgacagcga    240
cgtgggggag ttccgggcgg tgacgctgct gggctgcct ccgccgagt actggaacag      300
ccagaaggac atcctggaga gggaacgggc ggcggtggac agggtgtgca gacacaacta    360
ccagtttggag ctccgcacga ccttgcagcg gcgagtggag cccacagtga ccatctcccc   420
atccaggaca gaggccctca accaccacaa cctgctggtc tgctcggtga cagatttcta   480
tccagcccag atcaaagtcc ggtggtttcg aatgaccag gaggagacag ctggcgttgt    540
gtccaccccc cttattagga atggtgactg gaccttccag atcctggtga tgctggaaat   600
gactcccccag cgtggagacg tctacacctg ccacgtggag caccccagcc tccagagccg   660
catcaccgtg gagtggcggg ctcaatctga atctgcccag agcaagatgc tgagtggcat   720
tggaggcttc gtgctgggc tgatcttcct cgggctgggc cttatcatcc atcacaggag    780
tcagaaaggg ctcctgcact gactcgagga tc                                  812

SEQ ID NO: 66           moltype = DNA   length = 812
FEATURE                 Location/Qualifiers
source                  1..812
                        mol_type = other DNA
                        organism = synthetic construct
SEQUENCE: 66
gatcagatct accaccatgt cttggaaaaa ggctttgcgg atccccgag gccttcgggc      60
agcaactgtg accttgatgc tgtcgatgct gagcacccca gtggctgagg cagagactc     120
tcccgaggat ttcgtgtacc agtttaaggg catgtgctac ttcaccaacg gaacagagcg    180
cgtgcgtctt gtgagcagaa gcatctataa ccgagaagag atcgtgcgct tcgacagcga    240
cgtgggggag ttccgggcgg tgacgctgct gggctgcct ccgccgagt actggaacag      300
ccagaaggac atcctggaga ggacacgggc ggcggtggac agggtgtgca gacacaacta    360
ccagtttggag ctccgcacga ccttgcagcg gcgagtggag cccacagtga ccatctcccc   420
atccaggaca gaggccctca accaccacaa cctgctggtc tgctcggtga cagatttcta   480
tccagcccag atcaaagtcc ggtggtttcg aatgaccag gaggagacag ctggcgttgt    540
gtccaccccc cttattagga atggtgactg gaccttccag atcctggtga tgctggaaat   600
gactcccccag cgtggagacg tctacacctg ccacgtggag caccccagcc tccagagccg   660
catcaccgtg gagtggcggg ctcaatctga atctgcccag agcaagatgc tgagtggcat   720
tggaggcttc gtgctgggc tgatcttcct cgggctgggc cttatcatcc atcacaggag    780
tcagaaaggg ctcctgcact gactcgagga tc                                  812

SEQ ID NO: 67           moltype = DNA   length = 789
FEATURE                 Location/Qualifiers
source                  1..789
                        mol_type = other DNA
                        organism = synthetic construct
SEQUENCE: 67
gatcagatct accaccatgt cttggaaaaa ggctttgcgg atccccgag gccttcgggc      60
agcaactgtt accttgatgc tggcgatgct gagcacccca gtggctgagg cagagactc     120
tcccgaggat ttcgtgtacc agtttaaggc catgtgctac ttcaccaacg gacggagcg     180
cgtgcgttat gtgaccagat acatctataa ccgagaggag tacgcacgct tcgacagcga    240
cgtgggaggtg taccgggcgg tgacgccgct ggggccgcct gacgccgagt actggaacag   300
ccagaaggaa gtcctggaga ggacccgggc ggagttggac acggtgtgca gacacaacta    360
ccagtttggag ctccgcacga ccttgcagcg gcgagtggag cccacagtga ccatctcccc   420
atccaggaca gaggccctca accaccacaa cctgctggtc tgctcagtga cagatttcta   480
tccagcccag atcaaagtcc ggtggtttcg aatgaccag gaggagacaa ccggcgttgt    540
gtccaccccc cttattagga acggtgactg gaccttccag atcctggtga tgctggaaat   600
gactcccccag catggagacg tctacacctg ccacgtggag caccccagcc tccagaaccc   660
catcaccgtg gagtggcggg ctcagtctga atctgcccag agcaagatgc tgagtggcat   720
tggaggcttc gtgctgggc tcatcttcct cgggctgggc cttattatcc atcacaggag    780
tcagaaagg                                                             789

SEQ ID NO: 68           moltype = DNA   length = 835
FEATURE                 Location/Qualifiers
source                  1..835
                        mol_type = other DNA
                        organism = synthetic construct
SEQUENCE: 68
gatcagatct accaccatgt cttggaagaa ggctttgcgg atccctggag gccttcgggt     60
```

```
agcaactgtg accttgatgc tggcgatgct gagcacccog gtggctgagg gcagagactc    120
tcccgaggat ttcgtgtacc agtttaaggg catgtgctac ttcaccaacg ggacggagcg    180
cgtgcgtctt gtgaccagat acatctataa ccgagaggag tacgcacgct tcgacagcga    240
cgtgggggtg tatcgggcgg tgacgccgct ggggccgcct gacgccgagt actgaaacag    300
ccagaaggaa gtcctggaga ggacccgggc ggagttggac acggtgtgca gacacaacta    360
ccagttggag ctccgcacga ccttgcagcg gcgagtggag cccacagtga ccatctcccc    420
atccaggaca gaggccctca accaccacaa cctgctggtc tgctcagtga cagatttcta    480
tccagcccca atcaaagtcc ggtggtttcg gaatgaccag gaggagacaa ctggcgttgt    540
gtccaccccc cttattagga acggtgactg gaccttccag atcctggtga tgctggaaat    600
gactccccag cgtggagacg tctacacctg ccacgtggag cacccccagcc tccagaaccc    660
catcatcgtg gagtggcggg ctcagtctga atctgcccag agcaagatgc tgagtggcat    720
tggaggcttc gtgctggggc tgatcttcct cgggctgggc cttattatcc atcacaggag    780
tcagaaaggg ctcctgcact gactcgagga tcgctcctgc actgactcga ggatc         835

SEQ ID NO: 69         moltype = DNA   length = 812
FEATURE               Location/Qualifiers
source                1..812
                      mol_type = other DNA
                      organism = synthetic construct
SEQUENCE: 69
gatcagatct accaccatgt cttggaagaa ggctttgcgg atccctggag gccttcgggt    60
agcaactgtg accttgatgc tggcgatgct gagcacccog gtggctgagg gcagagactc    120
tcccgaggat ttcgtgtacc agtttaaggg catgtgctac ttcaccaacg ggacggagcg    180
cgtgcgtctt gtgaccagat acatctataa ccgagaggag tacgcacgct tcgacagcga    240
cgtgggggtg tatcgggcgg tgacgccgct ggggccgcct gccgccgagt actgaaacag    300
ccagaaggaa gtcctggaga ggacccggga ggagttggac acggtgtgca gacacaacta    360
ccagttggag ctccgcacga ccttgcagcg gcgagtggag cccacagtga ccatctcccc    420
atccaggaca gaggccctca accaccacaa cctgctggtc tgctcagtga cagatttcta    480
tccagcccca atcaaagtcc ggtggtttcg gaatgaccag gaggagacaa ctggcgttgt    540
gtccaccccc cttattagga acggtgactg gaccttccag atcctggtga tgctggaaat    600
gactccccag cgtggagacg tctacacctg ccacgtggag cacccccagcc tccagaaccc    660
catcatcgtg gagtggcggg ctcagtctga atctgcccag agcaagatgc tgagtggcat    720
tggaggcttc gtgctggggc tgatcttcct cgggctgggc cttattatcc atcacaggag    780
tcagaaaggg ctcctgcact gactcgagga tc                                  812

SEQ ID NO: 70         moltype = DNA   length = 812
FEATURE               Location/Qualifiers
source                1..812
                      mol_type = other DNA
                      organism = synthetic construct
SEQUENCE: 70
gatcagatct accaccatgt cttggaagaa ggctttgcgg atccccggag accttcgggt    60
agcaactgtc accttgatgc tggcgatgct gagctccgga ctgggctgagg gcagagactc    120
tcccgaggat ttcgtgtacc agtttaaggg catgtgctac ttcaccaacg ggacggagcg    180
cgtaaccagac acatctataa ccgagaggag tacgcgcgct tcgacagcga                240
cgtgggggtg taccggcgg tgacgccgca ggggcggcct gttgccgagt actgaaacag      300
ccagaaggaa gtcctggaga ggacccgggc ggagttggac acggtgtgca gacacaacta    360
cgaggtgggg taccgcggga tcctgcagag gagagtggag cccacagtga ccatctcccc    420
atccaggaca gaggccctca accaccacaa cctgctggtc tgctcggtga cagatttcta    480
tccaggccca atcaaagtcc agtggtttcg gaatgatcag gaggagacag ccggcgttgt    540
gtccaccccc cttattagga atggtgactg gactttccag atcctggtga tgctggaaat    600
gactccccag cgtggagatg tctacacctg ccacgtggag cacccccagcc tccagagccc    660
catcaccgtg gagtggcggg ctcagtctga atctgcccag agcaagatgc tgagtggcgt    720
tggaggcttc gtgctggggc tgatcttcct tgggctgggc cttatcatcc gtcaaaggag    780
tcagaaaggg cttctgcact gactcgagga tc                                  812

SEQ ID NO: 71         moltype = DNA   length = 827
FEATURE               Location/Qualifiers
source                1..827
                      mol_type = other DNA
                      organism = synthetic construct
SEQUENCE: 71
gatcagatct accaccatgg tgtgtctgag gctccctgga ggctcctgca tggcagttct    60
gacactgaca ctgatggtgc tgagctcccc actggctttg gctggggaca ccagaccacg    120
tttcttggag tactctacgt ctgagtgtca tttcttcaat gggacggagc gggtgcggta    180
cctggacaga tacttccata accaggagga gaacgtgcgc ttcgacagcg acgtggggga    240
gttccgggcg gtgacggagc tggggcggcc tgatgccgag tactgaaaca gccagaagga    300
cctcctggag cagaagcggg gccggtggga caactactga agacacaact acgggggttct    360
ggagagcttc acagtgcagc ggcgagtcca tcctaaggtg actgtgtatc cttcaaagac    420
ccagccctg cagcaccata acctcctggt ctgttctgtg agtggtttct atccaggcag    480
cattgaagtc aggtggttcc ggaatggcca ggaagagaag actggggtgg tgtccacagg    540
cctgatccac aatggagact ggaccttcca gaccctggtg atgctggaaa cagttcctcg    600
gagtggagag gtttacacct gccaagtgga gcacccaagc gtgacaagcc ctctcacagt    660
ggaatggaga gcacgtctg aatctgcaca gagcaagatg ctgagtggag tcggggcgtt    720
tgtgctgggc ctgctcttcc ttggggccgg gctgttcatc tacttcagga atcagaaagg    780
acactctgga cttcagccaa gaggattcct gagctgactc gaggatc                  827

SEQ ID NO: 72         moltype = DNA   length = 827
FEATURE               Location/Qualifiers
```

```
source                  1..827
                        mol_type = other DNA
                        organism = synthetic construct
SEQUENCE: 72
gatcagatct accaccatgg tgtgtctgag gctccctgga ggctcctgca tggcagttct   60
gacagtgaca ctgatggtgc tgagctcccc actggctttg gctggggaca ccagaccacg  120
tttcttggag tactctacgt ctgagtgtca tttcttcaat gggacggagc gggtgcggta  180
cctggacaga tacttccata accaggagga gaacgtgcgc ttcgacgcg acgtggggga   240
gttccgggcg gtgacggagc tggggcggcc tgatgccgag tactgaaca gccagaagga   300
cctcctggag cagaagcggg gcccgggtgga caactactgc agacacaact acggggttat  360
ggagagcttc acagtgcagc ggcgagtcca tcctaaggtg actgtgtatc cttcaaagac  420
ccagcccctg cagcaccata acctcctggt ctgttctgtg agtggtttct atccaggcag  480
cattgaagtc aggtggttcc ggaatggcca ggaagagaag actggggtgg tgtccacagg  540
cctgatccac aatggagact ggaccttcca gaccctggtg atgctggaaa cagttcctcg  600
gagtggagag gtttacacct gccaagtgga gcacccaagc gtgacaagcc ctctcacagt  660
ggaatggaga gcacggtctg aatctgcaca gagcaagatg ctgagtggag tcggggcgtt  720
tgtgctgggc ctgctcttcc ttggggccgg gctgttcatc tacttcagga atcagaaagg  780
acactctgga cttcagccaa gaggattcct gagctgactc gaggatc               827

SEQ ID NO: 73           moltype = DNA  length = 827
FEATURE                 Location/Qualifiers
source                  1..827
                        mol_type = other DNA
                        organism = synthetic construct
SEQUENCE: 73
gatcagatct accaccatgg tgtgtctgaa gttccctgga ggctcctgca tggcagctct   60
gacagtgaca ctgatggtgc tgagctcccc actggctttg gctggggaca cccgaccacg  120
tttcttggag caggttaaac atgagtgtca tttcttcaac gggacggagc gggtgcggtt  180
cctggacaga tacttctatc accaagagga gtacgtgcgc ttcgacgcg acgtggggga   240
gtaccgggcg gtgacggagc tggggcggcc tgatgccgag tactgaaca gccagaagga   300
cctcctggag cagaagcggg gccgcggtgga cacctactgc agacacaact acggggtttt  360
tgagagcttc acagtgcagc ggcgagtcta tcctgaggtg actgtgtatc ctgcaaagac  420
ccagcccctg cagcaccaca acctcctggt ctgctctgtg aatggtttct atccaggcag  480
cattgaagtc aggtggttcc ggaacggcca ggaagagaag actggggtgg tgtccacagg  540
cctgatccag aatggagact ggaccttcca gaccctggtg atgctggaaa cagttcctcg  600
gagtggagag gtttacacct gccaagtgga gcacccaagc ctgacgagcc ctctcacagt  660
ggaatggaga gcacggtctg aatctgcaca gagcaagatg ctgagtggag tcggggcgtt  720
cgtgctgggc ctgctcttcc ttggggccgg gctgttcatc tacttcagga atcagaaagg  780
acactctgga cttcagccaa caggattcct gagctgactc gaggatc               827

SEQ ID NO: 74           moltype = DNA  length = 827
FEATURE                 Location/Qualifiers
source                  1..827
                        mol_type = other DNA
                        organism = synthetic construct
SEQUENCE: 74
gatcagatct accaccatgg tgtgtctgaa gttccctgga ggctcctgca tggcagctct   60
gacagtgaca ctgatggtgc tgagctcccc actggctttg gctggggaca cccgaccacg  120
tttcttggag caggttaaac atgagtgtca tttcttcaac gggacggagc gggtgcggtt  180
cctggacaga tacttctatc accaagagga gtacgtgcgc ttcgacgcg acgtggggga   240
gtaccgggcg gtgacggagc tggggcggcc tgatgccgag tactgaaca gccagaagga   300
cctcctggag cagaagcggg gccgcggtgga cacctactgc agacacaact acggggttct  360
tgagagcttc acagtgcagc ggcgagtcta tcctgaggtg actgtgtatc ctgcaaagac  420
ccagcccctg cagcaccaca acctcctggt ctgctctgtg aatggtttct atccaggcag  480
cattgaagtc aggtggttcc ggaacggcca ggaagagaag actggggtgg tgtccacagg  540
cctgatccag aatggagact ggaccttcca gaccctggtg atgctggaaa cagttcctcg  600
gagtggagag gtttacacct gccaagtgga gcacccaagc ctgacgagcc ctctcacagt  660
ggaatggaga gcacggtctg aatctgcaca gagcaagatg ctgagtggag tcggggcgtt  720
cgtgctgggc ctgctcttcc ttggggccgg gctgttcatc tacttcagga atcagaaagg  780
acactctgga cttcagccaa caggattcct gagctgactc gaggatc               827

SEQ ID NO: 75           moltype = DNA  length = 827
FEATURE                 Location/Qualifiers
source                  1..827
                        mol_type = other DNA
                        organism = synthetic construct
SEQUENCE: 75
gatcagatct accaccatgg tgtgtctgaa gttccctgga ggctcctgca tggcagctct   60
gacagtgaca ctgatggtgc tgagctcccc actggctttg gctggggaca cccgaccacg  120
tttcttggag caggttaaac atgagtgtca tttcttcaac gggacggagc gggtgcggtt  180
cctggacaga tacttctatc accaagagga gtacgtgcgc ttcgacgcg acgtggggga   240
gtaccgggcg gtgacggagc tggggcggcc tgatgccgag tactgaaca gccagaagga   300
cctcctggag cagaagcggg gccgcggtgga cacctactgc agacacaact acggggttat  360
ggagagcttc acagtgcagc ggcgagtcta tcctgaggtg actgtgtatc ctgcaaagac  420
ccagcccctg cagcaccaca acctcctggt ctgctctgtg aatggtttct atccaggcag  480
cattgaagtc aggtggttcc ggaacggcca ggaagagaag actggggtgg tgtccacagg  540
cctgatccag aatggagact ggaccttcca gaccctggtg atgctggaaa cagttcctcg  600
gagtggagag gtttacacct gccaagtgga gcacccaagc ctgacgagcc ctctcacagt  660
ggaatggaga gcacggtctg aatctgcaca gagcaagatg ctgagtggag tcggggcgtt  720
```

```
cgtgctgggc ctgctcttcc ttggggccgg gctgttcatc tacttcagga atcagaaagg    780
acactctgga cttcagccaa caggattcct gagctgactc gaggatc                  827

SEQ ID NO: 76           moltype = DNA  length = 827
FEATURE                 Location/Qualifiers
source                  1..827
                        mol_type = other DNA
                        organism = synthetic construct
SEQUENCE: 76
gatcagatct accaccatgg tgtgtctgaa gttccctgga ggctcctgca tggcagctct    60
gacagtgaca ctgatggtgc tgagctcccc actggctttg gctggggaca cccgaccacg    120
tttcttggag caggttaaac atgagtgtca tttcttcaac gggacggagc gggtgcggtt    180
cctggacaga tacttctatc accaagagga gtacgtgcgc ttcgacagcg acgtggggga    240
gtaccgggcg gtgacggagc tggggcggcc tgatgccgag tactgaaaca gccagaagga    300
cctcctggag caggagcggg ccgaggtgga cacctactgc agacacaact acggggttgt    360
ggagagcttc acagtgcagc ggcgagtcta tcctgaggtg actgtgtatc ctgcaaagac    420
ccagcccctg cagcaccaca acctcctggt ctgctctgtg aatggtttct atccaggcag    480
cattgaagtc aggtggttcc ggaacggcca ggaagagaag actggggtgg tgtccacagg    540
cctgatccag aatggagact ggaccttcca gaccctggtg atgctggaaa cagttcctcg    600
gagtggagag gtttacacct gccaagtgga gcacccaagc ctgacgagcc ctctcacagt    660
ggaatggaga gcacggtctg aatctgcaca gagcaagatg ctgagtggag tcgggggctt    720
cgtgctgggc ctgctcttcc ttggggccgg gctgttcatc tacttcagga atcagaaagg    780
acactctgga cttcagccaa caggattcct gagctgactc gaggatc                  827

SEQ ID NO: 77           moltype = DNA  length = 827
FEATURE                 Location/Qualifiers
source                  1..827
                        mol_type = other DNA
                        organism = synthetic construct
SEQUENCE: 77
gatcagatct accaccatgg tgtgtctgaa gttccctgga ggctcctgca tggcagctct    60
gacagtgaca ctgatggtgc tgagctcccc actggctttg gctggggaca cccgaccacg    120
tttcttggag caggttaaac atgagtgtca tttcttcaac gggacggagc gggtgcggtt    180
cctggacaga tacttctatc accaagagga gtacgtgcgc ttcgacagcg acgtggggga    240
gtaccgggcg gtgacggagc tggggcggcc tgatgccgag tactgaaca gccagaagga    300
cctcctggag caggagcggg ccgcggtgga cacctactgc agacacaact acggggttgt    360
ggagagcttc acagtgcagc ggcgagtcta tcctgaggtg actgtgtatc ctgcaaagac    420
ccagcccctg cagcaccaca acctcctggt ctgctctgtg aatggtttct atccaggcag    480
cattgaagtc aggtggttcc ggaacggcca ggaagagaag actggggtgg tgtccacagg    540
cctgatccag aatggagact ggaccttcca gaccctggtg atgctggaaa cagttcctcg    600
gagtggagag gtttacacct gccaagtgga gcacccaagc ctgacgagcc ctctcacagt    660
ggaatggaga gcacggtctg aatctgcaca gagcaagatg ctgagtggag tcgggggctt    720
cgtgctgggc ctgctcttcc ttggggccgg gctgttcatc tacttcagga atcagaaagg    780
acactctgga cttcagccaa caggattcct gagctgactc gaggatc                  827

SEQ ID NO: 78           moltype = DNA  length = 827
FEATURE                 Location/Qualifiers
source                  1..827
                        mol_type = other DNA
                        organism = synthetic construct
SEQUENCE: 78
gatcagatct accaccatgg tgtgtctgaa gttccctgga ggctcctgca tggcagctct    60
gacagtgaca ctgatggtgc tgagctcccc actggctttg gctggggaca cccgaccacg    120
tttcttggag caggttaaac atgagtgtca tttcttcaac gggacggagc gggtgcggtt    180
cctggacaga tacttctatc accaagagga gtacgtgcgc ttcgacagcg acgtggggga    240
gtaccgggcg gtgacggagc tggggcggcc tagcgccgag tactgaaaca gccagaagga    300
cctcctggag caggagcggg ccgcggtgga cacctactgc agacacaact acggggttgg    360
tgagagcttc acagtgcagc ggcgagtcta tcctgaggtg actgtgtatc ctgcaaagac    420
ccagcccctg cagcaccaca acctcctggt ctgctctgtg aatggtttct atccaggcag    480
cattgaagtc aggtggttcc ggaacggcca ggaagagaag actggggtgg tgtccacagg    540
cctgatccag aatggagact ggaccttcca gaccctggtg atgctggaaa cagttcctcg    600
gagtggagag gtttacacct gccaagtgga gcacccaagc ctgacgagcc ctctcacagt    660
ggaatggaga gcacggtctg aatctgcaca gagcaagatg ctgagtggag tcgggggctt    720
cgtgctgggc ctgctcttcc ttggggccgg gctgttcatc tacttcagga atcagaaagg    780
acactctgga cttcagccaa caggattcct gagctgactc gaggatc                  827

SEQ ID NO: 79           moltype = DNA  length = 827
FEATURE                 Location/Qualifiers
source                  1..827
                        mol_type = other DNA
                        organism = synthetic construct
SEQUENCE: 79
gatcagatct accaccatgg tgtgtctgaa gttccctgga ggctcctgca tggcagctct    60
gacagtgaca ctgatggtgc tgagctcccc actggctttg gctggggaca cccgaccacg    120
tttcttggag caggttaaac atgagtgtca tttcttcaac gggacggagc gggtgcggtt    180
cctggacaga tacttctatc accaagagga gtacgtgcgc ttcgacagcg acgtggggga    240
gtaccgggcg gtgacggagc tggggcggcc tgatgccgag tactgaaca gccagaagga    300
cctcctggag caggagcggg ccgcggtgga cacctactgc agacacaact acggggttgg    360
tgagagcttc acagtgcagc ggcgagtcta tcctgaggtg actgtgtatc ctgcaaagac    420
```

```
ccagcccctg cagcaccaca acctcctggt ctgctctgtg aatgttttct atccaggcag    480
cattgaagtc aggtggttcc ggaacggcca ggaagagaag actggggtgg tgtccacagg    540
cctgatccag aatggagact ggaccttcca gaccctggtg atgctggaaa cagttcctcg    600
gagtggagag gtttacacct gccaagtgga gcacccaagc ctgacgagcc ctctcacagt    660
ggaatggaga gcacggtctg aatctgcaca gagcaagatg ctgagtggag tcgggggctt    720
cgtgctgggc ctgctcttcc ttggggccgg gctgttcatc tacttcagga atcagaaagg    780
acactctgga cttcagccaa caggattcct gagctgactc gaggatc                  827

SEQ ID NO: 80           moltype = DNA  length = 827
FEATURE                 Location/Qualifiers
source                  1..827
                        mol_type = other DNA
                        organism = synthetic construct
SEQUENCE: 80
gatcagatct accaccatgg tgtgtctgaa gctccctgga ggctcctgca tggcagctct     60
gacagtgaca ctgatggtgc tgagctcccc actggctttg gctggggaca cccaaccacg    120
tttcctgtgg cagggtaagt ataagtgtca tttcttcaac gggacggagc gggtgcagtt    180
cctggaaaga ctcttctata accaggagga gttcgtgcgc ttcgacagcg acgtggggga    240
gtaccgggcg gtgacggagc tagggcggcc tgtcgccgag tcctggaaca gccagaagga    300
catcctggag gacaggcggg gccaggtgga caccgtgtgc agacacaact acggggttgg    360
tgagagcttc acagtgcagc ggcgagtcca tcctgaggtg actgtgtatc ctgccaagac    420
tcagcccctg cagcaccaca acctcctggt ctgctctgtg agtgtttct atccaggcag     480
cattgaagtc aggtggttcc ggaacggcca ggaagagaag actggggtgg tgtccacagg    540
cctgatccag aatggagact ggaccttcca gaccctggtg atgctggaaa cagttcctcg    600
gagtggagaa gtttacacct gccaagtgga gcacccaagt gtgatgagcc ctctcacagt    660
ggaatggaga gcacggtctg aatctgcaca gagcaagatg ctgagtggag tcgggggctt    720
tgtgctgggc ctgctcttcc ttggggccgg gttgttcatc tacttcagga atcagaaagg    780
acactctgga cttcagccaa caggattcct gagctgactc gaggatc                  827

SEQ ID NO: 81           moltype = DNA  length = 827
FEATURE                 Location/Qualifiers
source                  1..827
                        mol_type = other DNA
                        organism = synthetic construct
SEQUENCE: 81
gatcagatct accaccatgg tgtgtctgaa gctccctgga ggctcctgca tggcagctct     60
gacagtgaca ctgatggtgc tgagctcccc actggctttg gctggggaca cccaaccacg    120
tttcttgaag caggataagt ttgagtgtca tttcttcaac gggacggagc gggtgcggta    180
tctgcacaga ggcatctata accaagagga gaacgtgcgc ttcgacagcg acgtgggggga   240
gtaccgggcg gtgacggagc tggggcggcc tgtcgccgag tcctggaaca gccagaagga    300
cttcctggag cggaggcggg ccgaggtgga caccgtgtgc agacacaact acggggttgg    360
tgagagcttc acagtgcaga ggcgagtcca tcctgaggtg actgtgtatc ctgccaagac    420
tcagcccctg cagcaccaca acctcctggt ctgctctgtg agtggtttct atccaggcag    480
cattgaagtc aggtggttcc ggaacggcca ggaagagaag actggggtgg tgtccacagg    540
cctgatccag aatggagact ggaccttcca gaccctggtg atgctggaaa cagttcctcg    600
gagtggagaa gtttacacct gccaagtgga gcacccaagt gtgatgagcc ctctcacagt    660
ggaatggaga gcacggtctg aatctgcaca gagcaagatg ctgagtggag tcgggggctt    720
tgtgctgggc ctgctcttcc ttggggccgg gctgttcatc tacttcagga atcagaaagg    780
acactctgga cttcagccaa caggattcct gagctgactc gaggatc                  827

SEQ ID NO: 82           moltype = DNA  length = 827
FEATURE                 Location/Qualifiers
source                  1..827
                        mol_type = other DNA
                        organism = synthetic construct
SEQUENCE: 82
gatcagatct accaccatgg tgtgtctgag gctccctgga ggctcctgca tggcagttct     60
gacagtgaca ctgatggtgc tgagctcccc actggctttg gctggggaca ccagaccacg    120
tttcttggag gaggttaagt ttgagtgtca tttcttcaac gggacggagc gggtgcgttt    180
gctggaaaga cgcgtccata accaagagga gtacgcgcgc tacgacagcg acgtggggga    240
gtaccgggcg gtgacggagc tggggcggcc tgatgccgag tactggaaca gccagaagga    300
cctcctggag cggaggcgtg ccgcggtgga cacctactgc agacacaact acggggttgg    360
tgagagcttc acagtgcagc ggcgagttca acctaaggtg actgtgtatc cttcaaagac    420
ccagcccctg cagcaccaca acctcctggt ctgttctgtg aatgttttct atccaggcag    480
cattgaagtc aggtggttcc ggaacggcca ggaagagaag actggggtgg tgtccacggg    540
cctgatccag aatggagact ggaccttcca gaccctggtg atgctggaaa cagttcctca    600
gagtggagag gtttacacct gccaagtgga gcacccaagt gtgatgagcc ctctcacagt    660
ggaatggaga gcacggtctg aatctgcaca gagcaagatc ctgagtggag tcgggggctt    720
tgtgctgggc ctgctcttcc ttggggccgg gctgttcatc tacttcagga atcagaaagg    780
acactctgga cttccgccaa caggattcct gagctgactc gaggatc                  827

SEQ ID NO: 83           moltype = DNA  length = 827
FEATURE                 Location/Qualifiers
source                  1..827
                        mol_type = other DNA
                        organism = synthetic construct
SEQUENCE: 83
gatcagatct accaccatgg tgtgtctgag gctccctgga ggctcctgca tggcagttct     60
gacagtgaca ctgatggtgc tgagctcccc actggctttg gctggggaca ccagaccacg    120
```

```
tttcttggag tactctacgt ctgagtgtca tttcttcaat gggacggagc gggtgcggtt   180
cctggacaga tacttctata accaagagga gtacgtgcgc ttcgacacgc acgtggggga   240
gttccgggcg gtgacggagc tggggcggcc tgatgaggag tactgaaaca gccagaagga   300
cttcctggaa gacaggcggg ccgcggtgga cacctactgc agacacaact acggggttgg   360
tgagagcttc acagtgcagc ggcgagtcca tcctaaggtg actgtgtatc cttcaaagac   420
ccagcccctg cagcaccaca acctcctggt ctgttctgtg agtggtttct atccaggcag   480
cattgaagtc aggtggttcc ggaatggcca ggaagagaag actggggtgg tgtccacagg   540
cctgatccac aatggagact ggaccttcca gaccctggtg atgctggaaa cagttcctcg   600
gagtggagag gtttacacct gccaagtgga gcacccaagc gtgacaagcc ctctcacagt   660
ggaatggaga gcacggtctg aatctgcaca gagcaagatg ctgagtggag tcgggggctt   720
tgtgctgggc ctgctcttcc ttggggccgg gctgttcatc tacttcagga atcagaaagg   780
acactctgga cttcagccaa gaggattcct gagctgactc gaggatc                827

SEQ ID NO: 84         moltype = DNA length = 827
FEATURE               Location/Qualifiers
source                1..827
                      mol_type = other DNA
                      organism = synthetic construct
SEQUENCE: 84
gatcagatct accaccatgg tgtgtctgag gctcccctgga ggctcctgca tggcagttct    60
gacagtgaca ctgatggtgc tgagctcccc actggctttg gctggggaca ccagaccacg   120
tttcttggag tactctacgt ctgagtgtca tttcttcaat gggacggagc gggtgcggtt   180
cctggacaga tacttctata accaagagga gtacgtgcgc ttcgacacgc acgtggggga   240
gttccgggcg gtgacggagc tggggcggcc tgatgaggag tactgaaaca gccagaagga   300
catcctggaa gacgagcggg ccgcggtgga cacctactgc agacacaact acggggttgt   360
ggagagcttc acagtgcagc ggcgagtcca tcctaaggtg actgtgtatc cttcaaagac   420
ccagcccctg cagcaccaca acctcctggt ctgttctgtg agtggtttct atccaggcag   480
cattgaagtc aggtggttcc ggaatggcca ggaagagaag actggggtgg tgtccacagg   540
cctgatccac aatggagact ggaccttcca gaccctggtg atgctggaaa cagttcctcg   600
gagtggagag gtttacacct gccaagtgga gcacccaagc gtgacaagcc ctctcacagt   660
ggaatggaga gcacggtctg aatctgcaca gagcaagatg ctgagtggag tcgggggctt   720
tgtgctgggc ctgctcttcc ttggggccgg gctgttcatc tacttcagga atcagaaagg   780
acactctgga cttcagccaa gaggattcct gagctgactc gaggatc                827

SEQ ID NO: 85         moltype = DNA length = 827
FEATURE               Location/Qualifiers
source                1..827
                      mol_type = other DNA
                      organism = synthetic construct
SEQUENCE: 85
gatcagatct accaccatgg tgtgtctgag gctcccctgga ggctcctgca tggcagttct    60
gacagtgaca ctgatggtgc tgagctcccc actggctttg gctggggaca ccagaccacg   120
tttcttggag tactctacgt ctgagtgtca tttcttcaat gggacggagc gggtgcggtt   180
cctggacaga tacttctata accaagagga gtacgtgcgc ttcgacacgc acgtggggga   240
gttccgggcg gtgacggagc tggggcggcc tgatgaggag tactgaaaca gccagaagga   300
cttcctggaa gacgagcggg ccgcggtgga cacctactgc agacacaact acggggttgt   360
ggagagcttc acagtgcagc ggcgagtcca tcctaaggtg actgtgtatc cttcaaagac   420
ccagcccctg cagcaccaca acctcctggt ctgttctgtg agtggtttct atccaggcag   480
cattgaagtc aggtggttcc ggaatggcca ggaagagaag actggggtgg tgtccacagg   540
cctgatccac aatggagact ggaccttcca gaccctggtg atgctggaaa cagttcctcg   600
gagtggagag gtttacacct gccaagtgga gcacccaagc gtgacaagcc ctctcacagt   660
ggaatggaga gcacggtctg aatctgcaca gagcaagatg ctgagtggag tcgggggctt   720
tgtgctgggc ctgctcttcc ttggggccgg gctgttcatc tacttcagga atcagaaagg   780
acactctgga cttcagccaa gaggattcct gagctgactc gaggatc                827

SEQ ID NO: 86         moltype = DNA length = 827
FEATURE               Location/Qualifiers
source                1..827
                      mol_type = other DNA
                      organism = synthetic construct
SEQUENCE: 86
gatcagatct accaccatgg tgtgtctgag gctcccctgga ggctcctgca tggcagttct    60
gacagtgaca ctgatggtgc tgagctcccc actggctttg gctggggaca ccagaccacg   120
tttcttggag tactctacgg tgtagtgtta tttcttcaat gggacggagc gggtgcggtt   180
actggagaga cacttccata accaggagga gctcctgcgc ttcgacacgc acgtggggga   240
gttccgggcg gtgacggagc tggggcggcc tgtcgccgag tcctgaaaca gccagaagga   300
catcctggaa gacaggcgcg ccgcggtgga cacctattgc agacacaact acgggcgtgt   360
ggagagcttc acagtgcagc ggcgagtcca tcctaaggtg actgtgtatc cttcaaagac   420
ccagcccctg cagcaccaca acctcctggt ctgttctgtg agtggtttct atccaggcag   480
cattgaagtc aggtggttcc ggaatggcca ggaagagaag actggggtgg tgtccacggg   540
cctgatccac aatggagact ggaccttcca gaccctggtg atgctggaaa cagttcctcg   600
gagtggagag gtttacacct gccaagtgga gcacccaagc gtgacaagcc ctctcacagt   660
ggaatggaga gcacggtctg aatctgcaca gagcaagatg ctgagtggag tcgggggctt   720
tgtgctgggc ctgctcttcc ttggggccgg gctgttcatc tacttcagga atcagaaagg   780
acactctgga cttcagccaa gaggattcct gagctgactc gaggatc                827

SEQ ID NO: 87         moltype = DNA length = 827
FEATURE               Location/Qualifiers
source                1..827
```

```
                mol_type = other DNA
                organism = synthetic construct
SEQUENCE: 87
gatcagatct accaccatgg tgtgtctgaa gctccctgga ggctcctgca tgacagcgct    60
gacagtgaca ctgatggtgc tgagctcccc actggctttg tctggggaca cccgaccacg   120
tttcctgtgg cagcctaaga gggagtgtca tttcttcaat gggacggagc gggtgcggtt   180
cctggacaga tacttctata accaggagga gtccgtgcgc ttcgacagcg acgtgggga    240
gttccgggcg gtgacggagc tggggcggcc tgacgctgag tactgaaaca gccagaagga   300
catcctggag cagaggcggg ccgcggtgga cacctactgc agacacaact acggggttgt   360
ggagagcttc acagtgcagc ggcgagtcca acctaaggtg actgtatatc cttcaaagac   420
ccagcccctg cagcaccaca acctcctggt ctgctctgtg agtggtttct atccaggcag   480
cattgaagtc aggtggttcc tgaacggcca ggaagagaag gctgggatgg tgtccacagg   540
cctgatccag aatggagact ggaccttcca gaccctggtg atgctggaaa cagttcctcg   600
aagtggagag gtttacacct gccaagtgga gcacccaagc gtgacaagcc ctctcacagt   660
ggaatggaga gcacggtctg aatctgcaca gagcaagatg ctgagtggag tcgggggctt   720
tgtgctgggc ctgctcttcc ttggggccgg gctgttcatc tacttcagga atcagaaagg   780
acactctgga cttcagccaa caggattcct gagctgactc gaggatc                 827

SEQ ID NO: 88           moltype = DNA   length = 827
FEATURE                 Location/Qualifiers
source                  1..827
                mol_type = other DNA
                organism = synthetic construct
SEQUENCE: 88
gatcagatct accaccatgg tgtgtctgaa gctccctgga ggctcctgca tgacagcgct    60
gacagtgaca ctgatggtgc tgagctcccc actggctttg tctggggaca cccgaccacg   120
tttcctgtgg cagcctaaga gggagtgtca tttcttcaat gggacggagc gggtgcggtt   180
cctggacaga tacttctata accaggagga gtccgtgcgc ttcgacagcg acgtgggga    240
gtaccgggcg gtgacggagc tggggcggcc tgacgctgag tactgaaaca gccagaagga   300
catcctggag caggcgcggg ccgcggtgga cacctactgc agacacaact acggggttgt   360
ggagagcttc acagtgcagc ggcgagtcca acctaaggtg actgtatatc cttcaaagac   420
ccagcccctg cagcaccaca acctcctggt ctgctctgtg agtggtttct atccaggcag   480
cattgaagtc aggtggttcc tgaacggcca ggaagagaag gctgggatgg tgtccacagg   540
cctgatccag aatggagact ggaccttcca gaccctggtg atgctggaaa cagttcctcg   600
aagtggagag gtttacacct gccaagtgga gcacccaagc gtgacaagcc ctctcacagt   660
ggaatggaga gcacggtctg aatctgcaca gagcaagatg ctgagtggag tcgggggctt   720
tgtgctgggc ctgctcttcc ttggggccgg gctgttcatc tacttcagga atcagaaagg   780
acactctgga cttcagccaa caggattcct gagctgactc gaggatc                 827

SEQ ID NO: 89           moltype = DNA   length = 827
FEATURE                 Location/Qualifiers
source                  1..827
                mol_type = other DNA
                organism = synthetic construct
SEQUENCE: 89
gatcagatct accaccatgg tgtgtctgaa gctccctgga ggctcctgca tgacagcgct    60
gacagtgaca ctgatggtgc tgagctcccc actggctttg tctggggaca cccgaccacg   120
tttcctgtgg cagcctaaga gggagtgtca tttcttcaat gggacggagc gggtgcggtt   180
cctggacaga tacttctata accaggagga gtccgtgcgc ttcgacagcg acgtgggga    240
gttccgggcg gtgacggagc tggggcggcc tgacgctgag tactgaaaca gccagaagga   300
catcctggag cagaggcggg ccgcggtgga cacctactgc agacacaact acggggttgt   360
ggagagcttc acagtgcagc ggcgagtcca acctaaggtg actgtatatc cttcaaagac   420
ccagcccctg cagcaccaca acctcctggt ctgctctgtg agtggtttct atccaggcag   480
cattgaagtc aggtggttcc tgaacggcca ggaagagaag gctgggatgg tgtccacagg   540
cctgatccag aatggagact ggaccttcca gaccctggtg atgctggaaa cagttcctcg   600
aagtggagag gtttacacct gccaagtgga gcacccaagc gtgacaagcc ctctcacagt   660
ggaatggaga gcacggtctg aatctgcaca gagcaagatg ctgagtggag tcgggggctt   720
tgtgctgggc ctgctcttcc ttggggccgg gctgttcatc tacttcagga atcagaaagg   780
acactctgga cttcagccaa caggattcct gagctgactc gaggatc                 827

SEQ ID NO: 90           moltype = DNA   length = 827
FEATURE                 Location/Qualifiers
source                  1..827
                mol_type = other DNA
                organism = synthetic construct
SEQUENCE: 90
gatcagatct accaccatgg tgtgtctgaa gctccctgga ggctcctgca tgacagcgct    60
gacagtgaca ctgatggtgc tgagctcccc actggctttg tctggggaca cccgaccacg   120
tttcctgtgg cagcctaaga gggagtgtca tttcttcaat gggacggagc gggtgcggtt   180
cctggacaga tacttctata accaggagga gtccgtgcgc ttcgacagcg acgtgggga    240
gttccgggcg gtgacggagc tggggcggcc tgacgctgag tactgaaaca gccagaagga   300
catcctggag cagaggcggg ccgcggtgga cacctactgc agacacaact acggggttat   360
ggagagcttc acagtgcagc ggcgagtcca acctaaggtg actgtatatc cttcaaagac   420
ccagcccctg cagcaccaca acctcctggt ctgctctgtg agtggtttct atccaggcag   480
cattgaagtc aggtggttcc tgaacggcca ggaagagaag gctgggatgg tgtccacagg   540
cctgatccag aatggagact ggaccttcca gaccctggtg atgctggaaa cagttcctcg   600
aagtggagag gtttacacct gccaagtgga gcacccaagc gtgacaagcc ctctcacagt   660
ggaatggaga gcacggtctg aatctgcaca gagcaagatg ctgagtggag tcgggggctt   720
tgtgctgggc ctgctcttcc ttggggccgg gctgttcatc tacttcagga atcagaaagg   780
```

```
acactctgga cttcagccaa caggattcct gagctgactc gaggatc              827

SEQ ID NO: 91           moltype = DNA  length = 827
FEATURE                 Location/Qualifiers
source                  1..827
                        mol_type = other DNA
                        organism = synthetic construct
SEQUENCE: 91
gatcagatct accaccatgg tgtgtctgaa gctccctgga ggctcctgca tgacagcgct    60
gacagtgaca ctgatggtgc tgagctcccc actggctttg tctggggaca cccgaccacg   120
tttcctgtgg cagcctaaga gggagtgtca tttcttcaat gggacggagc gggtgcggtt   180
cctggacaga tacttctata accaggagga gtccgtgcgc ttcgacagcg acgtggggga   240
gttccgggcg gtgacggagc tggggcggcc tgacgctgag tactgaaaca gccagaagga   300
catcctggag cagaggcggg ccgcggtgga cacctactgc agacacaact acggggttgg   360
tgagagcttc acagtgcagc ggcgagtcca acctaaggtg actgtatatc cttcaaagac   420
ccagcccctg cagcaccaca acctcctggt ctgctctgtg agtggttct atccaggcag    480
cattgaagtc aggtggttcc tgaacggcca ggaagagaag gctgggatgg tgtccacagg   540
cctgatccag aatggagact ggaccttcca gaccctggtg atgctggaaa cagttcctcg   600
aagtggagag gtttacacct gccaagtgga gcacccaagc gtgacaagcc ctctcacagt   660
ggaatggaga gcacggtctg aatctgcaca gagcaagatg ctgagtggag tcggggcttc   720
tgtgctgggc ctgctcttcc ttggggccgg gctgttcatc tacttcagga atcagaaagg   780
acactctgga cttcagccaa caggattcct gagctgactc gaggatc              827

SEQ ID NO: 92           moltype = DNA  length = 827
FEATURE                 Location/Qualifiers
source                  1..827
                        mol_type = other DNA
                        organism = synthetic construct
SEQUENCE: 92
gatcagatct accaccatgg tgtgtctgaa gctccctgga ggctcctgca tgacagcgct    60
gacagtgaca ctgatggtgc tgagctcccc actggctttg tctggggaca cccgaccacg   120
tttcctgtgg cagcctaaga gggagtgtca tttcttcaat gggacggagc gggtgcggtt   180
cctggacaga tacttctata accaggagga gtccgtgcgc ttcgacagcg acgtggggga   240
gttccgggcg gtgacggagc tggggcggcc tgacgctgag tactgaaaca gccagaagga   300
catcctggag cagaggcggg ccgcggtgga cacctactgc agacacaact acggggttgg   360
tgagagcttc acagtgcagc ggcgagtcca acctaaggtg actgtatatc cttcaaagac   420
ccagcccctg cagcaccaca acctcctggt ctgctctgtg agtggttct atccaggcag    480
cattgaagtc aggtggttcc tgaacggcca ggaagagaag gctgggatgg tgtccacagg   540
cctgatccag aatggagact ggaccttcca gaccctggtg atgctggaaa cagttcctcg   600
aagtggagag gtttacacct gccaagtgga gcacccaagc gtgacaagcc ctctcacagt   660
ggaatggaga gcacggtctg aatctgcaca gagcaagatg ctgagtggag tcggggcttc   720
tgtgctgggc ctgctcttcc ttggggccgg gctgttcatc tacttcagga atcagaaagg   780
acactctgga cttcagccaa caggattcct gagctgactc gaggatc              827

SEQ ID NO: 93           moltype = DNA  length = 827
FEATURE                 Location/Qualifiers
source                  1..827
                        mol_type = other DNA
                        organism = synthetic construct
SEQUENCE: 93
gatcagatct accaccatgg tgtgtctgaa gctccctgga ggctccagct tggcagcgtt    60
gacagtgaca ctgatggtgc tgagctcccg actggctttc gctggggaca cccgaccacg   120
tttcttggag ctgcgtaagt ctgagtgtca tttcttcaat gggacggagc gggtgcggta   180
cctggacaga tacttccata accaggagga gttcctgcgc ttcgacagcg acgtggggga   240
gtaccggggcg gtgacggagc tggggcggcc tgtcgccgag tcctggaaca gccagaagga   300
cctcctggag cagaagcggg ccgggtgga caattactgc agacacaact acggggttgg   360
tgagagcttc acagtgcagc ggcgagtcca tcctcaggtg actgtatatc ctgcaaagac   420
ccagcccctg cagcaccaca acctcctggt ctgctctgtg agtggttct atccaggcag    480
cattgaagtc aggtggttcc ggaacggcca ggaagagaag gctggggtgg tgtccacggg   540
cctgatccag aatggagact ggaccttcca gaccctggtg atgctagaaa cagttcctcg   600
gagtggagag gtttacactt gccaagtgga gcacccaagc gtaacgagcg ctctcacagt   660
ggaatggaga gcacggtctg aatctgcaca gagcaagatg ctgagtggag tcggggcttc   720
tgtgctgggc ctgctcttcc ttggggccgg gctgttcatc tacttcagga atcagaaagg   780
acactctgga cttcagccaa caggattcct gagctgactc gaggatc              827

SEQ ID NO: 94           moltype = DNA  length = 1115
FEATURE                 Location/Qualifiers
source                  1..1115
                        mol_type = other DNA
                        organism = synthetic construct
SEQUENCE: 94
gatcctcgag accaccatgc gggtcacggc gccccgaacc ctcctcctgc tgctctgggg    60
ggcagtggcc ctgaccgaga cctgggctgg ctcccactcc atgaggtatt ccacacctc   120
cgtgtcccgg cccggccgcg gggagcccgc tttcatcacc gtgggctacg tggacgacac   180
gctgttcgtg aggttcgaca gcgacgccgc gagtccgaga gaggagccgc gggcgccgtg   240
gatagagcag gaggggccgg agcattggga ccgggagaca cagatctgca aggccaaggc   300
acagactgac cgagaggacc tgcggaccct gctccgctac tacaaccaga gcgaggccgg   360
gtctcacacc ctccagaata tgtatggctg cgacgtgggg ccggacggc gctcctccg    420
cgggtaccac caggacgcct acgacggcaa ggattacatc gccctgaacg aggacctgag   480
```

```
ctcctggacc gccgcggaca cggcggctca gatcacccag cgcaagtggg aggcggcccg   540
tgtggcggag cagctgagag cctacctgga gggcgagtgc gtggagtggc tccgcagata   600
cctggagaac gggaaggaga cgctgcagcg cgcggacccc ccaaagacac acgtgaccca   660
ccaccccatc tctgaccatg aggccaccct gaggtgctgg gccctgggct tctaccctgc   720
ggagatcaca ctgacctggc agcgggatgg cgaggaccag ctgagcttgt                 780
ggagaccaga ccagcaggag atagaacctt ccagaagtgg gcagctgtgg tggtgccttc   840
tggagaagag cagagataca catgccatgt acagcatgag gggctgccga agcccctcac   900
cctgagatgg gagccgtctt cccagtccac cgtcccatc gtgggcattg ttgctggcct   960
ggctgtccta gcagttgtgg tcatcggagc tgtggtcgct gctgtgatgt gtaggaggaa  1020
gagctcaggt ggaaaaggag ggagctactc tcaggctgcg tgcagcgaca gtgcccaggg  1080
ctctgatgtg tctctcacag cttgagaatt cgatc                              1115
```

SEQ ID NO: 95    moltype = DNA length = 1115
FEATURE       Location/Qualifiers
source        1..1115
           mol_type = other DNA
           organism = synthetic construct
SEQUENCE: 95

```
gatcctcgag accaccatgc gggtcacggc gccccgaacc ctcctcctgc tgctctgggg   60
ggcagtggcc ctgaccgaga cctgggctgg ctcccactcc atgaggtatt tccacacctc  120
cgtgtcccgg cccggccgcg gggagccccg ctttatcacc gtgggctacg tggacgacac  180
gctgttcgtg aggttcgaca gcgacgccgc gagtccgaga gaggagccgc gggcgccgtg  240
gatagagcag gaggggccgg agtattggga ccgggagaca cagatctgca aggccaaggc  300
acagactgac cgagaggacc tgcggaccct gctccgctac tacaaccaga gcgaggccgg  360
gtctcacacc ctccagaata tgtatggctg cgacgtgggg ccggacgggc gcctcctccg  420
cgggtaccac caggacgcct acgacggcaa ggattacatc gccctgaacg aggacctgag  480
ctcctggacc gccgcggaca cggcggctca gatcacccag cgcaagtggg aggcggcccg  540
tgtggcggag cagctgagag cctacctgga gggcgagtgc gtggagtggc tccgcagata  600
cctggagaac gggaaggaga cgctgcagcg cgcggacccc ccaaagacac acgtgaccca  660
ccaccccatc tctgaccatg aggccaccct gaggtgctgg gccctgggct tctaccctgc  720
ggagatcaca ctgacctggc agcgggatgg cgaggaccaa actcaggaca ctgagcttgt  780
ggagaccaga ccagcaggag atagaacctt ccagaagtgg gcagctgtgg tggtgccttc  840
tggagaagag cagagataca catgccatgt acagcatgag gggctgccga agcccctcac  900
cctgagatgg gagccgtctt cccagtccac cgtcccatc gtgggcattg ttgctggcct  960
ggctgtccta gcagttgtgg tcatcggagc tgtggtcgct gctgtgatgt gtaggaggaa 1020
gagctcaggt ggaaaaggag ggagctactc tcaggctgcg tgcagcgaca gtgcccaggg 1080
ctctgatgtg tctctcacag cttgagaatt cgatc                             1115
```

SEQ ID NO: 96    moltype = DNA length = 1115
FEATURE       Location/Qualifiers
source        1..1115
           mol_type = other DNA
           organism = synthetic construct
SEQUENCE: 96

```
gatcctcgag accaccatgc gggtcacggc gccccgaacc ctcctcctgc tgctctgggg   60
ggcagtggcc ctgaccgaga cctgggctgg ctcccactcc atgaggtatt tccacacctc  120
cgtgtcccgg cccggccgcg gggagccccg ctttatcacc gtgggctacg tggacgacac  180
gctgttcgtg aggttcgaca gcgacgccgc gagtccgaga gaggagccgc gggcgccgtg  240
gatagagcag gaggggccgg agtattggga ccgggagaca cagatctgca aggccaaggc  300
acagactgac cgagaggacc tgcggaccct gctccgctac tacaaccaga gcgaggccgg  360
gtctcacacc ctccagaata tgtatggctg cgacgtgggg ccggacgggc gcctcctccg  420
cgggtaccac caggacgcct acgacggcaa ggattacatc gccctgaacg aggacctgag  480
ctcctggacc gccgcggaca cggcggctca gatcacccag cgcaagtggg aggcggcccg  540
tgtggcggag cagctgagag cctacctgga gggcgagtgc gtggagtggc tccgcagata  600
cctggagaac gggaaggaga cgctgcagcg cgcggacccc ccaaagacac acgtgaccca  660
ccaccccatc tctgaccatg aggccaccct gaggtgctgg gccctgggct tctaccctgc  720
ggagatcaca ctgacctggc agcgggatgg cgaggaccaa actcaggaca ctgagcttgt  780
ggagaccaga ccagcaggag atagaacctt ccagaagtgg gcagctgtgg tggtgccttc  840
tggagaagag cagagataca catgccatgt acagcatgag gggctgccga agcccctcac  900
cctgagatgg gagccgtctt cccagtccac cgtcccatc gtgggcattg ttgctggcct  960
ggctgtccta gcagttgtgg tcatcggagc tgtggtcgct gctgtgatgt gtaggaggaa 1020
gagctcaggt ggaaaaggag ggagctactc tcaggctgcg tgcagcgaca gtgcccaggg 1080
ctctgatgtg tctctcacag cttgagaatt cgatc                             1115
```

SEQ ID NO: 97    moltype = AA length = 15
FEATURE       Location/Qualifiers
source        1..15
           mol_type = protein
           organism = synthetic construct
SEQUENCE: 97
GQVELGGWSK MDQLA                15

SEQ ID NO: 98    moltype = AA length = 15
FEATURE       Location/Qualifiers
source        1..15
           mol_type = protein
           organism = synthetic construct
SEQUENCE: 98
GQVELGGGNA VEVLK                15

```
SEQ ID NO: 99              moltype = AA   length = 15
FEATURE                    Location/Qualifiers
source                     1..15
                           mol_type = protein
                           organism = synthetic construct
SEQUENCE: 99
GQVELGGGSS PETLI                                                       15

SEQ ID NO: 100             moltype = AA   length = 14
FEATURE                    Location/Qualifiers
source                     1..14
                           mol_type = protein
                           organism = synthetic construct
SEQUENCE: 100
SLQPLALEAE DLQV                                                        14

SEQ ID NO: 101             moltype = AA   length = 17
FEATURE                    Location/Qualifiers
source                     1..17
                           mol_type = protein
                           organism = synthetic construct
SEQUENCE: 101
AMMIARFKMF PEVKEKG                                                     17

SEQ ID NO: 102             moltype = AA   length = 14
FEATURE                    Location/Qualifiers
source                     1..14
                           mol_type = protein
                           organism = synthetic construct
SEQUENCE: 102
HLVEELYLVA GEEG                                                        14

SEQ ID NO: 103             moltype = AA   length = 13
FEATURE                    Location/Qualifiers
source                     1..13
                           mol_type = protein
                           organism = synthetic construct
SEQUENCE: 103
PKYVKQNTLK LAT                                                         13

SEQ ID NO: 104             moltype = AA   length = 15
FEATURE                    Location/Qualifiers
source                     1..15
                           mol_type = protein
                           organism = synthetic construct
SEQUENCE: 104
SHLVEALYLV CGERG                                                       15

SEQ ID NO: 105             moltype = AA   length = 15
FEATURE                    Location/Qualifiers
source                     1..15
                           mol_type = protein
                           organism = synthetic construct
SEQUENCE: 105
RSQVETDDLI LKPGV                                                       15

SEQ ID NO: 106             moltype = AA   length = 15
FEATURE                    Location/Qualifiers
source                     1..15
                           mol_type = protein
                           organism = synthetic construct
SEQUENCE: 106
SQVETDDLIL KPGVV                                                       15

SEQ ID NO: 107             moltype = AA   length = 15
FEATURE                    Location/Qualifiers
source                     1..15
                           mol_type = protein
                           organism = synthetic construct
SEQUENCE: 107
PGIAGFKGEQ GPKGE                                                       15

SEQ ID NO: 108             moltype = AA   length = 15
FEATURE                    Location/Qualifiers
source                     1..15
                           mol_type = protein
                           organism = synthetic construct
SEQUENCE: 108
```

```
IFDSRGNPTV EVDLF                                                    15

SEQ ID NO: 109          moltype = AA  length = 14
FEATURE                 Location/Qualifiers
source                  1..14
                        mol_type = protein
                        organism = synthetic construct
PEPTIDE                 4
                        note = X =
  which indicates a deiminated arginine
                           residue
SEQUENCE: 109
IFDXGNPTVE VDLF                                                     14

SEQ ID NO: 110          moltype = AA  length = 13
FEATURE                 Location/Qualifiers
source                  1..13
                        mol_type = protein
                        organism = synthetic construct
SEQUENCE: 110
SAVRLRSSVP GVR                                                      13

SEQ ID NO: 111          moltype = AA  length = 13
FEATURE                 Location/Qualifiers
source                  1..13
                        mol_type = protein
                        organism = synthetic construct
PEPTIDE                 6
                        note = X =
  which indicates a deiminated arginine
                           residue
SEQUENCE: 111
SAVRLXSSVP GVR                                                      13

SEQ ID NO: 112          moltype = AA  length = 13
FEATURE                 Location/Qualifiers
source                  1..13
                        mol_type = protein
                        organism = synthetic construct
SEQUENCE: 112
QDFTNRINKL KNS                                                      13

SEQ ID NO: 113          moltype = AA  length = 13
FEATURE                 Location/Qualifiers
source                  1..13
                        mol_type = protein
                        organism = synthetic construct
PEPTIDE                 6
                        note = X =
  which indicates a deiminated arginine
                           residue
SEQUENCE: 113
QDFTNXINKL KNS                                                      13

SEQ ID NO: 114          moltype = AA  length = 15
FEATURE                 Location/Qualifiers
source                  1..15
                        mol_type = protein
                        organism = synthetic construct
SEQUENCE: 114
ATEGRVRVNS AYQDK                                                    15

SEQ ID NO: 115          moltype = AA  length = 15
FEATURE                 Location/Qualifiers
source                  1..15
                        mol_type = protein
                        organism = synthetic construct
PEPTIDE                 5
                        note = X =
  which indicates a deiminated arginine
                           residue
SEQUENCE: 115
ATEGXVRVNS AYQDK                                                    15

SEQ ID NO: 116          moltype = AA  length = 15
FEATURE                 Location/Qualifiers
source                  1..15
                        mol_type = protein
                        organism = synthetic construct
SEQUENCE: 116
```

```
ATIKAEFVRA ETPYM                                                           15

SEQ ID NO: 117         moltype = AA  length = 15
FEATURE                Location/Qualifiers
source                 1..15
                       mol_type = protein
                       organism = synthetic construct
PEPTIDE                9
                       note = X =
 which indicates a deiminated arginine
                       residue
SEQUENCE: 117
ATIKAEFVXA ETPYM                                                           15

SEQ ID NO: 118         moltype = AA  length = 12
FEATURE                Location/Qualifiers
source                 1..12
                       mol_type = protein
                       organism = synthetic construct
SEQUENCE: 118
AVRLQGSVAG VR                                                              12

SEQ ID NO: 119         moltype = AA  length = 15
FEATURE                Location/Qualifiers
source                 1..15
                       mol_type = protein
                       organism = synthetic construct
SEQUENCE: 119
PYHFKYHEKH FANAI                                                           15

SEQ ID NO: 120         moltype = AA  length = 15
FEATURE                Location/Qualifiers
source                 1..15
                       mol_type = protein
                       organism = synthetic construct
SEQUENCE: 120
PVSKMRMATP LLMQA                                                           15

SEQ ID NO: 121         moltype = AA  length = 11
FEATURE                Location/Qualifiers
source                 1..11
                       mol_type = protein
                       organism = synthetic construct
SEQUENCE: 121
FFRDHSYQEE A                                                               11

SEQ ID NO: 122         moltype = AA  length = 10
FEATURE                Location/Qualifiers
source                 1..10
                       mol_type = protein
                       organism = synthetic construct
SEQUENCE: 122
LVRYWISAFP                                                                 10

SEQ ID NO: 123         moltype = AA  length = 19
FEATURE                Location/Qualifiers
source                 1..19
                       mol_type = protein
                       organism = synthetic construct
SEQUENCE: 123
ENPVVHFFKN IVTPRTPPP                                                       19

SEQ ID NO: 124         moltype = AA  length = 25
FEATURE                Location/Qualifiers
source                 1..25
                       mol_type = protein
                       organism = synthetic construct
SEQUENCE: 124
AQGTLSKIFK LGGRDSRSGS PMARR                                                25
```

POCKET ENGINEERING OF HLA ALLELES FOR TREATING AUTOIMMUNITY

CROSS-REFERENCE TO RELATED APPLICATIONS

This application is a continuation of U.S. application Ser. No. 17/741,438 entitled "HLA Engineering Methods and Compositions for Treatment of Autoimmunity," filed on 10 May 2022, which claims benefit of and priority pursuant to 35 U.S.C. § 119(e) of U.S. provisional patent application No. 63/186,770 entitled "HLA Engineering Methods, Compounds, and Compositions for Treatment of Autoimmunity," filed on 10 May 2021, which are hereby incorporated by reference in their entireties. This application is related to PCT applications PCT/US2022/028643 entitled "Methods of HLA Engineering and Treatments for Autoimmunity," PCT/US2022/028644 entitled "Engineered HLA Alleles for Treating Autoimmunity", and PCT/US2022/028645 entitled "Pocket Engineering of HLA Alleles for Treating Autoimmunity."

FIELD

The disclosed compositions, methods, and systems are directed to treatment and prevention of autoimmune conditions.

SEQUENCE LISTING

The instant application contains a Sequence Listing which has been submitted electronically in XML format and is hereby incorporated by reference in its entirety. Said XML copy, created on Jul. 18, 2022, is named P292109US07.xml and is 155 kilobytes in size. The Sequence Listing does not extend beyond the scope of the specification, and does not contain new matter.

BACKGROUND

Autoimmunity refers to pathologic conditions in which the body's immune system mistakenly identifies healthy tissues and cells as foreign and attacks them. Any disease that results from this mistaken immune response is termed an autoimmune disease, disorder or condition. While some autoimmune diseases such as rheumatoid arthritis (RA), Type 1 diabetes (T1D), and multiple sclerosis (MS) are more prevalent than others, collectively they pose a serious public health challenge impacting millions of people across the world. Commonly, patients with an autoimmune disease suffer from various symptoms that, without limitation, can range from mild including fatigue, fever, muscle aches, joint pain and swelling, skin problems, abdominal pain, and digestion problems, to more severe, which can include decreased mobility, loss of vision, and organ failure.

Autoimmune disease can have various molecular, cellular, and physiological bases. Generally, autoimmunity is the result of a dysregulated immune system, which may stem from genetic or environmental factors, resulting in a subject's immune system turning on itself. Ideally, under normal circumstances, a healthy immune system recognizes and fights off foreign bodies (e.g., microbes, viruses, proteins, and nucleic acids). However, to do this effectively, it must be trained to avoid attacking the subject's own tissues, cells, proteins, and nucleic acids.

Human leukocyte antigen (HLA) refers to a group of related genes coding for proteins involved in immune function. HLA Class I and II proteins are cell-surface proteins with peptide clefts for presenting peptides to T-cell receptors. The HLA complex of genes reside on the Short Arm of human Chromosome 6. Reference to alleles of the HLA proteins has a well-known nomenclature. For example, DRB1*01:01:01:01, as is well known to the skilled HLA researcher, refers to an allele of the DRB1 gene of the HLA complex, the first two values after the HLA gene designation and separated by the '*' (in this example the '01:01') refers to the allele group or level, and variations at the protein sequence level—for example, DRB1*01:01 and DRB1*01:02 differ by two amino acids in the peptide binding region. The 3rd field (here, the third '01') indicates a difference in the genetic sequence that, due to degeneracy of the genetic code, does not change the amino acids and are therefore immunologically identical—i.e., DRB1*01:02:01 is immunologically identical to DRB1*01:02:02. The last field (i.e., the final '01') indicates differences in the genetic sequence that occur outside of the coding region of the protein (introns, promoters, etc.)—thus, DRB1*01:01:01:01 and a hypothetical DRB1*01:01:01:02 would be identical at the immunological and genetic levels, within the coding sequence, but have different non-coding sequences. This type of change typically may affect expression levels. Thus, by convention, as referenced herein the engineered HLA alleles are generally described using the first two fields.

HLA is the main genetic factor related to autoimmune diseases, accounting for approximately half of known genetic predisposition. Although more than 200 associations between HLA and disease have been described, the underlying pathogenic mechanisms remain poorly defined. Initially, the particular genetic characteristics of HLA, and the complex interaction with other genes and environment have prevented further clinically meaningful developments in this field. There is a greater need for dissecting and understanding the role of HLA in disease susceptibility.

One autoimmune disease, rheumatoid arthritis, or RA, is characterized by inflammation of the joint capsule synovia, resulting in an infiltration of macrophages, neutrophils, T cells, and B cells. This culminates in extensive joint destruction, disability, and reduced quality of life. The persistent inflammation associated with RA also increases the risk of developing ischemic heart and respiratory disease, resulting in early mortality. RA occurs in approximately 1% of the world population, with an estimated 1.3 million affected in the United States of America (US) alone. RA occurs more frequently in women over the age of 40 and in long-term smokers. Billions of dollars of direct healthcare costs are associated with the treatment of RA annually, and total annual societal costs of RA (direct, indirect and intangible) are estimated to reach tens of billions of dollars in the US alone.

Treatment of RA requires a systematic approach with frequent monitoring of disease activity and medication side effects to determine the optimal therapeutic regimen appropriate for the patient. There are currently a diverse range of approved therapeutic agents to control symptoms, manage pain, and limit joint damage. Current medications for RA include non-steroidal anti-inflammatory drugs (NSAIDs), analgesics, corticosteroids, synthetic disease-modifying antirheumatic drugs (DMARDs), and biologic agents. DMARD treatments globally target major components of the immune system to halt progression of RA and require sustained administration to maintain remission. This puts patients at risk of developing unwanted side effects, serious infections, malignancy, and organ toxicity; patients can also develop anti-drug antibodies (ADAs) against biologics that neutralize their effects. Furthermore, between approximately 6% and 21% of patients fail to achieve sufficient response to adequately manage disease with current treatments. Such patients are commonly referred to as refractory RA patients.

Existing treatments for autoimmune diseases target the symptoms and not the root cause of the diseases. Many autoimmune diseases, like RA, are initiated by the presentation of modified self-peptides by a subset of HLA alleles.

Transplantation of hematopoietic stem cells (HSCs) to cure RA has been unsuccessful at safely conferring long-term remission. First, autologous transplants employ a short course of chemotherapy to reset the immune system and are relatively safe but, rather than address the root problem, they simply re-populate the bone marrow with the same, problematic cells that allowed RA to develop in the first place. Secondly, allogeneic bone marrow transplants from HLA-matched donors also exhibit a high rate of relapse due to the fact that the same HLA alleles were used to replace the patient's bone marrow. Moreover, this technique is associated with graft-versus-host disease (GVHD), making it an unacceptable therapeutic strategy. A recent meta-analysis of 17 studies involving 155 unique patients with RA who had undergone autologous HSC transplants demonstrated that remission was not maintained beyond 2 years.

The National Institutes of Health (NIH), in 2005, reported that as many as 23.5 million people in the U.S. may suffer from autoimmune diseases, which, in most cases, lack cures. The lack of cures results in many patients suffering from debilitating symptoms, loss of organ function, reduced productivity at work, and high medical expenses. What is needed are effective therapies to treat autoimmune diseases.

Herein, Applicants describe techniques that target the HLA allele associated with autoimmune diseases and use this information to create tailored treatments comprising one or more autologous HSCs wherein the target HLA allele has been engineered to have altered antigen binding affinity and/or specificity.

SUMMARY

Herein, to address the foregoing and other shortcomings in existing treatment and management of autoimmune disease, Applicants have developed methods that identify and target HLA alleles associated with the disease and use this information to create tailored treatments involving one or more autologous HSCs wherein the target HLA allele has been engineered to have altered self-antigen binding affinity and/or specificity.

Disclosed herein are methods and compositions useful in reducing autoimmunity in a subject suffering from or at risk of developing an autoimmune disease, disorder, or condition. Such diseases, disorders, and conditions include, without limitation, rheumatoid arthritis (RA), celiac disease, diabetes mellitus type 1, systemic lupus erythematosus (SLE), multiple sclerosis (MS), myelin oligodendrocyte glycoprotein antibody disorders (MOGAD), myasthenic syndromes and neuromyelitis optica (NMO), ankylosing spondylitis, Behçet's syndrome, Birdshot uveitis, narcolepsy, narcolepsy type 1 (NT1; previously termed narcolepsy with cataplexy), Kawasaki disease, Crohn's disease, psoriasis, dermatomyositis (DM), Addison's disease, irritable-bowl syndrome (IBS), Graves' disease, Henoch-Schönlein purpura (HSP), sarcoidosis, Sjögren's syndrome, eosinophilic granulomatosis with polyangiitis, Hashimoto's disease, idiopathic thrombocytopenic purpura, polymyositis (PM), paraneoplastic neurological syndromes (PNS), autoimmune encephalitis, lupus nephritis (LN), myasthenia gravis (MG), psoriatic arthritis, graft rejection, graft-versus-host disease (GVHD), an unwanted delayed-type hypersensitivity reaction, T-cell mediated pulmonary disease, neuritis, vitiligo, autoimmune pancreatitis, inflammatory bowel diseases, ulcerative colitis, glomerulonephritis, scleroderma, autoimmune thyroid diseases, asthma, autoimmune uveoretinitis, pemphigus vulgaris, pulmonary fibrosis or idiopathic pulmonary fibrosis, primary biliary cirrhosis, and pernicious anemia. Various autoimmune diseases are associated with the presence of one or more alleles of the human leukocyte antigen (HLA) genes, which is a group of related genes coding for proteins involved in immune function. HLA Class I and Class II proteins are cell-surface proteins with peptide clefts for presenting peptides to T-cell receptors. The HLA complex of genes reside on the short arm of human Chromosome 6.

In one aspect, methods of modifying an HLA allele associated with an autoimmune disease are provided. One such method includes the steps of identifying autoimmunity-susceptibility HLA alleles; identifying target amino acid positions within a binding cleft of a susceptibility HLA allele-coded protein, wherein the target amino acid position has an identity that is different in an auto-immunity-resistant HLA allele; modifying the amino acid identity of the target amino acid position to the identity of the same amino acid position in the auto-immunity-resistant HLA allele to create a modified autoimmunity-susceptibility HLA allele, wherein a protein coded by the modified autoimmunity-susceptibility HLA allele possesses altered binding affinity for at least one self-peptide.

In a related aspect of the present disclosure, methods of treating a subject suffering from or at risk of developing an autoimmune disease are provided. One such method includes the steps of identifying an autoimmunity-susceptibility HLA allele within an HLA complex of the subject; isolating a plurality of CD34+ immune cells from the subject; and modifying the CD34+ immune cells to create modified CD34+ immune cells expressing a modified autoimmunity-susceptibility HLA allele. The modified autoimmunity-susceptibility HLA allele encodes a protein with altered binding affinity for at least one self-peptide as compared to a protein coded for by the autoimmunity-susceptibility HLA allele.

In certain embodiments according to the present disclosure, methods are provided for identifying autoimmune conditions related to antigen presentation by HLA Class I and Class II proteins that are treatable with engineered autologous-HLA expressing hematopoietic cells. In many embodiments, the HLA loci are selected from Class I A, B, and C, and Class II DP, DR, and DQ. In some embodiments, HLA genes, alleles, and proteins may include one or more of HLA-A*02, HLA-A*03, HLA-A*29, HLA-B*07, HLA-B*08, HLA-B*27, B*27:03 B*27:05, B*27:09, HLA-B*51, HLA-B*54, HLA-B*57, HLA-C*06, HLA-C*18, HLA-DPA1*02, HLA-DPB1*13, HLA-DQA1*02, HLA-DQA1*03, HLA-DQA1*05, HLA-DQB1*02, HLA-DQB1*03, HLA-DQB1*06, HLA-DRB1*01, HLA-DRB1*04, HLA-DRB1*07, HLA-DRB1*08, HLA-DRB1*11, HLA-DRB1*15, HLA-DRB1*16, and variants of those HLAs. The disclosed methods include, in certain embodiments, the steps of identifying one or more HLA alleles associated with susceptibility (susceptibility allele) to a specific autoimmune disease and one or more alleles of the same HLA gene that are associated with resistance (resistance allele) to the specific autoimmune disease, identifying one or more variable amino acid positions within the antigen binding groove of the HLA gene, wherein the variable amino acid position of the susceptible allele has a first identity and the variable amino acid position of the resistance allele has a second identity.

Certain embodiments of the present disclosure are premised in part on the discovery of causal associations between specific autoimmune diseases and specific HLA alleles. For example, certain embodiments are based on the association of Type 1 diabetes with DQB1*02 and/or DQB1*03, and in particular with DQB1*02:01 and/or DQB1*03:02. In some embodiments, rheumatoid arthritis is associated with DRB1*04 and DRB1*01, in particular DRB1*04:01, DRB1*04:05, and DRB1*01:01. In some such embodiments, multiple sclerosis is associated with DRB1*15, in particular DRB1*15:01. In some such embodiments, celiac disease is associated with DQB1*02, in particular DQB1*02:01. In some such embodiments, NMO is associated with DRB1*03, in particular DRB1*03:01. In some such embodiments, Behçet's syndrome is associated with B*51 or B51. In some cases, psoriasis may be associated with C*06, B*57, DRB1*07, and/or DQB1*03. In some cases, Birdshot uveitis may be associated with A*29. In some cases, narcolepsy may be associated with DQB1*06, in particular DQB1*06:02. In some cases, myasthenia gravis may be associated with A*03, B*07, DR2 (DRB1*15 and/or DRB1*16) and and/or DR4 (DRB1*04). In some cases, Kawasaki disease may be associated with B*54, in particular amino acid positions 91, 104, and 329. In some cases, inflammatory bowel disease may be associated with DRB1*01, in particular DRB1*01:03. In some cases, systemic sclerosis may be associated with DRB1*11, DPB1*13, B*08, DQA1*02:01, DQA1*05, DRB1*08, DRB1*07, DPA1*02, DQB1*03, in particular DRB1*11:04, DPB1*13:01, B*08:01, DQA1*02:01, DQA1*05:01, DRB1*08:01, DRB1*07:01, DPA1*02:01, DQB1*03:01.

Also disclosed herein are compounds and compositions useful in treating or preventing autoimmune conditions. In many embodiments, the disclosed compounds and compositions include one or more engineered immune cell comprising a modified HLA allele. In most embodiments, the modified HLA allele is an edited protein molecule and contains at least one amino acid mutation within the peptide binding cleft of the HLA protein coded for by the modified HLA allele. In other embodiments, the modified HLA allele is an edited nucleic acid molecule coding for an edited HLA protein, wherein the edited nucleic acid contains at least one codon coding for an amino acid mutation within the peptide binding cleft of the edited HLA protein. In most embodiments, the amino acid mutation is not at the T-cell receptor interface. In many embodiments, the modified HLA allele may be carried, contained in, or expressed by an engineered immune cell. In many embodiments, the engineered immune cells are autologous cells—i.e., they are obtained from the subject being treated for the autoimmune disease. In many embodiments, the engineered immune cell may be comprised within a composition, for example a therapeutic composition that may be administered to a subject suffering from or at risk for an autoimmune disease. In many embodiments, the engineered immune cell may be an HSC.

Further disclosed are methods of making the disclosed compounds and compositions. In many embodiments the methods comprise identifying one or more HLA genes associated with an elevated incidence of a specific autoimmune disease, identifying one or more alleles of the HLA gene associated with susceptibility (susceptibility allele(s)) and/or one or more alleles associated with resistance (resistance allele(s)) to the specific autoimmune disease, identifying one or more variable amino acid positions within the antigen binding groove of the HLA molecule, wherein the variable amino acid position of the susceptible allele has a first identity and the variable amino acid position of the resistant allele has a second identity. In certain embodiments, the methods of making the disclosed compounds further comprise creating an engineered HLA molecule of the susceptible allele wherein the identity of the amino acid at the variable position is the second identity. In some embodiments, the engineered HLA molecule is coded for by an expression vector or an engineered genomic sequence.

Also disclosed are various methods of treating subjects in need with the disclosed therapies, wherein treatment comprises administration of one or more engineered antigen presenting cells having at least one mutated amino acid within an MHC antigen binding region (e.g., an antigen binding groove of an HLA protein). In many embodiments, the treatment methods include isolating one or more cells from a donor. In many embodiments, the isolated cell is a HSC. In many embodiments, the method further comprises the step of modifying the HSC to create an engineered HSC. The engineered HSC comprises an engineered HLA allele (edited HLA allele, variant HLA allele, modified HLA allele) having altered binding specificity or affinity for a self-antigen or a variant self-antigen. In some embodiments, the modified HSC comprises one or more of a nucleic acid sequence coding for the engineered HLA allele in its genomic sequence or one or more expression vectors comprising a nucleic acid sequence coding for the engineered HLA allele. In many embodiments, the modified HSC may engraft in the subject's bone marrow and produce one or more modified antigen presenting cells.

Disclosed herein are various compositions for treating a subject at risk of developing or suffering from an autoimmune disease. In representative, specific embodiments, the compositions comprise a DNA sequence selected from the group consisting of SEQ ID NO:59-96.

In some certain embodiments according to the present disclosure, susceptibility to the autoimmune disease is associated with an HLA-DRB1 gene, for example DRB1*01, DRB1*03, DRB1*04, DRB1*07, DRB1*09, DRB1*10, DRB1*11, DRB1*12, DRB1*13, DRB1*14, DRB1*15, and DRB1*16. In many embodiments the autoimmune disease is associated with an allele of HLA-DRB1 selected from DRB1*01:01, DRB1*01:02, DRB1*01:03, DRB1*03:01, DRB1*04:01, DRB1*04:02, DRB1*04:03, DRB1*04:04, DRB1*04:05, DRB1*04:08, DRB1*07:01, DRB1*09:01, DRB1*10:01, DRB1*11:01, DRB1*11:02, DRB1*11:03, DRB1*12:01, DRB1*13:01, DRB1*14:01, DRB1*15:01, DRB1*15:02, and DRB1*16:01. In related embodiments, the compositions comprise a DRB1*01:01 protein or DNA coding region therefor comprising a mutation at position selected from L67, Q70, V85, G86, R71 (positions of amino acids are in reference to the mature protein sequence as presented at ebi.ac.uk/ipd/imgt/hla), and combinations thereof, for example, without limitation, L671, Q70D, V85A, G86V, R71E, and combinations thereof. For example, in some embodiments, the composition comprises a variant DRB1*03:01 protein or coding region comprising a mutation at position V86, for example V86L or V86M. In some embodiments, the composition comprises a variant DRB1*04:03, DRB1*04:04 DRB1*04:05, and DRB1*04:08 protein or coding region comprising a mutation at position R71, for example R71E. In some embodiments, the composition comprises a variant DRB1*13:01 protein or coding region comprising a mutation at position V86, for example V86L or V86M. In some embodiments, the composition comprises a variant DRB1*15:01 protein or coding region comprising a mutation at position F47, A71, or V86, for example F47Y, A71R, V86L, V86M, and combinations thereof.

In some embodiments of the present disclosure, susceptibility to the autoimmune disease is associated with an HLA-DRB3, HLA-DRB4, or HLA-DRB5 gene, for example HLA-DRB3*01, HLA-DRB3*02, HLA-DRB3*03, DRB4*01, and DRB5*01. For example, in certain embodiments, the autoimmune disease is associated with an allele of HLA-DRB3/4/5 selected from DRB3*01:01, DRB3*02:02, DRB3*03:01, DRB4*01:01, DRB4*01:03, and DRB5*01:01.

In additional embodiments according to the present disclosure, susceptibility to the autoimmune disease is associated with the HLA-DQA and/or HLA DQB genes. For example, in certain embodiments, the autoimmune disease is associated with an allele of HLA-DQA1 and/or selected from DQA1*01, DQA1*03, DQA1*05, DQB1*02, DQA1*03, DQB1*05, DQB1*06, and combinations thereof, for example DQ5, DQA1*01:01 and DQB1*05:01; DQ6, DQA1*01:02 and DQB1*06:02; DQ2, DQA1*05:01 and DQB1*02:01; DQ2 Trans, DQA1*03:01 & DQB1*02:01; DQ8, DQA1*03:01 and DQB1*03:02; DQ8 trans, DQA1*05:01 and DQB1*03:02; DQA1*05:05 and DQB1*03:01; and DQA1*03:01 and DQB1*03:01. In some such embodiments, at least one modified or variant HLA is engineered having at least one substitution within the antigen binding groove, for example position 57 or 71, wherein the mutation is A57D, K71E, K71T, or combinations thereof.

In further embodiments according to the disclosure, susceptibility to the autoimmune disease is associated with the HLA-B gene. For example, in some embodiments, the autoimmune disease is associated with an allele of B27 and/or selected from B*27:03 B*27:05, and B*27:09. In many embodiments, the mutation may be at a position selected from any polymorphic position within the antigen binding groove, for example position 59 or 116, wherein the mutation is Y59H, D116H, or combinations thereof.

Further disclosed herein are methods for identifying positions of HLA alleles that, when mutated, may be useful in reducing or eliminating susceptibility to, or symptoms of, autoimmunity. The methods include, in many embodiments, comparing a cohort of individuals suffering from an autoimmune disease, identifying specific HLA gene allele(s) associated with disease susceptibility (susceptibility allele), identifying specific HLA gene allele(s) associated with disease resistance (resistance allele), identifying polymorphic amino acid positions, located within the antigen binding groove of the HLA molecule, between the resistant allele (or resistance allele) and the susceptibility allele (or susceptible allele)—that is, positions where the amino acid identity in the resistant allele is different than the identity in the susceptibility allele. As one example, residues of the DRB1 gene located within the antigen binding groove include 8-14, 16, 25-26, 28, 30-33, 37-38, 40, 47, 57-60, 67, 70-71, 73-74, 77-78, 85-86, and 93. In related embodiments, the methods further comprise engineering the susceptibility allele to include the resistant allele's amino acid identity at the polymorphic position. In certain embodiments according to the present disclosure, expressing such engineered HLA molecule or molecules on one or more antigen presenting cells (APCs) prevents, treats, or ameliorates autoimmune disease in a subject.

Also disclosed herein are engineered HLA molecules having altered antigen binding and/or specificity compared to a non-engineered HLA molecule. In many embodiments, the antigen may be selected from various peptides including modified peptides, citrullinated peptides, hybrid peptides, nucleic acids, etc. In some embodiments, the hybrid peptide is a hybrid insulin peptide. In some embodiments, the peptide is selected from ENPVVHFFKNIVTPRTPPP SEQ ID NO: 123, LVRYWISAFP SEQ ID NO: 122, FFRDHSYQEEA SEQ ID NO: 121, AQGTLSKIFKLG-GRDSRSGSPMARR SEQ ID NO: 124, GQVEL-GGWSKMDQLA SEQ ID NO: 97, GQVELGGG-NAVEVLK SEQ ID NO: 98, GQVELGGGSSPETLI SEQ ID NO: 99, SLQPLALEAEDLQV SEQ ID NO: 100, HLVEELYLVAGEEG SEQ ID NO: 102, AMMI-ARFKMFPEVKEKG SEQ ID NO: 101, SHLVEALYL-VCGERG SEQ ID NO: 104, RSQVETDDLILKPGV SEQ ID NO: 105, SQVETDDLILKPGVV SEQ ID NO: 106, PGIAGFKGEQGPKGE SEQ ID NO: 107, IFDSRGNPTVEVDLF SEQ ID NO: 108, IFDS{CIT}GNPTVEVDLF SEQ ID NO: 109, SAVRLRSSVPGVR SEQ ID NO: 110, SAVRL{CIT}SSVPGVR SEQ ID NO: 111, QDFTNRIN-KLKNS SEQ ID NO: 112, QDFTN{CIT}INKLKNS SEQ ID NO: 113, ATEGRVRVNSAYQDK SEQ ID NO: 114, ATEG{CIT}VRVNSAYQDK SEQ ID NO: 115, ATI-KAEFVRAETPYM SEQ ID NO: 116, ATIKAEFV{CIT}AETPYM SEQ ID NO: 117, AVRLQGSVAGVR SEQ ID NO: 118, PYHFKYHEKHFA-NAI SEQ ID NO: 119, PVSKMRMATPLLMQA SEQ ID NO: 120, PKYVKQNTLKLAT SEQ ID NO: 103, and combinations thereof, wherein {CIT} indicates a deiminated arginine residue, which may be referred to as a citrullinated residue.

Also disclosed are methods of occluding a pocket in a binding cleft of an HLA allele, the methods comprising the steps of identifying susceptible HLA alleles, and identifying target amino acid position at or near a pocket of the antigen binding cleft, wherein the pocket defines a recess at the bottom of the antigen binding cleft. The methods may further comprise substituting an amino acid having a side chain larger than the target amino acid to create an occlusion HLA allele, wherein the side chain of the second amino acid extends into the recess at the bottom of the antigen binding cleft, and thereby occluding the pocket of the HLA allele. In various embodiments, the HLA allele may be selected from HLA-DRB1, HLA-DRB3, HLA-DRB4, and HLA-DRBS, and the pocket may be pocket 1. In these embodiments, the target amino acid may be, for example, position 86, and the identity of the substituted amino acid may be selected from valine, methionine, and leucine. In many embodiments the HLA protein with the occlusion in the pocket may possess lower binding affinity for at least one self-peptide associated with an autoimmune disease, optionally wherein the at least one self-peptide is deiminated, and further optionally wherein the target amino acid is not at the T-cell receptor binding interface.

Throughout the present disclosure, various publications may be referenced. The disclosures of these publications in their entireties are hereby incorporated by reference into this application, to the extent allowed by law.

The present disclosure is sufficient to enable one skilled in the art to practice the present disclosure. The present disclosure is not to be limited in scope by the constructs described, because the described embodiments are intended as illustrations of certain aspects of the present disclosure and any constructs that are functionally equivalent are within the scope of this disclosure.

BRIEF DESCRIPTION OF THE DRAWINGS

Embodiments will be readily understood by the following detailed description in conjunction with the accompanying drawings. Embodiments are illustrated by way of example and not by way of limitation in the accompanying drawings.

FIG. 2 depicts a schematic depiction of a mouse TCR/CD4 interaction with an engineered humanized HLA-DR4/I-E$^d$, and at bottom is a graph of results from studies on collagen sensitization as detected by ex vivo proliferation of CD4$^+$ T cells, where symbols indicate samples from individual humanized DRB1*04:01, DRB1*01:01 and DRB1*04:01$^{K71E}$ mice and bars indicate means. Data was analyzed by One-way ANOVA.

FIG. 3A shows a three-dimensional depiction of DRB1*04:01 identifying position K71 within the cleft and the antigen binding cleft occupied by a collagen peptide (left); the figure at the right shows the structure of DRB1*04:01$^{K71E}$ and the absence of collagen peptide binding—acidic residues are shaded in blue and basic residues are shaded in red.

FIG. 9 depicts aquaporin 4 peptides 5 and 6 binding to DRB1*03:01 and DRB1*07:01.

FIG. 10 is a sequence alignment of *04:01 and *04:05 mature length proteins, according to embodiments of the disclosure.

FIG. 12 depicts native vs. A57D binding of the HIP8-NPY peptide across multiple concentrations, where closed circle is the native allele, open circle is the A57D mutation: Panel A, DQ2; Panel B, DQ8; Panel C, DQ2 Trans; and Panel D, DQ8 Trans.

FIG. 20 depicts binding of hybrid insulin peptides to DRB3, DRB4 and DRB5 alleles, according to embodiments of the disclosure. Numbers in upper left corner of boxes are binding ratios compared to negative controls. The 'common' serologic names of these alleles (e.g., HLA-DR52) are shown above the allele name.

FIG. 21 depicts binding of diabetogenic peptides to DRB3, DRB4 and DRB5 alleles, according to embodiments of the disclosure. Numbers in upper left corner of boxes are binding ratios compared to negative controls.

FIG. 22 is a list of various antigens used in the present studies to investigate binding by gene-edited HLA molecules, according to embodiments of the present disclosure.

FIG. 23A is a three-dimensional representation of a DRB1 structure showing location of Pocket 1, according to embodiments of the present disclosure, and a two-dimensional representation of amino acids' chemistry.

FIG. 28 is a list of representative HLA alleles, amino acid positions, and mutations according to embodiments of the present disclosure.

FIG. 29 lists mature protein sequences of various HLA alleles.

FIG. 30 lists cDNA sequences of various embodiments of susceptible and engineered HLA alleles.

DETAILED DESCRIPTION

Figure 1:
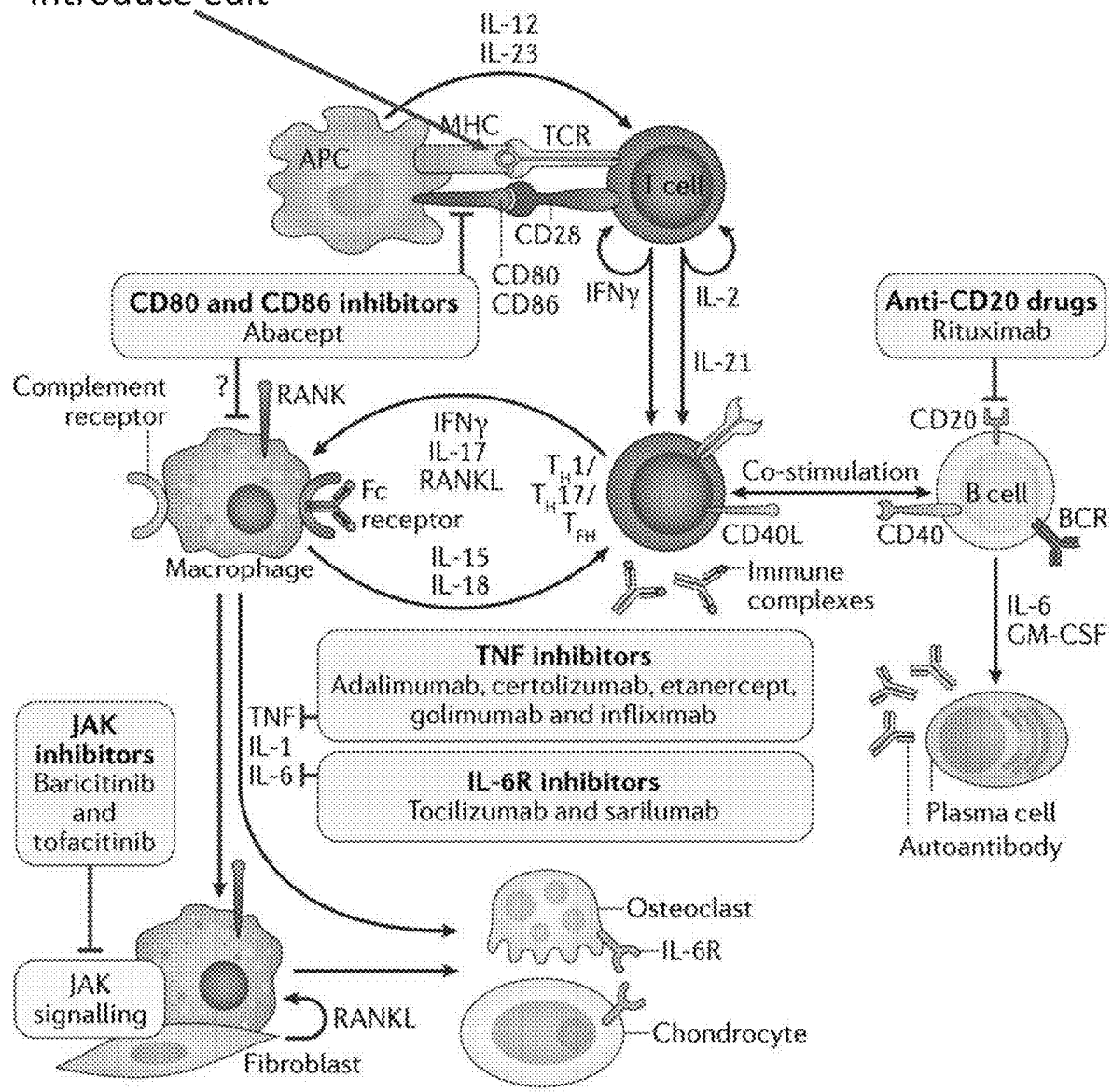
FIG. 1 is a schematic depiction of various pathways, interactions, and pharmaceutical interventions in autoimmunity.

Disclosed herein are various methods and compositions useful in treating, reducing, or eliminating autoimmune disease in a subject suffering from or at risk of developing the same. Such autoimmune diseases include, without limitation, rheumatoid arthritis (RA), celiac disease, diabetes mellitus type 1, systemic lupus erythematosus (SLE), multiple sclerosis (MS), myelin oligodendrocyte glycoprotein antibody disorders (MOGAD), myasthenic syndromes and neuromyelitis optica (NMO), ankylosing spondylitis, Behçet's syndrome, Birdshot uveitis, narcolepsy, narcolepsy type 1 (NT1; previously termed narcolepsy with cataplexy), Kawasaki disease, Crohn's disease, psoriasis, dermatomyositis (DM), Addison's disease, irritable-bowel syndrome (IBS), Graves' disease, Henoch-Schönlein purpura (HSP), sarcoidosis, Sjögren's syndrome, eosinophilic granulomatosis with polyangiitis, Hashimoto's disease, idiopathic thrombocytopenic purpura, polymyositis (PM), paraneoplastic neurological syndromes (PNS), autoimmune encephalitis, lupus nephritis (LN), myasthenia gravis (MG), psoriatic arthritis, graft rejection, graft-versus-host disease (GVHD), an unwanted delayed-type hypersensitivity reaction, T-cell mediated pulmonary disease, neuritis, vitiligo, autoimmune pancreatitis, inflammatory bowel diseases, ulcerative colitis, glomerulonephritis, scleroderma, autoimmune thyroid diseases, asthma, autoimmune uveoretinitis, pemphigus vulgaris, pulmonary fibrosis or idiopathic pulmonary fibrosis, primary biliary cirrhosis, and pernicious anemia.

In particular embodiments according to the present disclosure, the disclosed autoimmune diseases are correlated with the presence of one or more human leukocyte antigen (HLA) alleles. Applicants describe herein methods and compounds useful in ameliorating one or more symptoms of autoimmune disease in a subject suffering therefrom. In many embodiments, the methods may include identifying an autoimmune susceptible HLA allele expressed by the subject's antigen presenting cells comparing the amino acid sequence of that susceptible HLA allele with one or more HLA alleles associated with resistance to that same autoimmune disease. In most embodiments, hematopoietic stem cells are mobilized and isolated from the subject, and the susceptible HLA allele is modified or replaced with an engineered HLA allele comprising one or more amino acid substitutions within the antigen binding cleft of the protein coded for by the HLA allele, the specific identity of the substituted amino acid corresponds with the identity of that same amino acid position in the HLA allele associated with resistance.

In certain embodiments, targeted engineering of the antigen presenting cleft of the HLA gene modifies binding specificity and/or affinity to one or more self-antigens. In most embodiments, a single amino acid within the cleft, that is hidden from TCR interrogation is mutated to alter peptide biding without directly affecting TCR binding. In most embodiments, the disclosed HLA mutations result in HLA protein changes that fail to trigger either rejection or GVHD in the patient. In most embodiments, expression of the engineered HLA proteins on one or more antigen presenting cells in a subject suffering an autoimmune disease may result in amelioratin of one or more symptoms associated with the autoimmune disease.

Also disclosed are methods of occluding a pocket in a binding cleft of an HLA allele, the methods comprising the steps of identifying susceptible HLA alleles, and identifying target amino acid position at or near a pocket of the antigen binding cleft, wherein the pocket defines a recess at the bottom of the antigen binding cleft. The methods may further comprise substituting an amino acid having a side chain larger than the target amino acid to create an occlusion HLA allele, wherein the side chain of the second amino acid extends into the recess at the bottom of the antigen binding cleft, and thereby occluding the pocket of the HLA allele. In various embodiments, the HLA allele may be selected from HLA-DRB1, HLA-DRB3, HLA-DRB4, and HLA-DRB5, and the pocket may be pocket 1. In these embodiments, the target amino acid may be, for example, position 86, and the identity of the substituted amino acid may be selected from valine, methionine, and leucine. In many embodiments the HLA protein with the occlusion in the pocket may possess lower binding affinity for at least one self-peptide associated with an autoimmune disease, optionally wherein the at least one self-peptide is deiminated, and further optionally wherein the target amino acid is not at the T-cell receptor binding interface.

Applicant's present concept is presented in the diagram at FIG. 1. The HLA T cell receptor (TCR) interaction is central aspect in the pathogenesis of many autoimmune diseases, for example those described above. Current biologic agents targeting autoimmune disease tend to target and block innate and adaptive pathways downstream from this signal. This is problematic because these pathways engage in protective immune responses against myriad pathogens and blocking them or altering them leaving the patient at risk for various opportunistic infections.

APCs are derived from HSC progenitors in the bone marrow. The presently described engineered HSCs replace the subjects APCs that present antigens that lead to autoimmunity. The engineered HSCs express altered HLA molecules, which will reduce, prevent, and/or resolve, prior activation of autoreactive $CD4^+$ T cells and their subsequent effects on chronic inflammatory cytokine production, macrophage activation, and B cell autoantibody production.

Thus, in one aspect of the present disclosure, Applicants provide herein the ability to treat autoimmune diseases using engineered autologous HSCs comprising edited HLA proteins as presently described. The disclosed methods advantageously target specifically the underlying etiology of the patient's autoimmune disease while avoiding broad effects on other aspects of the patient's immune system.

Monocytes, macrophages, and dendritic cells (DCs) are the principal APCs that help to initiate and maintain the disease state in many autoimmune diseases. For example, in RA, the cells maintain the hyperinflammatory state in the joints associated with pain and debilitating progression of joint damage of the disease. However, these cells are short-lived and must be replenished from CD34$^+$ HSCs in the bone marrow on a regular basis. Monocytes, for example, typically survive in the blood for only a few days. However, if a monocyte migrates to an inflamed joint, they may progress to monocyte-derived DCs and macrophages and survive for weeks to months. Thus, Applicant's present disclosure describes replacing a subset of a patient's bone marrow with engineered HSCs that will produce new engineered monocytes, macrophages and DCs that no longer present auto-immunogenic antigens, thus preventing activation of T-Cells and/or causing autoreactive T cells to revert to a quiescent memory state.

The presently disclosed methods, compositions, and systems generally do not include depleting the patient's T cells and B cells prior to infusion of engineered HSCs. Thus, the presently disclosed therapeutic methods retain the patient's normal, innate, and adaptive immunity to infection by microbial pathogens and recognition tumor antigens.

Selecting HLA Allele, Position, and Mutation for Expression by Engineered HSC Disclosed herein are methods for selecting HLA alleles, target amino acid positions within those alleles, and mutations at those positions for expression by engineered HSCs. In some embodiments, the disclosed methods, compositions, and systems may include selecting and identifying more than one HLA allele, position, and/or mutation, modifying said allele to create an engineered HLA allele with altered binding affinity for at least one self-antigen as compared to an unmodified HLA allele. In many embodiments, the engineered HLA allele is expressed by engineered hematopoietic cells of a patient to be treated by the disclosed therapy.

The disclosed methods may include identifying and/or selecting an HLA allele that is closely associated with increased risk of autoimmunity, which may be referred to as a susceptibility allele or susceptible HLA allele. In certain embodiments, the susceptible HLA allele is found in greater than about 5% of patients with a specific autoimmune disease, for example greater than about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or more and less than about 90%, 80%, 70%, 60%, 50%, 45%, 40%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5%. In many embodiments, the susceptible HLA allele may be found in a smaller percentage of individuals that do not suffer from the identified autoimmune disease (i.e., a control population or controls), for example, less than about 35%, 30%, 25%, 20%, 19%, 18%, 17%, 16%, 15%, 14%, 13%, 12%, 11%, 10%, 9%, 8%, 7%, 6%, or 5%.

In the case of RA, DRB1*04:04, DRB1*01:01 or DRB1*04:01 may be selected as an HLA allele for engineering. For example, although several DRB1 alleles contain an arginine in position 71 and are at increased risk of developing RA, they are relatively uncommon. DRB1*01:01 is found at an allele frequency of 13% in RA patients, compared to 9.7% of controls and is the most common of these other 'shared epitopes'. The alleles DRB1*04:03 (0.6%), *04:04 (9.1%), *04:05 (1.2%), *04:08 (1.7%) and *10:01 (2%) are all relatively rare among RA patients. In contrast, DRB1*04:01 is seen in 31% of RA patients (compared to 10% of controls, $\rho=10^{-3}$). The frequency of DRB1*04:01 increases with the severity of the disease to greater than 50% of refractory RA patients and 88% of the most severe form of RA (Felty's Syndrome). In addition, DRB1*04:01 contributes the highest degree of susceptibility to RA.

The disclosed methods may include identifying and/or selecting a target amino acid position within the susceptible HLA allele to be mutated to create the engineered HLA allele. In certain embodiments, the selected target amino acid position (1) is not buried in HLA protein's structural core, (2) is positioned at or near the antigen binding cleft of the HLA protein, (3) within the groove/cleft and not directly accessible to the T-cell receptor, i.e., is not at the TCR:HLA binding interface, and/or (4) alters binding affinity of at least one antigen to the engineered HLA allele. In many embodiments, the disclosed target amino acid position in a protein encoded by the selected susceptible HLA allele molecule may have an identity that is different in another allele of the same HLA gene that is not associated with susceptibility. Instead, this other HLA allele may be associated with resistance to the same autoimmune disease; this HLA allele may be referred to as a resistant HLA allele. For example, target amino acid position 71 in the mature protein of RA-associated susceptible HLA allele DRB1*04:01 is lysine, while in the RA-associated resistant HLA protein, DRB1*04:02, position 71 is glutamic acid.

According to certain embodiments, HLA engineering is optimized to minimize or avoid entirely the consequences of HLA mismatching. Among recipients of allogeneic bone marrow transplants, any HLA disparity increases the risk of graft failure (rejection) and GVHD, so certain embodiments described herein include mutations within the antigen binding groove/cleft of the HLA molecule. For example, the location of K71 in DRB1*04:01 is below the upper surface (TCR interaction surface) of the HLA molecule and would not directly contact the TCR. Thus, mutations of K71 in DRB1*04:01 are unlikely to induce direct alloreactivity. In certain embodiments, suitable engineering sites are evaluated based on their inability to elicit T cell response, such as by in silico modeling, analysis of peptide binding, and/or in vitro characterization of T cell responses elicited by engineered HSCs.

Described herein are methods for generating edited HLA alleles that are sufficient to alter antigen binding but do not elicit rejection. Specifically, the edited HLA allele DRB1*04:01$^{K71E}$ is a variant that is not found in nature, its peptide repertoire and potential for alloreactivity was unknown.

Based on the presently disclosed methodology for identifying HLA target amino acid positions that may be changed while avoiding rejection by a subject's immune system, Applicants herein show that such amino acid changes do treat autoimmunity while avoiding rejection. Specifically, Applicants generated transgenic mice expressing either DRB1*04:01 or DRB1*04:01$^{K71E}$ and performed skin transplants between these strains. Skin grafts taken from one DRB1*04:01 mouse and applied to another DRB1*04:01 mouse will be accepted by the DRB1*04:01 immune cells as self. However, if the immune cells of DRB1*04:01 mice see DRB1*04:01$^{K71E}$ as foreign tissue, it will be rejected (and vice versa).

Herein, Applicants experimental results demonstrate that the presently disclosed methods of creating engineered HLA alleles based on the subject's own susceptible HLA allele and HSCs are not rejected. The disclosed engineered HLA-DRB1*04:01$^{K71E}$ alleles include one non-native amino acid substitution in the antigen binding cleft, wherein the substitution alters binding to at least one antigen (relative the native susceptible allele) but does not directly affect T-cell receptor interaction, such as the DRB1*04:01$^{K71E}$ edit, does not induce alloreactivity in native DRB1*04:01 recipients.

More than 100 genetic loci have been associated with RA. However, the strongest genetic association with RA pathogenesis is with the DRB1 gene within the major histocompatibility complex, contributing to approximately 50% of the genetic risk. More specifically, three amino acid positions (11, 71 and 74; note the aa positions within the HLA are relative to the mature protein, as presented at the Immuno Polymorphism Database-ImMunoGeneTics project/Human Leukocyte Antigen or IPD-IMGT/HLA website, available at website ebi.ac.uk/ipd/imgt/hla) in HLA-DRB1 account for most of the association of the HLA DRB1 locus with seropositive RA.

By cloning all the relevant RA-susceptible and RA-resistant alleles and then performing site-directed mutagenesis on individual amino acids, Applicants demonstrated that mutating position 71 from a K to E converted the peptide-binding profile to one that was similar to that of the resistant HLA allele DRB1*04:02 (below).

Using a peptide competition assay, Applicants identified HLA allele DRB1*04:01 as possessing the greatest preference for a set of RA-associated antigens—specifically, post-translationally modified "altered-self" peptides. These altered-self peptides may signal the initial breach of tolerance in pre-clinical RA. The collection of altered self-peptides includes a set of citrullinated peptide neoantigens that are upregulated during infection and inflammation. Human type II collagen is arthritogenic in animal models and in mice CD4$^+$ T cells that initiate arthritis recognize an immunodominant peptide located between amino acids 258-272 of collagen. CD4$^+$ T cells that recognize the collagen$^{258-272}$ peptide are found in RA joints, and their presence in the peripheral blood at disease onset is associated with rapid progression of joint disease and poor responsiveness to conventional synthetic and biologic disease modifying anti-rheumatic drugs (DMARDs). Applicants discovered that ionic attraction between the acidic K residue in position 71 and a basic E residue in the collagen$^{258-272}$ peptide enhance peptide binding to DRB1*04:01.

Refractory RA is a more severe form of the disease, in which the synovium of various joints is maintained in a state of constant inflammation. This state of inflammation is characterized by infiltrates of T cells macrophages, neutrophils, and B cells. The presently disclosed compositions, methods, and therapies result in engineered HSC engraftment in the bone marrow that will replenish myeloid APCs expressing the DRB1*04:01$^{K71E}$ allele.

Without wishing to be limited by theory, unlike native DRB1*04:01, the engineered DRB1*04:01$^{K71E}$ does not bind tightly to collagen$^{258-272}$ and may repel it, resulting in attenuation of the CD4$^+$ T cell response to this autoantigen. While a population of collagen-specific memory CD4$^+$ T cells may persist in the patient, those cells may no longer receive the necessary TCR signals required to maintain chronic joint inflammation.

The disclosed engineered HSCs will engraft in the bone marrow within days and begin to generate DRB1*0401$^{K71E}$-expressing myeloid cells within 10 days. In embodiments where the patients do not undergo immunosuppressive conditioning prior to administration of the disclosed engineered HSCs, they will retain acquired T and B cell immunity present before the procedure. In embodiments where patients are treated with non-myeloablative conditioning, using low-dose busulfan, patients may experience a brief period of neutropenia (7-10 days; low concentration of neutrophils, needed for mounting immune responses to infections, especially bacterial) and low platelet counts (20-30 days; possibly affecting blood clotting). These phenomena should not be life-threatening and severe adverse events (SAEs) are not expected.

Autoimmune Diseases Treatable With the Presently Disclosed Therapy

Rheumatoid arthritis (RA) is an autoimmune disease characterized by inflammation of the joint capsule synovia, resulting in an infiltration of macrophages, neutrophils, T cells and B cells that culminates in extensive joint destruction, disability and reduced quality of life. The persistent inflammation associated with RA also increases the risk of developing ischemic heart and respiratory disease, resulting in early mortality. RA occurs in approximately 1% of the world population, with an estimated 1.3 million affected in the US alone. RA occurs more frequently in women over the age of 40 and in long-term smokers. Billions of dollars of direct healthcare costs are associated with the treatment of RA annually, and total annual societal costs of RA (direct, indirect and intangible) are estimated to reach tens of billions of dollars in the US alone.

Behçet's syndrome is a chronic multisystemic inflammatory disorder characterized by relapsing and recurrent oral ulcers, genital ulcers, skin lesions, uveitis, and broader systemic manifestations, such as arthritis, and gastrointestinal or central nervous system involvement. The disease is categorized as a variable vessel vasculitis with multiple lesions in all sizes of arterial and venous vessels.

Birdshot uveitis (also known as Birdshot chorioretinopathy or Birdshot retinochoroidopathy) is a well-characterized form of autoimmune uveitis (inflammation of the uveal layer of the eye) mostly known for its ovoid light lesions, which appear 'shotgun pattern'-like distributed along the vascular arcades in the back of the eye (i.e., the 'fundus' of the eye where these lesions are visible by photography). Inflammation and extensive depigmentation of the choroid, macular edema, peripheral ischemia, degeneration of the retina, and the progressive formation of thin layer of scar tissue on the retina ("epiretinal membrane"), progressively impair vision in a substantial proportion of patients. Birdshot uveitis typically affects patients over 50 years of age of Western-European ancestry, with more women than men affected.

Celiac disease is a chronic immune-mediated enteropathy triggered by exposure to dietary gluten in genetically predisposed individuals (1). In celiac patients, the ingestion of gluten leads to the activation of both the innate and adaptive response of the immune system, with a subsequent chronic inflammation that determines changes in the mucosal structure including villous atrophy, crypt hyperplasia and lymphocyte infiltration. These changes in structure cause subsequent loss of function by the intestinal mucosa and the onset of symptoms brought by nutrient malabsorption.

Psoriasis is a chronic inflammatory disease mediated by T lymphocytes, with participation of dendritic cells. Genetic and environmental factors contribute or are required for the development of overt disease. The lesions are characterized by erythema and desquamation, configuring different clinical forms, from sharply delimited plaques to diffuse erythroderma. Up to 30% of patients may also have joint involvement, which may result, if untreated, in erosive disease and incapacity. It is considered a prevalent disease, affecting 2% of the population in Western countries.

Narcolepsy was first described by Westphal in 1877 and named by Gélineáu in 1880. After rapid eye movement (REM) sleep was discovered in 1953, several investigators studied sleep onset in patients with narcolepsy. Although healthy individuals typically enter their first REM sleep approximately 90 min after falling asleep, patients with narcolepsy frequently go directly into REM sleep at sleep onset. A malfunction of the mechanisms that regulate REM sleep can explain some of the symptoms of narcolepsy. Narcolepsy has no known cure at present. Although its symptoms can be managed with appropriate treatment, lifelong treatment is required for most patients.

Kawasaki disease (KD) is an acute systemic vasculitis that is a leading cause of acquired heart disease in children. The pathogenesis of KD remains unknown. It is likely that KD is caused by abnormal immune responses to unknown trigger(s) in genetically susceptible children.1 The HLA (human leukocyte antigen) genes, known as the most polymorphic gene in vertebrate animals, encode the protein on the cell-surface antigen-presenting proteins that is involved in the regulation of the immune system. The roles of HLA genes have been investigated in several immune-mediated vascular diseases, including Behçet disease, KD, and Wegener granulomatosis. A recent genome-wide association study demonstrated the significant association of HLA class II region (HLA-DQB2-DOB) with KD in a Japanese population.

Myasthenia gravis (MG), a rare disorder of the neuromuscular transmission, is increasingly acknowledged as a syndrome rather than a single disease. In the recent past, there has been an active search for new antigens in myasthenia gravis, whereas clinical and experimental studies have provided new insights into crucial pathways in immune regulation, which might become the targets of future therapeutics.

Systemic lupus erythematosus (SLE) is a severe autoimmune disease that involves multiple organ systems. Lupus nephritis (LN) is a complication of SLE and is associated with poor survival and high morbidity. Many genomic studies have been performed worldwide, and several histocompatibility leukocyte antigen (HLA) loci are linked to lupus susceptibility.

Crohn's disease (CD) has been known since 1932, when Crohn et al. reported fourteen cases of terminal ileitis. Crohn's disease is a relapsing inflammatory disease that mainly affects the gastrointestinal tract from mouth to anus. It involves any part of the gastrointestinal tract most commonly the terminal ileum or the perianal region in a non-continuous fashion.

Autoimmune neurology is an expanding field that has seen a huge development in recent years. Most of this progress is due to the discovery and characterization of autoantibodies (Ab) directed against antigens of the peripheral and/or central nervous system, and which are used as biomarkers of these diseases. Some of these Ab have allowed to better define already known entities, such as Ab against aquoporin-4 (anti-AQP4 Ab) in neuromyelitis optica (NMO).

Type 1 diabetes (T1D) is a multifactorial autoimmune disease that results in destruction of the insulin secreting R cells in the pancreas. Genome wide association studies have identified more than 50 loci linked to the risk of developing T1D. However, the inheritance of specific human leukocyte antigen (HLA) genes, such as DQ2 and DQ8, is most strongly linked to disease susceptibility.

Ankylosing spondylitis (AS) is a chronic inflammatory disease that results in immune-mediated arthritis of the spine and peripheral joints. The disease is more common in men and symptoms typically begin early in life. HLA-B*27:05 is strongly associated with AS but B*27:06 and B*27:09 are associated with resistance.

Multiple sclerosis (MS) is an autoimmune disease of the brain and central nervous system. In MS, the immune system attacks the myelin sheath that covers nerve fibers which can cause permanent damage or deterioration of the nerves. Susceptibility to MS is associated with the DRB1*15:01 allele.

Shown below at Table 1 are various HLA alleles associated with susceptibility to the above-described autoimmune diseases. Also shown at Table 1 are target amino acid positions that, when mutated to correspond to the amino acid at the same position in a resistant HLA allele, may aid in reducing or eliminating at least one symptom associated with the autoimmune disease. Table 1 also discloses specific mutations at the target amino acid position for treating the autoimmune disease.

Engineered HLA Molecules

Disclosed herein are various engineered HLA molecules. In some embodiments, the HLA molecule may be selected from one or more of H LA-A, HLA-B, HLA-C, HLA-DPA1, HLA-DPB1, HLA-DQA1, HLA-DQB1, HLA-DRB1, HLA-DRB3, HLA-DRB4, and HLA-DRB5.

In many embodiments the disclosed engineered HLA-A may include mutations at one or more of polymorphic positions selected from 9, 12, 17, 31, 35, 43, 44, 56, 62, 63, 65, 66, 67, 70, 73, 74, 76, 77, 79, 80, 81, 82, 83, 90, 95, 97, 99, 102, 105, 107, 109, 114, 116, 127, 142, 144, 145, 149, 150, 151, 152, 156, 158, 161, 163, 166, 167, 171, 184, and 186; specifically: 9, 31, 56, 62, 63, 66, 73, 77, 80, 81, 95, 97, 99, 114, 116, 150, 152, 156, and 171.

In many embodiments the disclosed engineered HLA-B may include mutations at one or more of polymorphic positions selected from 4, 9, 11, 12, 24, 30, 32, 33, 41, 45, 46, 52, 59, 62, 63, 65, 66, 67, 69, 70, 71, 73, 74, 76, 77, 80, 81, 82, 83, 90, 94, 95, 97, 99, 103, 109, 113, 114, 116, 131, 143, 145, 147, 152, 156, 158, 162, 163, 166, 167, 171, 177, 178, and 180; specifically: 9, 24, 33, 45, 46, 52, 59, 62, 66, 70, 73, 77, 81, 95, 97, 99, 114, 116, 143, 147, 152, 156, 163, 167, 171, and 178.

In many embodiments the disclosed engineered in HLA-C may include mutations at one or more of polymorphic positions selected from 4, 9, 11, 12, 24, 30, 32, 33, 41, 45, 46, 52, 59, 62, 63, 65, 66, 67, 69, 70, 71, 73, 74, 76, 77, 80, 81, 82, 83, 90, 94, 95, 97, 99, 103, 109, 113, 114, 116, 131, 143, 145, 147, 152, 156, 158, 162, 163, 166, 167, 171, 177, 178, and 180; specifically: 4, 24, 30, 33, 45, 52, 59, 62, 63, 66, 67, 70, 73, 74, 77, 80, 81, 95, 97, 99, 114, 116, 143, 147, 152, 167, and 171.

In many embodiments the disclosed engineered HLA-DQA1 may include mutations at one or more of polymorphic positions selected from 20, 26, 34, 40, 41, 44, 46, 47, 48, 50, 52, 53, 54, 55, 61, 64, 66, 69, 75, 76, and 80; specifically: 34, 44, 61, 64, 69, 76, and 80.

In many embodiments the disclosed engineered HLA-DQB1 may include mutations at one or more of polymorphic positions selected from 9, 13, 14, 26, 28, 30, 37, 38, 45, 46, 47, 52, 53, 55, 56, 57, 66, 67, 70, 71, 74, 75, 77, 84, 85, 86, 87, 89, and 90; specifically: 9, 26, 28, 30, 37, 38, 47, 53, 57, 67, 70, 71, 74, 86, 87, and 90.

In many embodiments the disclosed engineered HLA-DPA1 may include mutations at one or more of polymorphic positions selected from 11, 18, 28, 30, 31, 50, 72, 73, 83, and 96; specifically: 11, 28, 31, 72, 73, and 96.

In many embodiments the disclosed engineered HLA-DPB1 may include mutations at one or more of polymorphic positions selected from 8, 9, 11, 33, 35, 36, 55, 56, 57, 65, 69, 72, 76, 84, 85, 86, 87, and 91; specifically: 9, 11, 33, 35, 36, 55, 56, 65, 69, 72, 76, 84, 87, and 91.

In many embodiments the disclosed engineered HLA-DRB1, HLA-DRB3, HLA-DRB4, and HLA-DRBS may include mutations at one or more of polymorphic positions selected from 9, 10, 11, 12, 13, 14, 16, 25, 26, 28, 30, 31, 32, 33, 37, 38, 40, 47, 57, 58, 60, 67, 70, 71, 73, 74, 77, 78, 85, and 86; specifically 9, 11, 13, 26, 28, 30, 32, 33, 37, 38, 40, 47, 57, 58, 67, 71, 74, 78, 85, and 86.

In many embodiments, the disclosed methods may create one or more engineered HLA alleles from one or more susceptible HLA alleles selected from:

A*02, A*03, A*29;
B*07, B*08, B*08:01, B*27, B*27:03 B*27:05, B*27:09, B*51, B*54:01, B*57;
C*06, C*18;
DPA1*02:01;
DPB1*13:01;
DQ;
DQA1*02:01, DQA1*03:01, DQA1*05, DQA1*05:01;
DQB1*02, DQB1*02:01, DQB1*03, DQB1*03:01, DQB1*03:02, DQB1*06:02;
DR;
DRB1*01:03, DRB1*04, DRB1*07, DRB1*07:01; DRB1*15, DRB1*15:01; DRB1*16; DRB1*08, DRB1*08:01, DRB1*11:04.

Disclosed herein are various mutations at target amino acid positions within a mature HLA protein sequence. In many embodiments, the mutations are selected based on the criteria disclosed above. In some embodiments, specific allelic mutations may be selected based on the autoimmune disease or disorder to be treated. For example, treatments for: Type 1 diabetes may include mutations in DQB1*02:01 at A57D (where the native A, alanine, at position 57 is mutated to D, aspartic acid) and/or DQB1*03:02 of A57D; rheumatoid arthritis may include one or more mutations in DRB1*04:01 of L67I, Q70D, L67I+Q70D, K71E, K71R, L67F, A74L, L67F-A74F, G86V, G86M, G86L, G86F, and A74E; in DRB1*04:05 of R71E, in DRB1*01:01 of L67I, Q70D, R71E, V85A, and G86V, in DRB1*04:03 of R71E, in DRB1*04:04 of R71E, in DRB1*04:08 of R71E; multiple sclerosis may include one or more mutations in DRB1*15:01 of F47Y, A71R, A71R-V86G, V86L, and V86F; celiac disease may include one or more mutation in DQB1*02:01 of K71E, and K71T; neuromyelitis optica may include one or more mutation in DRB1*03:01 of V86L and V86M; Behçet's syndrome may include one or more mutation in B*51; psoriasis my include one or more mutations in C*06; B*57, and C*06; C*18, A*02.

Methods of Treatment

The present disclosure includes methods of treating or preventing an autoimmune disease by administering engineered APCs and/or APC precursors, i.e., engineered HSCs. In contrast to, for example, T cell therapies, the engineered cell compositions disclosed herein are provided to reduce or prevent T cell-mediated rejection responses, rather than elicit them. As such, the engineered compositions provide a relatively broad therapeutic window, while targeting the subject's specific condition. In certain embodiments, the methods comprise administration of a therapeutically effective amount of the engineered HSCs.

In certain embodiments, subjects receive $1\times10^6$, $2\times10^6$, $3\times10^6$, $4\times10^6$, $5\times10^6$, for example 1-5 million, or more engineered, autologous, HSCs per kg of body weight, such as by intravenous administration, in one or more doses, over one or more days.

The methods of the present disclosure include the production and administration of engineered HSCs as described. In certain embodiments, including presently certain embodiments, the engineered HSCs are autologous to the subject to be treated. Accordingly, some embodiments include isolating HSCs or HSC precursors from the subject, ex vivo engineering of the isolated HSCs, optional selection and/or expansion of the engineered HSCs, and administration of the engineered autologous HSCs to the subject.

HSCs or precursors can be isolated from subjects by methods known in the art. For example, PBMCs and/or bone marrow cells can be mobilized, isolated, and HSCs purified based on expression of CD34. HSC subpopulations can be selected based on expression of additional antigens as desired. Additionally, or alternatively, HSCs can be produced from precursor cells, such as pre-harvested stem cells or de-differentiated cells of the subject, as known in the art. Although autologous HSCs are presently certain, the present disclosure is not limited to autologous HSCs. For example, in certain embodiments, non-autologous (donor) HSCs engineered to express a desired HLA without expressing proteins capable of eliciting non-self-responses are provided.

Certain embodiments of the methods provided herein also include pre-conditioning, such as non-myeloablative conditioning, and/or post-treatment interventions, such as to promote engraftment of the engineered HSCs. Additionally, or alternatively, HSC engineering according to the present disclosure can be performed in vivo, such as by administration of viral vectors encoding, inter alia, expressed autoimmunity resistance alleles and/or gene editing constructs as described herein. Moreover, although reference is primarily made herein to single engineered HSC populations, multiple HSC compositions having discrete HLA allelic modifications may also be provided, separately or sequentially, such as in instances of multi-allelic autoimmune disease.

HLA Allele Engineering

The present disclosure includes systems, constructs, and techniques for gene editing, and the application of same to provide resistance to autoimmunity. In particular, certain embodiments of the present disclosure include constructs, systems, and vectors for HLA allele engineering as disclosed herein.

Many gene editing systems are available, suitable, and well-characterized in the art. For example, in certain embodiments, CRISPR-Cas systems containing a DNA-targeting polynucleotide complementing the HLA allele to be modified and a CRISPR-associated nuclease, such as Cas9, are provided. Related CRISPR-Cas9 systems for treatment of RNA are disclosed in PCT/US2018/029302, published as WO2019200635, hereby incorporated by reference herein in its entirety.

In other embodiments, CRISPR systems containing, for example, CasX, Cas12a, Cas13, or MAD7 are provided for HSC HLA allele engineering, for example as in PCT/US2019/043066, published as WO/2020/023529, PCT/US2018/028919, published as WO/2018/195545, etc. Certain CRISPR systems can be selected on the basis of protospacer-adjacent motif (PAM) specificity, allowing targeting of almost all genomic sequences, on-target selectivity, efficiency in human HSCs, and other considerations. In alternative embodiments, TAL effector nucleases (TALENs) or zinc finger nucleases (ZFNs) are employed for HLA allele engineering as disclosed at Nucleic Acid Res. 2011 Sep. 1; 39 (17):7879).

In further embodiments, HLA allele engineering is performed with fusion proteins, such as enzymatically inactive dCas9-based fusion proteins. These systems combine the programmable DNA-targeting capability associated with CRISPR with additional on-target selectivity and/or functional capabilities of other gene engineering platforms. For example, in certain embodiments, HLA allele engineering is performed with systems including a Cas-CLOVER fusion, as described in PCT/US2015/036226.

In additional embodiments, including certain certain embodiments, HLA allele engineering is performed with a nucleobase editing system. For example, certain embodiments provide an HLA-allele targeting polynucleotide and a fusion protein comprising dCas9 and a nucleobase editing enzyme, such as a deaminase. Such embodiments advantageously result in generation of specific point mutations sufficient to alter the amino acid encoded at the targeted HLA allele codon without resulting in or requiring DNA double-strand breakage and repair.

The principles of design for CRISPR-Cas systems and vectors for same are well known in the art, and in the present context essentially require only selection of a sequence complementary to the portion of the HLA allele to be engineered. The same is true with respect to CRISPR-Cas fusion-based systems including the examples described. The production of genetic engineering platforms involving protein-based DNA targeting, such as TALENs and zinc fingers, is also well-characterized, and suitable such systems for use with the present disclosure can be generated with no more than routine procedures and experimentation.

In additional and alternative embodiments, the HLA allele engineering systems include a homologous repair template. For example, in certain embodiments, the entire gene for the susceptible HLA allele, within the MHC locus, can be excised and replaced with the engineered HLA allele. In many embodiments, the gene coding for the susceptible HLA allele may be disrupted by insertion of the engineered HLA allele, which may be as an uninterrupted nucleic acid with the engineered HLA allele's cDNA sequence.

HLA allele engineering, and the systems therefore, according to the present disclosure can also include, for example, vectors, such as retroviral vectors for expression of the HLA allele engineering constructs disclosed. Transient transfection techniques and systems therefore can also be applied. Accordingly, the present disclosure is not limited by or to specific HLA allele engineering constructs or systems. In certain embodiments, including some certain embodiments, HLA allele engineering according to the table below is provided.

TABLE 1

| Autoimmune Disease | Engineered Allele | Target Amino Acid | Mutation |
|---|---|---|---|
| Type 1 Diabetes | DQB1*02:01 | 57 | A57D |
|  | DQB1*03:02 | 57 | A57D |
| Rheumatoid Arthritis | DRB1*04:01 | 67 | L67I, |
|  |  | 70 | Q70D |
|  |  | 71 | K71E; K71R, |
|  |  | 67 | L67F |
|  |  | 74 | A74L |
|  |  | 74 | A74E |
|  |  | 86 | G86L; G86F; G86V; G86M |
|  | DRB1*04:05 | 71 | R71E |
|  | DRB1*01:01 | 67 | L67I |
|  |  | 70 | Q70D |
|  |  | 71 | R71E |
|  |  | 85 | V85A |
|  |  | 86 | G86A |
|  | DRB1*04:03 | 71 | R71E |
|  | DRB1*04:04 | 71 | R71E |
|  | DRB1*04:08 | 71 | R71E |
| Ankylosing Spondylitis | B*27:05 | 116 | D116H |
| Multiple Sclerosis | DRB1*15:01 | 47 | F47Y |
|  |  | 71 | A71R |
|  |  | 86 | V86L; V86F |
| Celiac Disease | DQB1*02:01 | 71 | K71E; K71T |
| Neuromyelitis Optica | DRB1*03:01 | 86 | V86L; V86M |
| Behç et's Syndrome | B*51 |  |  |
| Psoriasis | C*06 |  |  |
|  | B*57 |  |  |
|  | C*18 |  |  |
|  | A*02 |  |  |

Engineered Hematopoietic Cells

Autologous immune cells may be engineered using various systems as disclosed herein, for example cells may be engineered to carry and express engineered HLA genes and molecules with various viral vectors and/or nucleases capable of genomic editing. Various protocols well known to those of skill in the art may allow for screening of the genomes of manipulated cells to assess the frequency and/or position of viral insertions, double strand breaks in DNA (DSBs) or other potentially mutagenic events (Li H, Haurigot V, Doyon Y, et al. In vivo genome editing restores haemostasis in a mouse model of haemophilia. Nature. 475(7355):217-21, 2011). In many embodiments, the systems may be useful in removing and or preventing expression of the susceptible HLA allele, as well as inserting the engineered HLA allele into the same locus. In many embodiments, the engineered HLA allele is expressed from a cDNA sequence. Particular specific cDNA sequences of susceptible HLA alleles and engineered HLA alleles are provided at FIG. 30, and SEQ ID NOs:59-96.

Therapeutically relevant levels of genetically modified engineered hematopoietic stem cells needed to effect clinical outcomes may be more readily achieved by expansion of large populations of cells ex vivo and reintroduction(s) into the patient.

Definitions

The following terms and phrases include the meanings provided below. The provided definitions are intended to aid in describing particular embodiments, and are not intended to limit the claimed compositions, methods, compounds, systems, and therapies. Unless otherwise defined, all technical and scientific terms used herein have the same meaning as commonly understood by one of ordinary skill in the art to which this disclosure belongs. If there is an apparent discrepancy between the usage of a term in the art and its definition provided herein, the definition provided within the specification shall prevail.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

"Amino acid identity," "residue identity," "identity," and the like, as used herein refers to the structure of the functional group (R group) on the poly peptide backbone at a given position. Naturally occurring amino acid identities are (name/3-letter code/one-letter code): alanine/ala/A; arginine/arg/R; asparagine/asn/N; aspartic acid/asp/D; cysteine/cys/C; glutamine/gln/Q; glutamic acid/glu/E; glycine/gly/G; histidine/his/H; isoleucine/ile/I; leucine/leu/L; lysine/lys/K; methionine/met/M; phenylalanine/phe/F; proline/pro/P; serine/ser/S; threonine/thr/T; tryptophan/trp/W; tyrosine/tyr/Y; and valine/val/V. Amino acid positions, as used herein to designate a position on an HLA molecule reference the mature protein sequence as provided at website ebi.ac.uk/ipd/imgt/hla. Thus, for example, DRB1*04:01$^{K71E}$, refers to position 71 in the mature protein of allele *04:01 of DRB1, wherein the native identity is lysine, K, and the non-native, edited identity is glutamic acid, E.

"Autoimmune disease, disorder, or condition" refers to a disease, disorder, or condition in which the immune system produces an immune response (e.g., a B cell or a T-cell response) against an endogenous antigen, leading to injury one or more tissues. Such diseases include, but are not limited to, rheumatoid arthritis (RA), celiac disease, diabetes mellitus type 1, systemic lupus erythematosus (SLE), multiple sclerosis (MS), myelin oligodendrocyte glycoprotein antibody disorders (MOGAD), myasthenic syndromes and neuromyelitis optica (NMO), ankylosing spondylitis, Behçet's syndrome, Birdshot uveitis, narcolepsy, narcolepsy type 1 (NT1; previously termed narcolepsy with cataplexy), Kawasaki disease, Crohn's disease, psoriasis, dermatomyositis (DM), Addison's disease, irritable-bowl syndrome (IBS), Graves' disease, Henoch-Schönlein purpura (HSP), sarcoidosis, Sjögren's syndrome, eosinophilic granulomatosis with polyangiitis, Hashimoto's disease, idiopathic thrombocytopenic purpura, polymyositis (PM), paraneoplastic neurological syndromes (PNS), autoimmune encephalitis, lupus nephritis (LN), myasthenia gravis (MG), psoriatic arthritis, graft rejection, graft-versus-host disease (GVHD), an unwanted delayed-type hypersensitivity reaction, T-cell mediated pulmonary disease, neuritis, vitiligo, autoimmune pancreatitis, inflammatory bowel diseases, ulcerative colitis, glomerulonephritis, scleroderma, autoimmune thyroid diseases, asthma, autoimmune uveoretinitis, pemphigus vulgaris, pulmonary fibrosis or idiopathic pulmonary fibrosis, primary biliary cirrhosis, and pernicious anemia. When used herein, the terms "disease," "disorder," and "condition" are interchangeable.

"HLA" or "human leukocyte antigen" refers to human gene that encodes a major histocompatibility complex (MHC) protein on the surface of cells that are responsible for regulation of the immune system. "HLA-I" or "HLA class I" refers to human MHC class I gene including HLA-A, HLA-B, HLA-C, HLA-E, HLA-F, HLA-G, and β2-microglobulin loci. "HLA-II" or "HLA class II" refers to human MHC class II gene including HLA-DPA1, HLA-DPB1, HLA-DQA1, HLA-DQB1, HLA-DRA1, HLA-DRB1, HLA-DRB3, HLA-DRB4, HLA-DRB5, HLA-DM, HLA-DOA, and HLA-DOB loci.

"Intravenous" administration refers to administering a drug or therapy, for example one or more of the disclosed engineered HSCs into a vein of a patient, e.g. by infusion (slow therapeutic introduction into the vein) for therapeutic purposes. "Infusion" or "infusing" refers to the introduction of a drug, therapy, and/or solution into the body of a patient through a vein for therapeutic purposes. Generally, this may be accomplished via an intravenous (IV) bag.

An "intravenous bag" or "IV bag" is a bag that can hold a solution which can be administered via the vein of a patient. In one embodiment, the solution may be a saline solution (e.g. about 0.9% or about 0.45% NaCl), or any therapeutically useful solution for administration of the disclosed engineered HSCs.

By "co-administering" is meant intravenously administering two (or more) drugs during the same administration, rather than sequential (i.e. one after the other) infusions of the two or more drugs. Generally, co-administration may involve combining the two (or more) drugs into the same IV bag, or adding the second drug to an I.V. bag comprising the first drug, prior to co-administration thereof.

The term "amelioration" as used herein refers to any improvement of a disease state (for example improvement of a symptom of an autoimmune disease, for example a symptom of rheumatoid arthritis) of a patient suffering therefrom, by the administration of one or more treatments, drugs, and/or compositions, according to the present disclosure, to such patient or subject in need thereof. Such an improvement may be seen as a slowing down of the progression, or a cessation of the progression, of the disease of the patient, a decrease in the frequency, duration, and/or severity of any symptom, and/or an increase in frequency or duration of disease symptom-free periods or a prevention of impairment or disability due to the disease.

"Antigen" refers to a compound, composition, substance, protein, peptide, nucleic acid, nucleo-peptide, etc., whether native, modified, or synthetic, that can stimulate the production of antibodies or a T-cell response in an animal, including compositions that are injected or absorbed into an animal or modified by an animal. As used herein, an antigen may be defined by its ability to bind within the antigen binding cleft of a native or engineered HLA molecule. In some aspects, an antigen may react with one or more products of specific humoral or cellular immune system. The term "antigen" includes all related antigenic epitopes and antigenic determinants.

"Antigen Presenting Cell," (APC), refers to a cell that can process and present antigenic compounds, including peptides, in association with class I or class II MHC molecules to a T-cell. In many cases, the APC can deliver a co-stimulatory signal necessary for T-cell activation. Typical APCs include monocytes, macrophages, dendritic cells, B cells, thymic epithelial cells, and vascular endothelial cells.

"Antigen binding region," "antigen binding cleft," "antigen binding groove," "antigen cleft," and the like refer to the region of the HLA molecule that interacts with and binds the antigen presented by the HLA. As discussed in Nguyen, A. et al., "The pockets guide to HLA class I molecules," Biochemical Society Transactions (2021) 49 2319-2331, which is incorporated herein, the HLA-I peptide binding cleft is closed at the N and C termini (restricting the length of peptide antigens to about 8-10 amino acids), while the ends of the HLA-II cleft is open, allowing for longer peptide antigens (for example >13 amino acids in length). K. J. Smith et al., "Crystal Structure of HLA-DR2 (DRA*0101, DRB1*1501) Complexed with a Peptide from Human Myelin Basic Protein," Vol. 188, No. 8, Oct. 19, 1998, 1511-1520, which is incorporated herein, discuss binding cleft and pocket structures in HLA Class II molecules. In general, specific binding pockets bind specific components of an antigen bound within the antigen binding cleft. As used herein, the 'bottom' of the cleft may be the surface of the cleft nearest the core of the molecule and farthest from the TCR interface, the cleft may have sides extending generally upward from the bottom toward the TCR interface. In most embodiments, the antigen is a peptide and the components are amino acids. Three-dimensional structures of HLA molecules are available to the skilled artisan for reference (for example at ebi.ac.uk/ipd/imgt/hla), allowing for identification of the antigen binding region for any HLA molecule.

cDNA (complementary DNA) are poly nucleic acids lacking internal, non-coding segments (introns) and regulatory sequences that determine transcription. cDNA is synthesized in the laboratory by reverse transcription from messenger RNA extracted from cells.

The terms "dosage" or "dose" as used herein denote any form of the active ingredient formulation that contains an amount sufficient to produce a therapeutic effect with a single administration.

The phrase "therapeutically effective amount" means an amount of a drug, composition, compound, treatment, or therapy of the present disclosure that alone, or in combination with other therapies, (i) treats the particular disease, condition, or disorder, (ii) attenuates, ameliorates, or eliminates one or more symptoms of the particular disease, condition, or disorder, or (iii) prevents or delays, the onset of one or more symptoms of the particular disease, condition, or disorder described herein. The term can encompass an amount that improves overall therapy, reduces, or avoids symptoms or causes of disease, or enhances the therapeutic efficacy or synergizes with another therapeutic agent. In the case of the targeted autoimmunity, the therapeutically effective amount of the drug, composition, compound, treatment, or therapy may reduce the number of reactive or active immune cells, such as T-cells; reduce inflammation; inhibit (i.e., slow to some extent and preferably stop) immune-based attack or degradation of cells, tissues, or organ; and/or partially or fully relieve one or more of the symptoms associated with the autoimmune response.

"Immune response" refers to a response of a cell of the immune system, such as a B cell, or a T-cell, to a stimulus. In one embodiment, the response is specific for a particular antigen (an "antigen-specific response"). In another embodiment, an immune response is a T-cell response.

"Autoimmune response" refers to an immune response directed against an auto- or self-antigen. In many cases, the autoimmune response is a result of self-reactive T cells, which recognize one or more auto- or self-antigens. The immune system ordinarily functions to direct protective immune responses against microorganisms and other harmful foreign materials. In an autoimmune response, antigens present in a patient's own tissues become targets for autoreactive immune responses that cause cell, tissue, or organ deterioration, destruction, or dysfunction.

The term "mammal" includes, but is not limited to, humans, mice, rats, guinea pigs, monkeys, dogs, cats, horses, cows, pigs and sheep.

A "patient" or "subject" includes a mammal or animal, such as a human, cow, horse, sheep, lamb, pig, chicken, turkey, quail, cat, dog, mouse, rat, rabbit, or guinea pig. The animal can be a mammal such as a non-primate or a primate (e.g., monkey and human). In one embodiment, a patient is a human, such as a human infant, child, adolescent, or adult of any or indeterminant sex.

"Pharmaceutically acceptable composition" is an organic or inorganic solution for maintaining or supporting the viability of a mammalian cell.

"Prevention" as used herein means the avoidance of the occurrence or of the re-occurrence of a disease, disorder, or condition as specified herein, by the administration of a composition, compound, treatment, or therapy according to the present disclosure to a subject in need thereof.

"Recombinant" refers to a nucleic acid or polypeptide that has a sequence that is not typically found or expressed in a patient or has a sequence that is the result of artificial manipulation, such as mutation of one or more nucleic acids or amino acids. Artificial manipulation may be accomplished by chemical synthesis or, more commonly, by the editing (insertion, deletion, mutation, etc.) of isolated segments of nucleic acids, e.g., by genetic engineering techniques.

Similarity between amino acid or peptide sequences is expressed in terms of the similarity between two sequences, otherwise referred to as sequence identity. Sequence identity is frequently measured in terms of percentage identity (percentage of identical residues for peptides or bases for nucleic acids; or similarity or homology); the higher the percentage, the more similar the two sequences are. Complete identity is 100% identical over a given sequence, for example 50, 100, 150, or 200 bases or residues.

The term "specifically binds" is "antigen specific," is "specific for," "selective binding agent," "specific binding agent," "antigen target" or is "immunoreactive" with an antigen refers to an molecule or polypeptide that binds a target antigen with greater affinity than other antigens of similar sequence. It is contemplated herein that the antigen specifically binds HLA molecules at the surface of an APC.

"Subject in need," "patient" or those "in need of treatment" include those already with existing disease (i.e. autoimmune disease, for example, without limitation, rheumatoid arthritis (RA), celiac disease, diabetes mellitus type 1, systemic lupus erythematosus (SLE), multiple sclerosis (MS), myelin oligodendrocyte glycoprotein antibody disorders (MOGAD), myasthenic syndromes and neuromyelitis optica (NMO), ankylosing spondylitis, Behçet's syndrome, Birdshot uveitis, narcolepsy, narcolepsy type 1 (NT1; previously termed narcolepsy with cataplexy), Kawasaki disease, Crohn's disease, psoriasis, dermatomyositis (DM), Addison's disease, irritable-bowel syndrome (IBS), Graves' disease, Henoch-Schönlein purpura (HSP), sarcoidosis, Sjögren's syndrome, eosinophilic granulomatosis with polyangiitis, Hashimoto's disease, idiopathic thrombocytopenic purpura, polymyositis (PM), paraneoplastic neurological syndromes (PNS), autoimmune encephalitis, lupus nephritis (LN), myasthenia gravis (MG), psoriatic arthritis, graft rejection, graft-versus-host disease (GVHD), an unwanted delayed-type hypersensitivity reaction, T-cell mediated pulmonary disease, neuritis, vitiligo, autoimmune pancreatitis, inflammatory bowel diseases, ulcerative colitis, glomerulonephritis, scleroderma, autoimmune thyroid diseases, asthma, autoimmune uveoretinitis, pemphigus vulgaris, pulmonary fibrosis or idiopathic pulmonary fibrosis, primary biliary cirrhosis, and pernicious anemia), as well as those at risk of or susceptible to the disease. The terms also include human and other mammalian subjects that receive either prophylactic or therapeutic treatments as disclosed herein.

"Tolerance" refers to a diminished or absent capacity to make a specific immune response to an antigen. Tolerance is often produced as a result of contact with an antigen in the presence of a two domain MHC molecule, as described herein. In one embodiment, a B cell response is reduced or does not occur. In another embodiment, a T-cell response is reduced or does not occur. Alternatively, both a T-cell and a B cell response can be reduced or not occur.

The terms "treat," "treating," and "treatment" refer to eliminating, reducing, suppressing, or ameliorating, either temporarily or permanently, either partially or completely, a clinical symptom, manifestation or progression of an event, disease or condition associated with immune disorders and diseases described herein. As is recognized in the pertinent field, methods and compositions employed as therapies may reduce the severity of a given disease state but need not abolish every manifestation of the disease to be regarded as useful. Similarly, a prophylactically administered treatment need not be completely effective in preventing the onset of a condition to constitute a viable prophylactic method or agent. Simply reducing the impact of a disease (for example, as disclosed herein, reducing inflammation, T-cell activation, etc. and/or reducing the number or severity of associated symptoms, or by increasing the effectiveness of another treatment, or by producing another beneficial effect), or reducing the likelihood that the disease will occur or worsen in a subject, is sufficient. One embodiment of the present disclosure is directed to a method for determining the efficacy of treatment comprising administering to a patient therapeutic treatment in an amount, duration, and repetition sufficient to induce a sustained improvement over pre-existing conditions, or a baseline indicator that reflects the severity of the particular disorder.

As used herein, the terms "protein" and "polypeptide" are used interchangeably to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

An amino acid within an HLA molecule may be substituted to create an engineered HLA molecule. The amino acid (aa or a.a.) residue can be replaced by a residue having similar physiochemical characteristics, that is a 'conservative substitution'—e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, for example based on size, charge, polarity, hydrophobicity, chain rigidity/orientation, etc., are well known in the art of protein engineering. Polypeptides comprising conservative amino acid substitutions can be tested in any one of the assays described herein to confirm that a desired activity, e.g. binding, specificity, and/or function of a native or reference polypeptide is achieved.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: leucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

"T-cell" refers to immune cells that have matured in the thymus. An activated T-cell is a T-cell that has left Go and is synthesizing DNA, upregulating CD25, and/or up-regulating CD "T-cell receptor," or "TCR," as used herein refers to a cell surface protein on T-cells that recognizes/interacts with an HLA molecule on an APC.

"T-cell receptor:HLA binding interface," T-cell receptor binding interface," "TCR:HLA binding interface," "TCR: HLA interface," as used herein refers to the surface of the TCR and the surface of the HLA molecule in close proximity during TCR:HLA binding, in most cases, the TCR:HLA binding interface does not include amino acids within the antigen binding cleft of the HLA that are not in direct contact with the TCR.

"Variant," as used herein refers to a polypeptide, nucleic acid, gene, sequence, or molecule that is substantially homologous to a naturally occurring or reference member, but which is different from that of the native or reference member because of one or a plurality of deletions, insertions, substitutions, molecules, expression levels, etc. Variant polypeptide-encoding DNA sequences encompass sequences that comprise one or more additions, deletions, or substitutions of nucleotides when compared to a native or reference DNA sequence, but that encode a variant protein or fragment thereof. A wide variety of cloning, PCR-based site-specific mutagenesis, and genomic editing approaches are known in the art, and can be applied by the ordinarily skilled artisan.

Variant HLA genes and molecules include those naturally occurring variants, as listed at the IPD-IMGT/HLA Database (website ebi.ac.uk/ipd/imgt/hla; the "IPD Database"). For example, HLA-A Variants include all HLA-A alleles from *01 through to *80, listed at the IPD Database.

Variant amino acid or nucleic acid sequences can be at least 70%, at least 75%, at least 80%, at least 85%, at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and variant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and understood by those of skill in the art.

"Nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA, cDNA, or vector DNA. Suitable RNA can include, e.g., mRNA.

"Expression" as used herein, refers to cellular processes involved in producing, displaying (e.g., on or at a cell's surface/outer membrane), or secreting RNA and proteins including where applicable, but not limited to, for example, transcription, transcript processing, translation and protein folding, modification and processing. Expression can refer to the transcription and stable accumulation of sense (e.g., mRNA) or antisense RNA derived from a nucleic acid fragment or fragments and/or to the translation of mRNA into a polypeptide.

"Vector" refers to a nucleic acid molecule which is capable of transporting another nucleic acid linked, typically covalently using gene engineering methods, thereto. One type of vector is a "plasmid," which refers to circular double-stranded DNA into which an additional DNA segment can be ligated. Another type of vector is a phage vector. Yet another type of vector is a viral vector, where an additional DNA segment can be ligated into the viral genome. Certain vectors are capable of autonomous replication in a host cell into which they are introduced (for example, bacterial vectors having a bacterial origin of replication and episomal mammalian vectors). Other vectors (for example, non-episomal mammalian vectors) can be integrated into the genome of a host cell upon introduction into the host cell, and thus are replicated along with the host genome. In addition, certain vectors are capable of directing expression of genes to which they are operatively linked. Such vectors are referred to herein as "recombinant expression vectors" or simply "expression vectors." In general, expression vectors useful in recombinant DNA techniques are often in the form of plasmids. In the present specification, "plasmid" and "vector" may be used interchangeably as the plasmid is the most commonly used form among vectors.

"Engineered" as used herein may refer to the aspect of having been manipulated by human intervention. Disclosed herein are engineered cells, HSCs, peptides, polypeptides, proteins, molecules, HLA proteins, nucleic acids, genes, etc. In one example, an HLA protein is considered to be "engineered" when at least one aspect of the polypeptide, e.g., its sequence, has been intentionally manipulated by human intervention (directly or indirectly) to differ from the aspect as it exists in a patient/subject or in nature. As is common practice and is understood by those in the art, progeny of an engineered cell are typically still referred to as "engineered" even though the actual manipulation was performed on a prior entity. In contrast, "native" or "wild-type" as used herein refers to un-engineered and/or un-modified cells, genes, proteins, nucleic acids, nucleic acid sequences, alleles, and amino acid sequences, and portions thereof.

Abbreviations: ACR, American College of Rheumatology; ADA, Anti-drug Antibody; AE, Adverse Event; ANC, Absolute Neutrophil Count; APC, Antigen Presenting Cell; AUC, Area Under the Concentration-Time Curve; DMARD, Disease-Modifying Anti-Rheumatic Drug; CBC, Complete Blood Count; cGCP, Current Good Clinical Practices; CD, Cluster of Differentiation; CMP, Complete Metabolic Panel; cGMP, Current Good Manufacturing Practices; cGTP, Current Good Tissue Practices; DC, Dendritic cell; DM, dermatomyositis; DMSO, Dimethyl Sulfoxide; DRB1*04:01, HLA DR Beta 1 chain of HLA, 04:01 Allele; E, Glutamic Acid; EBMT, European Bone Marrow Transplant Registry; G-CSF, Granulocyte Colony Stimulating Factor; GVHD, graft-versus-host disease; GWAS, Genome Wide Association Study; HLA, Human Leukocyte Antigen; HLA-DRB1, Human Leukocyte Antigen—DR Beta 1; HSA, Human Serum Albumin; HSC, Hematopoietic Stem Cell; HSP, Henoch-Schönlein purpura; IBS, irritable-bowel syndrome; IL, Interleukin; IV, Intravenous; K, Lysine; LN, lupus nephritis; MG, myasthenia gravis; MHC II, Major Histocompatibility Complex Class II (HLA in Humans); MOGAD, myelin oligodendrocyte glycoprotein antibody disorders; MS, multiple sclerosis; MTX, Methotrexate; NIS, National Inpatient Sample Dataset; NMO, neuromyelitis optica; NSAIDs, Non-Steroidal Anti-Inflammatory Drugs; NT1, narcolepsy type 1; PNS, paraneoplastic neurological syndromes; PM, polymyositis; RA, rheumatoid arthritis; SC, Subcutaneous; SAE, Serious Adverse Event; SLE, systemic lupus erythematosus; TCR, T Cell Receptor; TNF, Tumor Necrosis Factor.

"Susceptible HLA allele," "susceptibility allele," and the like as used herein refers to a given HLA allele that is associated with susceptibility to one or more autoimmune diseases in a given population.

"Resistant HLA allele," "resistance allele," and the like as used herein refers to a given HLA allele that is associated with resistance to one or more autoimmune diseases in a given population.

"Genome" as used herein refers to all genetic information of an organism, including both coding (i.e. genes) and noncoding deoxyribonucleic acids (DNA). "Genomic sequence" is the nucleotide sequence of the genome's DNA. "native genome" as used herein refers to refers to the original genomic sequence of an individual, such as a subject or patient, before any modification or engineering as described herein.

Certain terms referring to like subject matter may be used interchangeably herein. For example, reference to HLA proteins encoded by a specific allele of a specific gene may be identified with reference to the HLA allele. Similarly, specific codons in an HLA allele may be identified with reference to the amino acid encoded thereby. For example, a specific position in the amino acid sequence of an HLA protein encoded by an HLA allele may be identified by reference to the corresponding position in the HLA allele, and vice versa.

EXAMPLES

Example 1—Materials and Methods

Cell Lines

Figure 30:
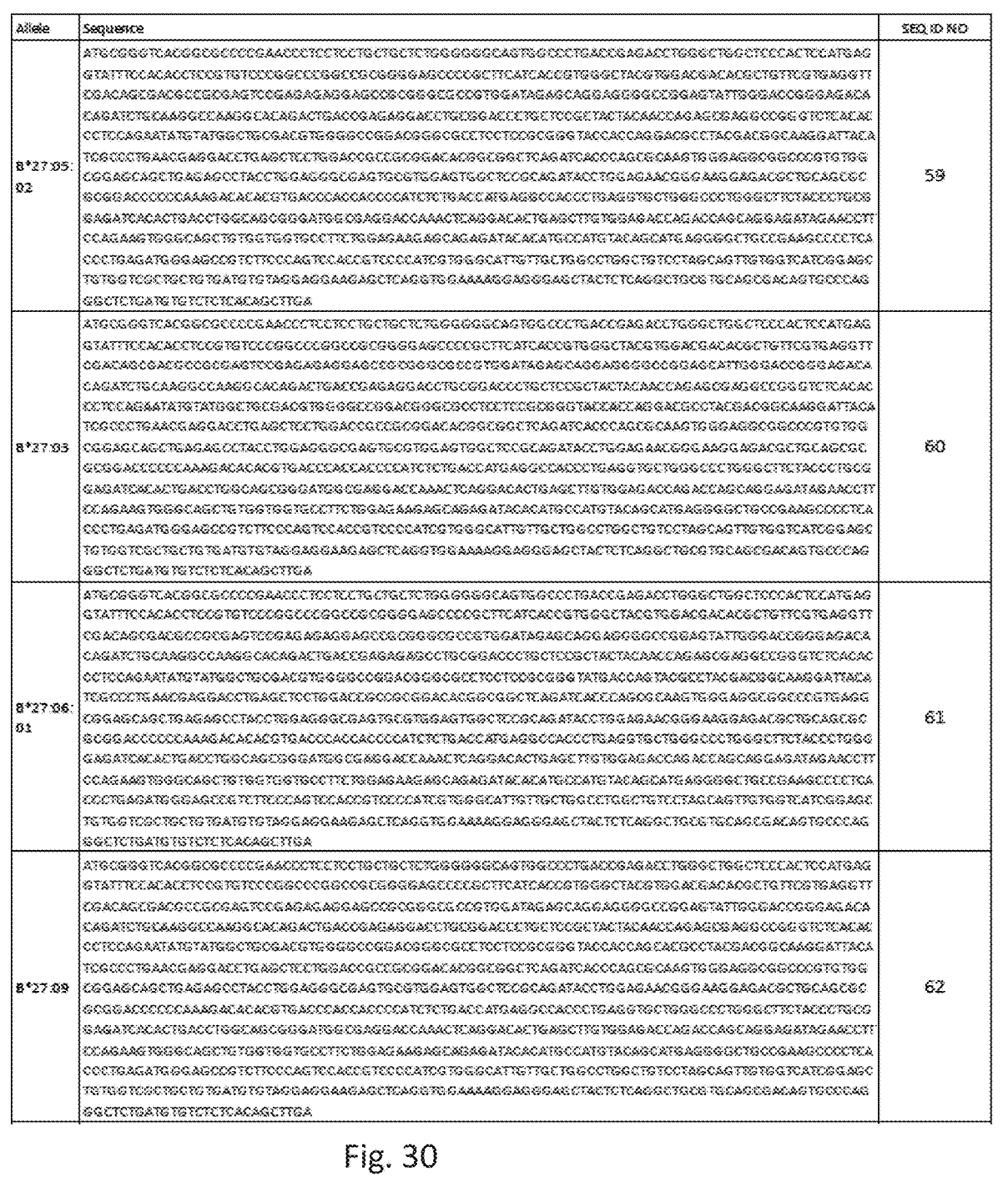

Briefly, cDNA expression constructs were obtained either by cloning the allele of interest directly from cells expressing that allele, or by obtaining 'gBlock' sequences (based on IPD-IMGT/HLA Database sequences, available at website ebi.ac.uk/ipd/imgt/hla/) from Integrated DNA Technologies (Coralville, IA). Various gBlock sequences, with RE sites are shown at FIG. 30. For testing, cDNA was cloned into a murine stem cell virus (MSCV) plasmid for retroviral transduction and expression. Various alleles were individually packaged as retrovirus by transient transfection of Phoenix 293T cells with GFP+MSCV plasmids as previously described (Bowerman 2011). HLA Class II proteins were expressed in human class II negative T2 cell line (T2 Parent). Below is described class II expression.

RNA was isolated from individuals expressing DRB1*03:01, DRB3*02:02, DQA1*05:01, DQB1*02:01, DQA1*03:01, DQB1*03:02, DRB1*15:01, DQA1*01:02, or DQB1*06:02, and complementary DNA (cDNA) for each individual HLA-DR, DQA1 or DQB1 allele was made. HLA-DRB1*04:01, DRB3*03:01, DRB4*01:03, and DRB5*01:01 T2 cell lines were made previously (Anderson et al. 2016). cDNA sequences for DRB1*11:03, DRB3*01:01, DQA1*05:05, and DQB1*03:01 were obtained from the IPD-IMGT/HLA Database (website ebi.ac.uk/ipd/imgt/hla/) and were obtained as gBlocks from Integrated DNA Technologies (Coralville, IA). cDNA was cloned into a murine stem cell virus (MSCV) plasmid for retroviral transduction of the human class II negative T2 cell line (T2 Parent). The HLA-DRB1, -DRB3, -DQA1, and -DQB1 alleles were individually packaged as retrovirus by transient transfection of Phoenix 293T cells with GFP+MSCV plasmids as previously described (Bowerman et 2011). For the HLA-DRB1 and -DRB3 alleles, the retrovirus in the supernatant was used to transduce $1\times10^5$ T2 cells expressing DRA1*01:01 and sorted for high expression of HLA-DR+/GFP+ seven days post transduction (Anti-DR-APC (LN3) Invitrogen Cat #17-9956-42). For the -DQ alleles, the retrovirus of the HLA-DQB1 alleles was used to transduce $1\times10^5$ HLA Class II negative T2 cells and sorted for high GFP+ expression seven days post transduction. Then, the retrovirus for the corresponding HLA-DQA1 allele for the cis and trans dimer was used to transduce $1\times10^5$ DQB1+ T2 cells and sorted for high HLA-DQ+/GFP+ expression seven days post transduction (Anti-Human HLA-DP/DQ/DR Starbright Blue (WR18) 700 BioRad Cat #MCA477SBB700). Post-sort, RNA was isolated from each cell line to verify the HLA sequences for both cis and trans HLA alleles by Sanger sequencing (Quintara Biosciences). All cell lines were grown in IMDM-GlutaMAX (Life Technologies) supplemented with sodium pyruvate, thio-penicillin/streptomycin, and 10% fetal bovine serum (FBS).

Peptide Design and Synthesis for Peptide Binding Assays

Hybrid Insulin Peptides HIP1-WE14 (GQVELGGWSKMDQLA SEQ ID NO: 97), HIP6-IAPP2 (GQVELGGGNAVEVLK SEQ ID NO: 98), HIPS-NPY (GQVELGGGSSPETLI SEQ ID NO: 99), and HIP11-C peptide (SLQPLALEAEDLQV SEQ ID NO: 100) were synthesized with a biotinylated PEG3 linker on the N-terminus to >98% purity with Trifluoroacetic acid (TFA) removal by Genscript (Piscataway, NJ) (Delong 2016, Baker2019). The HIPs used in this study were selected because of their capability to stimulate available T cell clones (Table 2). Biotinylated GAD65$^{265-281}$ (AMMIARFKMFPEVKEKG SEQ ID NO: 101), Insulin Mimotope (HLVEELYLVAGEEG SEQ ID NO: 102), and Influenza A (PKYVKQNTLKLAT SEQ ID NO: 103) peptides were also synthesized as controls for HLA-DR and DQ binding [S. Dai, at doi.org/10.1073/pnas.1716527115]. All peptides, except HIP6, were reconstituted in Dimethyl Sulfoxide (DMSO), then equal parts water, and finally Dulbecco's phosphate buffered saline (DPBS) (Life Technologies) to 400 μM concentration and kept frozen at −20° C. until use in peptide binding and T cell studies. HIP6 was reconstituted in 3% ammonia water, then equal parts water, 75 uL of 1M HCL to restore a neutral pH, and finally DPBS to 400 μM.

Patient Specific HLA-Class II Expressing T2 Cells Peptide Binding

T2 cell lines expressing the HLA-Class -DR and -DQ genotype of Pt3977 were harvested, resuspended, plated with 100 μM HIP1, and cultured overnight as mentioned above. Plates were washed twice with DPBS to remove unbound peptide, then resuspended in 100 μL 1:1000 diluted eBioscience™ Fixable Viability Dye eFluor™ 780 for 30 min at 4° C. Then, the cells were processed and stained as before. Data were acquired on the Canto II flow cytometer (BD Biosciences) and analyzed by FlowJo Version X (Tree Star). The average binding ratio (MFI of HLA Class II+T2 cells/MFI T2 parent HLA Class II−)±SEM for 3 independent experiments was determined using GraphPad Prism software version 9.1.

Peptide Synthesis for T cell Stimulation Assays

Hybrid Insulin Peptides HIP1 (GQVELGGWSKMDQLA SEQ ID NO: 97), and HIP11 (SLQPLALEAEDLQV SEQ ID NO: 100) were synthesized to >98% purity with Trifluoroacetic acid (TFA) removal by Genscript (Piscataway, NJ) [Baker et al. 2019]. The peptides were reconstituted in DMSO to a final concentration of 10,000 μM. For the stimulation assays, the peptides were diluted 1:100 for a working concentration of 100 μM.

Resistant and Susceptible HLA-Class II Expressing T2 Cells Peptide Binding

Peptide binding assays were conducted as described previously (Anderson et al. 2016, Roark et al. 2016). Briefly, T2 cell lines expressing T1D resistant and susceptible HLA-DR and -DQ alleles were harvested and resuspended in media (IMDM-GlutaMAX, 10% FBS, thio-pen/strep and sodium pyruvate) at $4\times10^6$ cells/mL. In a 96-well round-bottom plate, resuspended cells, 100 μM biotinylated stock peptide, and DPBS were combined. Negative control wells contained resuspended cells with DPBS alone. Plates were incubated overnight at 37° C. Plates were washed twice with DPBS to remove unbound peptide, then resuspended in 1× Zombie Aqua (Biolegend Zombie Aqua™ Fixable Viability Kit cat #423102) for 15 min at room temperature. Cells were lightly fixed for five minutes in 1% formaldehyde in DPBS to prevent loss of peptide from the cell surface. To detect peptide binding, 1× PE-labeled streptavidin (One Lambda LT-SA-PE) was added for 30 min at 4° C. Prior to acquisition on the Canto II flow cytometer (BD Biosciences), cells were again fixed. Data were analyzed by FlowJo Version X (Tree Star) and the average binding ratio (MFI of HLA Class II+T2 cells/MFI T2 parent HLA Class II−)±SEM for 3 independent experiments was determined using GraphPad Prism software version 9.1 (Graph Pad).

For the titration of HIP11, the T2 Parent, HLA-DQ2, and -DQ2 trans were harvested and resuspended as mentioned above. Then, in a 96-well round bottom plate, the reaction was setup as before except the final concentrations of peptide were 5 µM, 10 µM, 20 µM, and 50 µM. The cells were cultured overnight, and washed twice with DPBS. Cells were resuspended in 100 µL 1:1000 diluted eBioscience™ Fixable Viability Dye eFluor™ 780 (cat #65-0865-18) for 30 min at 4° C. Then, the cells were processed, stained, and analyzed as mentioned above.

T cell Stimulation Assay

T cells were cloned and expanded as described previously (Baker 2019). For HIP11, HLA-DQ2 and -DQ2 trans expressing T2 lines or autologous EBV-transformed B-cell line (EBV3537) were either unloaded or preloaded with varying concentrations of HIP11 (5 µM, 10 µM, 20 µM, and 50 µM). The antigen presenting cells were preloaded by incubating the antigen at the selected concentrations with the cells for 1 hr at 37° C. Then, excess antigen was removed by washing with DPBS to ensure only the antigen bound and presented by the HLA alleles was capable of stimulating the T cell clones. Then, $1 \times 10^5$ CD4+ T cell clones (E2) were incubated with $5 \times 10^4$ of the antigen presenting cell lines overnight then stained with viability dye (eBioscience™ Fixable Viability Dye eFluor™ 780) for 30 min at 4° C. The cells were washed then stained with anti-CD4-PE (Biolegend PE anti-human CD4 Antibody cat #317410), and anti-CD25-BV421 (BD Biosciences BV421 Mouse Anti-Human CD25 cat #562443) for 30 min at 4° C. Cells were washed then fixed before acquisition on the Canto II flow cytometer (BD Biosciences). Data were analyzed by FlowJo Version X (Tree Star). GraphPad Prism software version 9.1 was used to calculate the mean CD25 MFI±SEM of 3 independent experiments.

For HIP1, $1 \times 10^5$ CD4+ T cell clones (D11) were incubated with $5 \times 10^4$ patient specific HLA-Class II T2 lines or autologous EBV-transformed B-cell line (EBV 3977) in the absence or presence of antigen. The HLA-Class II T2 cell lines and EBV line were preloaded as mentioned above with a concentration of 20 µM. The cells were co-cultured overnight, and they were processed and analyzed as mentioned above.

Example 2—Humanized DRB1*04:01$^{K71E}$ Transgenic Mice are Resistant to Collagen Sensitization Collagen-induced arthritis (CIA) is a well-established mouse model of autoimmune arthritis that recapitulates key features of RA, including an important role of MHC II molecules and collagen specific T cell responses. HLA-DR4 transgenic mice injected with heterologous type II collagen protein emulsified in Complete Freund's Adjuvant (CFA) develop potent collagen-specific CD4+ T cell responses (collagen sensitization), an essential first step required for development of CIA.

In order to determine if a DRB1*04:01-K71E gene edit is sufficient to prevent collagen sensitization in vivo, chimeric HLA-DR4/I-E$^d$ transgenic mice on an H-2 class II knockout background were used. FIG. 2, top, shows a diagram showing the distal/human DRα1 and DRβ1 domains in the chimeric MHC II molecules mediate peptide binding and interaction with the mouse T cell receptor (mTCR), while the proximal murine I-E$^d$α2 and I-E$^d$α2 domains mediate interactions with the mouse CD4 co-stimulatory molecule. Three transgenic lines were used in these experiments: one carrying the DRB1*04:01 gene one carrying the DRB1*01:01 gene (see, for example (J. Exp. Med., Vol. 180, 1994, pp. 173-18, and J. of Exp. Med., Vol. 185, No. 6, 1997, p. 1113-1122, both of which are incorporated by reference in their entireties), and one carrying the DRB1*04:01$^{K71E}$ gene (based on the methods in PLOS ONE, Vol. 8, 12, 2013, e84908, which is incorporated by reference). All three lines were immunized on Day 0 and Day 21 with soluble type II collagen protein emulsified in CFA. On Day 56, mice were sacrificed, lymph nodes were harvested, and cultured with collagen$^{258-272}$ peptide (Pep) or in media alone (No Pep) in the presence of the thymidine nucleoside analog 5-ethynyl-2'-deoxyuridine (EdU) that incorporates into the DNA of proliferating cells.

Fluorescent azide and Cu(I)-catalyzed [3+2] cycloaddition "click" chemistry was used to detect EdU incorporation in proliferating cells. Cells were also co-stained with fluorescent antibodies for CD3 and CD4. The frequency of CD4+ T cells that proliferated ex-vivo in response to collagen$^{258-272}$ was used to quantify sensitization. As shown in FIG. 2, bottom, DRB1*04:01 mice developed collagen$^{258-272}$ specific CD4+ T cell responses, while CD4+ T cells from DRB1*01:01 transgenic mice exhibited a weak proliferative response, commensurate with its reduced ability to bind collagen$^{258-272}$ and weaker association with RA compared to DRB1*04:01. In contrast, there was no proliferative response in CD4+ T cells from DRB1*04:01$^{K71E}$ transgenic mice. This demonstrated that expression of DRB1*04:01$^{K71E}$ in otherwise sensitive mice prevented the mice from becoming sensitized to collagen.

Example 3—DRB1*04:01$^{K71E}$ Skin Transplants Achieve Stable Engraftment in DRB1*04:01 Mice To verify that the K71E edit would not induce alloreactivity in DRB1*04:01 recipients, skin transplants were performed from either DRB1*01:01 and DRB1*04:01$^{K71E}$ mice onto DRB1*04:01 recipients. Skin grafts contain an abundance of APCs making it a difficult tissue to engraft. Assessment of skin engraftment is a robust model to test for potential alloreactivity. This pre-clinical model was used to determine the frequency of DRB1*04:01$^{K71E}$ skin graft rejection in DRB1*04:01 recipients.

Figure 3B:
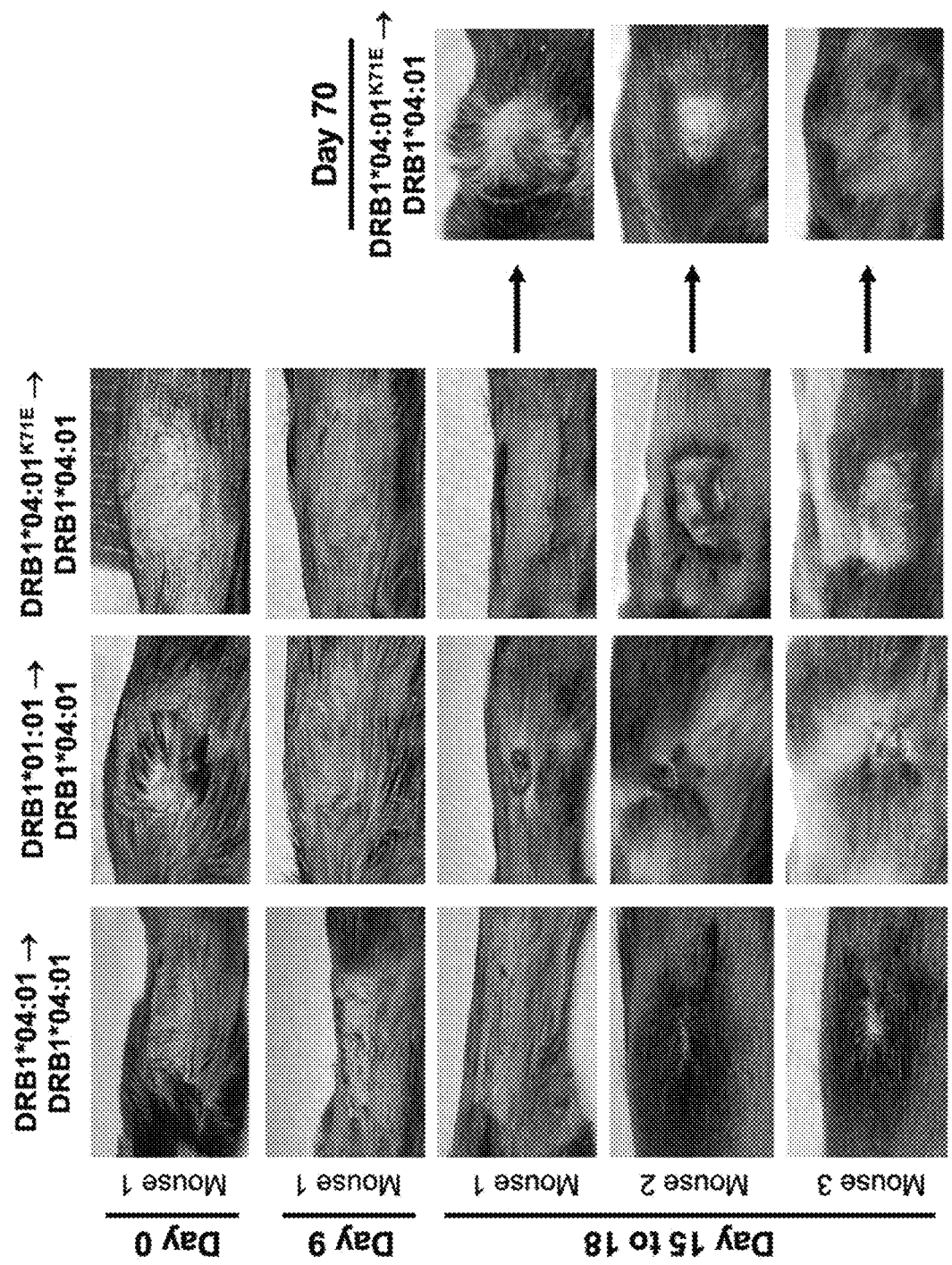
FIG. 3B shows skin grafts in DRB1*04:01 recipients for representative mice on days 0 and 9 and all mice on days 15-18 are shown. Long-term engraftment is shown for DRB1*04:01$^{K71E}$ transplants (day 70) in lower right panels. Red scabbing indicates rejection of the graft.
Figure 4:
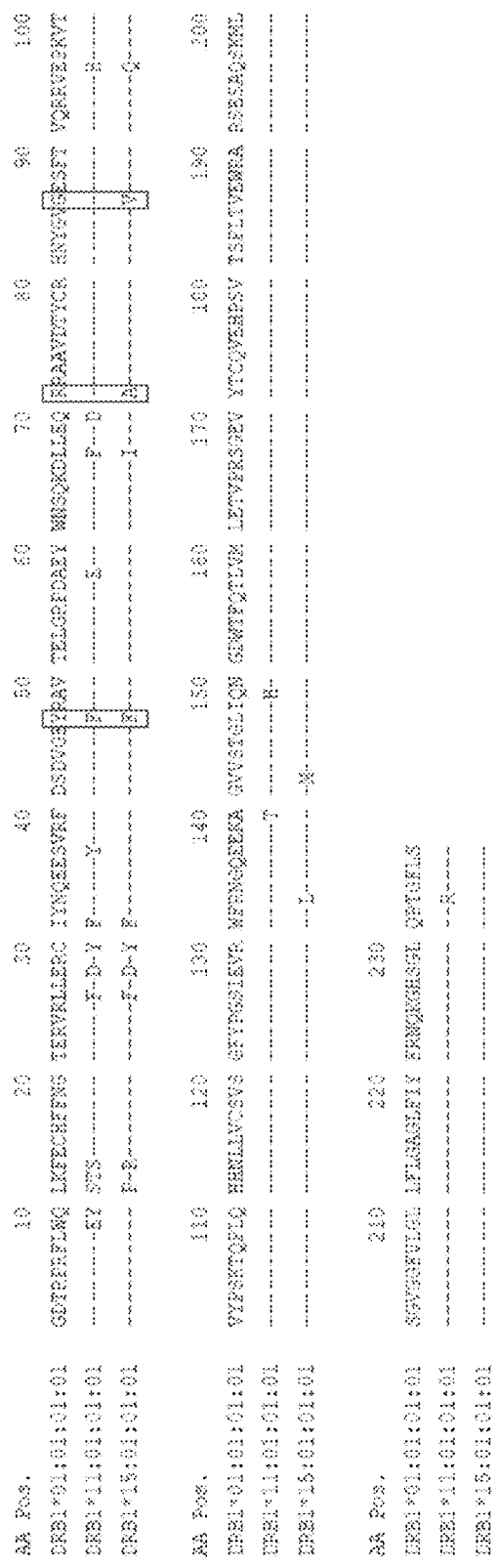
FIG. 4 is a sequence alignment of DRB1*01:01, DRB1*11:01 and DRB1*15:01 mature length proteins, according to embodiments of the disclosure.

As shown in FIG. 3, bottom, DRB1*01:01 skin grafts were completely rejected by day 14 (n=3), but the DRB1*04:01 (n=3) and DRB1*04:01$^{K71E}$ (n=3) grafts both remained stably engrafted. The fact that the DRB1*04:01$^{K71E}$ allografts survived indefinitely indicates that DRB1*04:01$^{K71E}$ expression does not induce either acute or chronic rejection. Therefore, once engrafted into the bone marrow, long-term progenitor HSCs expressing DRB1*04:01$^{K71E}$ should not be rejected or induce an immune response in the DRB1*04:01 recipient.

Example 4—HLA Alleles Involved in MS

Alleles associated with MS resistance and susceptibility were investigated. Two DRB1 alleles, *01:01 and *11:01 were identified as alleles conferring resistance, while *15:01 is associated with susceptibility. The mature protein sequence of the three alleles was submitted to alignment, and polymorphic positions matching the criteria described above were identified for the DRB1*15:01 allele: F47, A71, and V86. Mutations were made at one or more of these positions (F47Y, A71R, and V86G) against 4 peptides: MOG97-109 (FFRDHSYQEEA SEQ ID NO: 121), which is related to MOGAD; RASGRP$^{278-87}$ (LVRYWISAFP SEQ ID NO: 122), which is expressed in the brain and may activate memory T cells in MS, leading to characteristic brain inflammation (Jelcic et al., 2018, Cell 175); MBP[83-101] (ENPVVHFFKNIVTPRTPPP SEQ ID NO: 123), an immunogenic peptide that binds DRB1*15:01; and MBP[146-170]) AQGTLSKIFKLGGRDSRSGSPMARR SEQ ID NO: 124), which may play a role in resistance to MS, it binds DRB1*01:01 and does not activate MS T cells (Mamedov et al., Front. Immunol. 2020.)

Figure 5:
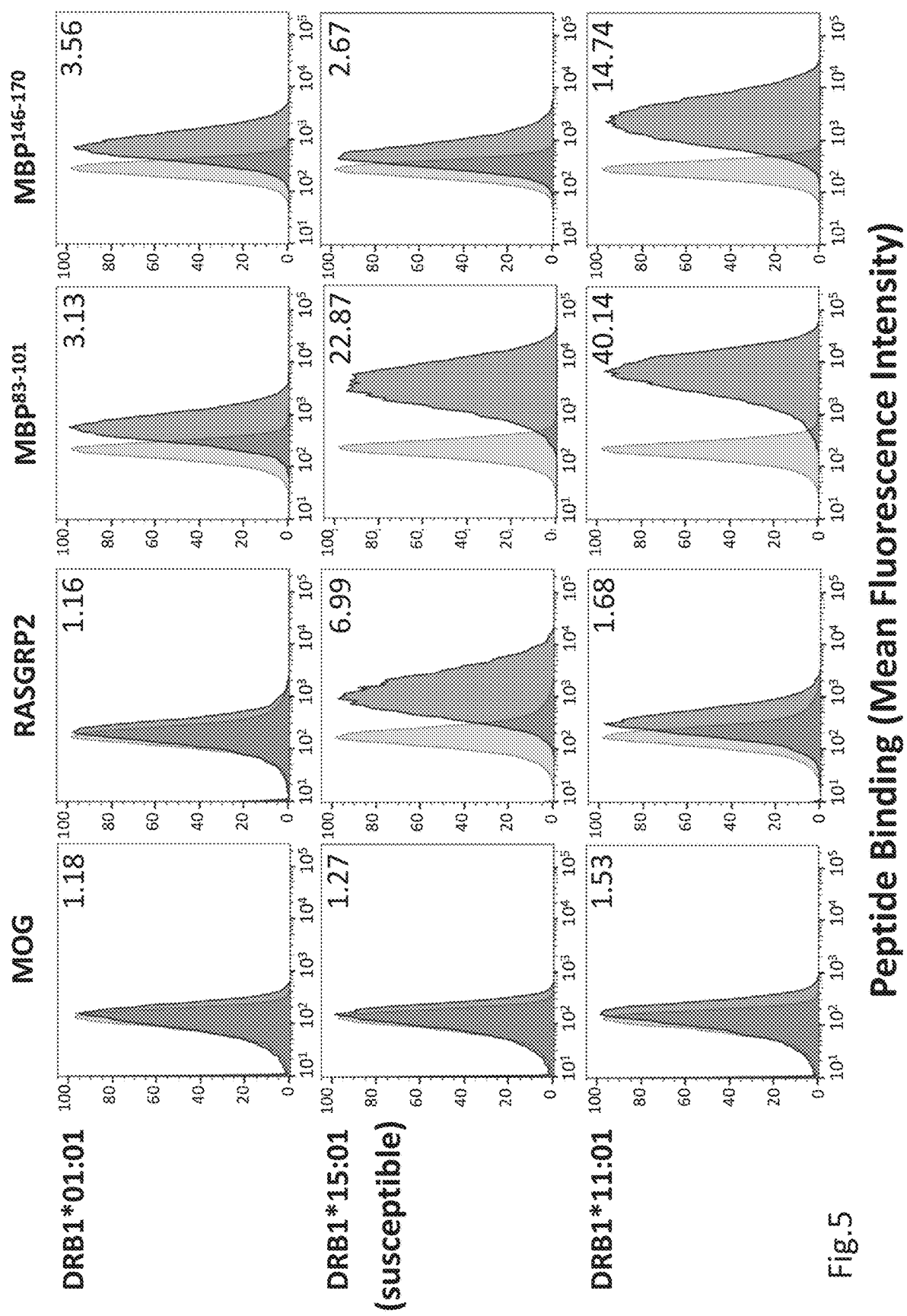
FIG. 5 depicts antigen binding studies of DRB1*01:01, *15:01 and *11:01 alleles, numbers in upper left corner of boxes are binding ratios of the peptide compared to cells that do not express any HLA Class II molecule and therefore do not bind peptide (negative control).
Figure 6:
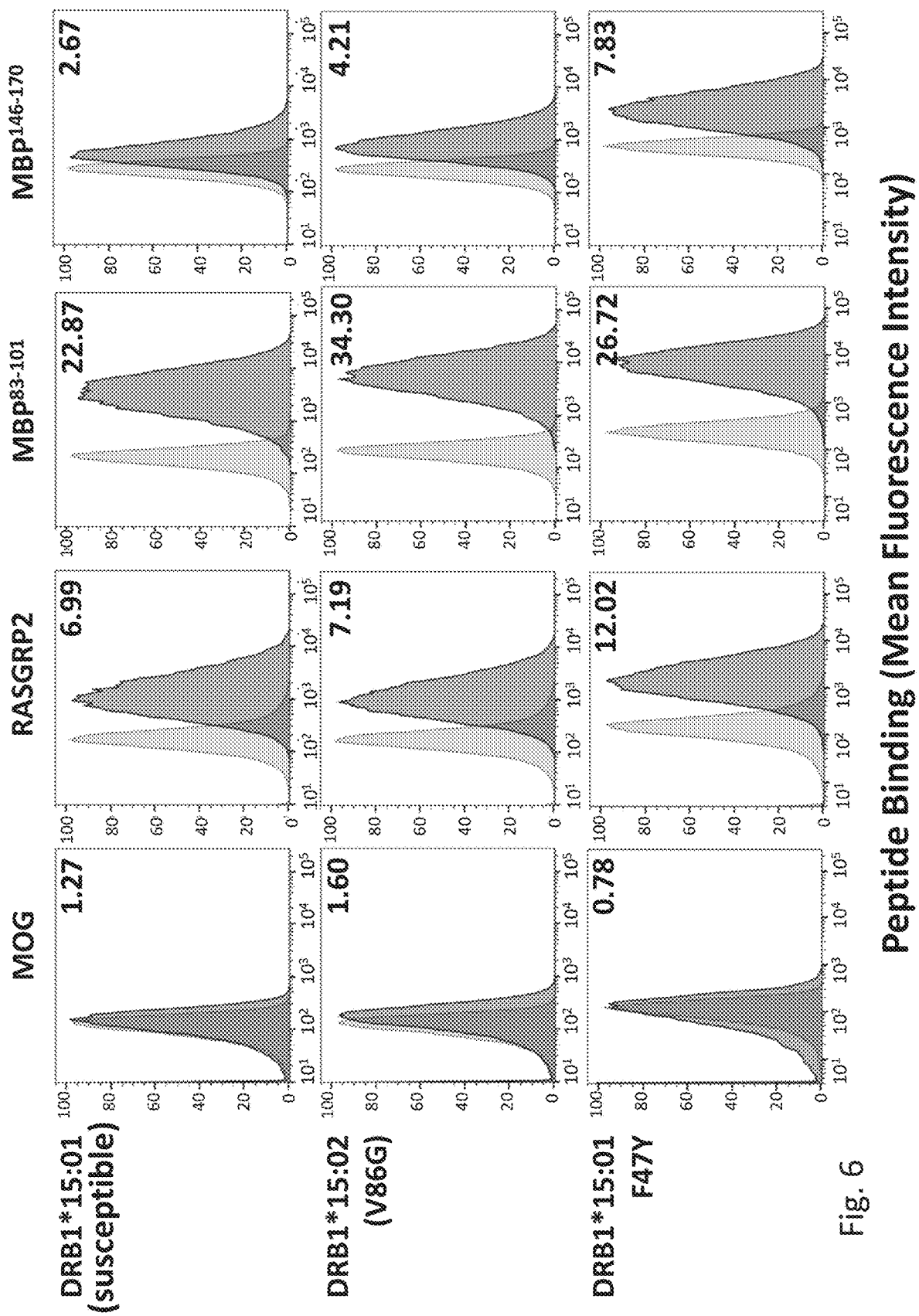
FIG. 6 depicts binding of autoimmune demyelination-associated peptides to DRB1*15:01 and 15:02 single and double mutant embodiments, numbers in upper left corner of boxes are binding ratios compared to negative controls (light gray).
Figure 7:
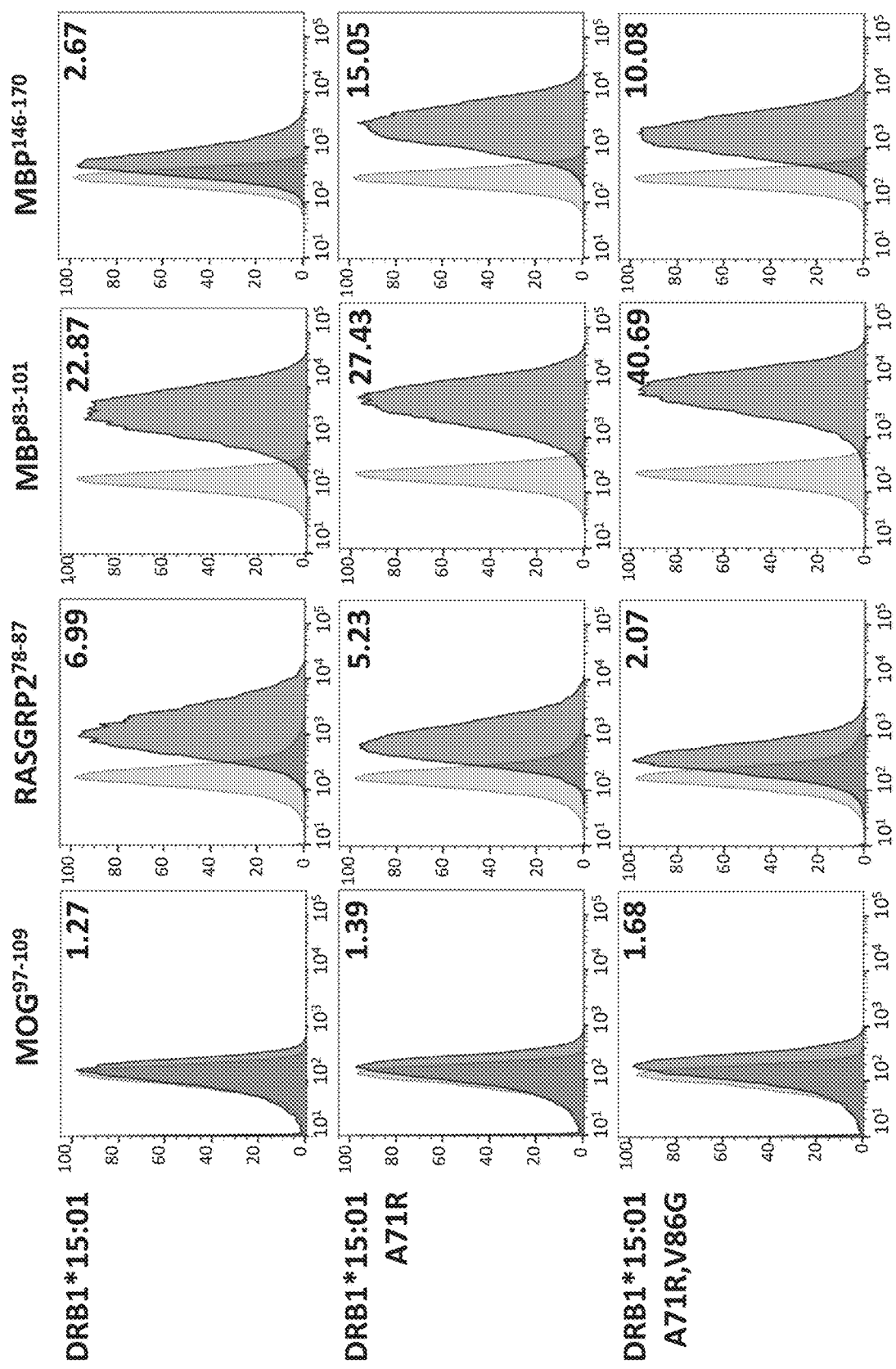
FIG. 7 depicts binding autoimmune demyelination-associated peptides to DRB1*15:01alleles, and the effects of edits at positions 71 and 86; numbers in upper left corner of boxes are binding ratios compared to negative controls.

The collected data (FIGS. 5-7) indicate that DRB1*15:01, which confers susceptibility to MS, binds the RASGRP2 better than the two resistant alleles—it also binds the MBP[83-101] peptide strongly, but not the MBP[1146-170] peptide. These data also suggest that the V86G and F47Y mutations affected the binding pattern mildly, except with the MBP[146-170] peptide, where binding is better, suggesting that this peptide may play a role in resistance. Finally, The A71R mutation alone in DRB1*15:01 does not change peptide binding except to increase the binding of MBP 146-170 (FIG. 6). The double mutation, A71R-V86G, shows a decrease in RASDRP2 binding as well (FIG. 7), suggesting that double mutations may provide additional benefits in addressing MS autoimmunity.

Example 5—HLA Alleles Associated with NMO (Neuromyelitis Optica)

The clinical syndrome of NMO is characterized by acute optic neuritis and transverse myelitis, caused by pathogenic serum IgG autoantibodies to aquaporin 4 (AQP4). AQP4 is the most abundant water-channel protein in the central nervous system (>80% of cases). Susceptibility to NMO is associated with HLA-DRB1*03:01, while resistance is associated with the allele DRB1*07:01. Two AQP4 peptides were tested for their binding to both alleles.

Figure 8:
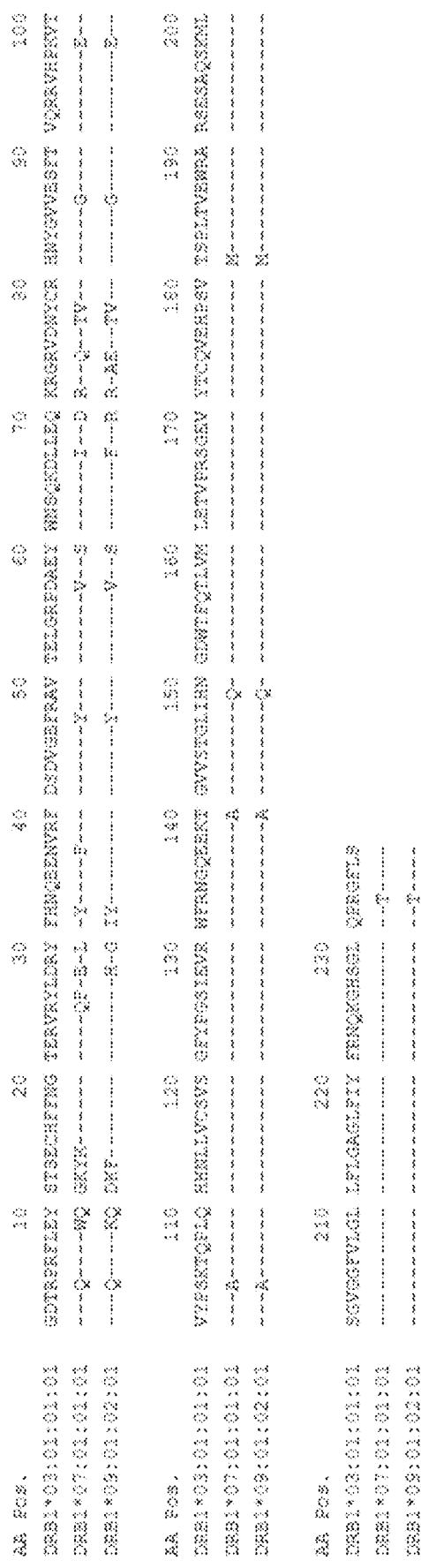
FIG. 8 is a sequence alignment of DRB1*03:01, DRB1*07:01, and DRB1*09:01 mature length proteins, according to embodiments of the disclosure.

The collected data indicate that the AQP4-5 peptide binds to the susceptible allele and not the resistant allele (FIG. 9). The same is seen with the AQP4-6 peptide, which also binds the susceptible allele, but not the resistant allele. These results suggest that the peptide binding profile of DRB1*03:01 may be affected by mutating positions in the peptide binding groove, to prevent or lessen binding of AQP4 peptides, and thus prevent autoimmunity. Candidate positions (e.g. as disclosed elsewhere target amino acid positions 9, 11, 13, 26, 28, 30, 32, 33, 37, 38, 40, 47, 57, 58, 67, 71, 74, 78, 85, and 86) for such a mutation can be identified from the sequence alignment of DRB1*03:01 and DRB1*07:01 (FIG. 8; note positions 38, 40, and 85 are not polymorphic indicate 03:01 and 07:01; note also that aligned sequence positions are numbered based on mature protein sequence).

Example 6A— HLA Alleles Associated with RA

Figure 10:
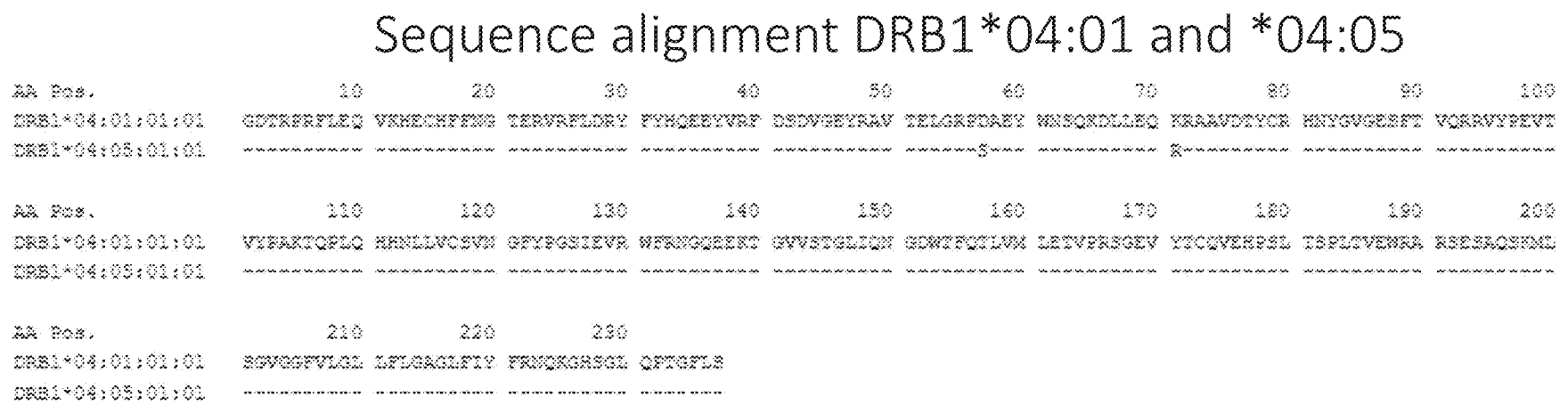

The HLA-DRB1 allele *04:05 also shows susceptibility to RA. In particular, this allele shows a strong association with RA in Japanese population. For these studies, position 71 in DRB1*04:05 was mutated from R to E (see FIG. 10).

Figure 11:
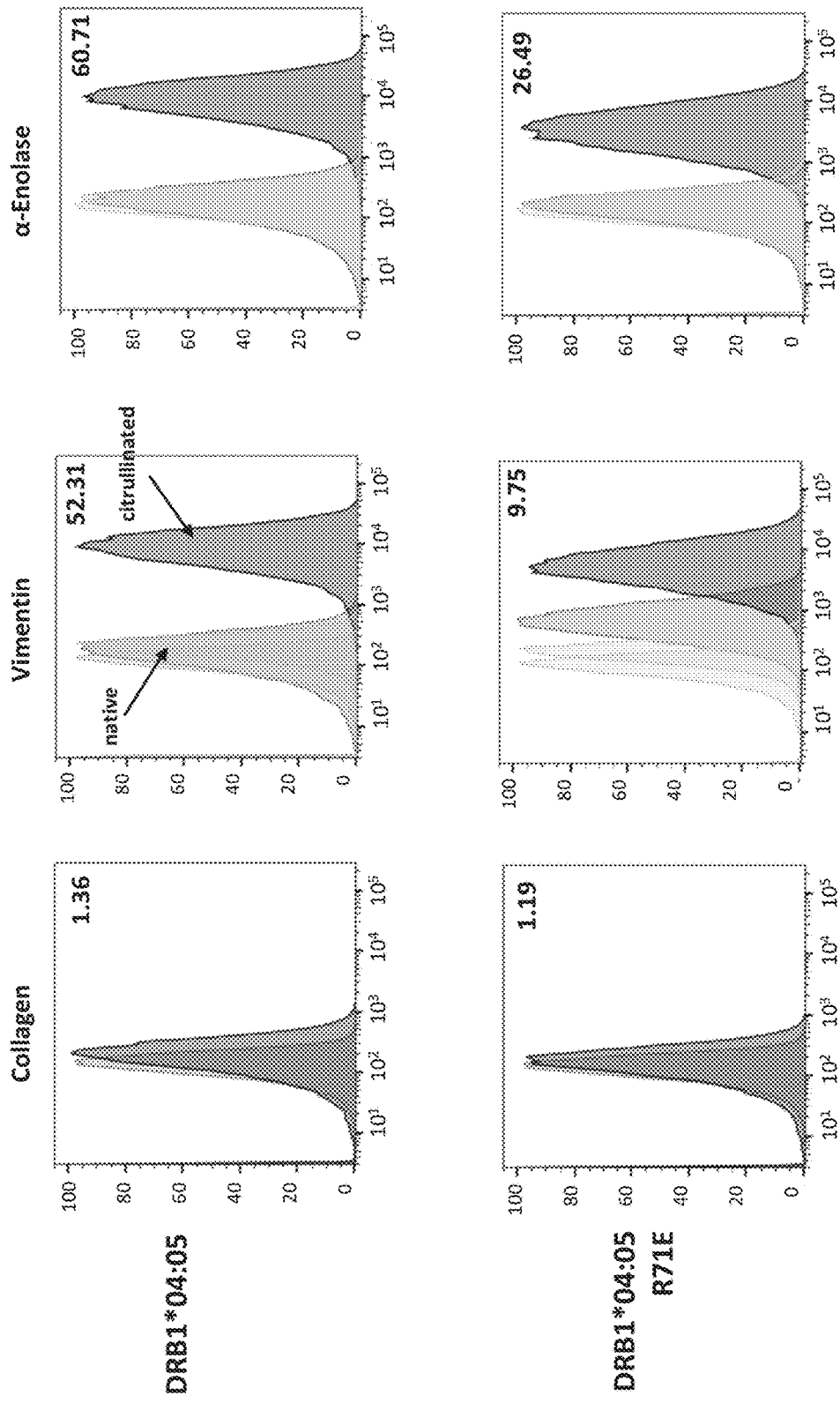
FIG. 11 depicts binding of three peptides associated with rheumatoid arthritis to the DRB1 allele *04:05 allele and the effect of a R71E edit, according to embodiments of the disclosure. The ratios in the upper right corner of the box refers to a comparison with the negative control (collagen) or compared to native form of vimentin and α-enolase.

These studies indicate that DRB1 allele *04:05 does not show a strong preference for binding the immunodominant collagen peptide (FIG. 11). However, when position 71 is mutated to glutamic acid (R71E), the low level of binding is further reduced. In the case of vimentin and α-enolase, the *04:05 allele preferentially binds the citrullinated versions over the native versions. As with to the K71E mutation, this preference is reduced by changing arginine at position 71 in DRB1*04:05 to glutamic acid (R71E). MFI Binding Ratio averages for 2 experiments.

As disclosed herein, other DR4 alleles susceptible to RA, for example DRB1*04:03, *04:04, and *04:08, may confer resistance (i.e. resistant alleles) when position 71 is changed from arginine (R) to glutamic acid (E).

Example 6B— HLA Alleles Associated With Type I Diabetes—T1D

DQB1 alleles associated with susceptibility to Type I diabetes were tested for the ability to confer resistance with one or more mutations in the antigen binding groove. Specifically, several DQB alleles and corresponding A57D variants were cloned into T2 cell lines. Aspartic acid is found at position 57 in several resistant alleles.

TABLE 2

Selected Hybrid Insulin Peptide Information (See also FIG. 22)

| Hybrid Insulin Peptides | Abbreviations | Sequences | References | SEQ ID NO |
|---|---|---|---|---|
| HIP1-WE14 | HIP1 | GQVELGG-WSKMDQLA | Delong et al. 2016 | 97 |
| HIP6-IAPP2 | HIP6 | GQVELGGG-NAVEVLK | Delong et al. 2016 | 98 |
| HIP8-NPY | HIP9 | GQVELGGG-SSPETLI | Delong et al. 2016 | 99 |
| HIP11-C | HIP11 | SLOPLAL-EAEDLQV | Baker et al. 2019 | 100 |

Peptide Selection—Hybrid Insulin Peptides HIP1-WE14 (GQVELGGWSKMDQLA SEQ ID NO: 97), HIP6-IAPP2 (GQVELGGGNAVEVLK SEQ ID NO: 98),), HIPS- NPY (GQVELGGGSSPETLI SEQ ID NO: 99), and HIP11-C peptide (SLQPLALEAEDLQV SEQ ID NO: 100) were synthesized with a biotinylated PEG3 linker on the N-terminus to >98% purity with Trifluoroacetic acid (TFA) removal by Genscript (Piscataway, NJ) (Delong 2016, Baker2019). The HIPs used in this study were selected because of their capability to stimulate and availability of T cell clones (Table 2). Biotinylated GAD65[265-281] (AMMI-ARFKMFPEVKEKG SEQ ID NO: 101), Insulin Mimotope (HLVEELYLVAGEEG SEQ ID NO: 102), and Influenza A (PKYVKQNTLKLAT SEQ ID NO: 103) peptides were also synthesized as controls for HLA-DR and DQ binding [S. Dai, available at doi.org/10.1073/pnas.1716527115].

Hybrid insulin peptides were tested for their binding to these cell lines at various concentrations. Specifically, peptide binding of the native HLA DQB1 allele was compared with its A57D mutated form. Susceptible alleles were hypothesized to bind the hybrid insulin peptides.

Figure 13:
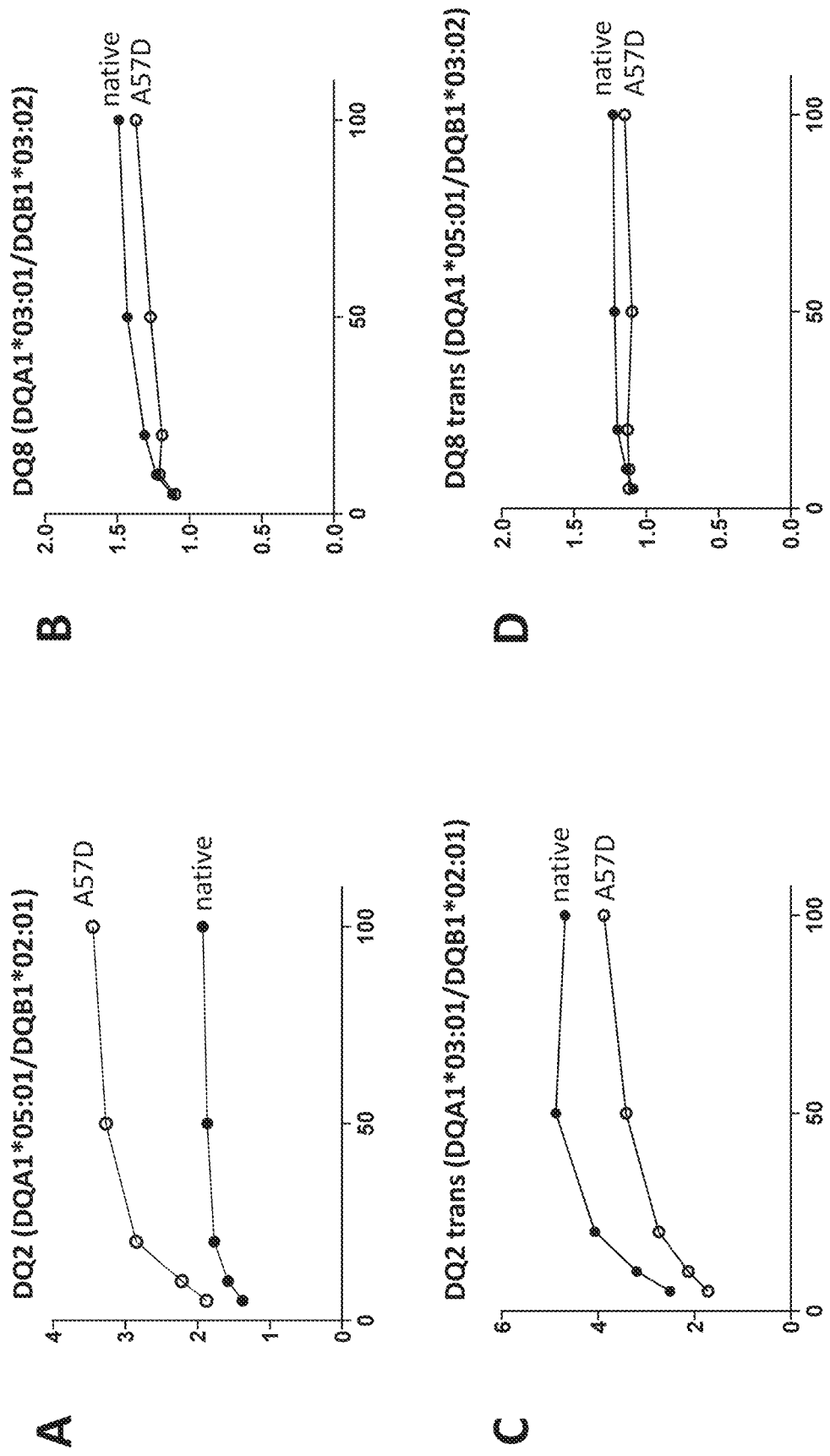
FIG. 13 depicts native vs. A57D binding of the HIP11-C peptide across multiple concentrations, where closed circle is the native allele, open circle is the A57D mutation: Panel A, DQ2; Panel B, DQ8; Panel C, DQ2 Trans; and Panel D, DQ8 Trans.
Figure 14:
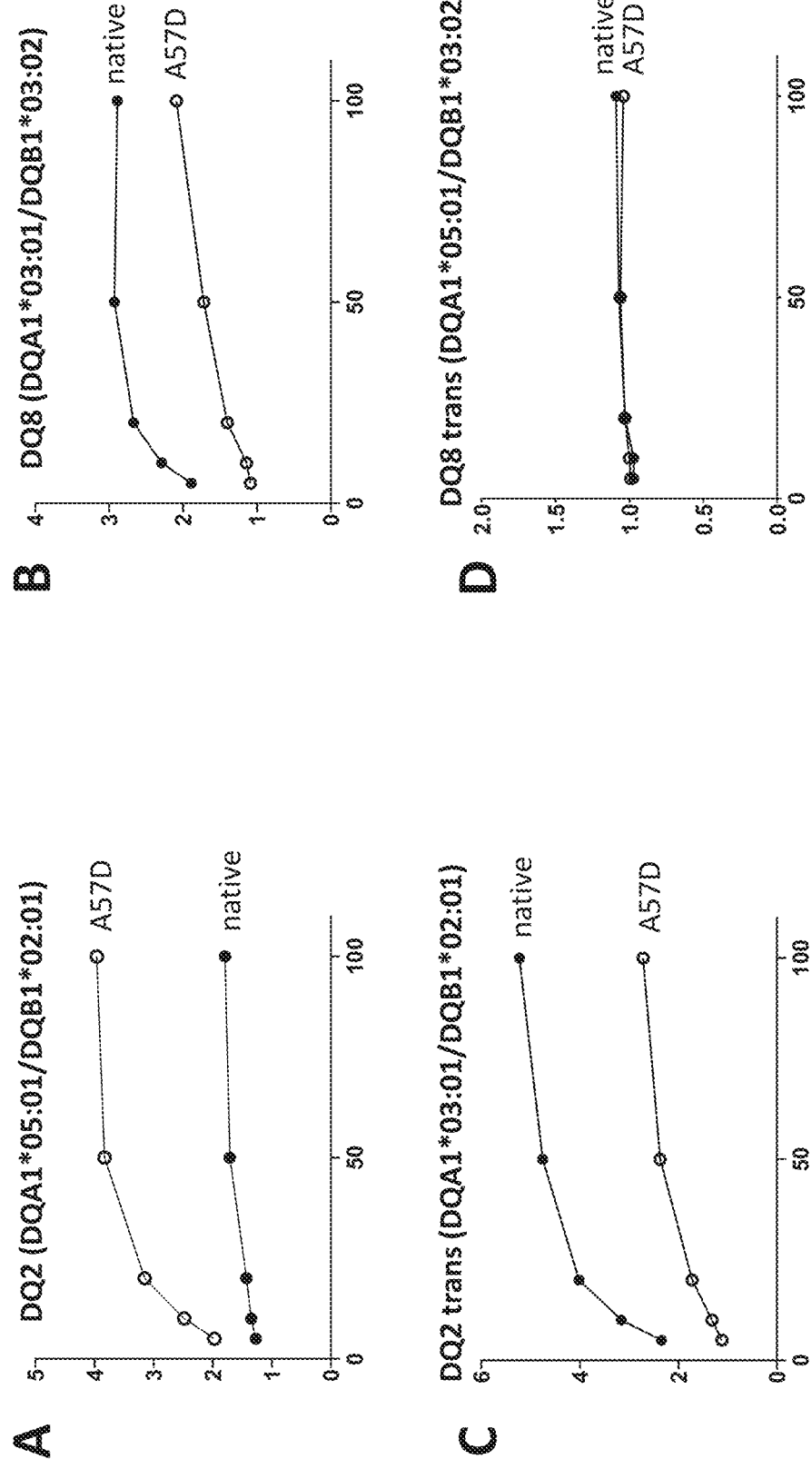
FIG. 14 depicts native vs. A57D binding of the Insulin Mimotope across multiple concentrations, where closed circle is the native allele, open circle is the A57D mutation: Panel A, DQ2; Panel B, DQ8; Panel C, DQ2 Trans; and Panel D, DQ8 Trans.

These studies showed that the susceptible DQ2 and DQ8 alleles do not bind the HIP8-NPY peptide, but the DQ2 trans HLA molecule does (FIG. 12). When position 57 is changed from A to D, the binding of this hybrid insulin peptide is increased on DQ2 and DQ8 but is reduced on DQ2 trans. Similarly, DQ2 and DQ8 do not bind the HIP11-C peptide (FIG. 13), but the DQ2 trans molecule does. When A57D is introduced, DQ2 shows peptide binding. While DQ2 trans binds this peptide less, binding is not abolished. Binding of the insulin mimotope peptide follows a similar pattern as to the above peptides (FIG. 14). Specifically, DQ2 does not bind the mimotope peptide, but DQ2 trans and DQ8 bind the peptide. When the A57D mutation is introduced, DQ2 and DQ2 trans now bind the peptide. While the mutation reduces binding to the DQ8 molecule.

The effect on T cell stimulation by the A57D mutation was also tested. Specifically, E2 T-cells, restricted to DQ2 and specific for the HIP11-C peptide, were obtained. These T cells were stimulated in culture with T2 cells expressing DQ2 or the DQ2 trans molecule in the presence of different concentrations of the HIP11-C peptide overnight. Both molecules with the A57D mutations, were also tested. T cell stimulation was then measured by staining the cells for the IL-2R (CD25) on the surface of the cells.

Figure 15:
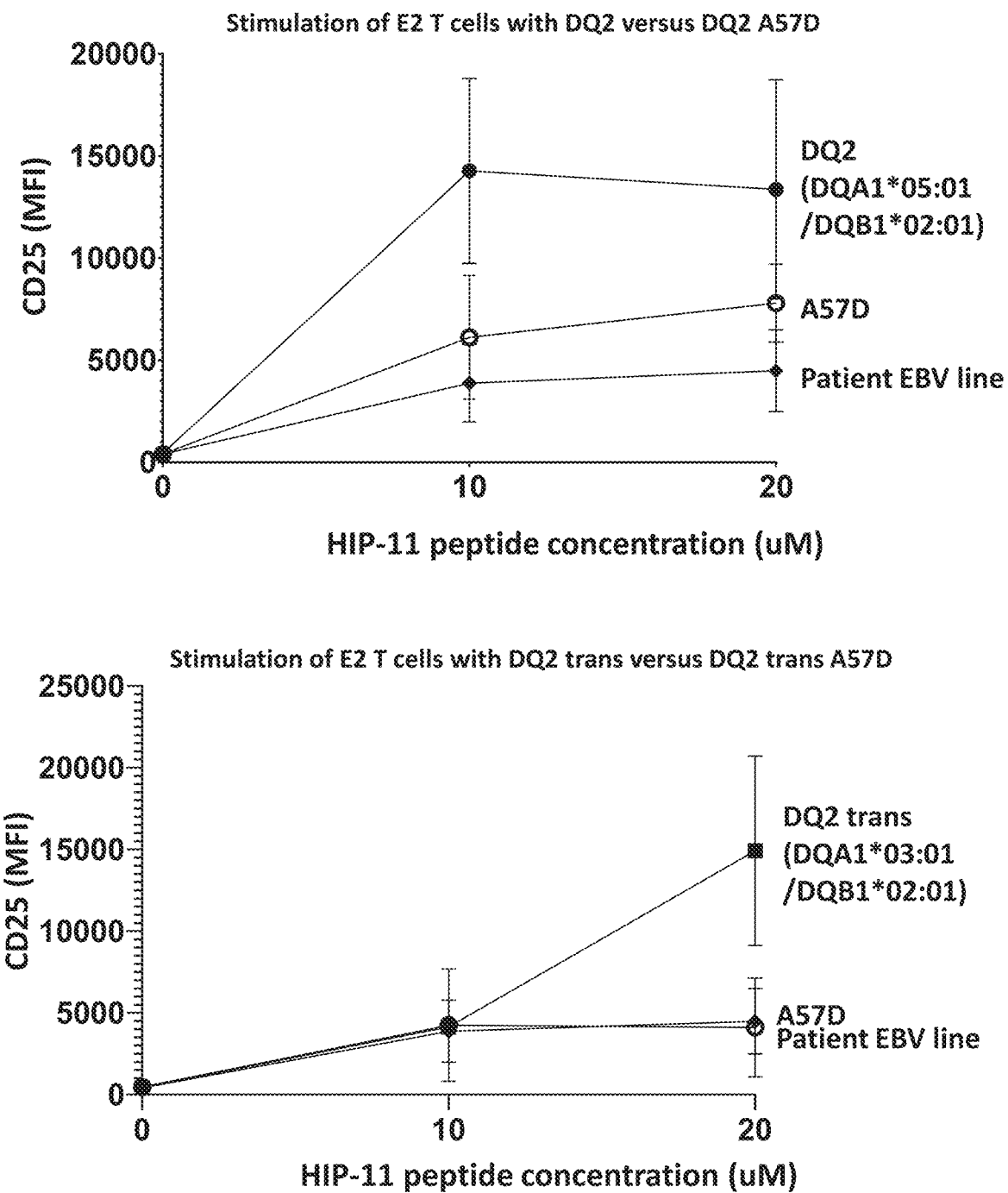
FIG. 15 (top) shows that the DQ2 T2 cell lines stimulates the E2 T cell clone much better than the parent EBV line. Introducing the A57D mutation results in less stimulation of the E2 T cell: stimulation of E2 T cell with DQ2 and DQ2 A57D at 10 uM and 20 uM preload concentrations of HIP11 peptide, solid circles are DQ2, open circles are DQ2 A57D, and diamonds are patients EBV transformed B cell line (bottom) shows stimulation of E2 T cell with DQ2 Trans and DQ2 Trans A57D at 10 uM and 20 uM preload concentrations of HIP11 peptide, where solid circles are DQ2 Trans, open circles are DQ2 Trans A57D, diamonds are patients EBV transformed B cell line.
Figure 16:
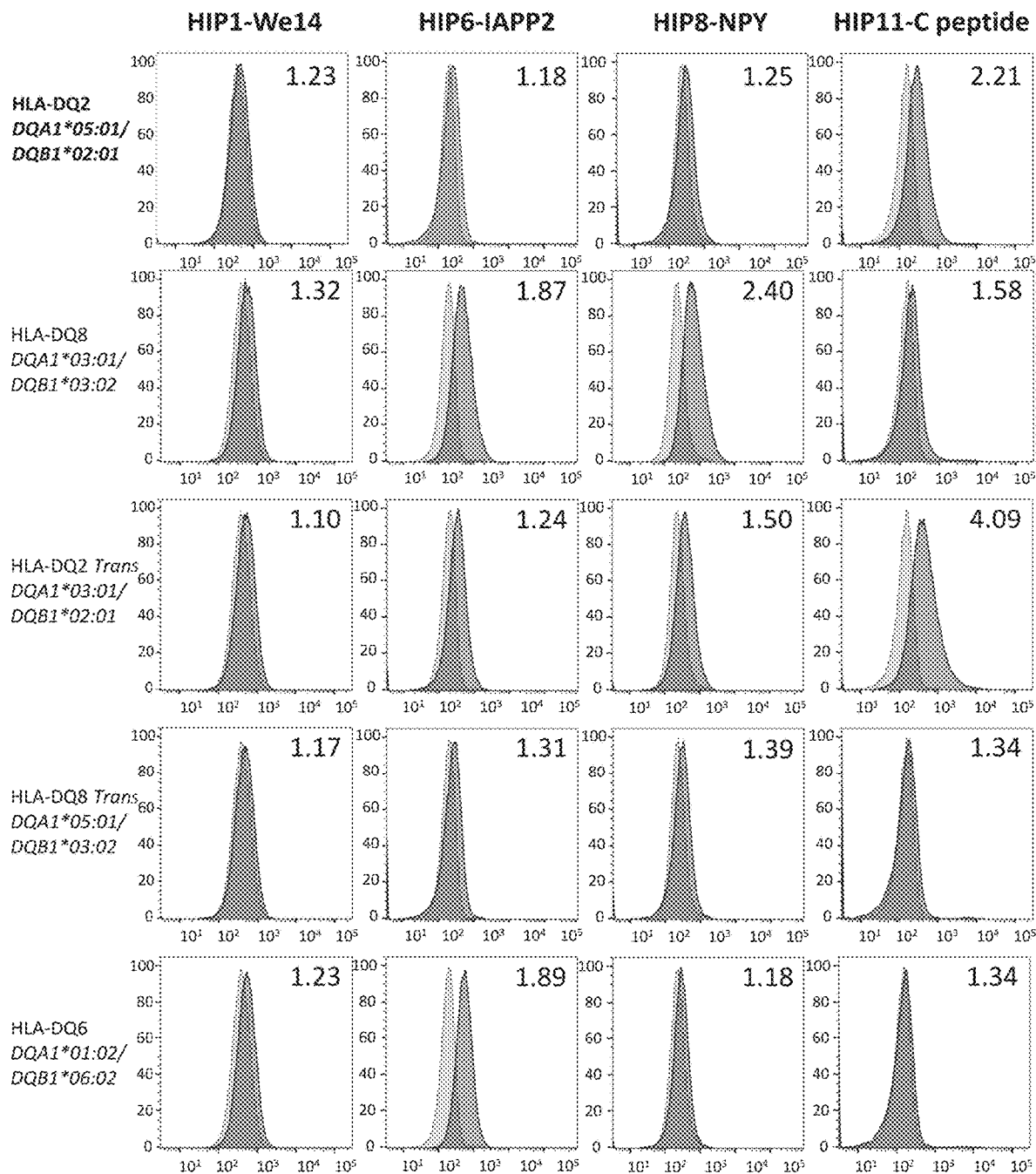
FIG. 16 depicts various HLA-DQ alleles binding hybrid insulin peptides, numbers in upper left corner of boxes are binding ratios.
Figure 17:
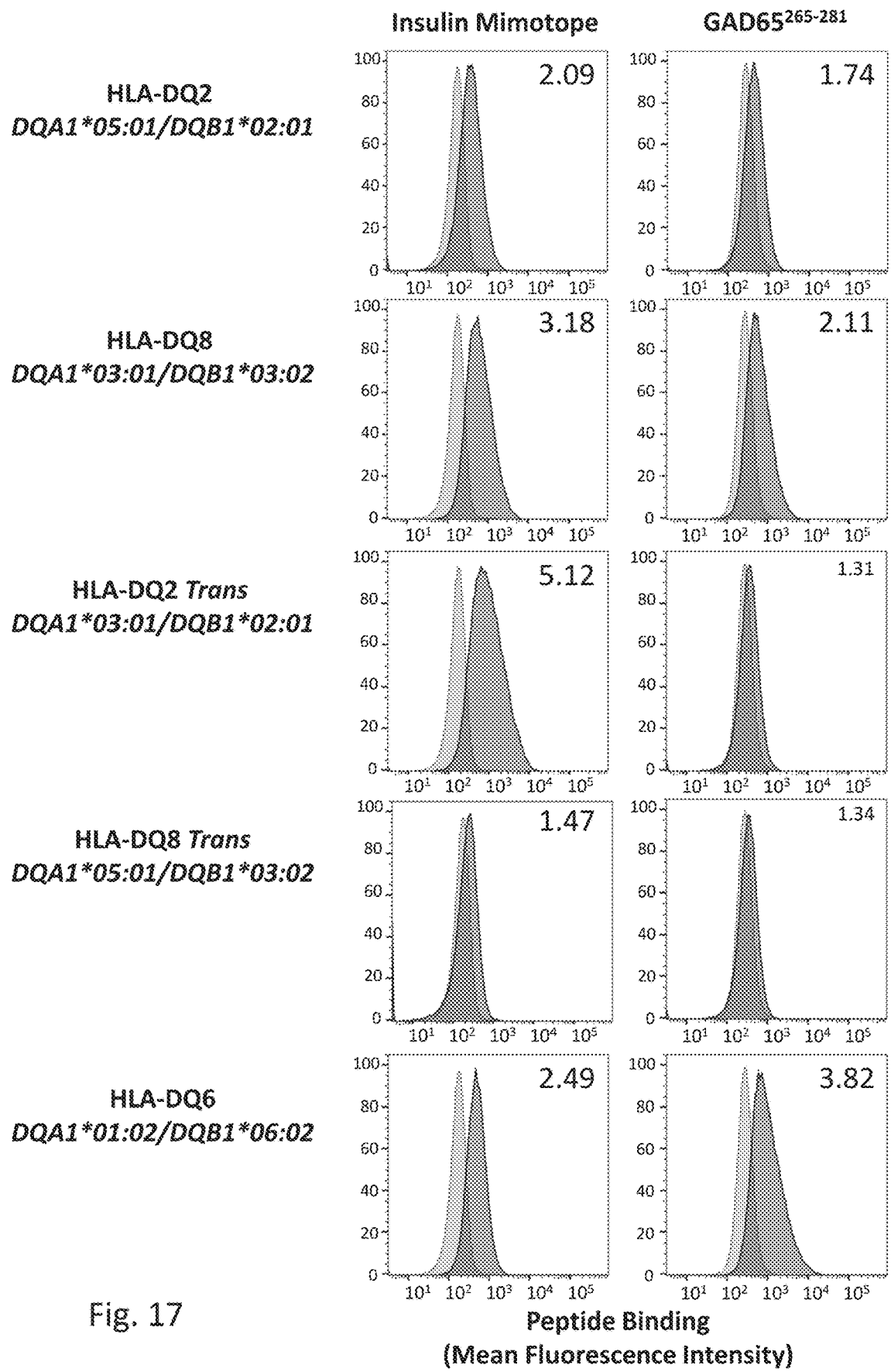
FIG. 17 depicts various HLA-DQ alleles binding diabetogenic peptides, according to embodiments of the disclosure. Numbers in upper left corner of boxes are binding ratios compared to negative controls.
Figure 18:
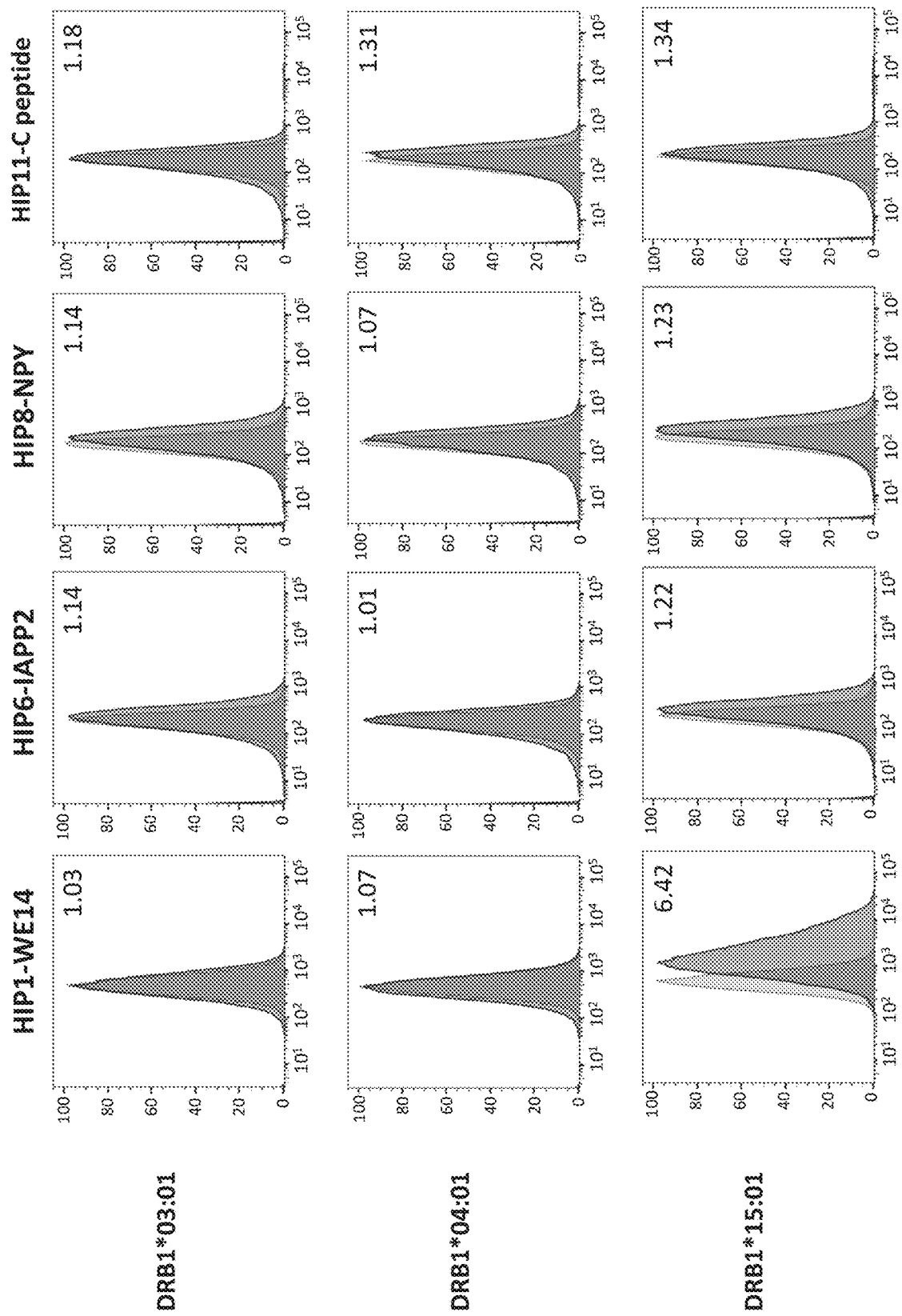
FIG. 18 depicts binding of hybrid insulin peptides to DRB1*03:01, *04:01 and *15:01, according to embodiments of the disclosure. Numbers in upper left corner of boxes are binding ratios compared to negative controls.
Figure 19:
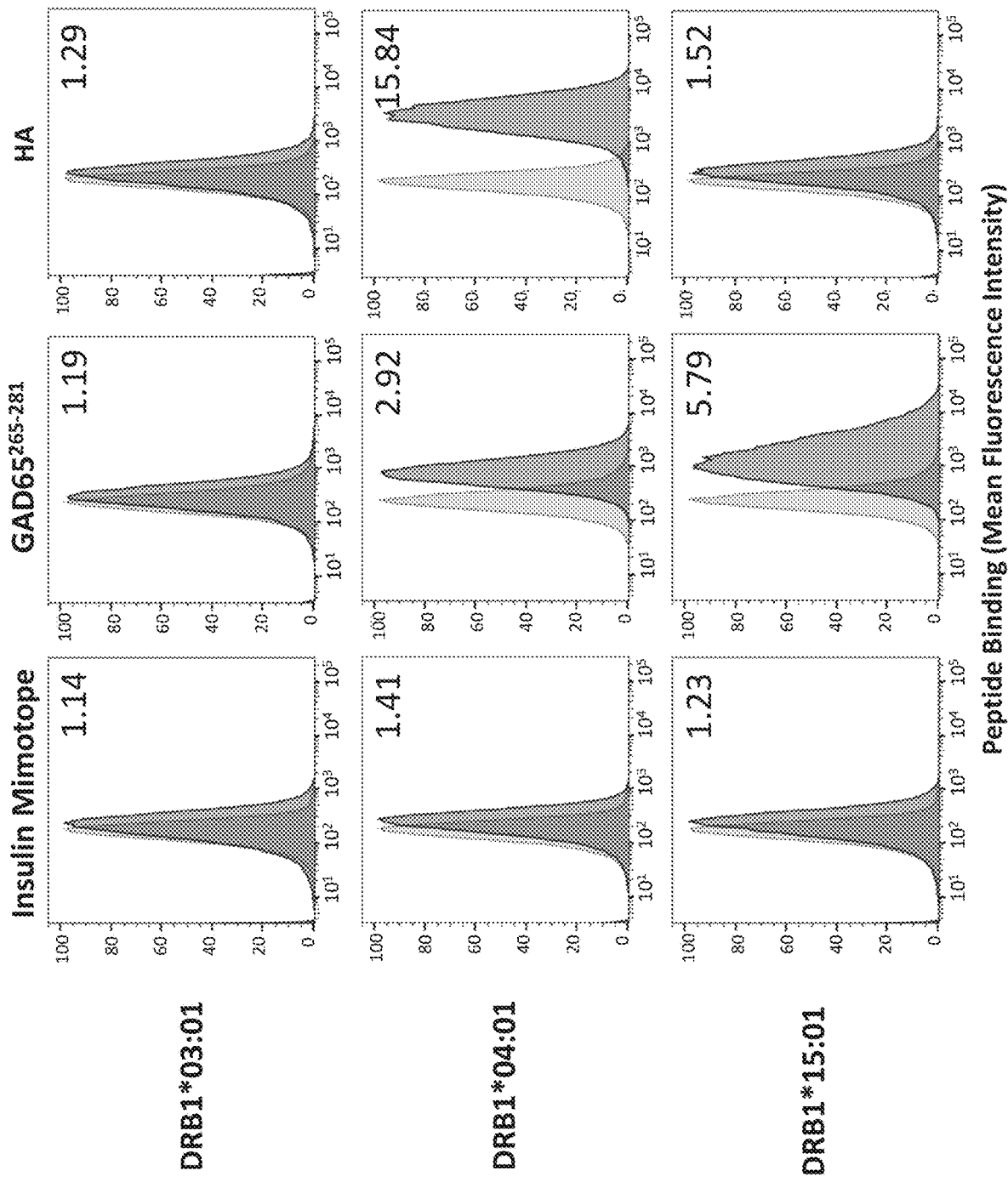
FIG. 19 depicts binding of diabetogenic peptides and influenza hemagglutinin peptide to DRB1*03:01, *04:01 and *15:01, according to embodiments of the disclosure. Numbers in upper left corner of boxes are binding ratios compared to negative controls.
Figure 23B:
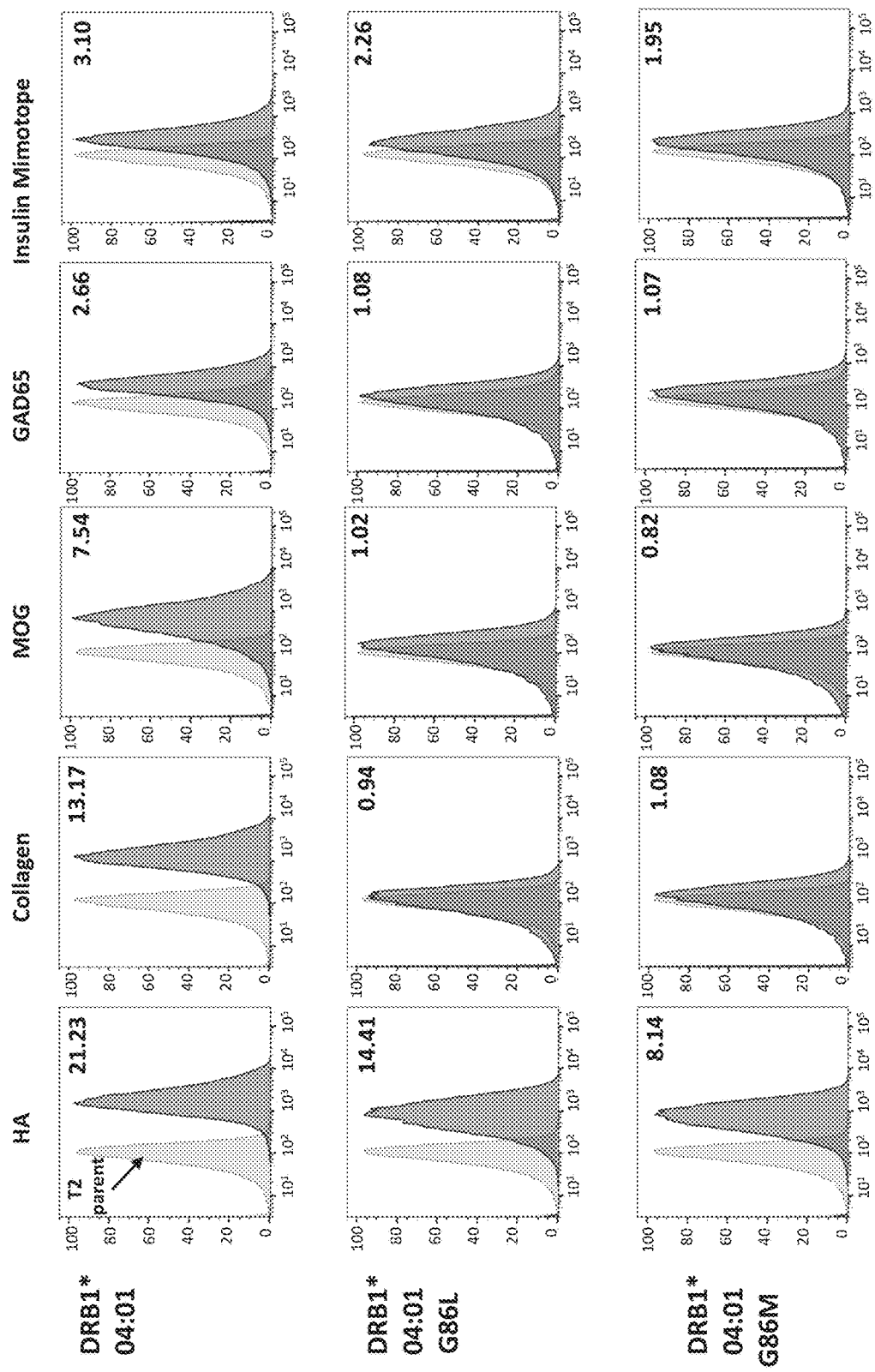
FIG. 23B depicts antigen binding studies of DRB1*04:01 and edited alleles of the present disclosure with pocket 1 mutations G86L and G86M, according to embodiments of the disclosure. Numbers in upper left corner of boxes are binding ratios compared to negative controls.

These studies showed that the DQ2 T2 cell lines stimulate the E2 T cell clone much better than the parent EBV line (FIG. 15, top panel). Introducing the A57D mutation into these alleles results in less stimulation of the E2 T cell. As shown in the bottom panel of FIG. 15, the E2 T cell clone is stimulated by the DQ2 trans molecule but the introduction of A57D into the DQ2 trans molecule results in less stimulation of the T cell clone.

FIG. 16 shows HLA-DQ alleles binding Hybrid Insulin Peptides. Binding of biotinylated HIP1-WE14, HIP6-IAPP2, HIP9-NPY, and HIP11-C peptide were measured on T2 cells expressing the risk alleles of DQ2 (A1*05:01/B1*02:01), DQ8 (A1*03:01/B1*03:02), DQ2 trans (A1*03:01/B1*02:01), and DQ8 trans (A1*05:01/B1*03:02). The resistant allele of DQ6 (A1*01:02/B1*06:02) was also tested. The light gray is the background binding of the peptide to the HLA-Class II (−) T2 Parent line while the darker gray is peptide binding to the specific HLA-Class II (+) T2 line. The rows represent different alleles, and the columns are different peptides. The number in the upper right corner is the average binding ratio (SA-PE MFI T2 HLA Class (+)/SA-PE MFI T2 parent). The number represents the average binding ratio from 3 independent experiments.

FIG. 17 shows HLA-DQ alleles binding control native peptides. Binding of biotinylated Insulin Mimotope and GAD65265-281 were measured on T2 cells expressing the risk alleles of DQ2 (A1*05:01/B1*02:01), DQ8 (A1*03:01/B1*03:02), DQ2 trans (A1*03:01/B1*02:01), and DQ8 trans (A1*05:01/B1*03:02). The resistant allele of DQ6 (A1*01:02/B1*06:02) was also tested. The light gray is the background binding of the peptide to the HLA-Class II (−) T2 Parent while the darker gray is signal of the HLA-Class II (+) T2 line. The number in the upper right corner is the average binding ratio (SA-PE MFI T2 HLA Class (+)/SA-PE MFI T2 parent). The number represents the average binding ratio from 3 independent experiments.

FIG. 18 shows susceptible and resistant HLA-DRB1 alleles binding HIPs. Binding of biotinylated HIP1, HIP6, HIP8, and HIP11 were measured on T2 cells expressing the susceptible alleles of DRB1*03:01 and DRB1*04:01 and resistant DRB1*15:01. The light gray is the background binding of the peptide to the HLA-Class II (−) T2 Parent line while the darker gray is signal of the HLA-Class II (+) T2 line. The number in the corner is the mean binding ratio of 3 independent experiments.

FIG. 19 shows susceptible and resistant HLA-DRB1 alleles binding native control peptides. Binding of biotinylated insulin mimotope, GAD65265-281, and Influenza HA were measured on T2 cells expressing either susceptible or resistant HLA-DRB1 alleles, specifically DRB1*03:01, DRB1*04:01, and HLA*DRB1*15:01. The number in the corner is the mean binding ratio.

FIG. 20 shows various HLA-DRB3/4/5 alleles binding HIPs. The ability of the HLA-DRB3/4/5 alleles to bind biotinylated HIP1, HIP6, HIP8, and HIP11 were measured on T2 cells expressing the alleles of DRB3 (*01:01, *02:02, *03:01), DRB4*01:03, and DRB5*01:01. The light gray is the background binding of the peptide to the HLA-Class II (−) T2 Parent line while the darker gray is signal of the HLA-Class II (+) T2 line. The number in the corner is the mean binding ratio of 3 independent experiments.

FIG. 21 shows various HLA-DRB3/4/5 alleles binding native control peptides. Binding of biotinylated insulin mimotope, GAD65265-281, and Influenza HA were measured on T2 cells expressing DRB3 (*01:01, *02:02, *03:01), DRB4*01:03, and DRB5*01:01. The light gray is the background binding of the peptide to the HLA-Class II (−) T2 Parent line while the darker gray is signal of the HLA-Class II (+) T2 line. The number in the corner is the mean binding ratio of 3 independent experiments.

Example 7—Effect of Mutations in Pocket 1 of DRB1

Disclosed herein are methods and compositions for occluding the antigen binding position, pocket 1, of an HLA class II protein. In many embodiments, the HLA class II protein is DRB, for example DRB1, DRB3, DRB4, or DRB5. In many embodiments, variant DRB molecules are described where one or more amino acid positions in pocket 1 are edited. In many embodiments, the edit may include changing a glycine to a larger amino acid identity, for example valine, methionine, or leucine. In many embodiments, the amino acid position is 85 or 86 in the mature DRB protein.

Position 86 is located within pocket 1 of the peptide binding region of DRB1, and may act as a peptide anchor position deep in the binding groove. Pocket 1 (or P1) of DRB molecules may form a deep recess, depression, or hole for receiving one or more large amino acid side chains to aid in anchoring the peptide antigen. Studies were designed to investigate the effect of replacing glycine at position 86 of DRB1 with other amino acids. Specifically, larger, non-polar amino acids, valine, methionine, and leucine, were substituted to reduce the size of this peptide anchor position.

In these studies, a specific amino acid position within the binding cleft of DRB1*04:01, position 86, was changed from glycine to either methionine (G86M) or leucine (G86L). T2 cell lines were transfected with engineered genes coding for the variants and the novel HLA molecules were expressed. Cell lines were incubated overnight with 100uM biotinylated peptide. The next day, cells were washed and lightly fixed before the addition of streptavidin-PE to detect bound biotinylated peptide. Cells were analyzed by flow cytometry using the BD Canto instrument. A variety of peptides were tested to see how changing pocket 1 might affect peptide binding: increase, decrease or remain the same.

T2 cell lines expressing either DRB1*04:01 or DRB1*04:01 where position 86 was changed from glycine to methionine (G86M) or glycine to leucine (G86L) were tested for their ability to bind a variety of peptides. Position 86 is located in pocket 1 of the peptide binding region of DRB1 and we hypothesized that replacing glycine with a larger, non-polar amino acid, we could essentially block peptide binding by filling up this anchor position.

DRB1*04:01 binds all peptides listed here (FIG. 23). When position 86 is changed to a methionine or leucine, inhibition of peptide binding is observed for collagen, MOG, and GAD65. A reduction in peptide binding is seen for the insulin mimotope and the viral influenza HA peptide. The light grey peak is binding by the T2 parent cell line A. The dark peak is peptide binding by the specific HLA allele. Number in the right-hand corner is the MFI ratio over background binding to the T2 parent line that does not express class II HLA. Bold number is the binding ratio for two experiments for HA, collagen, MOG, and GAD65; Insulin Mimotope only has one experiment.

Figure 24:
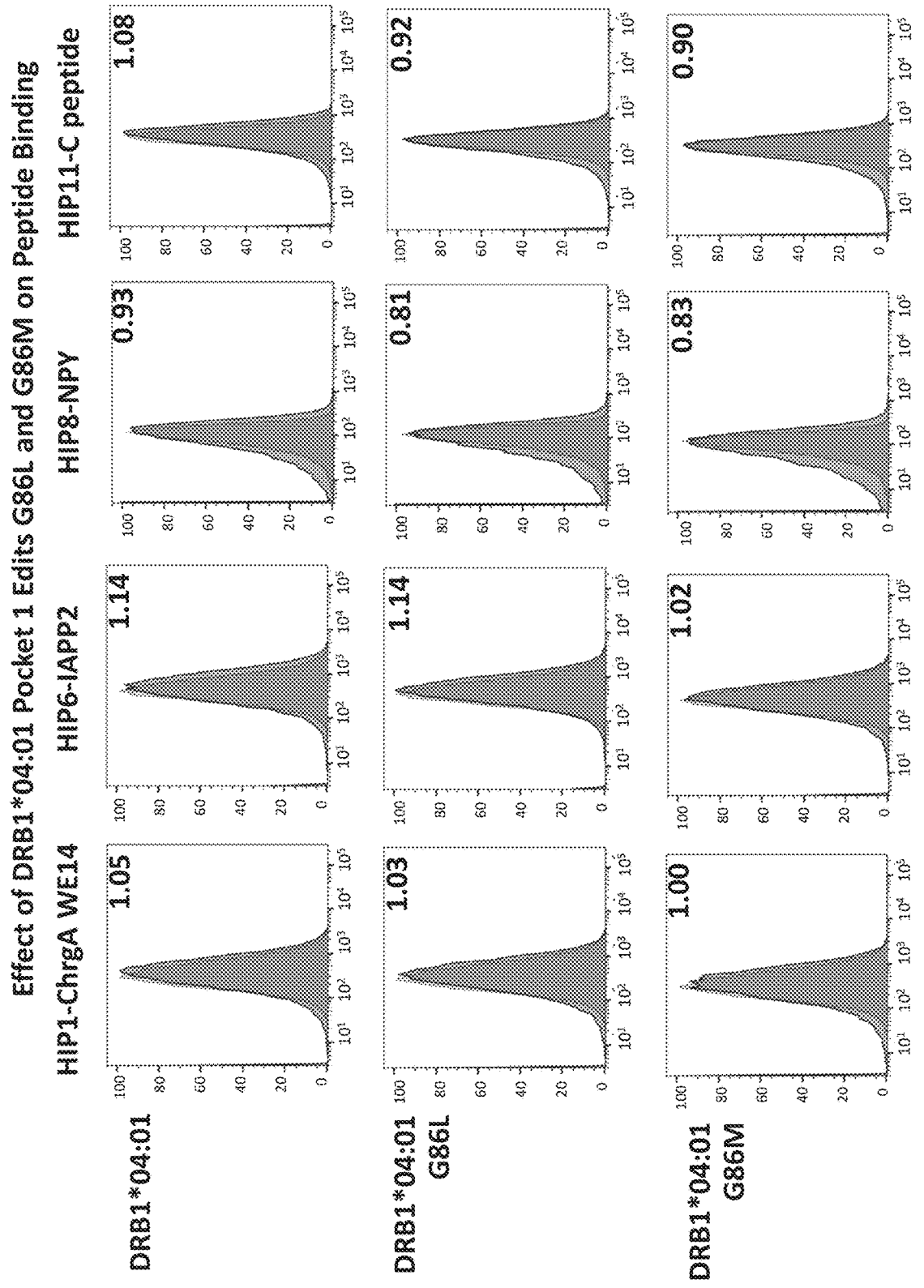
FIG. 24 depicts binding of hybrid insulin peptides to DRB1*04:01 and two edited alleles of the present disclosure with pocket 1 mutations G86L and G86M, according to embodiments of the disclosure. Numbers in upper left corner of the boxes are binding ratios compared to negative controls.

The same cell lines were tested with hybrid insulin peptides (FIG. 24). Changing position 86 from G to M or G to L did not result in a gain of function for these hybrid insulin peptides. They do not bind to DRB1*04:01 or the two mutants.

Figure 25:
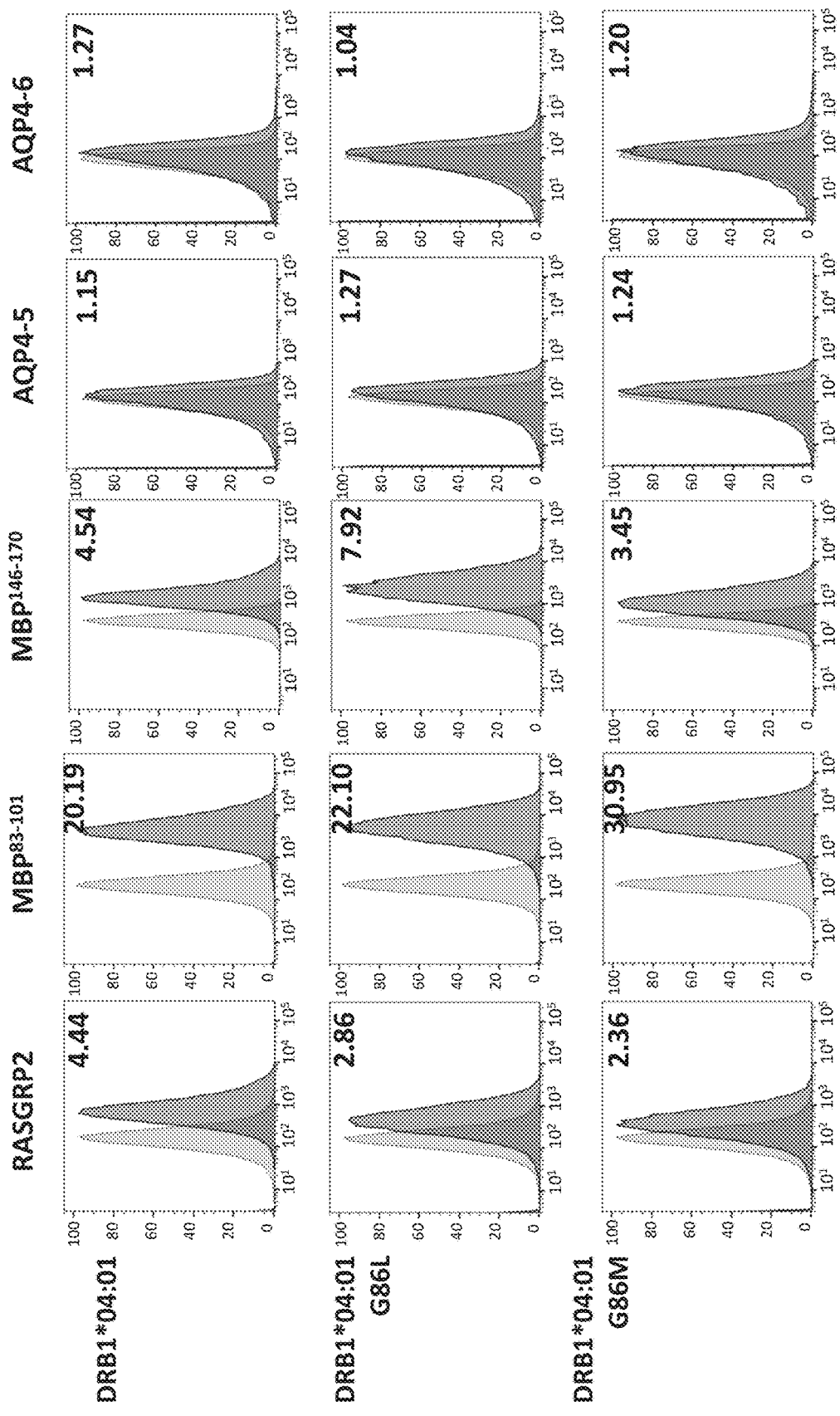
FIG. 25 depicts binding of neuroautoimmune peptides binding to DRB1*04:01 and edited alleles of the present disclosure with pocket 1 mutations G86L and G86M, according to embodiments of the disclosure. Numbers in upper left corner of boxes are binding ratios compared to negative controls.

As shown in FIG. 25, binding of RASGRP2 peptide, which is thought to play a role in MS, was reduced on the two mutants. However, the mutant cell lines still bound MBP peptides. The AQP4 peptides (NMO) bound similarly to DRB1*04:01 and the two mutants.

Figure 26:
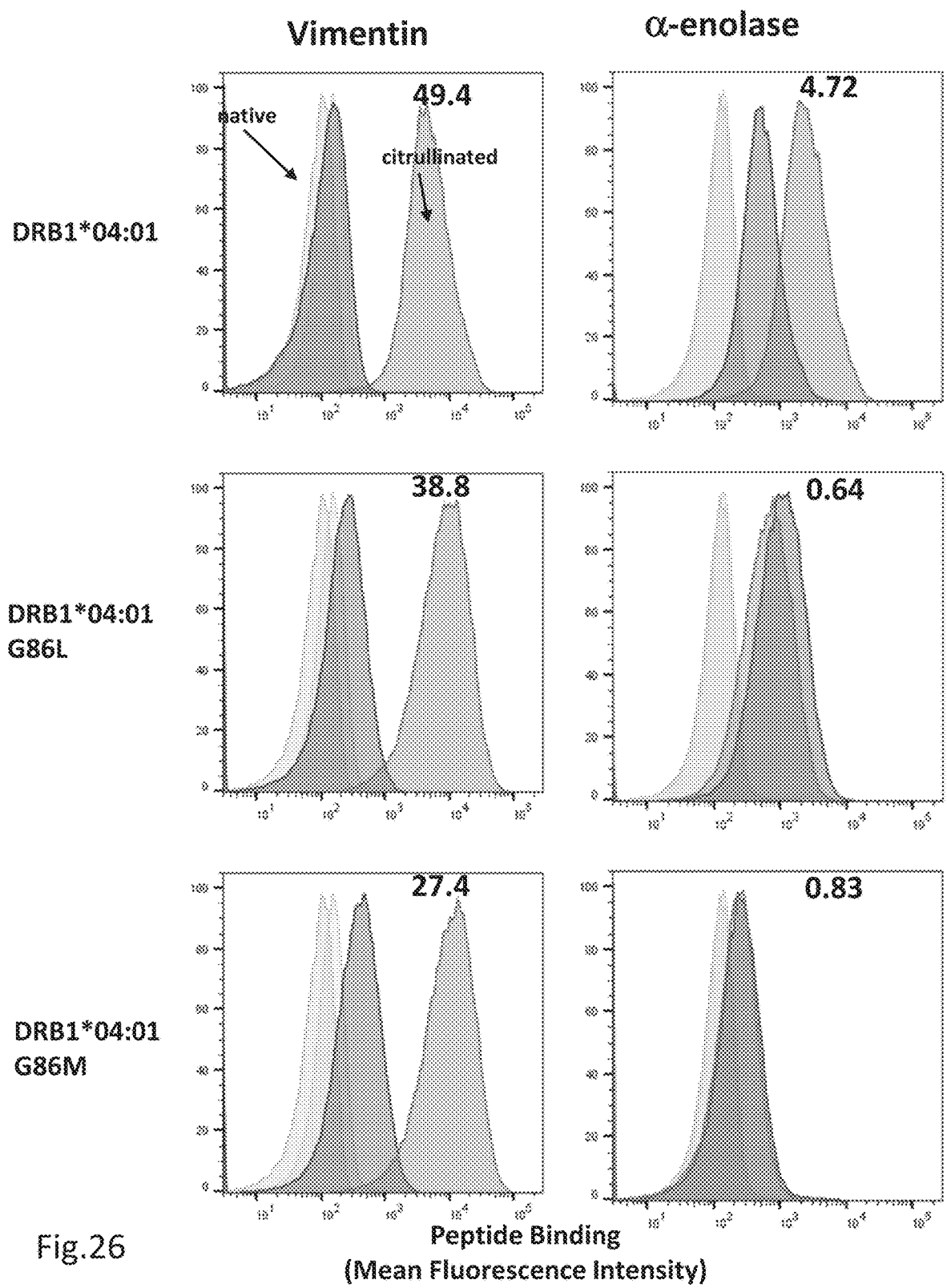
FIG. 26 depicts binding of arthritogenic peptides to DRB1*04:01 and engineered alleles of the present disclosure with pocket 1 mutations, according to embodiments of the disclosure. Numbers in upper left corner of boxes are binding ratios of citrullinated peptides compared to native peptides.

There is a preference for binding citrullinated vimentin and citrullinated a-enolase peptides are reduced when position 86 is changed to M or L. FIG. 26 depicts these binding with the a-enolase peptides. These mutations do not block all peptide binding. Light gray is citrullinated, dark gray is native peptide. The very light grey peak is background binding of the peptide to a T2 cell that does not express the HLA molecule. Ratio of citrullinated to native peptide binding is shown in the right-hand corner.

Figure 27:
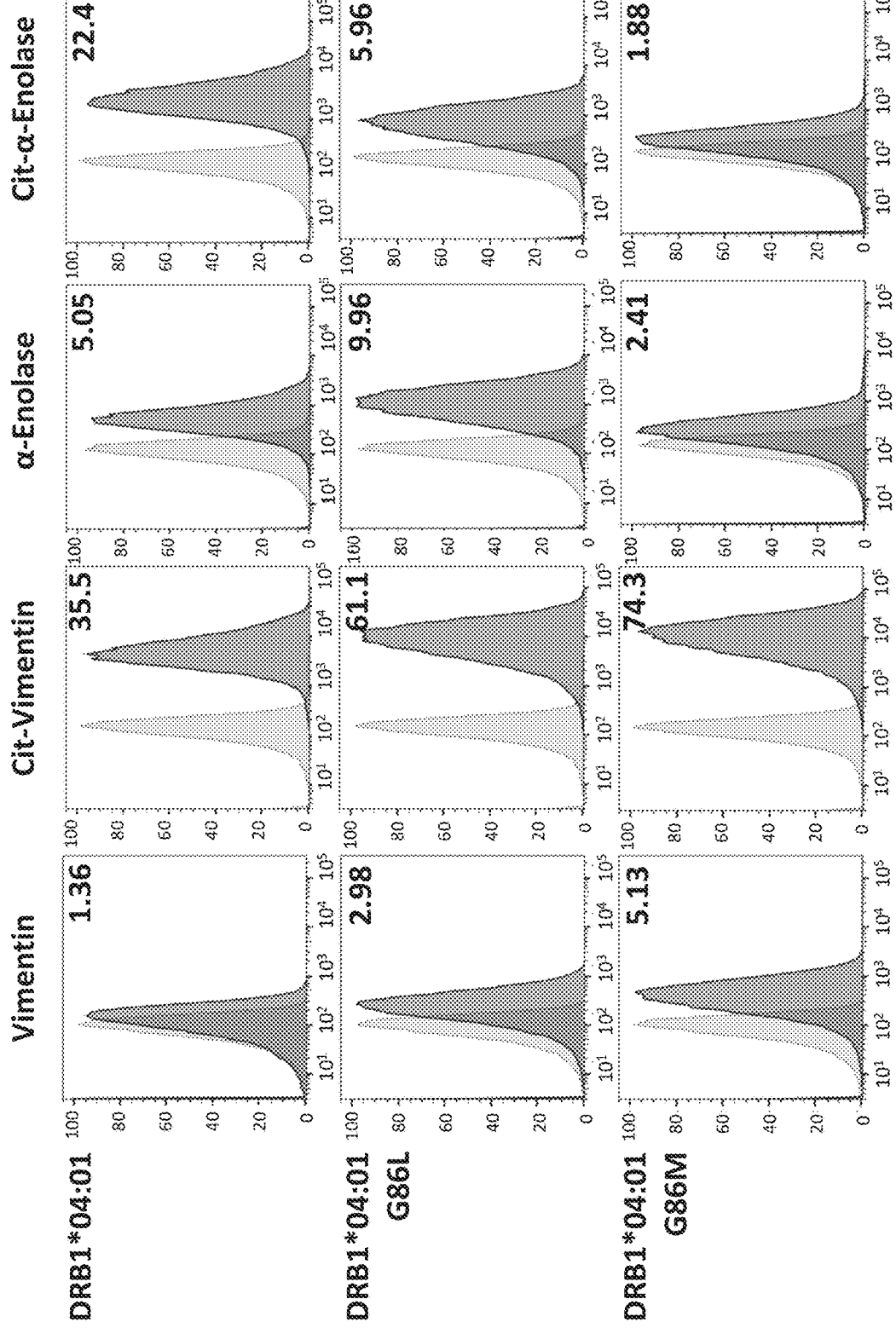
FIG. 27 depicts binding of native and citrullinated arthritogenic peptides to DRB1*04:01 and engineered alleles of the present disclosure with pocket 1 mutations, according to embodiments of the disclosure. Numbers in upper left corner of boxes are binding ratios compared to the negative controls.

Arthritogenic peptides were tested against DRB1*04:01 and the two mutants. FIG. 27 shows comparisons of the native versus citrullinated versions of the peptides on these cell lines. These studies show that the native and citrullinated versions of vimentin bind better when position 86 is mutated. Native a-enolase binding is increased on the G86L cell line but both mutants bind less of the citrullinated from. Here the ratio is calculated over the T2 parent background.

Example 8—Bone Marrow Treatments

At least 48 hrs before the experiment, mice were fed Baytril water (Baytril at 22.7 mg/ml: 50 ml tube with 1135 mg enrofloxacin, 45 ml water, 1.25 ml 1-butanol (n-butanol) and add dropwise (50% NaOH, 19M) 45% KOH (11.7M) until enrofloxacin dissolves (~150-200 µl); check pH, adjust to pH 8.9-10.9 with HCl, and qs to 50 ml with water) at 2 ml of Baytril water per water bottle (~375 ml). Bone marrow cells were isolated from the donor K71E mice and transferred into irradiated DR4 recipients. Recipient mice were irradiated with 2 doses @ 6 hrs apart to achieve total dose.
Bone Marrow Reconstitution Bone marrow cells were isolated from bones after washing in ethanol and dissecting away all the muscle tissue and tendons. Ends of the bone were cut and flushed using a 10 ml syringe with a 25-gauge needle to remove bone marrow cells. Cells were flushed into a 10 ml tissue culture plate with fresh PBS. Bone marrow cells were disrupted by passaging the cells through an 18-gauge needle/10 mL syringe with the PBS in the plate. Single cell suspension was transferred to a 50 ml conical tube, which was centrifuged to pellet cells. Red blood cells were lysed by incubating 1min with 2 ml RBC lysis buffer, and then composition was filtered through a 70 uM filter into a fresh 50 ml tube. 10 ul aliquot was diluted 1:2 in trypan blue for staining. Non-RBC cells were counted and total number of cells for each type of donor tallied. Cells were again centrifuged at 400×g and resuspend in PBS to $2-5\times10^7$ cells/mL. 100 ul was transferred to each irradiated recipient mouse by retro-orbital injection.
Monitoring and Checking for Reconstitution and Chimerism Mice were monitored daily for the first 2 weeks and thereafter on a weekly basis. Baytril water was replaced once a week for 4 weeks. Blood samples from mice were checked for reconstitution, by staining for B and T cells after 6 weeks. Mice with donor cell markers were checked for chimerism using flow cytometry. If no cell surface marker is available, samples were submitted for genotyping to test for the presence of altered gene or gene disruption.
Bone Marrow Transplant Using Anti-CD117 or Other Reagents to Remove Cells in the Recipient for the Transplant.

Anti-CD117 antibodies may aid engraftment of the disclosed engineered HSCs because they target HSCs (2019 May 9; 133(19):2069-2078 doi: 10.1182/blood-2018-06-858159). Anti-human CD117 mAb, SR-1, inhibits normal cord blood and bone marrow HSCs in vitro. SR-1 and clinical-grade humanized anti-human CD117 mAb, AMG 191, deplete normal and MDS HSCs in vivo in xenograft mouse models. These anti-CD117 mAbs are also useful in facilitating engraftment of normal donor human HSCs in MDS xenograft mouse models, restoring normal human hematopoiesis and eradicating aggressive pathologic MDS cells, in some cases the anti-CD117 antibody helps to block binding of hematopoietic stem cells to the bone marrow stroma, thus releasing them from the bone marrow into the peripheral circulation. For this reason, one method of treating a subject having or at risk of developing an autoimmune disease may include prior treatment with an anti-CD1117 antibody comprising to aid engraftment of engineered HSCs comprising the disclosed variant HLA molecules. Alternatively, subjects may be subjected to mobilization of immune cells with GCF treatments, prior to administration of engineered cells, as disclosed for harvesting of HSCs above.

Mice are placed into two groups. For these experiments, Group I were DR4+ mice, which were given two retrorbital iv injections of anti-CD117 (day 0 and day 2). These mice then received bone marrow cells from DRB1*04:01K71E donors on day 8. There after blood from recipients was collected at two time points (day 14 and day 28 after BMT) and analyzed. Group II mice were also DR4+, but received no anti-CD117 (day 0 and day 2). However, they did receive K71E bone marrow cells on day 8. Thereafter, blood was collected at two time points (day 14 and day 28 after BMT) as for Group I. Final samples collected on day 56

Blood samples are analyzed using digital PCR to look for the single amino acid difference between DR4 mice and K71E mice.

Busulfan, an alkylating chemotherapeutic agent, may also be used to prepare subjects for receipt of allogenic engineered HSCs. In some embodiments, busulfan is also used to treat recipient mice prior to transfer of bone marrow cells from donor mice carrying the engineered DRB1*04: 01K71E allele.

Discussion

The experiments and data disclosed herein provide original proof of concept for treatment of autoimmune diseases, including RA as well as Type 1 diabetes, multiple sclerosis, neuromyelitis optica, and other disorders arising from undesirable HLA protein-mediated binding and presentation of self-peptides to immune effector cells. The present disclosure is also to Applicant's knowledge the first description of treatment of an autoimmune disease other than RA. As such, the present disclosure is to Applicant's knowledge the first to broadly enable and demonstrate possession of treatment of autoimmunity by HLA engineering as disclosed.

The present disclosure further provides the novel HLA engineering strategy of steric occlusion of the antigen binding pocket (Pocket 1) of an HLA class II protein to modify binding and presentation of peptides, including self-peptides recognized as antigenic in autoimmune disease. In particular, the present disclosure describes and exemplifies (see Example 7) the strategy of replacing a relatively small amino acid (e.g., glycine) with a relatively large amino acid (e.g., methionine) to generally reduce the amount and affinity of peptide binding by an HLA protein associated with autoimmunity.

Thus, as broadly embodied, the present disclosure provides, inter alia, methods of treating or preventing autoimmunity by HLA engineering and methods of designing an HLA engineering treatment for autoimmune disease. The HLA engineering, which can be performed in vivo or ex vivo, reduces binding of one or more self-peptides associated with autoimmune response, and is designed and conducted to replace one or more amino acids that contribute to binding of that self-peptide(s) by the HLA protein, wherein the one or more amino acids are relatively 'immunoprivileged' by virtue of their location(s) within the HLA protein's antigen binding cleft.

The substituted or replacement amino acid can be identified by reference to an HLA allele associated with resistance to autoimmunity, such as a particular autoimmune disease by which a subject is afflicted or to which the subject is considered vulnerable. In certain embodiments, for example, candidate HLA protein amino acid residues for engineering are identified by comparison of the sequences and/or three-dimensional models of the autoimmune disease-associated HLA protein and an HLA protein associated with resistance to the same autoimmune disease. Such three-dimensional models include crystal structures of the HLA proteins in complex with a peptide or peptides associated with the autoimmune disease. Additionally or alternatively, the replacement amino acid can be identified de novo, such as by in silico modeling and/or high-throughput in vitro assays to identify substitutions that reduce binding of the HLA protein to the autoimmunity-associated peptides (e.g., peptides derived from insulin, collagen, RASDRP2, in diabetes, RA, and MS, respectively).

In some embodiments, the methods comprise identifying a small amino acid, such as glycine, at a suitable location, such as Pocket 1, of an HLA protein associated with an autoimmune disease, and engineering the corresponding HLA allele to express a replacement amino acid that is larger in size. The methods can further include assaying binding of self- and/or nonself peptides to the engineered HLA protein, as well as the functional assaying discussed above.

As contemplated herein, and as expressly described at, for example, Example 4, the HLA engineering can include replacement (or mutation) of two or more amino acids in an HLA protein, and the methods of designing treatment can be applied and optimized accordingly.

Certain embodiments provide methods of treating or preventing an autoimmune disease and methods of designing a treatment for autoimmune disease by HLA engineering. Certain embodiments provide methods of treating or preventing RA, T1D, MS, neuromyelitis optica, Behçet's syndrome, celiac disease, and psoriasis, and methods of designing a treatment for same. Certain embodiments provide methods of treating or preventing T1D, MS, neuromyelitis optica, Behçet's syndrome, celiac disease, and psoriasis, and methods of designing a treatment for same. In certain embodiments, the HLA engineering does not comprise DRB1*04:01$^{K71E}$ mutation. In certain embodiments, the HLA engineering does not comprise mutation of position 71 of the DRB1*04:01 allele. In certain embodiments, the HLA engineering does not comprise mutation of the DRB1*04:01 allele.

Significantly, many embodiments of the present disclosure, including certain embodiments, do not require, and can exclude, post-treatment immunosuppression. Accordingly, certain methods of designing a treatment for autoimmune disease by HLA engineering according to the present disclosure comprise, for example, in vitro T cell stimulation assays and/or skin graft experiments to confirm efficacy and non-rejection of candidate mutations, wherein such efficacy and/or non-rejection identifies a suitable mutation for HLA engineering as disclosed herein.

While multiple embodiments are disclosed, still other embodiments of the presently disclosed concepts, compounds, compositions, methods, processes, systems, and therapies will become apparent to those skilled in the art from the following detailed description. As will be apparent, the present disclosure is capable of modifications in various obvious aspects, all without departing from the spirit and scope of the present disclosure. Accordingly, the detailed description is to be regarded as illustrative in nature and not restrictive.

All references disclosed herein, whether patent or non-patent, are hereby incorporated by reference as if each was included at its citation, in its entirety. In case of conflict between reference and specification, the present specification, including definitions, will control.

Although the present disclosure has been described with a certain degree of particularity, it is understood the disclosure has been made by way of example, and changes in detail or structure may be made without departing from the spirit of the disclosure as defined in the appended claims.

What is claimed is:

1. A method of treating a subject suffering from or at risk of developing multiple sclerosis, comprising:

identifying a susceptible HLA DRB1*15:01 allele of the subject, wherein the susceptible HLA allele is associated with susceptibility to multiple sclerosis;

isolating a plurality of CD34+ hematopoietic stem cells from the subject;

modifying the HLA complex of the CD34+ hematopoietic stem cells to create engineered CD34+ hematopoietic stem cells, wherein the engineered CD34+ hematopoietic stem cells do not express the susceptible HLA allele, and express an engineered HLA allele, wherein a protein encoded by the engineered HLA allele differs from a protein encoded by the susceptible HLA allele by presence of an occlusion within a pocket of an antigen binding cleft of the protein encoded by the engineered HLA allele, and alters binding affinity for at least one self-peptide as compared to a protein encoded by the susceptible HLA allele;

isolating a plurality of the engineered CD34+ hematopoietic stem cells;

administering the isolated, engineered CD34+ hematopoietic stem cells to the subject; and thereby treating the subject suffering from or at risk of developing multiple sclerosis.

2. The method of claim 1, wherein the pocket is pocket 1.

3. The method of claim 2, wherein the occlusion within the pocket of the antigen binding cleft results from an amino acid substitution at position 86 of the protein encoded by the engineered HLA allele as compared to the protein encoded by the susceptible HLA allele.

4. The method of claim 1, wherein the occlusion within the pocket of the antigen binding cleft results from an amino acid substitution at position 86 of the protein encoded by the engineered HLA allele as compared to the protein encoded by the susceptible HLA allele, the amino acid substitution being replacement of the amino acid at position 86 with leucine.

5. The method of claim 4, wherein the protein encoded by the engineered HLA allele possesses lower binding affinity for the at least one self-peptide associated with multiple sclerosis.

6. The method of claim 5, wherein the self-peptide is selected from a peptide comprising at least one deiminated residue.

7. The method of claim 5, wherein the engineered HLA allele has an amino acid sequence of SEQ ID NO: 74.

8. The method of claim 1, wherein administering the isolated, engineered CD34+ hematopoietic stem cells to the subject does not elicit a rejection or graft-versus-host disease in the subject.

9. The method of claim 1, wherein the occlusion within the pocket of the antigen binding cleft results from an amino acid substitution at position 86 of the protein encoded by the engineered HLA allele as compared to the protein encoded by the susceptible HLA allele, the amino acid substitution being replacement of the amino acid at position 86 with phenylalanine.

10. The method of claim 1, wherein the occlusion within the pocket of the antigen binding cleft results from an amino acid substitution at position 71 of the protein encoded by the engineered HLA allele as compared to the protein encoded by the susceptible HLA allele.

11. The method of claim 10, wherein the occlusion within the pocket of the antigen binding cleft results from an amino acid substitution at position 71 of the protein encoded by the engineered HLA allele as compared to the protein encoded by the susceptible HLA allele, the amino acid substitution being replacement of the amino acid at position 71 with arginine.

12. The method of claim 1, wherein the occlusion within the pocket of the antigen binding cleft results from an amino acid substitution at position 47 of the protein encoded by the engineered HLA allele as compared to the protein encoded by the susceptible HLA allele.

13. The method of claim 12, wherein the occlusion within the pocket of the antigen binding cleft results from an amino acid substitution at position 47 of the protein encoded by the engineered HLA allele as compared to the protein encoded by the susceptible HLA allele, the amino acid substitution being replacement of the amino acid at position 47 with tyrosine.

* * * * *